US009644207B2

(12) United States Patent
Rigo et al.

(10) Patent No.: US 9,644,207 B2

(45) Date of Patent: May 9, 2017

(54) COMPOSITIONS AND METHODS FOR MODULATING TAU EXPRESSION

(71) Applicant: Ionis Pharmaceuticals, Inc., Carlsbad, CA (US)

(72) Inventors: Frank Rigo, Carlsbad, CA (US); Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/776,561

(22) PCT Filed: Mar. 14, 2014

(86) PCT No.: PCT/US2014/029752

§ 371 (c)(1),
(2) Date: Sep. 14, 2015

(87) PCT Pub. No.: WO2014/153236

PCT Pub. Date: Sep. 25, 2014

(65) Prior Publication Data

US 2016/0032285 A1 Feb. 4, 2016

Related U.S. Application Data

(60) Provisional application No. 61/785,177, filed on Mar. 14, 2013, provisional application No. 61/943,931, filed on Feb. 24, 2014.

(51) Int. Cl.

| | |
|---|---|
| ***C07H 21/02*** | (2006.01) |
| ***C07H 21/04*** | (2006.01) |
| ***A61K 31/70*** | (2006.01) |
| ***C12N 15/113*** | (2010.01) |
| *C12N 5/00* | (2006.01) |

(52) U.S. Cl.

CPC ........ *C12N 15/113* (2013.01); *C12N 2310/11* (2013.01); *C12N 2310/31* (2013.01); *C12N 2310/315* (2013.01); *C12N 2310/3181* (2013.01); *C12N 2310/32* (2013.01); *C12N 2310/321* (2013.01); *C12N 2310/3231* (2013.01); *C12N 2310/3233* (2013.01); *C12N 2310/3341* (2013.01); *C12N 2310/345* (2013.01); *C12N 2310/346* (2013.01); *C12N 2310/351* (2013.01); *C12N 2320/33* (2013.01)

(58) Field of Classification Search

None

See application file for complete search history.

(56) References Cited

U.S. PATENT DOCUMENTS

| | | | |
|---|---|---|---|
| 3,687,808 | A | 8/1972 | Merigan et al. |
| 4,845,205 | A | 7/1989 | Huynh Dinh et al. |
| 4,880,635 | A | 11/1989 | Janoff et al. |
| 4,906,477 | A | 3/1990 | Kurono et al. |
| 4,911,928 | A | 3/1990 | Wallach |
| 4,917,951 | A | 4/1990 | Wallach |
| 4,920,016 | A | 4/1990 | Allen et al. |
| 4,921,757 | A | 5/1990 | Wheatley et al. |
| 5,034,506 | A | 7/1991 | Summerton et al. |
| 5,130,302 | A | 7/1992 | Spielvogel et al. |
| 5,134,066 | A | 7/1992 | Rogers et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,185,444 | A | 2/1993 | Summerton et al. |
| 5,367,066 | A | 11/1994 | Urdea et al. |
| 5,432,272 | A | 7/1995 | Benner |
| 5,457,187 | A | 10/1995 | Gmelner et al. |
| 5,459,255 | A | 10/1995 | Cook et al. |
| 5,484,908 | A | 1/1996 | Froehler et al. |
| 5,502,177 | A | 3/1996 | Matteucci et al. |
| 5,525,711 | A | 6/1996 | Hawkins et al. |
| 5,552,540 | A | 9/1996 | Haralambidis |
| 5,587,469 | A | 12/1996 | Cook et al. |
| 5,594,121 | A | 1/1997 | Froehler et al. |

(Continued)

FOREIGN PATENT DOCUMENTS

| | | |
|---|---|---|
| CN | 1696294 | 11/2005 |
| WO | WO 98/39352 | 9/1998 |

(Continued)

OTHER PUBLICATIONS

Agrawal et al, "Site-specific excision from RNA by Rnase H and mixed-phosphate-backbone oligodeoxynucleotides" Proc. Nat'l Acad. Sci (1990) 87:1401-1405.

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Allshire, "RNAi and Heterochromatin—a Hushed-Up Affair" Science (2002) 297: 1818-1819.

(Continued)

*Primary Examiner* — Sean McGarry

(74) *Attorney, Agent, or Firm* — Ionis Pharmaceuticals, Inc. Patent Dept.

(57) ABSTRACT

Disclosed are methods for modulating splicing of Tau mRNA in an animal with Tau antisense compounds. Also disclosed herein are methods for reducing expression of Tau mRNA and protein in an animal with Tau antisense compounds. Such compounds and methods are useful to treat, prevent, or ameliorate neurodegenerative diseases in an individual in need thereof. Examples of neurodegenerative diseases that can be treated, prevented, and ameliorated with the administration Tau antisense oligonucleotides include Alzheimer's Disease, Fronto-temporal Dementia (FTD), FTDP-17, Progressive Supranuclear Palsy, Chronic Traumatic Encephalopathy, Epilepsy, and Dravet's Syndrome.

26 Claims, 1 Drawing Sheet

(56) References Cited

U.S. PATENT DOCUMENTS

| | | | |
|---|---|---|---|
| 5,596,091 A | 1/1997 | Switzer | |
| 5,614,617 A | 3/1997 | Cook et al. | |
| 5,645,985 A | 7/1997 | Froehler et al. | |
| 5,681,941 A | 10/1997 | Cook et al. | |
| 5,698,685 A | 12/1997 | Summerton et al. | |
| 5,750,692 A | 5/1998 | Cook et al. | |
| 5,763,588 A | 6/1998 | Matteucci et al. | |
| 5,801,154 A | 9/1998 | Baracchini et al. | |
| 5,830,653 A | 11/1998 | Froehler et al. | |
| 5,837,853 A | 11/1998 | Takashima et al. | |
| 6,005,096 A | 12/1999 | Matteucci et al. | |
| 6,268,490 B1 | 7/2001 | Imanishi et al. | |
| 6,525,191 B1 | 2/2003 | Ramasamy | |
| 6,582,908 B2 | 6/2003 | Fodor et al. | |
| 6,670,461 B1 | 12/2003 | Wengel et al. | |
| 6,673,661 B1 | 1/2004 | Liu et al. | |
| 6,770,748 B2 | 8/2004 | Imanishi et al. | |
| 6,794,499 B2 | 9/2004 | Wengel et al. | |
| 7,034,133 B2 | 4/2006 | Wengel et al. | |
| 7,053,207 B2 | 5/2006 | Wengel | |
| 7,084,125 B2 | 8/2006 | Wengel | |
| 7,217,805 B2 | 5/2007 | Imanishi et al. | |
| 7,314,923 B2 | 1/2008 | Kaneko et al. | |
| 7,399,845 B2 | 7/2008 | Seth et al. | |
| 7,427,672 B2 | 9/2008 | Imanishi et al. | |
| 7,547,684 B2 | 6/2009 | Seth et al. | |
| 7,569,575 B2 | 8/2009 | Sorensen et al. | |
| 7,696,345 B2 | 4/2010 | Allerson et al. | |
| 7,741,457 B2 | 6/2010 | Seth et al. | |
| 7,858,747 B2 | 12/2010 | Woldike et al. | |
| 8,178,503 B2 | 5/2012 | Rigoutsos et al. | |
| 8,329,890 B2 | 12/2012 | Davidson et al. | |
| 2001/0053519 A1 | 12/2001 | Fodor et al. | |
| 2002/0018995 A1 | 2/2002 | Ghetti et al. | |
| 2003/0228597 A1 | 12/2003 | Cowsert et al. | |
| 2004/0054156 A1 | 3/2004 | Draper et al. | |
| 2004/0171570 A1 | 9/2004 | Allerson et al. | |
| 2004/0241651 A1 | 12/2004 | Olek et al. | |
| 2005/0130923 A1 | 6/2005 | Bhat et al. | |
| 2005/0153336 A1 | 7/2005 | Bennett et al. | |
| 2005/0244851 A1 | 11/2005 | Blume et al. | |
| 2005/0255487 A1 | 11/2005 | Khvorova et al. | |
| 2006/0216722 A1 | 9/2006 | Betsholtz et al. | |
| 2007/0031844 A1 | 2/2007 | Khvorova et al. | |
| 2007/0203333 A1 | 8/2007 | McSwiggen et al. | |
| 2007/0287831 A1 | 12/2007 | Seth et al. | |
| 2008/0003570 A1 | 1/2008 | Rogers et al. | |
| 2008/0039618 A1 | 2/2008 | Allerson et al. | |
| 2008/0249058 A1 | 10/2008 | Roberson et al. | |
| 2008/0318210 A1 | 12/2008 | Bentwich | |
| 2009/0012281 A1 | 1/2009 | Swayze et al. | |
| 2009/0176725 A1 | 7/2009 | Morrissey et al. | |
| 2009/0176728 A1* | 7/2009 | Yague | C12N 15/113 514/44 R |
| 2011/0054005 A1 | 3/2011 | Naito et al. | |
| 2011/0150897 A1 | 6/2011 | Meyer et al. | |
| 2011/0244561 A1 | 10/2011 | Davidson et al. | |
| 2011/0263687 A1 | 10/2011 | Mattick et al. | |
| 2013/0046007 A1 | 2/2013 | Bennett et al. | |
| 2013/0123133 A1 | 5/2013 | Ward et al. | |

FOREIGN PATENT DOCUMENTS

| | | |
|---|---|---|
| WO | WO 99/14226 | 3/1999 |
| WO | WO 99/62548 | 12/1999 |
| WO | WO 00/63364 | 10/2000 |
| WO | WO 01/32703 | 5/2001 |
| WO | WO 02/081494 | 10/2002 |
| WO | WO 03/004602 | 1/2003 |
| WO | WO 2004/017072 | 2/2004 |
| WO | WO 2004/035765 | 4/2004 |
| WO | WO 2004/058940 | 7/2004 |
| WO | WO 2004/106356 | 12/2004 |
| WO | WO 2005/017143 | 2/2005 |
| WO | WO 2005/021570 | 3/2005 |
| WO | WO 2005/040180 | 5/2005 |
| WO | WO 2006/047673 | 5/2006 |
| WO | WO 2007/027775 | 3/2007 |
| WO | WO 2007/107789 | 9/2007 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036698 | 4/2010 |
| WO | WO 2010/148249 | 12/2010 |
| WO | WO 2011/017521 | 5/2011 |
| WO | WO 2011/131693 | 10/2011 |
| WO | WO 2011/139702 | 11/2011 |
| WO | WO 2013/148260 | 10/2013 |
| WO | WO 2013/148283 | 10/2013 |
| WO | WO 2013/173647 | 11/2013 |
| WO | WO 2014/114937 | 7/2014 |
| WO | WO 2015/010135 | 1/2015 |
| WO | WO 2016/151523 | 9/2016 |

OTHER PUBLICATIONS

Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16: 917-926.

Altmann et al., "Second Generation of Antisense Oligonucleotides: From Nuclease Resistance to Biological Efficacy in Animals" Chimia (1996) 50: 168-176.

Altmann et al., "Second-generation antisense oligonucleotides: structure-activity relationships and the design of improved signal-transduction inhibitors." Biochem. Soc. Trans. (1996) 24: 630-637.

Altschul et al., "Basic Local Alignment Search Tool" J. Mol. Biol. (1990) 215:403-410.

Andorfer et al., "Hyperphosphorylation and aggregation of tau in mice expressing normal human tau isoforms" Journal of Neurochemistry (2003) 86: 582-590.

Australian Patent Examination Report for Application No. 2013202595 dated Jul. 4, 2014 (15 pages).

Badiola et al, "Tau phosphorylation and aggregation as a therapeutic target in tauopathies" CNS Neurol Discord Drug Targets (2010) 9(6):727-740.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem., (1997) 272: 11944-12000.

Baker et al., "Effects of oligo sequence and chemistry on the efficiency of oligodeoxyribonucleotide-mediated mRNA cleavage" (1990) 18(12):3537-3543.

Bevins et al., "Object recognition in rats and mice: a one-trial non-matching-to-sample learning task to study 'recognition memory'" Nature Protocols (2006) 1: 1306-1311.

Bi et al., Tau-Targeted Immunization Impedes Progression fo Neurofibrillary Histopathology in Aged P301L Tau Transgenic Mice Plos ONE (2011) 6(12):e26860.

Boiziau et al., "Antisense 2'-O-alkyl oligoribonucleotides are efficient inhibitors of reverse transcription" Nucleic Acids Research, (1995) 23(1):64-71.

Braasch et al., "Locked nucleic acid (LNA): fine-tuning the recognition of DNA and RNA" Chem. Biol. (2001) 8:1-7.

Braasch et al., "Novel antisense and peptide nucleic acid strategies for controlling gene expression" Biochemistry (2002) 41(14):4503-4510.

Branch et al., "A good antisense molecule is hard to find," TIBS (1998) 23:45-50.

Caceres et al., "Inhibition of neurite polarity by tau antisense oligonucleotides in primary cerebellar neurons" Nature (1990) 343:461-463.

(56) References Cited

OTHER PUBLICATIONS

Caceres et al., "The Effect of Tau antisense Oligonucleotides on Neurite Formation of Cultured Cerebellar Macroneurons" J. Neuroscience (1991) 11(6):1515-1523.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Craig et al., "Towards a small molecule inhibitor of tau exon 10 splicing: Identification of compounds that stabilise the 5'-splice site stem-loop" Alzheimer's & Dementia: The Journal of the Alzheimer's Association (2012) 8(4): P636.
Crooke et al., "Basic Principles of Antisense Therapeutics" Antisense Research and Application (1998) Chapter 1:1-50.
Crooke et al., "Pharmacokinetic Properties of Several Novel Oligonucleotide Analogs in mice" J. Pharmacol. Exp. Ther. (1996) 277(2):923-937.
Dawson et al., "The tau N279K exon 10 splicing mutation recapitulates frontotemporal dementia and parkinsonism linked to chromosome 17 tauopathy in a mouse model." (2007) 27(34):9155-9168.
Dawson, "Tau Exon 10 Splicing Tauopathy", presentation given at CurePSP 2010 International Research Symposium, Nov. 18, 2010, San Diego, CA.
Dawson, "The Effects of the CBD-Associated Tau Gene H1 Haplotype on Tau Expression," Abstract presented at CurePSP 2010 International Research Symposium, Nov. 18, 2010, San Diego, CA (retrieved online Jan. 13, 2016).
Deacon, "Assessing nest building in mice" Nat. Protocol. (2006) 1:1117-1119.
Devos et al., "Antisense oligonucleotides: treating neurodegeneration at the level of RNA" Neurotherapeutics (2013) 10(3): 486-497.
Devos et al., "Antisense Reduction of Human Tau in the CNS of P301S mice both Prevents and Reverses Hyperphosphorylated Tau Deposition" abstract presented at Keystone Symposium: Long Noncoding RNAs: Marching toward Mechanism, Feb. 27-Mar. 4, 2014, Santa Fe, NM.
Devos et al., "Antisense Reduction of Tau in Adult Mice Protects against Seizures" J. Neuroscience (2013) 33(31): 12887-12897.
Devos et al., "Antisense Reduction of the Human Tau Transgene in the CNS of P301S mice Robustly Decreases Tau Deposition" abstract presented at Keystone Symposia: New Frontiers in Neurodegenerative Disease Research, Feb. 3-8, 2013, Santa Fe, NM.
Devos et al., "Reducing Human Tau in the CNS of P301S mice Dramatically Reverses Tau Pathology" abstract presented at14th International Conference on Alzheimer's Drug Discovery, Sep. 9-10, 2013, Jersey City, NJ.
Devos et al., "Using antisense oligonucleotides to knockdown endogenous brain tau in vivo" Alzheimer's & Dementia: The Journal of the Alzheimer's Association (2012) 8(4): P205.
Devos et al., "Using antisense oligonucleotides to knockdown endogenous brain tau in vivo" poster presentation at AAIC 2012; Jul. 14-19, 2012.
Donahue et al., "Stabilization of the Tau Exon 10 Stem Loop Alters Pre-mRNA Splicing" J. Biol. Chem. (2006) 281(33):23302-23306.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Angewandte Chemie, International Edition (1991) 30(6): 613-629.
European Examination Report for Application No. 13770075.3 dated Oct. 2, 2015.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Frost et al., "Retinal Screening for Early Detection of Alzheimer's Disease" Digital Telerential Screening, K. Yogesan eds., 2012, 91-100.
Furdon et al., "RNase H cleavage of RNA hybridized to oligonucleotides containing methylphosphonate, phosphorothioate and phosphodiester bonds" Nucleic Acids Res. (1989) 17(22): 9193-9204.
Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.
GenBank Accession No. AK226139.1 (retrieved online Apr. 10, 2015).
GenBank Accession No. NM_001123066.3 (retrieved online Apr. 10, 2015).
GenBank Accession No. NM_001123067.3 (retrieved online Apr. 10, 2015).
GenBank Accession No. NM_001203251.1 (retrieved online Apr. 10, 2015).
GenBank Accession No. NM_001203252.1 (retrieved online Apr. 10, 2015).
GenBank Accession No. NM_005910.5 (retrieved online Apr. 10, 2015).
GenBank Accession No. NM_016834.4 (retrieved online Apr. 10, 2015).
GenBank Accession No. NM_016835.4 (retrieved online Apr. 10, 2015).
GenBank Accession No. NM_016841.4 (retrieved online Apr. 10, 2015).
GenBank Accession No. NT_010783.14 (retrieved online Apr. 10, 2015).
GenBank Accession No. NT_010783.15 (retrieved online Apr. 10, 2015).
Goedert et al., "Cloning and Sequencing of the cDNA Encoding a Core Protein of the Paired Helical Filament of Alzheimers Disease: Identification as the Microtubule-Associated Protein Tau" PNAS (1988) 85(11):4051-4055.
Goedert et al., "Monoclonal antibody AT8 recognises tau protein phosphorylated at both serine 202 and threonine 205." Neurosci. Lett. (1995) 189(3): 167-169.
Gupta et al., "Retinal tau pathology in human glaucomas" Can. J. Ophtalmol. (2008) 43: 53-60.
Hall et al., "Establishment and Maintenance of a Heterochromatin Domain" Science (2002) 297: 2232-2237.
Hatta et al., "Mechanisms of the inhibition of reverse transcription by unmodified and modified antisense oligonucleotides" FEBS Lett. (1993) 330(2): 161-164.
Ho et al., "Review: Tauopathy in the retina and optic nerve: does it shadow pathological changes in the brain?" Molecular Vision (2012) 18: 2700-2710.
International Search Report for application PCT/US2013/31500 dated Jun. 5, 2013 (12 pages).
International Search Report for application PCT/US2014/029752 dated Sep. 18, 2014.
Jenuwein, "Molecular biology. An RNA-guided pathway for the epigenome." Science (2002) 297(5590): 2215-2218.
Jiang et al., "Aberrant Splicing of tau Pre-mRNA Caused by Intronic Mutations Associated with the Inherited Dementia Frontotemporal Dementia with Parkinsonism Linked to Chromosome 17" Mol. Cell Biol. (2000) 20(11):4036-4048.
Jones et al., "RNA Quantitation by Fluorescence-Based Solution Assay: RiboGreen Reagent Characterization" Analytical Biochemistry (1998) 265: 368-374.
Jones et al., "Targeting hyperphosphorylated tau with sodium selenate suppresses seizures in rodent models" Neurobiology of Disease (2012) 45:897-901.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.
Kalbfuss, B. et al., "Correction of Alternative Splicing of Tau in Frontotemporal Dementia and Parkinsonism Linked to Chromosome 17," Journal of Biological Chemistry, (2001) 276:42986-42993.

(56) References Cited

OTHER PUBLICATIONS

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, The Concise Encyclopedia of Polymer Science and Engineering, John Wiley & Sons, 1990, 858-859.
Kumar et al., "The First Analogues of LNA (Locked Nucleic Acids): Phosphorothioate-LNA and 2'-Thio-LNA" Bioorg. Med. Chem. Lett. (1998) 8:2219-2222.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.
Manoharan et al., "Chemical Modifications to Improve Uptake and Bioavailability of Antisense Oligonucleotides" Ann. N.Y. Acad. Sci. (1992) 660:306.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Martin, "Ein neuer Zugang zu 2'-O-Alkylribonucleosiden and Eigenschaften deren Oligonucleotide" Helv. Chim. Acta (1995) 78: 486-504.
Mishra et al., "Improved leishmanicidal effect of phosphorotioate antisense oligonucleotides by LDL-mediated delivery" Biochim. Biophys. Acta (1995) 1264:229-237.
Morita et al., "Synthesis and Properties of 2'-O,4'-C-Ethylene-Bridged Nucleic Acids (ENA) as Effective Antisense Oligonucleotides" Bioorganic Medicinal Chemistry (2003) 11: 2211-2226.
New England Biolabs 1998/99 Catalog (cover page and pp. 121 and 284).
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3:239-243.
Pal-Bhadra et al., "Heterochromatic silencing and HP1 localization in *Drosophila* are dependent on the RNAi machinery." Science (2004) 303(5658): 669-672.
Peacey et al., "Targeting a pre-mRNA structure with bipartite antisense molecules modulates tau alternative splicing" Nucleic Acids Research (2012) 40(19):9836-9849.
Pizzi et al., "Antisense Strategy Unravels Tau Proteins as Molecular Risk Factors for Glutamate-Induced Neurodegeneration" Cellular and Molecular Neurobiology (1994) 14(5):569-578.
Reynolds et al., "Rational siRNA design for RNA interference" Nature Biotechnology (2004) 22(3):326-330.
Rodriguez-Martin et al., "Reprogramming of tau alternative splicing by spliceosome-mediated RNA trans-splicing: implications for tauopathies." Proc Natl Acad Sci USA (2005) 102(43): 15659-15664.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi et al., "Heterocyclic Base Modifications in Nucleic Acids and Their Applications in Antisense Oligonucleotides" Antisense Research and Applications (1993) pp. 273-288.
Sapir et al., "Tau's role in the developing brain: implications for intellectual disability" Human Molecular Genetics (2012) 21(8):1681-1692.
Schoch et al., "Antisense oligonucleotide-mediated tau splicing reduces behavioral deficits and tau pathology in a tauopathy model" abstract presented at Keystone Symposium: Alzheimer's Disease, Mar. 2-7, 2014, Keystone, CO.
Schoch et al., "Antisense oligonucleotide-mediated tau splicing reduces behavioral deficits and tau pathology in a tauopathy model" poster presented at Keystone Symposium: Alzheimer's Disease, Mar. 2-7, 2014, Keystone, CO.
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Smith et al., "Comparison of Biosequences" Adv. Appl. Math. (1981) 2: 482-489.
Sproat et al., "Highly efficient chenical synthesis of 2'-O-methyloligoribonucleotides and tetrabiotinylated derivatives; novel probes that are resistant to degradation by RNA or DNA specific nucleases" Nucleic Acids Res. (1989) 17(9): 3373-3386.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Usman et al., "Exploiting the chemical synthesis of RNA," Trends in Biochemical Sciences, Elsevier, Haywards, GB (1992) 17(9): 334-339.
Verdel et al., "RNAi-Mediated Targeting of Heterochromatin by the RITS Complex" Science (2004) 303: 672-676.
Volpe et al., "Regulation of Heterochromatic Silencing and Histone H3 Lysine-9 Methylation by RNAi" Science (2002) 297: 1833-1837.
Wahlestedt et al., "Potent and nontoxic antisense oligonucleotide containing locked nucleic acids" Proc. Natl. Acad. Sci. USA (2000) 97: 5633-5638.
Walder et al., "Role of RNase H in hybrid-arrested translation by antisense oligonucleotides." Proc. Natl. Acad. Sci. USA (1988) 85(14): 5011-5015.
Wang et al., "A Novel Tau Transcript in Cultured Human Neuroblastoma Cells Expression Nuclear Tau" J. Cell Biol. (1993) 121(2):257-267.
Wolfe M.S., "The Roll of Tau in Neurodegenerative Diseases and Its Potential as a Therapeutic Target" Scientifica (2012) 1-20.
Woolf et al., "Specificity of antisense oligonucleotides in vivo" Proc. Natl. Acad. Sci. USA (1992) 89:7305-7309.
Yamada et al., "In vivo microdialysis reveals age-dependent decrease of brain interstitial fluid tau levels in P301S human tau transgenic mice." Neurosci. (2011) 31: 13110-13117.
Yoshiyama et al., "Synapse Loss and Microglial Activation Precede Tangles in a P301S Tauopathy Mouse Model" Neuron (2007) 53: 337-351.
Zhang et al., "PowerBLAST: A New Network BLAST Application for Interactive or Automated Sequence Analysis and Annotation" Genome Res. (1997) 7:649-656.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Davies et al., (2003) "Hyperphosphorylation and aggregation of tau in mice expressing normal human tau isoforms" Journal of Neurochemistry 86:582-590.

(56) References Cited

OTHER PUBLICATIONS

Duff et al.,"Characterization of Pathology in Transgenic Mice Over-Expressing Human Genomic and cDNA Tau Transgenes" Neurobiology of Disease (2000) 7:87-98.
Supplementary European Search Report for Application No. 14767904.7, dated Sep. 19, 2016, 10 pages.
Gordon et al., "Antisense Suppression of Tau in Cultured Rat Olgodendrocytes Inhibits Process Formation," Journal of Neuroscience Research (2008) 86:2591-2601.
Spicakova et al., "Expression and Silencing of the Microtubule-Associated Protein Tau in Breast Cancer Cells," Molecular Cancer Therapeutics (2010) 9:2970-2981.
Wolfe M.S., "Tau Mutations in Neurodegenrative Diseases" J. Biol Chem (2009) 284(10):3021-3025.

* cited by examiner

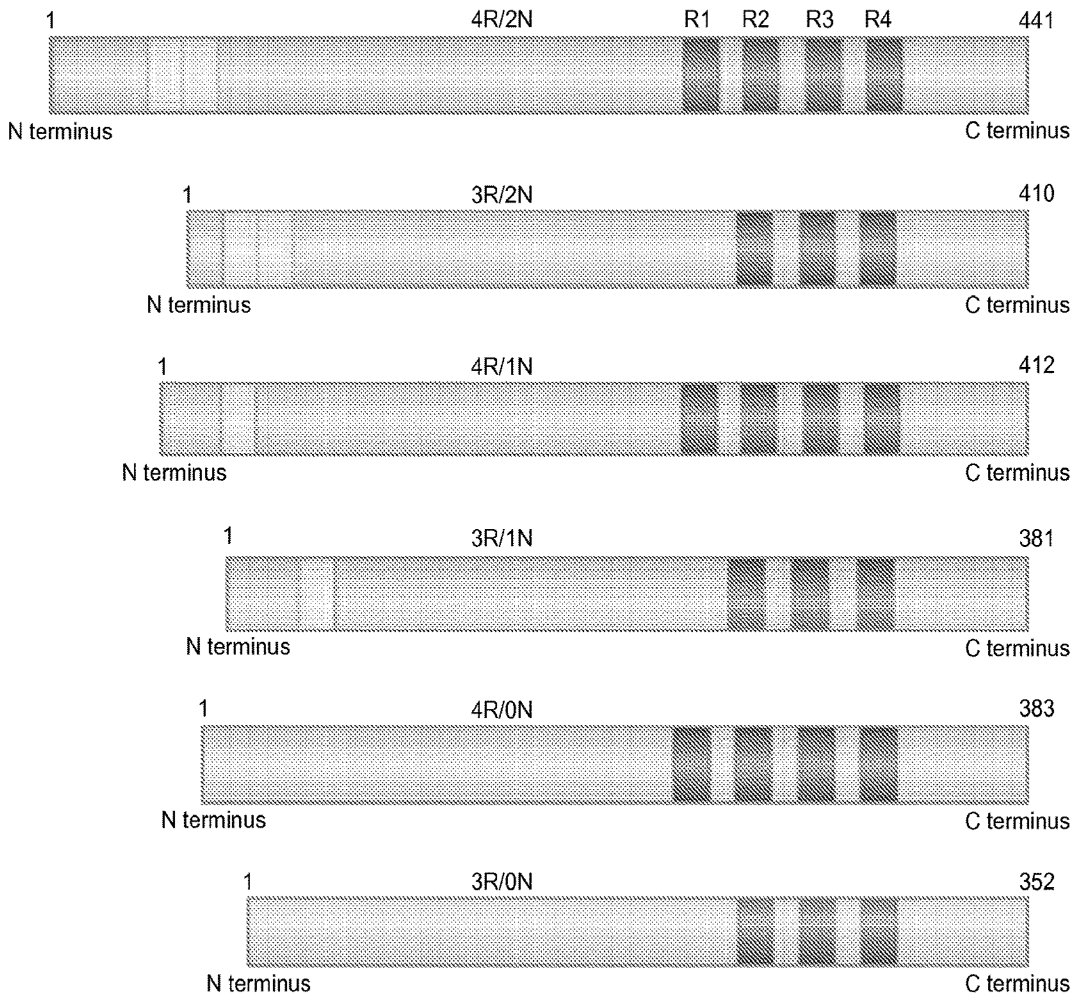
1
4R/2N
R1
R2
R3
R4
441
N terminus
C terminus
1
3R/2N
410
N terminus
C terminus
1
4R/1N
412
N terminus
C terminus
1
3R/1N
381
N terminus
C terminus
1
4R/0N
383
N terminus
C terminus
1
3R/0N
352
N terminus
C terminus

SEQUENCE LISTING

```
<160> NUMBER OF SEQ ID NOS: 232

<210> SEQ ID NO 1
<211> LENGTH: 141001
<212> TYPE: DNA
<213> ORGANISM: Homo sapiens

<400> SEQUENCE: 1

aatttataaa ggaaaaaggt ttaattgact cacagttcag catgtctggg gaagtgttag     60

gaaacttaca atcatggcag aagagaaagc aaaccatcct ttctcacatg gtgacaggaa    120

gagcaaagcg gggtaagccc cttacaaaac caccagatct catgagaact cactatcacg    180

agaacaccat ggaggtaact gcccccatga ttcaattacc tcccaccagg tccctcccac    240

gacatgtggg gattatgcga actccaactc aagatgagat ttgggtgggg acacagccaa    300

accatatcag aagcttaacc ttctttggag catgattatt cagttgaacc taagttcagt    360

agtcacccag ttatgctgtc ttcagctact attttccata tgtttctcaa acatctgata    420

tatcacactg gctagtgcac tttcttccac cagcatacca tctcaattta ccactttaac    480

aattggactg ccactttgtg tcagggacta tctgtgctcc aactactaca agtgataagg    540

tcctcactga cagccaggga gcaagtgatc cagctctaaa actcacctta tcatctgctt    600

tcctagacca ctcctaacaa ccaactattc tgggttgagt tctccaagag gcagagagtt    660

caggatacag aatgttgttt tgtttttgtt gttgttgctg ttgttgtttg tgtgtgtgtt    720

tgggcttttt tgagacggag tctcactctg ttgcccaggt agaagtgcag tggcatgatc    780

tcagctccct gcaacctcca cctcctgggt ttaagtgatt cccctgcctc cacctcctga    840

gtagctggga ctacaagtgt gcgccaccac acccagctaa tttttgtgtt tttagtagaa    900

atggggtttt accatgttgg ctaggctgct cccaaactcc tgacctccag tgatccacct    960

acctctgcct cccaaagtgc tgggattaca ggcgtgagcc accacaccca gcccagaatg   1020

tttattagaa tgcacaatta ataccagagg cagtggggaa ggaaggactg agcagaggag   1080

gaagttgagt tgtgattcaa cccaacaact gcctggctgg catggggagc tctggagtta   1140

aatagggcca tcagactttc ccagtgtggg gccaacatga ctgggtcttt atacccccac   1200

ctctgtcagt cactcaacgt ggtctccctg caacaaggtg actcttgcag ccgagacaat   1260

ccctgaaggg acagagggct gaagcctgtc tgccaacagc actcccagtg gctggaacaa   1320

gtccttccct ataggggaat ctgggcggca cacctccatc tccatgtcca tcacatacga   1380

tatcacagac atttaaatat tttgataact gtacataaga gtttccttta taatcttata   1440

gatcttattt tatgcatttg aaaatattct tctgagacag ggcttttatc atattgccat   1500

agggtgccac gatataaaaa aggttaaata ctctctgatt cagaagtatc caatgatgac   1560

ttctctctca tgcatttaat tgaaaatctg gtttttctcc ttctctgcta gttctctacc   1620

tctctcccca cctcccacat catagcctat tcacatatgt ctgaatctca tgatagacaa   1680
```

-continued

```
gttcaggttc ttttcccagg ttctttttac cacatccccc cacccccaca taaaaagtat   1740
atatggcaca gcctaggttc cacccaaatc ctttctcctc ttcttcctgg gcccacaact   1800
ctcctacata cattggtata ccttgcgctt agggatggcc atgtgactaa gttctaacag   1860
tggaacatga tcagatgcca cttccagcct ctaagacagc cagtgtgttt cctccataag   1920
ctccttctct tcctcccaac tggagactct aaatgatgac cctgcctcaa gcaagcaaac   1980
aacaagtccc tcaggggtgg tgtaggctgc aaatggaagg agcttgagtc ccaaaccttc   2040
cacggagaag gctggctacc aacctggatc actcacccaa gactgctcga agagttggtt   2100
tgaaccattg tgttttgggg tctatttatt acaacagttt agcttgcttt gtgaatagat   2160
ttagtggcag agcctccaaa ttctatagat acattgatct cagtcctaac cgcatctgga   2220
acaccattaa ataaaggaat tgcaaaccca gagaaggtaa tgaatttgtc taaggtcata   2280
caagatggct aggatcagga cccaactctc cagttttctt tcttctctgc tattctgcct   2340
tctgtgatcc tacataagtg ggcatgattg tataacatat gcggccatga gatttctctt   2400
tcagcaagag aaagggacag gaagaaagag agggaatgca ttttcttggc ctgaattagt   2460
gtgagccatt agttacctac attgactaaa ttatctggaa tgaacattca actctacatc   2520
acatatagtt aaaatgacag atctgcttaa gattgtttct agcatacgtt atttcaattt   2580
aggcaaatgt gaccattcag tgtgagggga ccatactgtc attaggtccc tgtcagttct   2640
caattatact gttatcttag agggggaaaa atgtgaaatt tgaatgtaga cgagtgttga   2700
tttgactgct acagtttatt ttacgtatag aaataaaata atgtgtagca aaagcattat   2760
tacaaagatg ataatgaaat aactagtatt tataatagta taatagtata gtatttataa   2820
tagtatgata gtttaatgac tatttgtcag atgttgtgta agaaacttta tacacacaca   2880
cacacacacc tcatttaatt cctgtatcaa tcaggataca ggacgctgtg gtaacaactc   2940
ctcaaatctc ggtggcttgc acaacaaatg cttatttctt tttttttttt gacaccaagt   3000
cttgctctgt aacaggctgg agtgcaatgg tgcaatctcg gctcactgca gcctctgcct   3060
cctgggttca agcgattctc ctgcctcagt ctctcgagta gctgggaaca caggcacgcg   3120
ccaccacatc tggctaattt ttgtgatttt agtagagatg ggatttcacc atgttgctca   3180
ggctggcctt gaactcctga cctcaagcga tccacccacc tcagcctccc aaagtgctgg   3240
gattacaggc atgagccact gcgcccagcc ccaaatgttt atttcttgct catgtgacat   3300
gtacttcctc gagtttttcc ttcctgagat ctaagctgaa ggaacagctc tctggagcca   3360
cgccattctg gtggcggaaa ggaagagtaa aagtggtaga accttgcaat gctcttgaag   3420
cgcctatttg gaatgtctac atcatgtaaa tggtaatgga caagtatgta taatccccac   3480
accaaaaaaa ggggacacta ttggggacaa taaccacatt tcaatgctgc aagacggata   3540
ttgactgcac cccctctccca ctttcagaaa gaagaagagt aattttgctg aactccttct   3600
agagactgga aatgtccctt ccagttgggg tgattaggga aggctttggt aaaatttgag   3660
ctagagtttg aaggttaggt agactactgg tgggtgaaga aagaacaagg acctttgtag   3720
gcaaaggaaa acctcagaat tacagaggtg gaaaaagagt tctagtcaag ccacttcagc   3780
tggctacaga gtaggtggga aagaaaatgg gaggacaagg gctcagatga tggggggttg   3840
gggcattggg gggacacttg aaagctaaac taaggggttg aacttaattt aggaggcagt   3900
tagaagcttt tacatatttt tgagcaagag agtgacataa ttaaaatgat ctgggccagg   3960
tgtggtggct cacacctgta atcccagcac tttgggaggc tgaggagctt gggtcacctg   4020
```

-continued

```
aggtcaggag atcgagacca gcctggccaa catggtgaaa tcccgtccta ctaaaaatac   4080
aaaaattagc cgggagtggt ggcatatgcc tgtaatccca gtagctggga ggctgagaca   4140
ggaaaatcgc ttgaacccgg gaaacaggtt gcagtgagcc gagatcgtgc cactgcactc   4200
cagcctgggc aacagagcga gactccatct caaaaaaaca aaacaaacac acacaaaaaa   4260
ccaaaaataa ataaataaaa tgatcacttc tgaatactga tctaactagg ggttgcaggg   4320
tgggctgata tagggagaaa ctggagagca aggagatcac taaggtccct acatgtccag   4380
aaccaagata gaggtcttga actaggatgg tggcagttag aacaacaaca acaaaaagtc   4440
aattccaggc tgagtgcagt ggctcatgcc tgtaatccca acgctttggg aggctgaggt   4500
gggagttaga aagcagcctg ggcaacactg caagacctcc tctctaaaaa aaaaaaaaaa   4560
aaaaagttag ccaggtgtgg tggtgcccac ctgtagtccc agcaactcag aaggctgagg   4620
tgggaagatt gcttgagccc caggagttca agcttgccgt gagctacgat tgtgccactg   4680
cactccagcc tgagcaagac cttgtctcca aaaaaaggtc aattccactg acttttctaa   4740
ggtgtacacc atcaaggggc agctccatct ccaggccatt ggctcatgag acattctgta   4800
gtcagaaggc tagggcagat tgctttgagc aagcccccat ggtggttctc actcctactt   4860
ctttgggtat atgcccctct gtttaaaaat aaagttaata tgcatttaaa aaaaaaaagg   4920
agaaaaaggt cagttccaga aactgtgtga ataaagcatt ttacttgctt tttctattaa   4980
tctataacat atgttgattt tttaaaaaga atataagagc tatgcaaatt ggagcttcaa   5040
gacaacttcc catctcccta ggaggagatg gctgccctaa acccccctac atagaaatca   5100
tcccactgct tgggcttaaa cttgatgttg gggaaatgaa aaatccaagc taaggccgaa   5160
gcctggggcc tgggcgacca gcagaatgag gaccactggt cagtttcagg ctgaggtgcg   5220
tcttccaggg gacaatctct agctggccct taaacattca gacttcaagc tctatttaca   5280
gcataaaggt gtttcaaaag acgtgataca aataactgca aatgctctgc gatgtgttaa   5340
gcactgtttg aaattcgtct aatttaagat tttttttct gacgtaacgg ttagattcac   5400
gtttcttttt ttttaagtac agttctactg tattgtaact gagttagctt gctttaagcc   5460
gatttgttaa ggaaaggatt caccttggtc agtaacaaaa aaggtgggaa aaaagcaagg   5520
agaaaggaag cagcctgggg gaaagagacc ttagccaggg gggcggtttc gggactacga   5580
agggtcgggg cggacggact cgagggccgg ccacgtggaa ggccgctcag gacttctgta   5640
ggagaggaca ccgccccagg ctgactgaaa gtaaagggca gcggacccag cggcggagcc   5700
actggccttg ccccgacccc gcatggcccg aaggaggaca cccacccccg caacgacaca   5760
aagactccaa ctacaggagg tggagaaagc gcgtgcgcca cggaacgcgc gtgcgcgctg   5820
cggtcagcgc cgcggcctga ggcgtagcgg gagggggacc gcgaaagggc agcgccgaga   5880
ggaacgagcc gggagacgcc ggacggccga gcggcagggc gctcgcgcgc gcccactagt   5940
ggccggagga gaaggctccc gcggaggccg cgctgcccgc cccctcccct ggggaggctc   6000
gcgttcccgc tgctcgcgcc tgcgccgccc gccggcctca ggaacgcgcc ctcttcgccg   6060
gcgcgcgccc tcgcagtcac cgccacccac cagctccggc accaacagca gcgccgctgc   6120
caccgcccac cttctgccgc cgccaccaca gccaccttct cctcctccgc tgtcctctcc   6180
cgtcctcgcc tctgtcgact atcaggtaag cgccgcggct ccgaaatctg cctcgccgtc   6240
cgcctctgtg cacccctgcg ccgccgcccc tcgccctccc tctccgcaga ctggggcttc   6300
gtgcgccggg catcggtcgg ggccaccgca gggcccctcc ctgcctcccc tgctcggggg   6360
ctggggccag ggcggcctgg aaagggacct gagcaaggga tgcacgcacg cgtgagtgcg   6420
```

-continued

```
cgcgtgtgtg tgtgctggag ggtcttcacc accagattcg cgcagacccc aggtggaggc   6480
tgtgccggca gggtggggcg cggcggcggt gacttggggg agggggctgc ccttcactct   6540
cgactgcagc cttttgccgc aatgggcgtg tgtgtgtgtg tgtgtgtgtg tgtgtgtgtg   6600
tgtgtgtgtg gaggggtccg ataacgaccc ccgaaaccga atctgaaatc cgctgtccct   6660
gccgctgttc gccatcagct ctaagaaaga cgtggatcgg gttctagaaa agatgactcc   6720
ctgcacgccc ctccctgcac ctcccgagca gtgattccga cagggccttc actgcccctg   6780
attttaggcg ggggccggcc ccctcccctt ttcctccttc agaaacccgt aggggacatt   6840
tgggggctgg gagaaatcga ggagatgggg aggggtccac gcgctgtcac tttagttgcc   6900
cttcccccctg cgcacgcctg gcacagagac gcgagcagcg ccgtgcctga gaacagtgcg   6960
cggatcccac tgtgcacgct cgcaaaggca gggttcacct ggcctggcga tgtggacgga   7020
ctcggcggcc gctggtcccc gttcgcgggc acgcacagcc gcagccacgc acggatgggc   7080
gcggggctgc aggtgcatct cggggcggat ttctttctca gcgctcggag cgcagggcgc   7140
ccggcgtgtg cgctccctgc cggaggcgcg gggctggcgc gcagggctcg cccctcactg   7200
cggcagtggg tgtggaccct ggtgggcgag gaagggggag gataggctgt gcctcctccc   7260
actcccgccc ccagcccccc ttttttttccc cctcggaacg cgaggtgcca tctttttttcg   7320
gcgtgtcacg tctttacggt gccatgccaa accgggtggc cgggcttcat aggacagggc   7380
ggggcctggc attaaaggga gggggacaat cagcgctgaa atcttggcgt tttgctgctg   7440
cgggcgtgag cactgggggc gttcgcccag caccttcttc gggggctctt tgctttgtct   7500
gtagaggtta cgtgatctgc gctcccagcc ctggtttctg gcttttattc tgagggtgtt   7560
cagtcaacct ccccccctacg cccatgcgcc tctctttcct ttttcgctcc tcatttccga   7620
gcccattgtt ggatctcgag gcttgctggg ttcgatgaac tcgagtcaac cccccgaccc   7680
ccggcacgca tggaacgggc gtgaccgcgc gcagcctcgt ctcggagtct gccggcgccg   7740
ggaagcttct gaagggatgg gattcgagtc tccgtgcgcg ctgcgggcgg cggcagaggg   7800
atctcgcccc tccctacacc ccaagtgtcc tgagggccac gccacaccag gttgcccagc   7860
gagggacgct ggctacccat ccggggatgg gtggggagcc ctggcggggc ctctccggct   7920
ttacgccctg ttgcttcgcc tggccggaga atgtgaggaa ggggcataag gttactggtg   7980
cttcggccac acccatcttt ctgagcccac tggactgggc gcagaggggg gattgccatg   8040
gaaaccacag gtgtccggag aggggatctt ggggctggcc tcacccccttc cctgcggaga   8100
ttggggaccc tggggtaggg ggagccgcgc ccagtcggcc tcctggagga cacgggagga   8160
agccccgaac ccccgcgcct gaggctgttt ctgattggcc cctggaggcc gcagacacgc   8220
agataggcgg ccctgggtgt atttttatta atattatgtc cgtactgatt aatattattt   8280
atcttaaata aatttcaccc gtgtccaagt tcaccgcgcc cccaaaaccg agtctggggc   8340
ggcaggggga actcctggcc aacgaatcca tgcctcgccc tcctgtgatg aacctggtac   8400
gcacggtttt ctggttaatt ctatcgctga aaactggtgc ggggggcgca cttctgagac   8460
ggaagagcat ctaggagctg aatcctccac gcgggtcgcc caggttgatc tgaatttctg   8520
gggaatggct tggctgcccg cccgggacca ggccgacccct ccttgacggt ggcgtagagg   8580
gctggagcct gggtactgcg aggctcctcg catggctggg cccgccgcga ggggttgcag   8640
agcggctcag ggatcgattc aagcatcgtc tctcctccct cgcccccaga cagagctggg   8700
cgcggggttc cccttccaga tggagcgagg gtctcggggt ggccccggaa aaggggagcc   8760
```

-continued

```
cgcggccacg gctacgtatt gccatctcgc gagcagagat gtcacctcct gcctttggag   8820
gaaagggagc ccggtgggga tgagcgcatt tagcccaatg ctgggaacaa agcgcactcc   8880
gcgcttctgc gatttcgctc cattttgaaa tgtgttggcg ctttggtggg gccgctgcgg   8940
tgggcaaggc cgggggcgct gttaatggag gaacctcagg gggacggtcc ttcgtaggaa   9000
actctatcct ggctctgcgc gcgctttaag gaaatggctt ccctccagga cctcgaggga   9060
tgcagctttt gcgcggatga cggtggggtg ctgaaccagc cggtgcgcct ctggaaatgt   9120
ctgggcacgg atcctggggc catcgacgac tcctccccat tcccagcagg cgggagctct   9180
tacattccga gcgagtgacc cctctcaccc tctggcgctc acacacctgt aactccaaac   9240
ctccgtctca gaatggtcca ggctggaagg gatgatgggg gctccgacag cgactgccta   9300
gctcacccct ctgcgtgctc aggctccagg ctcagcagga ccaatttgag ttctatctga   9360
tccccctcgg ccccttaact gacccatcct acaggagaca gggaaatgtc tttcctaccg   9420
cggttgattc tggggtgtca ttttgtgttt tgtgatggct gcttatattt actgtataag   9480
cattgtattt actgtataag cattgtatta taattactgt ataagctgct tatatttact   9540
gtataagcat ctccaaatcc tccctctacg taaacaaatt aatggataaa cagataagtg   9600
tatcccctgc cccccacccct gctacgcagg tccggagtga ctcttgaagc tcatacattc   9660
cttggccaag tttgcttctc taacagatgt ttatatagca ataacctggc ttggctcttg   9720
ggttcacctt tggacgattt ggggaagggg cttgttggct ttgctgggtt ttggatgagt   9780
gacagtccat gactgttcct gctggaaggg cgtgactttt aagtggtttc taatatcagg   9840
cattgctcct ccgacaggaa caaaagaaat ggatactgcc cataaattgt tagaaaactt   9900
agaatcgctt tgattgagga aaggttagat ttattccggt tggaaaaagt ggcctttcta   9960
ttaaacgtgc cctttgaccc tcatgccctt ggaggtcggt gccagcctgg agatgggata  10020
agattgtggt tttccttctg cctttttaac atctgttgtt acagtccatt tgttgaaaat  10080
ttaaagaaac tgttttattc cactttccct cagcatttat gtgtgtggtt tcagtagctc  10140
tgtggctata tgtacgaaca cgtgttattt ttccaattgg acatgtgata attttccaac  10200
tggaccttgc cttctattga tgtatttatt tagcatcttc cttactccct ccttgaaaaa  10260
gaatcactca aaaacaaata aaaacagccg taggggccta atacagtgct agacatacaa  10320
gaggtattcg gtccatacca aatggatttt atccatgaag gataaatggg gaaatacagt  10380
gggaagcagg tgggaaactg cgtttgactc tgctctttcc tccaccacca ctttcctcat  10440
caccgtgttc agagaccccc aaagccccct cacactccca gaaacacccc cctggccact  10500
cctaacttgc catgcccagg agttaggtgc ttccactagt gacatggagc tggcgtttgg  10560
ggggcacctc agcaggtgac gggaagagaa gaccccagcc tcaccagctg ggctgcagca  10620
gggagaggag tcctcatgtt ccagcaggga ctctcagctg ttttcctgta aaaccatggt  10680
tctcaactgg gggccactga gatgtctaga gagatgtttt tgttttcaca actcggggag  10740
ggtgctactg acatcttgtg ggtagaggcc aggaatgctg ttaaacatcc tacaaggaag  10800
gcacaggaca gtctcctaca tcaaaatatg acccagtccc aatgtcacca ctgctggggt  10860
tgacactggc actgctatct taattacatt cattgagtgt cttttaggag gccctattct  10920
aagtgcttgc taagattatc tcatttaatc ctcacaacac ttccgctatg tagcaggtgc  10980
tgttattatc tccgtgatgg ggaaactgaa gcacagagag ggttagtaac ttgctaaagg  11040
tcacagagcc agtgggtggt ggagctggtt gcctgacact agttccctcc cctctcagcc  11100
acatgtgggt ttacttggcc attgtggact agtctgggaa cccagatatg atctataaca  11160
```

-continued

```
ttgacccagt agaatattga ttccaaaacc actgtctcac aaatgaattt ttacaagagt  11220
ctgtaatcgg agcatgaccc agaataaggt tagggagatg tggagttaaa gctctcaatt  11280
tcttatctgg ccccgacaca gagagcaagg catttcactc tacattggtg ctctgtttat  11340
aaaacaaaga gcaaatatct cttcctaagg tccttaaacc tcttccccca atccagggtt  11400
tctggactgc tctgccatat gacggggcag ctggtttgat tgacccaggg aaggctggaa  11460
atcaagactg gggatcaag acgtagattc agtgtggcca aggtcaagtc tctgaggttt  11520
agggacatca gatccccagc ttaggttctg tacctcggca aggtgaaagc gttggcgccc  11580
actgatgagg cctgctctga gattgtgggt gtgggttgag ttgggtgggc ataggcaagt  11640
cctcttgtaa gaatcttttg gcaaagatgg gcctgggagg cttttctcac ttcctggggc  11700
ccaggctttg caataagtat tccattatac tgtggtacct tggggctacc tgagaatcct  11760
ctgtctcgcc cctgttgcct tgccaaagag tttgctgtcc aagaattcct ttcctgtctc  11820
caggtgccat gctcctgcca cctctgccag gttccctgcc tgcccagatg gctcccaact  11880
gagtgtgagg aggaatttga gacaggtttt gagctttctg ggttctccag ttaggaaact  11940
ttctgtaagc atgcagatag aatgggcttc agcaaaatac aaactcgaac aacttccatg  12000
tatagtccct taattttctt tgctttttc atatttcatc aggctccatg ctgagcccaa  12060
tcagggaccc gatagaaatc caaacaccat gtcagcgagt ccccaagaaa tgcattttgt  12120
gccaaggcta ttcaaggaag gtttgggagc agctcaaggg cagacactgt taccctcccc  12180
caggtcccca gtgcagggca gtgttctgca tgtggaggca gtttggccta atggttaagg  12240
aggtaggctc tgatcgggcc tcctgggcac aaatcccagc tccctgctca ctgtgagacc  12300
taagccatat tgtttagctg cttggagagt tttttgtcat ccacaacttg gagtatgatg  12360
gtacctgtct cacgggttgc catggggttc acacaagcta acccggtact cactagggcc  12420
aagcacatag taactgctca gtaaatggca tcatcggcgg tgtcctgtgg atgagtgctt  12480
gtgattggct gaatgaccag aggggtctaa agatcctggt gatggaatca gttgtacaga  12540
taaattgtta cactgagtag ggatcaagat aggaaaagtc ggcaactacc cagctcccct  12600
gcaccaaact gggcagaagt ggatcctctg aaaattgcac acacccatgt ttaaatgtac  12660
acacagaact cttgccacag gcaagcggag atttgtcatc tgctgtccct gcctcatctt  12720
cttcctgaaa tccactccat gccaggaata aactgcatgc tctccaccag cccaaactga  12780
cctgccttcc cgccagccat cccgggcagg gtgacctggc ttagtacatc gggttcagag  12840
atctttccag tttactcgtt gaataaaaag tgagggctga tcgagaaagt aatggcagtc  12900
agggaaggcg aaggaggtaa agaagagatt ttacaaatga agtaattcaa cagagtgctg  12960
acattggtaa actggcaaac agatttcagg gtggttggtt gagagtagag tagaaaagga  13020
ttaaataaag caaacttgtg gtgtactgaa tcttaggaat tccatgtatc caataagtat  13080
agtcatttat gaattaataa attcggccta agaagccttc ttatcgctta aatcaagact  13140
aagtaacaat atatcagttt taaaaagtca ttatatcaga aaatcattta aatgatacac  13200
atagatttcc aagattttac tttaaccgaa actatataaa tgtgaatttg ttcacccatc  13260
ttttgacaca gggctcaggt cttctcttgg tgtctggatc agccagttga aatttcttgt  13320
ctgttttgcc tatgccacat taataatgca ctgtctgggt cctccgattt cagtttggat  13380
tttgggttta cattgtggag tcatctgaat gcagaatcct tcagggattt tacttttttt  13440
tttttttttc atggtcttta ccatcccatt tgatagtaaa tattactcac ctttatgaag  13500
```

-continued

```
tctttccaaa acattcaact aaattttctt aaaatcattg aatgatttga agagcttatt  13560
cctcagcact tttactccat cagcttgcac cttatttttt aatctttttt tgagacggag  13620
tctcgctcta tcgcccaggc ttaagtgcaa tggcgcgatc ttggctcact gcgacctcca  13680
cctcctgggt tcaagcaatt ccgcctcagc ctccgccgta gccgggacta caggtacaca  13740
ccataatgct cggctgattt ttgtattttt gtagggatgg ggtatcgcca tgttggccag  13800
gctggtcccg aacttctgac ccaagtgatc cacccacctc ggcctcccaa agtgctggga  13860
ttacaggtgt gagccaccgc gcccggccag cttgcacctt atttaggata tgtgattatt  13920
atagcaagtc tggtgtacat acaagatttt gaatgggcac agatgacctt tagtaagtgc  13980
ttggctgtga taagaggcag tcctgactgc agatcaggct gtgtggaccc cagccttgca  14040
tgtttacaga ccttcatgtc ttattcttac agggtatcag aagaacacct actggggaaa  14100
cttataaatt agtaaaaggt gggcattctc cccgcccatc ttctgtctgt ctgccaggac  14160
tagcacagca ctttgaagtc attcacatag aatcccaact taagagggta aaatcctcct  14220
caacagactg aaaataagtt taaattccct ttgctatatt aactcccctg aggaaagagt  14280
cttagatcaa tgtccaacac taaaaacagt tttaaatcag caagtgagaa ttaaatctga  14340
agcaattgat aataatgttt cattcattcc tctcctttgg ccccgtccac cctactgcta  14400
aatccaggca tcaaagagaa gagggacata attatctcta gtcccagctg ctggttttcc  14460
ttccagccta tggcccagtt ttctgtttta ctgagaaggc tggtgatgtt atcttgggat  14520
ctaagtctgc agtttcacca caaaaagtcc agggatgcac tttcatgctt gtgtcctcct  14580
ccctgggata gcaaggatat tagaagaccc ctggctctgt aattgcttgt catgtgctct  14640
acagacgcca cagaatgcca agaacgaagt gctgggaagg acaaattcat ggaaccgtgg  14700
gacggtgctc ctcccccagc gtaaaggaca gctcctcctc ctgaattgga gccagcgttc  14760
taaatcatgt gtcaacagag ttgtcctgga tcggatccag ttctgccatt gatttgcagg  14820
tcatttcagt ggtacctgtt tccagttgtt cttaattgaa cagtggcacc aaactattgt  14880
cttgcctcat ccccctccca tggcctgtcc cccaaaaaga gacttcttgg gtaattaatc  14940
agggcaacat caggcagtct gggcgcggtg gctcacgcct gtaatcccag cactttggga  15000
ggccgaggcg ggcagatcat gaggttagga gattgagacc atcctggctt tgtgaaaccc  15060
cgtctctact aaaaatacaa aaaattagcc gggcgtggtg gcgggcgcct gtagtcccag  15120
ctactcgaga ggctgaggca ggggaatggc gtgaacccgg gaggtggagg ttgcagtgag  15180
ccgagatcgc accactgcac tctagcctgg gcgacagagc tagacttctt ctcaaaaaaa  15240
aaaaaaaaaa ggaatctctt tggttttata tatatttttt ttatatatat aatatatatt  15300
aaaatataat atatatattt atataatata atatataaat atattatata ttatatattt  15360
tatatattat atattatata tattatatat tatatattta tatatttata tattatatat  15420
atttatatat tatatattta tatatattat atatttatat ataatatata ttatatatta  15480
tatattatat attatatatt atatatttat atatattata tattatatat attatatatt  15540
atatatttat atattatata tttatatata ttatatatta tatattatat atttatatat  15600
tatatattta tatattatat atatttatat atattatata ttatatatta tatatgtata  15660
tattatatat gttatatatt atatatattt atatatataa tatattgtat atattatata  15720
tctaatatat tatatatatt atatatatta tatattataa tatatattat atattatata  15780
ttatatatat ttttatatat ataatatgta taatatataa tatatataaa aacatatata  15840
atatatatta tatattatat atatattata tatattatat atattaaata tattttatat  15900
```

atattatata tatatacaca tatatatata taaatgaggc caggctcggt ggctcacact 15960
tgtaatccca gcactgtggg aggatcactt gaagccagga gtctgagact agcctgggca 16020
acaaaacaag atcctgtctc tacaaaagga aactgtaaaa attagctggg catgatggca 16080
tgtgtctgta gccctagcta cttgggaggc cgaagcagga ggatcgcttg agcccaggag 16140
ttcaaggcta cagtgagcta tgattgtccc atagcactcc agcctgggta acacagcaag 16200
gccctgtctc taaacttttt ttttttaatt ctatttatat ttacatgtat ttaaatgtga 16260
atattcacta cctatttgtt gcatgcctgc atttttttata ctgggcttgc caaaaacccg 16320
aacagctttc tactttgaca atgtatcaga atttaaatca gcaatatgtt aataagccaa 16380
gcaaaggtta tatatgcaaa taaaactgtt gtctataacc tcctgttaca ctggggcaca 16440
gcaaaagtca tggtgtagtc gcatgtgaac ctgtcccttt catagctgct cattgccagg 16500
aaacatcagg aatagccatt tggaagagtc atcagccctc ccaccatccg ttttctgtct 16560
tgtcttttcc ctatgagcag gggaaattcc acgctggccc caatccccag tgcagcggct 16620
cagcctctgc ctctgctgct ggtccccatg aggccagctt agaaacggag gatttttgcag 16680
aacatcccta aatccgcttg aataatgaag tgatcattca taaactcacc tgaaccttat 16740
taaaacctat ttaatatttt tcctggataa tcctataggg ataacttgcc tcctgggctt 16800
ctctccaccg ggttcagttc ttcctttagt ggtgaagttc ctcccttctt agcatctcaa 16860
ctgtgcctga gaaaaggcca gtggcggctg cactctgttc cctgtggagt gttaataaag 16920
actgaataaa ttgaaataaa tccctttcaa tgtcattaag tgctataaat aatcatgaac 16980
caatgttcga tggctgatga gaaatgcaag aaaaaatttt taatcagtag gattcataag 17040
ttgacaatct gggccaagtt aaaaaaaata aaaataaaaa gacttttaaa aagatcttat 17100
cgtttgttac cagtaagact gaattccaga agcaagctac tccctcattt gtgggcccct 17160
gttatcactg gctgcttagg gttgccaagc cctgaattca tttgtcaact aagagatttt 17220
tggccaagat taagatttcc catgcctcca tatttccatc tgagaaatgg agattatact 17280
gtcttccccc tcagaatgga tgataatgtg gtctctcttc tgttcgcata gtcatagaac 17340
tgaaataaaa caacttaaga gaattccttt gagcttctca gaagtgctgc agggctgggg 17400
gatgcctccc aggagccgca gtcaggtgct gatctgaagt ctttggtggg ctgactttag 17460
cctgacctga aatagtatag ctgctgccac ctggctccct tagcgtcagt cagacggtgc 17520
agctggttcc taggggtgag ggctgagcca gcagggtccg tgcccaggag ggatgcatgg 17580
gtggccacag cccagcctgc actgatcttg tctgtcccct tctttggaag gaaggagccc 17640
caaaccaggg tgcaagacag tgggtggggg tgccttgagc atgacctcaa gtgatttcca 17700
gcccctgcca gtgctgactt ctctggggaa gggctgggac ttccttctgg gctcaagtca 17760
cgacccttgg atggaatttc ctgggagctt ttctgttttt tctggagttt tcagtttttt 17820
cctaaccaga cagggacttg gtacagaatc tcatattcta attatgccta ggagcagcct 17880
ctccccacca ctcacagtgt ttagcatgtg acaggaatcg attaaggcat gagtgattaa 17940
attaaagcca ggcattgact tggatggtgt aatattctga catctgtttg gtgtcaaagg 18000
cacggggcag gcgcgttaat tgaactgctt gcacctggca tttgaattga gccagagcgg 18060
ggctaaagtc agtttgcctt caccctgtaa atggagggtt tctccggagc gtggatggtg 18120
ggaggtattt cagggtgtat gcataacccc caccctgaca atggcccatc tcttctccag 18180
cgtggccagg tttgagtgcc agtcctgggt gtccagtggc cccatagcct tgcgttttag 18240

-continued taaaatgctg cccccattac cacctggtct gtgcacttcg gtcactggaa tttgccatct 18300
tccagtcccg aatgtggcaa gccatggagc cttaagctct tctccctcca catcctggaa 18360
cagacccgcc agtttcttcc aggcattgcc tcagtttgcc cctctgtttc cagtcacact 18420
ctcaccagcg ataaaatgat tttagacctt atcatctcac cctcggatcc ttatggaaac 18480
aataatgagt tgttccctgt ttcaattcca aaattcatat ccaatccgtt ttgcatgcca 18540
ttgccaaatt cctcccagag caaccccgtc acctgccctg gccctctcca agtgtggtcc 18600
tgccatgggc atcgcctgct aagccaagct ggcctcgagc tgcctgcccg ggtccccaca 18660
ccttggctca cctccctgcc cagtcccgcc tcctgccagc ctgccctgtg gctccttcat 18720
agatgccgtg ctctttctgc cccttgctca cccatggcag ccttgcccct ctctccctgc 18780 cccacccccct atttaaattg acctgacctt cctcagtgtc catcttcccc gaagctttcc 18840
ccagccttgg cactcaaggt ccagaggcta cgcgtttcct ctcacctgtg gcagcgccgt 18900
gctccccagt gcctcacagt ttccttcttg cccccgcttc ctgtgtagga ctcatctgcc 18960
cacaggttgc acgtcctgtg agggcaagga ctgtgtctta tgtgactttc cttctccagt 19020
cacagagctg ggcacataga tagctcaaaa ccctctttat taacacagtt ggatgttgag 19080
aaatcaaaca ggccaatgtc aaatgagctc tccttattta aatcaagtca gttctccacc 19140
tcctagcact cagttccagt actctatata catggaaata ataaaaaaca catttccttt 19200
gaaacattct ataatcgttc ctttgcccta cttcagacca acttaacgca ctccccattg 19260
gtccaaatga gttttgctat acgaagatgc tgataataat agcagcagtg gattattctg 19320
ctaaaaccat tgcctcgtta atcctcagtc ccgaggtggg gattattatc ctcattttgc 19380
agagaagcaa actgagactc agagatttca cagctgggga gggagccagc tcatccctct 19440
gtccaggccc aagctctctc ccgcttgcct tcctgcctct gcaacctcag agcatccccc 19500
atctggttct actgcctgtg ctagtcgtgc aggagccaaa agacacgtct ttagtgctaa 19560
ggactggaga agccatgccc tccagcctct gtgaatgggt catatgtaac atgagcctgg 19620
agaaattatt tgaaaccaaa ggcaagcctc taaaccaggc tgctgcttca tggcgccggt 19680
gacggcagaa ccaaatttag tgctgtgggc aggtccacac ttatcaaata gagaagctca 19740
tttttcttcc ggctcacatc aagcatgaaa aatgttcaca cataccccccc acacacacat 19800 gctttccgga ggggtccatg tggctagagg ctggaagatg tggatgagag gagcctggca 19860
ggtaagccca gggaagatga cattcagctt cccagacagc atctacaggg agaaatttaa 19920
ttaaaagtgg ggcggtttcc ctgagcaagg cagacaaagt cagccctcta ctgttaagaa 19980
aaagggtcac agtgagaggg gaggtgagga gactgagtct gtattttcta gtctgttggg 20040
ctacactacc tgatcccccct tcctcaaaaa tccactttac tttccccatg tctacaccaa 20100
tgtggttcac actctgggac caggaaaagg gggagtgatg gggaacagag aagggaggag 20160
ctcacacagc tgaggctggg gttatgcata tcgaattact tagaatttgc aacctcacag 20220
ggtactttca tggcgttgaa atacacttcc cacagccacc ctccctctaa ctaaaagcaa 20280
gagtcatttc tcagttctgg tcttgcctcc cacgttctcc tccacattta agaaaatcca 20340
ccagctacaa agtgaagata ccatatgtga tatcccaccc tagtttctgt tttatcaggg 20400
tttggagcag gtggagcagg cagagggatc atttcagcct ataaattgta ttaagggtga 20460
gtactgagtc attcttcaag aaaagtttta gaagcatcca aaactgaagg gtggagccac 20520
ctggagacag tatcatcagt cctggccccg agcatggcct gcataggccc ccatggatcc 20580
cagcgggagc tgcagagtgc gggcaccttg gcacacagcc ctgagtgcaa aattaggagc 20640

-continued

```
tgggcagagg gcatctctct gtcgccattg ggcagcccag ggcacactgg tcatagcctt  20700
agaccacgaa caccctgtgc ccgggggaca gatgcaacca gtgtgccctg ggctgcccaa  20760
tggcaacaga gagatcgaca cctggacccc atgtcacggg gactccacta ctaaggctcc  20820
taagactgcc accttccagt gggataagcc ctgcctccta ctgggcccac aatgtgcaga  20880
gaacacttgg gactacctgg ctttctggat acacaaatat tgatccaatc tggactaatt  20940
agaaggtcag tcccaataac aaatcgaagt cagctgggcg tgatggctca ctcctataat  21000
cccagcactt tgggaggctg aggtgggcag atcatttgaa gccagaagtt caagaccagc  21060
ctgggcaaca tagcaaaacc ctgtctctac taaaaataca aataattagg ctgggtgtgg  21120
tggctcatgc ctgtaatccc aacagtttgg gaggctgagg caggtggtca cctgaggtca  21180
ggagtttgag accagcctgg ccaacagggt gaaaccccgt gtctactaaa aacataaaaa  21240
ttagccaagc atgatggcat gtgcctataa tcctggctac tagggaggct gagacaggag  21300
agaatcgctt gaatccagga ggtggttgca gtgagctgag atggtgccac tgcactccag  21360
cctggttgac agagcaagac tctgtctcaa aaaaaaaaaa aaaaaaaaaa aagccatgcc  21420
tggtggagca ctacgtgtaa tctcagctat ttgggaggct gaggcacgag aatcacttga  21480
acctgggagg cagtggttgc agtgagctga gatcgcgcca ctgcactcca gcctgggcga  21540
cagagtgagt gagactccat ttcaaaaaaa taataaatct gagtcacttt aatattgtta  21600
tttggatgtc aacctctagg tgtttgagac aggagagtga tatgggggca ctggaaacac  21660
acaggcacgg ggtgtcctca cacttgggta gcccacacga tgtgatttca gggtgctggg  21720
aggtcccccc actccccaaa ttactaacaa gtggatagta ctttacagtt tatatgatct  21780
catttgattc ttaacatgag cctgtgagtg aaaaattcct tcccctcttc tacagattag  21840
gacgttgaga ttcagggagg ttcagaggga ttcagggaag tcaagtggca cctggagtcc  21900
cgtggctaat ttgaggccgg taggggattc gaacccagga tttgtgcttc ttatgcctgg  21960
gcttctgctc cctggggcat ggtcttcccc ctagctttcc cattcactgc tttagcctag  22020
gggtcctacc ctttattaaa ctgccagtgc ctcactgctt ttctccccca aagacaaaaa  22080
aaaagtgttt ttgcttttgt tttgtttttc atgggcagag acctggaatt tcagcttgag  22140
aatttgtgcc atatgataaa taaatcaaca gatggctttt tccttaaaaa aaaaaaaaaa  22200
aaaaactaag atgtatttgc agtgaggcat aatttgtacc aaaaagtgct caccacactg  22260
tagtcatggg ggcaggaggc agccgcgggt gaagggagaa atcttggagt ccaggcagcc  22320
cccttctggg ctgaactggg gagctggggg tgctgccagc cctgccaggt tctcctagga  22380
ggcggcagct catatggctg tgggaggagg cagagggagc ctcatatgca cccacatttc  22440
cagggatcta gaagacagaa ggaggaaaac caccatcatg ttaaagcaga cagttaggta  22500
acacatcctg taatacaagt tattttttcc acatctaaag gctaaaaata gttgttagaa  22560
tttaaagata attggtaaat gagtttctat ccttctagtt tcacatcaaa tggaatcatg  22620
ctgccttcac atcactagtg cccgttattt gtgtttaatt tccacaatgt tgtctaattc  22680
cactctttgg gcttccccag ggatccagcc tccctcactc gcccatcgca gggagatgct  22740
ttattcatct ttgtgtcttc tgtgccgggc atagcgcatg gcacagaata agcactcagt  22800
aattgattca cgagtgaata aatggatgag tgggtgagtt caatattgac tacaaaaacc  22860
ctaaggccac actggtgagt ggctgcgcct gtagtcccag ctgctgggga atctgaggca  22920
ggaggatctc ttgagcccag gagtttgaaa ctagcctggg cgatatagcg agaacctgtc  22980
```

-continued

```
tcaaatgaca aaaacagggc caggtgcagt ggctcacgcc tggaatccca gcactttagg  23040
aggccaagat gggaggatca cttgaggcca ggagtccgag accagcctgg gcaacatagg  23100
gagaccctgt ctctacaaaa aatttttaa aaattagctg ggcatggcgg tgtgcgcttg  23160
tagtcccagc tactcaggag gctgaggcag gaggatcact tgagcccagg aaattgaggc  23220
tgcagcgagc catgatggca ccactgcact gcagcctggg cgtcagaacg agacctgctc  23280
tcaaaaaaac aaacaaacaa caaaaaaaaa ggctttctta aagagacttg agaacagaaa  23340
ggggaacaga tacataactt atatatttat ttgttcatct ttccaccttc ctggagggtg  23400
gaggggaaca ggtctgtatt tggagttttg aatgctaaaa gtgggaatac atgtactgtt  23460
tgccatgatc tgttcaaaag ttaagccaaa tgccttagat tctcctgaaa actggaatgc  23520
cactgtaaac tataagcccc acttcaaaga taaaagatct tgatgaacag ggctgggtct  23580
gtggactggg cctctcccca ccacacaagg aagggtggtg ccagttgaag gaaaatcact  23640
taaatccttg ctgtctccta ataaggtgtg gtcccaggta gggctgtcag aattagcaaa  23700
ttaaaacaca gggcatctgt gaaaattaga atttcagata acaacaaata attggcatag  23760
gctgcataat gtccctcaaa gatatcaggt cctaatctcc agaacctgta aatgtgatct  23820
tatttggaaa aggggtcttt gtagatgtgg ttaaattaag gattttgaga tggggggatt  23880
atcctgtatt atctaggtag gtcctaaatg cagtcacact catccttgta agaggaagga  23940
agagagagat ggaaaacaca gaagagaaga caatgtggtg atggaggcag agattggagt  24000
gaggtggcca caagccaagg actgctggca gctaccagca gccagaaaag tccaggaacc  24060
aattctctct tggagctcca gagggagtgt ggccctgctg acaccttagc ttcaacctag  24120
tgatcctgat tttggacttt ggccttcaga agtgtgaggg aatgaatatc tgttgtttta  24180
agccaccaag tttatggtca tttcctacag cagccacagg aatcaaaaac agtaagtatg  24240
tcccatgcaa tgtttgtgac acacaccaaa aatattactt gttgttcacc tgaaattcaa  24300
atttaactgg gtctcctgta ttttatttgg ccaacctagt tcccaggccc aaagaaagag  24360
gcttttgaaa tttgcaagaa agctggttgg agctgtcaga aagtggactt tgtaaacaca  24420
gtaccaccga accaatttga actgtactac ctctagacaa aagagagggc agtcagacag  24480
ttgttcgtga tttcttcttt caacagtcat ttgagcactt actacaaaac agaagctatg  24540
tgtaagggtg gaggcgttag ctgttaatca ggacctccag gctaagtttc tgtattagtc  24600
cgttttcacg ctgctgataa agacataccc gagactgggg aatttacaaa agaaagaggt  24660
ttaattggac ttacagttcc aagtggctgg ggaagcctca caatcatggc agaaggcaag  24720
gaggagcaag ccacatctta catggatggc agcagacaga cagggagaga gagcttgtgc  24780
aggggaactc ctctttttaa aaccatcaga tctcgttaga cttattcact atcaagagaa  24840
cagcacagaa aagacctgcc cccatgattc agttacttcc caccagatcc ctcccacaac  24900
atgtgggaat tcaagatgag atttgttacc atatcagtta ccaacccttc cagataaatc  24960
acgtgaaata tcgccattaa cagagtgagc tcaggtggtt cttcagtgca tttctgatac  25020
ctgaaccttc cctgggaatt tcacagacca tcaggctctc cacccctttga tagcaggata  25080
gcagggccca ggttctgcag gaggagatgt taccacaggc ctgaaaggga gggaggggca  25140
gatgctacag gaagatgctg gctctggatt cgctggagga gctttcaagg gaagtagata  25200
cacactgtct ccatcatttc atgtccatca cactctaaaa tgctttggac aagaagcaaa  25260
tgttaaagac aaatgtggcc cattttcctg tacaaagagg gctgctccca tgccaggcta  25320
ttggcactgg tgggcatgag gcttctctgc tgccctggcc ggggggttct ctcactcacc  25380
```

-continued

```
attggctctc tgacacctgg agagaccacc acccttgggc tttcatgatg ctcacagaat  25440
ccacactgtt ggagctttaa ggagcctgga tcaactggaa caggcaggga gtactaggac  25500
agcccagcat tgccccaaaa tatccaggcc tgataaaaga gaaaaacagg tagctcacag  25560
gaaaaggata aaaaaaggag gagggattta acatgaaaag gtgcttgatc tccctcataa  25620
taaaaagact gctgattcca tccaggcaag tgacagaaaa aaaaaaatta atttaaaaag  25680
actgctgata aaaccacagc gagacactgc tgctcaggga tctgagggtg tgggcagcca  25740
ggctgccacg catcatgggt cggagaggaa gaccacaccc ctggagcaga gggcggctga  25800
tctgtcagat gccctttgac agcacctcag cttccaagaa ttaacccttt ctatgtgagc  25860
agaggcatcc atggggggac acactggtga atcatctgtt atgtagaagt ctggaaaaca  25920
tcaggatgga actggtgaaa taagtgtggc ctctgacgga atggagcggt ccgtctgcac  25980
tgctgcgggt gcccctcaga tcctgtgggt cagtgagaaa agcagtgagg aacaaggcag  26040
gtactgtgta ctgtcctctg cgtgcaagga aggccagcgc atgcaacaga gtccacacag  26100
acatagccta actctggaag gaagaatgag aatgcagttt cagtggtggc ctctggtggg  26160
gagaaactgg gtgaagggag atgtcatttc catttctcta ctattaattt tgtattacca  26220
tgcttaaatg ttacttttta cctttttttt tttttttgag acagggtctc tctctgttgc  26280
ccaggcagga gtgcagtggt acaatcatgg ttcactgcag cctgaacctc ccaggctcaa  26340
gcaatcctcc cacctcagcc tcctgagtag ctgggactat aggcacgcat accaccgtgc  26400
ccagctattt tttttaatca agatggagtt tttctatgtt gcccaggctg gtctcaagct  26460
cctggactca agcaatcctc ctgcctcagc ctcccaaagg gctgagatta aaacgtgagt  26520
caccctgccc agccaattgc tttttaaaaa agattaaatg catgtatacg ctcaggcatc  26580
agcacacttg gaaaggatga aaatatccgg aagaagggtt cttttaaaag gctcctcaag  26640
tgatgctggc aggcatgacg aatgtccctg gtcacaaaag ctctgatctg gcctaaccct  26700
gtcatgttag agactggagt gcgtgtgtgt gcgcgcaaag tgtgggggga tgggggtgag  26760
tgtgtgtggt gtgtaagcat gagtgtgtat gtgtgtggtg tgggggtgtg tgctgtgtga  26820
gcgtgtgtga gtctgtgtgt gtagtgtgtg tgtgaagtat gtggtgtgta tgtgtgacgt  26880
gaggtgtgtg tggtgtgtga gttgtgtatg gtgtgtgcat gagcatgtgt gtgggcatgt  26940
gatgtgtgtg tggtgtgtaa gcatgtgtga gtgtgtatgt ttgagcatgt gtggtgtgtt  27000
gtgatatgtg tgtggtgtgt gagcatgtgt gtgtgatgtg tctgtgtgtg gtgtgtgtga  27060
gcatgtgtgt tgtgtgtgtg gtgcatgtgt gtggcgtgtg agcgtgtgtg tgcattgtgt  27120
ctgtgagcat gtgtgagtgt gtgtgtgttc agcatatata aggcatgtaa ctgaacacag  27180
cactttagag ggctctcctg gagtcagagg gggtgggtag gaggagaagg gaggtgggct  27240
agtgtgctga agtatctact ccttgtcata gtctgtgaca acccagacta gcccatgagc  27300
caccctgttc cctgcatttc caatgagacc tcggtggaca tgttccctga ggtgaggctg  27360
actgatgtca tttgacgatc ttgatgccaa atccttttat atcaaaaaca accagaacac  27420
tctcttttct cttagtgctt tcacccagat gaccacattt catcctccca gccactctgg  27480
gccaggtggc actgctggtt tgaaagggag gtctcccctg gagtaacttc cgtgggcgga  27540
ttcacaccct gcccacagtc ctgtcccagt cagcccacca tggtggtctc cggttcctcc  27600
agaattcccg cttttcagct catccccaca ttcccggagg gactgagagc gcagccccag  27660
ggccctgctc tttgggggcc gtctctacac ccagagaagc agcaaggcat tcctaggttt  27720
```

-continued ctctttcaga tgcagaactt cagtgttcag agatgttccc actggtcctg agagggctca 27780
gttcagcttt aatgactgcg ctgttgcgtg tgctctgcag agggcgggtg gcccagcgtg 27840
gctgactgca gttttcctga cgtggagccc gagcctgccc cgctgtttat taattaagga 27900
tcactctgct tgcagaaccc tgaactcccc agaactgtga ggtgggagaa ccccgagagg 27960
ccacctggcc ccacttccca cctgctgccc aaaccccctc tctgccttcc tgacagtcac 28020
cccaactccc agtgatcccc atcaaccatc tgacaagggg actgagaggg aagagaaagg 28080
aggggcccaa agaggaaggt aaaactgtcg ggaacagccc ccaaatgtgt gacagccttc 28140
agtggagttg cccactttcc cttttctcct ccctgcagga cctcccttct ccccagtcct 28200
ccccaacttc tgaggttaca ttgagaaaag tctgcagaga ggtgccagca tcacaaggtg 28260
ttaaggacca cgagtttggc attttaacag atgccagagc cacttgagaa atgtggtaac 28320
taagcccaga gaggtacagt taacctcccc agagtcacac agcaggttca tggcaaagct 28380
ggactagcac aggtgtcctt cccctgcaga tccccttctg tgccccacat cacctccctc 28440
cagtgtctgg gccacctgga gatgggccct cagactcacc cggccagagg tgccatctca 28500
tgggagaggt ctggccagga agcatcgata tttgagatcc caagaaatga agacttggcc 28560
tgtcagatga cagacttcgg tcatgggaac acgtgatctg ttttacacat gcgtcccctc 28620
agcagcagct ttccagaaca ttcccacttt cttctgtagt gagaagaact ctttccctgc 28680
agcctcctgc ccaactcctc cttcagtgtc tttgcttcag tgtctttgat aaaccattct 28740
gctttgcaga gtgcgagctc tgccttgcag ggttcgcatc tgcctgtgct gagtaaccaa 28800
cgctaaggtc gagtggtcgg tcacctctca taagagctag ggttgtctca tgctgatgac 28860
taggacttgc cctcaaggag aaaaataaat caaaacaaaa gcaaaaacag caaacatgca 28920
tctcttaaag aaggctctga gtccaggtaa atttccttcc actgaagcag ccaggctgaa 28980
ttcgaattat ctttgcccct gcttaaaaac taatgcaaat tttcctagag aatatccact 29040
aattcctgga gggggcatgg gcattcctga tgcccatgag aggaccattt gctcttccct 29100
cagtatgcta aataacagaa gcgacatttg ttgctggaaa gtatcagtga agttaataag 29160
gtttttcttg cccagggtga gggaacagtt cccaatgaca aatgctgtat gggaaggggc 29220
tgtagaactg ccagcccctt tggtccatcc gtaaagtgaa ctctgtggat cctggaggat 29280
tccagcgtct tttttttttt ttcttttttt ttaagacaga gccttgctgt cacccaggct 29340
ggagtgcagt ggcacgatct cagttcactg caacctccgc ctcccgggtt caagcgattc 29400
tcatgtctcg gcctcccgag cagcaagact acaggtgcgc accaccatgc ccgactaatt 29460
tttgtattat tagtagagac gggggtttca ctctgttggc caggctggtc tcaaactcct 29520
gacctcaggt gatccacccg cctcagcctc ccaaagtgct gggattacag gcatgagcca 29580
ccatgcccag ccagcatctt tcatttttct gtctgctttg gccctttcct ctctcactgt 29640
cttccttttc catttccaaa gtcagtccat ctcactatta gcacaaaaac tgctagagcg 29700
cttgtcattg gtcatctctc cctgcacctg gctggtctgt tcttggccac tgaagcgttt 29760
cccccagctg ttgctttaat cattttattg ttattatgcc ttacttaaga aatggatatg 29820
agatgcattt acctgtctct tcctgccact ctgcagagcc agtaagatgt ggtggaaagg 29880
gcccaggctt tggaggaggg ctggctgggg ttggatcttg gctgccccct actagctgtg 29940
tgaccttggg taagtagctg gacctctctg agcctggttc ggaatcatag cacctctctt 30000
tcagggctgc tgtaaggaat agcagtggtg tgtataaagc agagcgcaca gccagcaact 30060
ggcccctagc cacactgctg agcacctact gtgataagct gccattgtgg tgtgtgaagc 30120

-continued

```
aaaggggaaa catgcctgct gtagtgagct tcctgtaggg caggttgtag aaccagaggt  30180
gggttccaag gttacaaagg gactcttagt gtattagtct gttctcacat tactataaag  30240
acctacctga gactggatca tttataaaga aaagaggttt aattggctca cattggctgg  30300
gtgcggtggc tcacgcctgt aatcccagca ttttgggagg ccaaggccgg cggatcactt  30360
gaggtcagga atttgagacc agcctggcca acatggtgaa accctgtctc ttctaaaata  30420
aaatacaaaa attagctggc catggtggtg tgcgcctgga atcccagcta ctcaggaggc  30480
tgaggtggaa gaattgcttg agcccgggag gtggaggttg cagtgagcca agatcgcccc  30540
actgcactct agcctgggca gcagactgag actctgtctc aataaaaaaa aaaaaaaaga  30600
aaagaaaaag aattgcaaga aataaattat tgtttatgag ctatatggtc tgtggtacct  30660
tgttgtggga ctgggagtct tggcgtctcc ctgaccctgc ctgttgctgc agcaccgctc  30720
agccctgcct gctccctacc tgcctcccct cggcctctcc tgcctccacc gggcccctgg  30780
tgcctcctct agagacagtc ctcctgggac cgattgtgtt ctcacttaca cgaggcatcc  30840
aggactacag ataaccagag gaaggggcgc cccccccgcc tgccctcctc cctggcatcc  30900
tcacgctgca gaggtcagag cctcatccca gccccttacc tgcccctact ctgtggagaa  30960
ccgtggtcag ttcgccaggc cggatccacg aacggccttg tggaagatgg tgagctcaca  31020
cccagagctg gctccgatga ccctgtctcc tttacatgtt tctaccttcc cctccctacc  31080
ttcccccact gctgggcgca gagtggaggc agatgaggtt taaagctcag aagggcttaa  31140
acgggttggg gcgcagtggc tcatgcctgt aatcccggca ctttgggagg ccaaggcaga  31200
ggatcacttg agcccaggag ttcgagacca acctgagcaa catagtgaga ccgcgtctct  31260
acaaaaaata aaataaataa aattagcttt gcagggtggc atgcacctgc agtccctgct  31320
actcagaagg ctgaggtggg aggatcgctt gtgcccagga gtttgaggct gcagtgagct  31380
atgctggcac cacagcactc cagcctgagt aacagaatga gatcctgtct caaaacaaac  31440
aaacaaacaa acaaaagaag gcttaaaggg ggctccaggt gggcttggca gcacaaagct  31500
atgaagttct atcttagaca caagttctgt tactgggcct ttgcaggctg gcctgggtac  31560
ctggctgcca tagacaggga accttccaga tgagctgcag gcgtggagca caggagccag  31620
ggtgctcttc ctgggctctg tccacaggca gaacgtacac agtctttgta cacgtccggc  31680
ggctctggtg cctatttttg tttgtgtttt tcttttgttt ggggggatgg atttggtttc  31740
ccccgagccc tctgtcctcc tgtcacctgg ctggtgctcg gcaatgttga ccagctgcct  31800
ggctggagtt ggcagtggct aaggctgtga cagctaacat gttcctgagt cctctcattt  31860
cttcaccata atgccctgtt gagtttgcag atactgtctc tgtttttatc tcccggggaa  31920
actgaggctc agagtggcta ggccaccttc ccatggtccc tcagctcatg agggccacac  31980
agggcattgc ggtggccttc tcctcagcct tgaccctccg gccccagcat tgctgcctca  32040
aggggtctcc tctgctgagc cgtgcacctt ctgcctggca gctccaactc tgtggctgtg  32100
ttcagtggct cagcactgcc ccttgaccct ccctggcctt ctgcggatgc cagactggag  32160
cactctgaca aggtctgggg tggttgtatg ggtcctgtga cctctataca cctcccagtg  32220
cctgggaatc ctgcagatac accctcctta gccgtcccta accatagagg acatttctga  32280
ggtccccgag agagtggggc acccctgcag gatccaactg ctgggcccag gaaggatagc  32340
agcagcatga ggggttccat tagccacaaa ctcacggcat ggaaccttca cccacctcgc  32400
ccctcatctg ctgtttagca cctggcacgc cgtgtatact tactgattat tacattttaa  32460
```

-continued tggcaaatta tagtggcaaa cgtatgcatc tttgcacaat tgttgtacag catgatgaac 32520
aagtcattaa tagtaaagaa taaatgtgaa agtgagaaaa atctgactgc caaagttttt 32580
actccttcct tccctcccca gacttttaaa tgaaagttta gggataatcc cttagttgtc 32640
ctgctagtag gacttgcaat taaaagaatt gggccaagaa cacttctacg cttctccttt 32700
taggtttggg tgtaaattcg gggtatttct cactgatgaa agcctggtgc agggcagacc 32760
gtgggaagct ttcatttccg gaatggacca tcaacatccc ttggagaaga attctcttct 32820
ccagacccag acctggtgtc ctggcaccca ttgggcaagt gggtcctaga agacaaacct 32880
ggtcagagcc tggaggctgc ttagcattcc ccacgcacat tagcagctcg gagagctcag 32940
gaagccgcag cccctccttg cctcaccagc ctggatcagg acagcatccc ctggaagaca 33000
cacagggcct ggcctctgat tacccagcct ggagggaaag ctcaatcgag catcatgtca 33060
cccggtgccc ccatgcaggg tggcactggt gagaccccca agccaatgat accacctcac 33120
aggagtgcag gcccattgtg gccagatcat cttgactttt caagataaat cagaaatcgt 33180
atttccatga gatatcccta tttgcaagtg atggtgacta aattagaagt ttttgaatat 33240
tgtaacatgt tcgtaggctg tttgtctggt ttaaactcta tctggaggaa ttcaagctag 33300
acttcaggaa taacttcttg aggcaaggat tttgagacct tagggaaaga aggacgtctt 33360
gggggtattc tgactgttgt cctcctggaa gggaagaaca gagaactaga agactgccct 33420
tagcgaagtt caaagcacct aagcccggga ccctcagcaa gtgttcttga gtcacagatt 33480
ctccctgagg cgcctctttc tggctccata gaatggctga ttctgtaact cggtgagttt 33540
gctttttttt tttcctccat cacccaggct ggagtgcagt gaagctggag tgccgtggag 33600
cgatcactgc aacctctgtc tcccaggttc aagcaattct ccttcctcag cctcccaagt 33660
agctgggatt acaagcatgc agcaccacac ctggctaatt tttgtgtttt taatagagac 33720
ggcccgaagt gctaggatta caggcatgag ccaccgcggc cagccataac tctgtgactc 33780
ttgttacaaa ggccttatat tttgctcttt gagggtggtt ttggtttgat gcctgttggt 33840
tgccatcttt taactaggga tgttttatca aaatgcccag ccaaagtgtc caaacaaatt 33900
ataccttaaa gtttgaaaat gtctggcact tctaattcaa tgcctgttgt gccaggcact 33960
gggctgctga ggaactgagt cccgtccctg caggctagct agagaacaca cacacacaca 34020
cacacacaca cacacacaga gtggtcttac aagtcagttt tatattctac ctatatgcaa 34080
taaaggtatt attatgttga ggtgccttga tataaaaatt tttcttaaag gagaggatgc 34140
ctaaaacagg cattacctga aacctcctct ctccagcatt ggttgtcttc tgtcatgact 34200
cagggttttc actgagaatg ggatggaaat gtggtctaaa gatagggcca atgttgggac 34260
tggatcccct ctgggaagtc agaccaggct agggcaggtc cttgaagcca tcaggaaaag 34320
cctctggagc cagaaacaaa acaaaaaaaa aatggtgtta actaaactca gtctcaaatc 34380
ctgaatagga ctcaagtcaa gcaaaataat taaaggagtt agcaaagggc aagtcagaga 34440
gaccgagcaa caccaatgtc ttccgggagc cctgtggcga gtgacagagc ctggactctg 34500
gagtagaact catcttgtgt cttcttctgc cactcgttag ctgggtgacc ttgagccaag 34560
ccccttaacc tcttggaccc tatgttctta tctctaagta ggggctggta atatcttccc 34620
ctttgaggaa tgccctctaa ggggtgttgt gaagattcgg taaggtggca ggggtaggac 34680
tcctggccag aaacaggcac ataataaatg ctaagtctct ccttctctcc acctgctgga 34740
tgctgtagat actaaggatt tcgatgtgaa tgagacaaaa cccctgcctt ccaggagcct 34800
ttgagaatca gagaactaga cccatttcca gaacaagggg atgcagggtc tggataaagt 34860

```
tttggggatc aatagagcag agggctccca gaggatccca tagggttgac tcctaactca  34920
agggcatgag acaaccccca ggaagggcac cctggaaggg gtccggctgt ccctgattta  34980
cttgtgggca ctgggggaat gcccggagcc atccagccct cagggctctg tgtgattctg  35040
ggttcctccc ataaaagata atcagattct ttcacgttaa tgtctttctc cacctcattg  35100
cacatcatgc agctattcat tgactcagca agtatcagct ttgcatgcga ccttggccta  35160
cccactttag cttttagtaa tagctccctt cttgaataat acaaccagtg gggaaacaga  35220
acctaactct tacctctggg aggcttattt gctttgagaa catatgtcct gcagttttgt  35280
tcatatggca gtgaagtttc gtgcacacac tctagagcca ggcagcctgg gttcaaagcg  35340
cagctctgcc aggtcctaac tgcatgaatt tgggcaagtc gctcaacctc tccatgcctg  35400
agtttcctca tctgtaagat tggagcaatg gtaatacctg ctttttaggg ttgagaagag  35460
aattaaatga attaagatgg gtaaagtgct tagagtggag ctttgcaagt agtaagtgct  35520
atgtaagtgt tcgatttaaa atgaaagacc cttaaataca ttctttgttc atttcacaag  35580
cccttcattt cacaacctta catttcacaa ccaagctctg tctcccctgg aatccagcca  35640
taactctgct cacaagtgtg agacaggccc cagcagagct gcacgaagag gagagaaggc  35700
agccccccag actcccaacc ccctgtccaa gatggcaaaa ccagaacaca gcctctgtac  35760
caccccagca ggtattcaga atctgcaatc tccaaagccc acttcaattg taaatgtaga  35820
gccacgtgcg ctttaagtca cctgtcactc tggaggctct tttgctcagt tcctcaccat  35880
tagcagggat gacagggagt gcaggagtgc ggtcgactcc cagatattgg agagcgctgg  35940
gctagctgcc cattctcccg gcctccactc ctctttgctg tccagccatc acttgctctt  36000
tgaaggcaaa caaaacagaa aacagtgcca aaagtatggg aagaaagcca gcttctcccc  36060
tggggtgcct gtgatgccat gcccaccctc cctgaccacg cagcccctgt ggaccctcag  36120
ggccccaagc ccccatttcc atcacatgcg tacacccatg tgtgtccata gccgcccatc  36180
tcagtcaata aggctgctcc tgcccacttg gaatagtggt gacaaccagg agtggcttat  36240
gggaactatc ccaatggcct gacagcatgt ccgctgcaaa ccgctgaggt aggacactgc  36300
cctcatgtct agctgatcag caagaggcgc agttgctttc ttaggtaaca ttgctgctgt  36360
gtcctggcca ttgctggggg gtggcactta atctacacca gaattttccc tcctgtatct  36420
tccaagctgc ttggatcttg gtgctgaatt aggttggact ttgtcttgtg gggaagggag  36480
gactatagac cctcaacgta agcaatggtc agactattct aagaaaactc gccgaattaa  36540
agcatgaggt aaatttagtt ctgacttctg tccaccccac tgccactgtc cccttttatc  36600
ccatgatccc ttgcttttct tttcctcctc tctccctatc tcttgtgttt gacgcatgat  36660
aggaattcag aaatatatgt ttgtggattt gtttattcac gtagcaaacc atttcttgag  36720
tgcctaccat gggccaggta gaatgggcgg ccccgggctg cagtggtttc ttcagcccct  36780
ctccagggtt tacactgtgc aagacggttt gtgatgggtc ctcccatcga ggaccacact  36840
cttctttctc tgtgcccctt ggtcctcagt ctctgacccc acttcaaagg cagcattcac  36900
tcagggaagc tcccatacaa tgctagtcag agtaaaagtt tggacaaatt gccaggaagc  36960
agcttgtcag tatgcataaa cagcctttaa aatattacta ctctttgacc cagaatttca  37020
cttctaggaa tctgtcctaa ggaagtagtc acatgcaaaa gatttatgta ccaagatgtt  37080
catcaaagtg ttgttttata acaggaagtc tcagaagctg gataaatatc caacctctgg  37140
aaatggttag atagaatagt atgtagccat tagaaaatta tgtctatggg gtttaaaatg  37200
```

-continued

```
tcatgggaaa acacttctga cataaaagag catgagaact gtatatttag cataatctta  37260
actatgtttt agaatgcaca ggaaaaaaat gtacaaacat attcatagtg atgtctctgg  37320
tggtaggatt atgatcagta agtacttctg tctcttcata ttttcctgta tttgataata  37380
catgcatatg ttgtttttaa aataagaaaa attttaagtt taaaattgga gctgaaaagt  37440
gtttttaggt caggcgaggt ggctcacacc tgtaatagca ccactttggg aggctgaggc  37500
agtcagatca cttgagccca ggagttcgag accagcctgg ccaacatggt gaaaccccat  37560
ctctactaaa aataaaaaaa ttagccatgt gtggtggcac acatctgtaa tcccagctac  37620
ttgggaggct gaggcatgag aattgcttga acccaggagg tggaggttgc agtgagccaa  37680
gatcgtgcca ctgcactcta gtctgggcaa cagagtaaga ctctatgtca aagaaaaaaa  37740
aaaaagaaaa gcctttttaa acagtagcag acataactat ataatcctta ctaagctgtc  37800
ggtcaaattt ttatttatat atttatttta ttcatttatt atttttagac agggtctcac  37860
tctgttgccc aggctggagt acagtggcgt gatcatggct ctcttcaaac ttgacctccc  37920
gggctcaagt gatcctccca tcttagcctc ccaagtagat gggaccacag gtgcatacca  37980
ccacacctgg ctaatttttt ttattttttta tttttagaga tggtgtttac tatgttgccc  38040
aggctagtct caaactcctg ggctcaagct atcctcccac ctcggcctcc cgaagtgctg  38100
gggttaccag catgagccac tgtacccagc cctcaaattt ttaaaaatct ataagagaca  38160
ttattggaca attagagaaa ttcacatatg gacttataat agtatcagag tgtgtggtgt  38220
gatggttctg gagggaatgg actttttctt tggagacagg cttttctatg cccacccttt  38280
tatcttgcta acttatcatc atccaggttc cagcagaaac attacttccc ccaggaaatt  38340
tcttaagggt gcagtatcat gatgtctgca gcaaattctc aaatagctca ggaaaaaagt  38400
acgtgtgtgg tatgagtgtg tgtatgtatg tgtgtatata tatacacata tatacacata  38460
tatatacata tatgtgtata tatatacata tatgtgtata tatatacaca cacatacaca  38520
tatatataca cacacacata catacatgta tttttatata attatatatg cagagagtgc  38580
aaatgttgcc aagttaaaga ttggtgagtc taggtgaagg gaatatggta tttattgtat  38640
tatttgtgca acttttctta agtttgaaaa ttttcaaaac aaaaaattgg aggaagaagg  38700
catgccagtc taccccaagc cctccattgg aatgctgaaa atctaaacaa tgtgatttgg  38760
caatttcatt tcttttctgt tgtgggccag tagtccttag atgttgggga agggggtagt  38820
cgctgaggtg tggttgactt aggatggaag aagcagaagt caagactccc agggtcaaag  38880
tggtttgctc tgctgaccca agtgtgggag gcccagagtc agcgtttcag gtgtgctaat  38940
tcagcatggt tctattcacg gccaaagtcc accctgggca cctctctggc agcaatcttg  39000
ggtgactcta ctaaggccag gcctccatga ccctatgtct ggatcccata tctccacctc  39060
tcccactgtc tcaggaacgg tgcttagctt tttcttttcc ctctcctgtc ttctttgcca  39120
gcatgtagaa agtttaaata attcccctct ttacaacaaa acaaaacata ccccccttcag  39180
tcaaccaccc tagctctctt ctccttttcc cagccagatt tttttaaaag catcctaggc  39240
caggcgcggt gactcacgcc tgtaattcca gcactttggg aggccaaggt gggtggatca  39300
caaggtcagg agatcgagac catcctggct aacatggtga aaccccatct ctactaaaaa  39360
tacaaaaaag tagccgggag tggtggcagg tgcctgtagt cccagctact cgggaggctg  39420
aggcaggaga atggcgtgaa cctggtaggc ggaggttgca gtgagccgag atggcgccac  39480
tgcactccag cctgggtgac agagtgagac tccgtctcag gaaaaaaaaa aaaaaaaaaa  39540
aaaaaagcat cctcagcact ttggcaactc catctcctcc caacatgtcc ctgttactgg  39600
```

```
aatccagcca ggactcagcc ccgatctttc tactctaacc agttgtctca gttaacaagg  39660
acaggtttat gctgcagtga caaacaagat cccaaattct tgtggcttca cacatctggc  39720
accacctcat cttccagcct taggagtcat cttttagttc cttgaaaact ctttacagtt  39780
ttctgttggg gccttgtcat atactattcc cctggaatgt tctttcctat cccctccctt  39840
tcaccttgct aacttgtgcc catccttcag gtctcagcag aaacatcact tccttgggga  39900
agttttctcc aacacccaca ctacacaggt gtcccatcta cactcctatg actttgtggt  39960
acttgtctca cttcattttc cactgccttc cccacaaggc acctgcacaa gggcaaggac  40020
cgtaccactg tacctatgtc actcattgct gtggtcacct gcactctggc tgcctacctt  40080
aactacacat tagaatcacc tgaggagctt ttaaagccac aatgcaagac tccaccctag  40140
gccaattgga tccaaatccc tggggtaggg ccagacatca gtggagttat atatacatat  40200
atatattttg tttgtttgtt tgtttgtttt ttgagacaga gttttgctct gtcacccagg  40260
ctggagtgca gtggcgcgat cttggctcac tgcaagctcc gcctctcggg ttcacaccat  40320
tctcctgcct cagcctcctg agtggctgga actacaagtg ctcgccacca cgcccagcta  40380
atttttttgt gtttttagta gagatggggt ttcaccgtgt tagccaggat ggtctcgatc  40440
tcctgacctc atgatctgcc tgcctcatca gcctcccaga gtgctgggat tacaggcatg  40500
agccactgca cccggccatc agtggatata tttttaaagc actgcagaga attctgttgc  40560
atcagcttga gaaccactga tctgccttgt gcttcacatt taaaactttt ttttaatgaa  40620
taaataaacc ccaaaaaatt aatctcccta agcctcccta gaagatagga tggtaaggat  40680
atttcctag gtaaaaatat gttaatttca tatttcatga aatttcatgt ttcatttcaa  40740
tcaagctctg tcatacacct tacatggggc aagcccagtg cctgggcagg gtgtaattat  40800
actcattaca caggcaagga aaagtcacat taggtgatgg agcacaaata ggcagttaat  40860
ggtttcaggg ctagttagga tatgtttgtc tttcaattgc aagtaataga agcccaaaga  40920
aattggttat ttatataata taattgattg gttcccaaat ttgaaaaatt caggaataga  40980
cccagcttag gtacagctgg atccagtcac tcaaacaatg tcacaaagaa ccctttgaca  41040
ggaatgtatc ctgtgttgac tctactttgc tctgagtagt ctttccccag gtgatgataa  41100
aaatggtcat catcgccagg cttgtgtcct gtttagtagg aatatacaag aagagctcag  41160
taaatgctgg ccccaccact aagcaaaaac aaaacttttg ttgttgttat tgttgtttta  41220
aataacagct tagacctttc ttctttcctt gttattctct ttcatctgta atccagtttt  41280
ctacttctga agtatagaat gttctgatga tttattcttc attacccaca acttgcacat  41340
gtttatttaa aaatgccagg attgcctggc cgttgtgtgc tgttaacctt tgtttgctgt  41400
tagtggatcc ctgaagttca ggctcccagg ggagcagata atgggtatcc agttcctgca  41460
atatccaccc tctggcaagc caagttcctt cctgggtaag gttttgccta cctgcattcc  41520
tagggaagtt tctgggcctg accaccaagc cagctctgag aaggggtgca taagccccac  41580
catgctttgg ctctgtccct atagaatatt ttatgttgtt actgaaaact aaaggaagat  41640
gggtgcggtg gctcatgcct gtaatcccag cactttggga ggccaagaca gattgatcac  41700
tcgatgccag gagttcaaga ccagcctggc caacatggtg aaaccttgtc tctacaaaaa  41760
caaaacaaaa caaaaattag ccgggtatgg tggcatgcac ctgtggtacc agctactcaa  41820
gaggctgagg cacaagaatc tcttgaacct gggaggtaga ggttgcagtg agccgagatc  41880
gcactactgc attccagcct gggtgacaga gcaagattct gtctccaaaa aaaaaaaaaa  41940
```

-continued

```
aaagaaaagg aaagctaaag gagagagact aaaatgatat caggttcctg gagaacaaac  42000
agacatgatt ttgcttcatg gcaggacagc cggaagaagt gggattatat cctcacatta  42060
caaataagaa aactgagact cagaatggtt aagtcacttg tcccaggcca cacagccagt  42120
aaattacaga aacagaattt gaacccaaat cttccagctc caaagcttgt gttcttttca  42180
ctacctcctg cttaattttt taatttctaa gattagaccc ttcatctatc catgacacct  42240
gcctgtcatc ccctgaaaaa aggtgaacgc cgttcagaaa tttttctagc ctgagctcac  42300
tcccagttca cttatttttg ctttgtcatg gctgcccagt ccccacttgt agaccaggaa  42360
taggtcatgg ctgcggggac tacacgctgt cgctgctgca agggccggcc tctgtttccg  42420
gggctgagtg ggggccagac ctgccaggag caccatcttc tgtgggtcct gcctggatgt  42480
cacatcccgg ccccaagaag tcactgcaaa ccttcgtatt attgagcttc acatcctaga  42540
atttgctgtc actgtggctg ctgcatgaag ttgtcctgag agaaacgggc attgtcatta  42600
acagggaaat tgatggtctg ggggaaaagt catcctcatt ctcttgcaga tctatgggtg  42660
attgagactg gctgatgttg aaggggtttc tcagccatcg tgtgccatgt tatggaacag  42720
tggtgtagcc agccatttga cacccagcgc tgacctttgt ttaacaacct cacctatata  42780
tgacaaaatg attgtcagaa ataatcgtgt aatgaaatga ctgtaataat ggccagaaaa  42840
gaaacgcaga tagtaaaatg tttctcttgt tgaactctgt acatataatt gcaccaggat  42900
tttttcaaa taaaaagtaa atattatact acaaaaaagg gaaaaagcac aagcatttat  42960
taaatagctt tctatatctt tctgagtttt gatcctttga ttgcagactg atgtaatatt  43020
ttatgtaaat cattgcttgg ttactaagtg aactttaaga aaagtgagac gtctgcagaa  43080
gttgcccata atttagcagc tactgtattg taccattgat gtacggcttt attttcttga  43140
ttaattattt aaacaatata attcacaatt ttaaaataat aaatttccac ttaaaatggt  43200
atttaaactc agcaaaatat atcatctatg agtaaaattt gtatttacca agcaaaaata  43260
ttacagtttg tggttcacat gctgtctcac tgttttaaat tttaaataca aaaactccaa  43320
gtaggctggg tgtggtggct cacacctgta atcccagtac tttgggaggc tgaggcaggc  43380
atatcgcttg agttcaggag ttcaagattt gcctgggcaa catagtgaga tcctgtctct  43440
actgaaaaca attagctggg tgtggtggca catgcctgcg gtcccagcta ctcaggaggc  43500
tgagatagga ggatcacttg aaccctgggg gacagaggtt gcagtgaggc aagattgcac  43560
cactgcactc cagcctgggt gacagattga gaccctgtct caaaaaaaga aaaaaaaaaa  43620
agaaacacaa aaactccagg tggtcgcaca gaatgacagg actgaagtaa cttagctcca  43680
atttctgtct tcataatcac tgtcctacca ttgtctgtgc ttagaatcta cttgcttaat  43740
gcaggaacat gtgttctcac agagatggaa aatgcaaatg gcgccagaag caagctggaa  43800
attctgaacc attaagaatt tactctctgc caggcacggt ggctcacgcc tgtaatccca  43860
ggactttggg aggctgaggc aggcagatca tctgaggtca ggagttcaag accagcctgg  43920
ccaacatggt gaaacttcat ctctacaaaa atacaaaaat tagccaggca tgatggtggg  43980
tgcctgtaat cccagctact cgggaggctg aggcaggaga atcgcttgca cctgagaggt  44040
ggaggttgca gtgagccgag atctatctgc accattgcac ttcagcctgg gagacagagt  44100
aagactccat ctcaaaaaaa aaaaaaaaaa aaaagaactt actctcaaaa taaatacgtg  44160
tggctgactc cacatatggt agggccaact gtataactag aagttctcca aataacttct  44220
gtggagaaaa aaaagtttat taaaggttaa ctttttttaaa gtgctaacta gaaccttact  44280
aacactgaga tcgcaccaat tgtttataac ttagacaggg ccgggtgcag tggctcatgc  44340
```

ctataatccc aacactttgg gaggccgagg caggtggatc acttgatgtc aggagttcga 44400
gaccagccta accaacatga tgaaacccca tctctactaa aaatacaaaa attagccagg 44460
cacggtggta cacgcctgta atcccagcta ctggggaggg tgaggcagga gaatctcttg 44520
aacccaggag gcggagattg cagtgggcca agatcgcacc attgcactct agccccagca 44580
acaagagtga aactctgttt caaacaaaca aacaaaaaaa aaaacctctt ggaccaggaa 44640
aatatttttt aagggaggag tattttatca ctggcattgt ttaggattgc aggcacatga 44700
tgctaatgaa aagcagacta actattagtt ggttttatta ctgtttttga actctctctc 44760
tcccttttt tttttttga gacagagtct ctctctctgt cacccaggct ggaatgcagt 44820
gactgcagtc tcagctcact acatcctctg cctcctcagt tcaagtgatt ctcgtgcctc 44880
agcctcccga gtagctggga ttacagggca ccacaccagg ctaagttttt gtatttttag 44940
tagaggcagg gtttcaccat gttgcccagg ctggtctcaa actcctggcc tcaagcgatc 45000
tgcccatctt gacctcccaa agtgttggga ttacaggcgt gagccaccgt gcctagccct 45060
gtttttgaac tctctagaga cagtccagcc ccttattact tgtcctgagg cagctgctcc 45120
cttcacctgg ccccccgcat tgtgttccgg acccttgtcc tggtggtgct aaagaatatc 45180
tctgtcgatc ctttggggac tggggaaact gaggcccagt gccacgcgat gccatttgtt 45240
cagggaagat taggtcatct gctaggtccc cagtcacttg accttcttcc cagacaggaa 45300
gaagctgctc tgggtctctc agtgctccac gtgtctttgc acattgaaat gttttctgat 45360
ttttttttt tttttttgct gttacattta cttttaaaaa ataacaagca ataaaatgtt 45420
acatttgaga aggttgaaat gagaattgat ttgagttaaa ttctagcaga tttttcttag 45480
aagaatgata tcatcatctc cagctacctg caattgatct actctgaatt aagaaagaga 45540
cttccatttg ttgtttatat tttgcactct tgatgtgttt ctttaaatta tggtcatggg 45600
ccaggtgtag gagctcacac ctgtaatccc agcaccttgg gactctgagg agggaggatc 45660
actggaggcc aggagttcaa gacctcgtct gtacagtaaa ttttaaaaat tagccaggca 45720
tggtagcatt cacctgtagt cttagctact tgggaggctg agatgggagg attgcttgag 45780
ccagaacttt gaggctacag tgagttattt tcacgccact gccctctagc ctggctgaca 45840
gagcaagacc tgcctcaaaa aaataagtaa aaaataaatt aaatttcaat cattagcagt 45900
cattaggata tttaaataca gtatgttgaa tcaaagttac gcatgtgtgt attttttttt 45960
ccagagagtt gtttatcatg tgggttttaa tttaacttta aaaaaatgtt ggctggacag 46020
ttgcccaaat ggtatcatca gccatttggt tgagaacgta tgtcctgcgg gctcctctgt 46080
cactggagtt ttgctagctg acagccactg gctagttaga gactgcagtc agcacagatg 46140
caggcgtgga cttgcgcacg taaccatgtc aatgcaaagc catcacttct taaaaattct 46200
gaaccctgct gtctgagatg gtggtgcagc ggatagaact ctgctctaag aggcagtagc 46260
taattccatg tcttctttgc ccttgactag ctgagtgact ttgcacatgg ggcttgcctc 46320
tctgttgcct tgtctgcaaa gtggaatcat cttttccttg ctagacagaa ggtggaccct 46380
ggacctatgg cctttttgag tttccccccc gcttcttaga aggacctctg atcctactga 46440
gtttaatacc cacgggttaa taattgggaa aagcaaagga agcgcttctg tttaggtaat 46500
tatatgcatg tttttgtctt tttctggctg gaaagatatc caagccactg ggaaggtccg 46560
tggctaccca gggtagccct ctctggggag ggctgctata tccaagagcc cctcatgaga 46620
atttgaaaat cgaccatggt agggcctgct gacttttgac agctaatggt gtgctgagaa 46680

-continued

```
ttgtccctcc aaagatgcct ttccattccc tcgggagagt ctgggcagcc cctactgggg  46740
gctgggatgc tggctcttcc ctcagcctcc accccaactg ctctcttccc tcctcccctc  46800
cccagccccc taatttctct cacaaggctt tgttctgcag caacctttcc taatgcagtc  46860
ctggcctctt cgcagcttca ttacataacc ttccgtggac tcctggtcca aggatcaccc  46920
cagaaagcca gtcagaggta ggcacgcagc tggggtccat ttacttacct tccccacccc  46980
ctcggaactc agaggtggtg caggaatttg gactccaaga attaacagct ccaccaccat  47040
caccagagcc aaaactcagg atgcatgtgc ttcatctgct gcttatttcc agctgagagc  47100
cagtggtgcc atggttcctt agggagccgg tcccctgatg ccggctcctg gccccaaatc  47160
tctctgatcc gggctcttcc agaatgtctt gtctccacca tcgcctttga ccaatggtgt  47220
ccctttgcct ggtaatgtcc cctttgcctg atgatggccc tgtcactcct ctctttagca  47280
cagaggaggc tgtttcatcc cttcaagcct gccctccctt caagtcttag ctcaagttca  47340
ccttctccgc agagccttct ccaatcttct tgactacgtc tcctctcagc tccagcaacc  47400
tctgtctctg gcactgattc cttacttagc taagagaatc acagacactt ggggctcagg  47460
acaatctgct ttctctcttc ttacccatgg ccttggactg tgtgtacctc tttgtctcca  47520
ctcccaaacc caacccccag agggcagaga gcatgttgtc tgtccctttg ctcagcatga  47580
agccatgcgt gtggtagatc ggcagagttc cataacttgt gttgaccgag gggtcacttt  47640
gctctgaaat tacccctgtg tccttcagta tttgcacaga tagcttcctg gccagaccga  47700
atatatccaa gggcatggcc cacctctgct cctgtttcca ggtccctggt gggggttagt  47760
tcatgccttc ctcataatct gcccactggc ctggtcctca aggtcttccc aactgctcag  47820
ccagagttga gaaaatgggt cgctccatcc tgtttgtgtc gttctctcct tcctggccca  47880
ctctcctgcc cacaggtatc caggggctgc ctgtagcatt agaggacata catgcacatg  47940
cgtgggcatg ggacactcac gtagcctcca agcacagcat caataatgca ttctgtgctt  48000
tatagcatgg aaagctgctc taaactttat tacacagtgg acatgtctga agcagctccc  48060
aaatccaccc ctgagtgtgt tggaattggc aagcctatca cttgggagtc tagttttttt  48120
gttcgttaat aatagatgct tcctgtggcc ccagcttggc aattttgatt taaagtgatc  48180
ttaactgaag agactaatgg acgggtctga atttgtgcct tttaagcaca aagtattgct  48240
cttaattaac tggattctat cctttgagca ggcagaggcc ttcccccaag ggcgtcatta  48300
acgatccaca tctggacatc ttccaaagcc ttcttctgtt tcaggccaac cgcaggtgtg  48360
ttcctgaaca cccaggaggc tatgagagcc acatatgcct cccaaataca cacagtgtgc  48420
atgcccaggg acatagagca gtgtgcaaag tcccattcca tctctctcca cctgggagag  48480
gatggctctt ctgtctgatt catggctcaa agtggtaaag gagctcccca ctccccgtcc  48540
cacgcctact cagagtctgc aaatatgtat gcgatatgag agctcgtcag ttagctgtct  48600
tcagtgtggc gcacatttga ggagtctgac tcccctccag cacaggccaa tgtgcactgc  48660
tctcctatct ttgtaccccc actgttgcac tgtgcagagg ttggagccat agaagtacca  48720
gagctgtgaa aggagaggcc ccctctcacc tctgccctgg tctccatccc cactttctct  48780
aggaagctag taggtgctga caggggagag aagggagggg aggggtccag aaacagtggc  48840
tcatgcctgc aatcctagca ctttgggagg ctgaggcagg aggatcattt gaggtcagga  48900
gtttgagacc agcctgggca atgtagcaag accctatctc tacaaaaaga aaaaatgtaa  48960
ttagctgggt gtggtggtgg gcacctgtag tcctagctac ttgggaggat gaggtgggag  49020
gattgcttga gcccaagagt ttgaggttac agtaagctgt gattgcacca ctgcactcca  49080
```

gcctgggcaa cagagctgag accctatctc aaaaaaagaa aaaaaaaaag aaaggagaga 49140
gagagaaaga aaagaaaaga aaaaaaaaaa agaagggaag ggaaagccca gaagagtgtg 49200
gggagaggag gcggccgtca ttctggggcc ctcagtgtgc acaaccagat aacacatgct 49260
ctgtgggctt ttgtaccatt ttgcttgagc ataaagaaag gaaggctgcc cctaaataga 49320
aagcactctg gaggcaaaca aatctgactc caatcctggc cctgccactt tcccagctga 49380
ggacttagac aagcacccta gcctcttgga cattctcaga gccatctgct gcaagtgggt 49440
gctgccatac ccaccttact gggcaggctt gggggaccaa gggtggtaaa tggctcagtc 49500
tttcatgatg cggccacaca gcaggtgcgc catccaggtc catttctttc cttcctttcc 49560
cccaaatcaa gttgtcatta aagtactagt ccacattaat gaaatcaact gtattaattt 49620
tctatttgct gctataataa atcatcagaa atttagtggc ttaaaccaac acaaatgtat 49680
taccttacag ttctggaggc cagaagccct ccataggtgt cactgggctg aaatcaaggt 49740
tttggcaagg ttgcggtcct ttctggaggg tccaggggag aatccatttt cttccttttt 49800
ccagcttcta aaggtttcat gcattccttg gctcatgatc ttctatagct atagtcagaa 49860
aaattttcca tcaatcatct tcaaagccag caatggcagg atgagtcctc acatcacctt 49920
gctctgacac cagttctctg cctccctctt ccacatgtca ggaccctcat gattactttg 49980
ggctcactct gataatctgg gatgatctct ctattttaga gtcagctgac tgggaacctt 50040
aattccatct acaaccccaa ttcctctttg ccatgtacag tgacatattc acaggttctg 50100
gggattagga cgagcctgtc tctgaaaggc tactttacat gaaaattcat ttttttaatt 50160
aagatttttt tttcctcttg agacaaggtc tcactctatg gttcaggctg gagtgcagtg 50220
gtatgatcac agctcactgc agcctcgacg tctctgggct caggtgatcc tcccacctca 50280
gcttccctag tagctggaac tacaggggtg agccccccatg cccagctaat tttttttttt 50340
tttttttttt gagacagagt ctcactcagt cacccaggct ggtgtgcagt ggtgcaatct 50400
cagctcacag caacctccgc ctcctgggtt caagtgattc ttgtgcctca gcctcccaag 50460
gagctgggac tacaggtgtg caccaccacg cccgactaat ttttgtattt ttagtaaaga 50520
tggggtttca ccatgttggc caggctggtc tcaaactcct gatctcaagt gatccaccaa 50580
cctcagcctc tcaaagtgct gggattacag gtgtaagcca acatgcccgg ccccagctaa 50640
tttttaaata ttttttttgt agagatgggg ttttaccatt ttgtctaggc tggtcttgaa 50700
ctcctgggct caagcaaacc tcccaccttg gtctcccaaa gtgctgggat tacagcatga 50760
gccactgcac tcggccttaa gagaagattt aataattaat actttacaac aagatctgga 50820
agaggtggga tgagtaacta aatgaggata caagtaaccc gggtcatatt tgctaatacc 50880
cttggtcaca ttgaacttga tatcttatca gatttttccta atcagctcct ttagcagcag 50940
tgttgcagca tcttatctca ttttgttttt tgttttttttg cctagcacat gcctgtaaat 51000
cactggattg aggtgtttag atgtttgttg tcctttggat gcttcttata aatccatatt 51060
tcatggctcc ctggaaagtg ctatgcaaat gataagctgc aaggatggaa aggaaattgc 51120
agtgctcctg aattgtaaat gggcttttac gaggaggttt ctaattactc gctctttctc 51180
ttgaactgag gagttgaagt gtaggtggca gatccataac agataatcat gtgtgtgatg 51240
tgacttcagc ctgagcgtcg aggaccaagt cacagagcag gaacagccac tctccagtgt 51300
ccttggggct acgtctgagg agaacctggg atttcatata tgacctgcac tggctggggg 51360
gctctcttga cgtaacgtgt tccctctgag catgttacag attctgacat tcttatgttc 51420

```
cttctgtgga gagacatgta cttagtgacc taactcactt tagcatattt ttgctcatcg  51480
tttgtgtagc ttaaaggaat cagataatta ccccctcccc actactttcg gaagcacaaa  51540
tgcaatgccc tagaattgta ctggggactc aaaaagaaaa gagagtagta aaatctatta  51600
aaggggacaa agacagccta tatactacaa gctttctatt tttatggcag agaatgccat  51660
tttctaagta aacagagaac tgcatttgac ctgcaatatc aaatgcatgg atttgatgct  51720
ttggaaagca actgttttct gcgttaatct gggtgtcttc cgtgaaatgt cctcctgcct  51780
ttggcttaaa cactagcttt gtctacagcc attccatcct gaacctgccc aatcttgtct  51840
gaatcctggt ttcaccactg acaagctgtg tgtccttggg caagttactt cacctgtctg  51900
tgcttcagag tcctcatctg tgagttgggg aatctggaca gaatctaccc catagggcgt  51960
agtgaggatg tgttgaatta tcccaagtgg ctacacagag taagcactca aatgatgtca  52020
tcgttgtcat gattgctgtt accagagcct agagttcatt ctgatactcg agtctgtggc  52080
ccatccagcc caggtaagga atagttggag gagttgggca tgttcagctt gaagaggaga  52140
cgacagggga tatgggatag ttgaatctgt gaagggcccc ctgggatgaa gaactggcat  52200
gttctgtgtg gctccagggc actgagcagg acccatttgc caaagtctca gggacacagt  52260
ttctagctat agacagaaaa attttctgtc actcagagga tgaaaataga atgagccccc  52320
ttaagaggta atgagctccc tgtcattgga aggattccag aagagctagg taaccacttt  52380
aggtgctatc aaggggcttt tttctttaaa gtcctttcca aaagcttctg agattgcata  52440
aacaatagga agccatcttg gtgctttaac acaaactctc cccagtgatg agggttgagc  52500
caaagccaga ttggcaagca gagaggagac ttgtgtacaa ggagttcctc gagtcaattg  52560
ctttttcctt gttctagcca gccagagggc tcctgttgga aaacaggaga ccggagaggc  52620
tgaggcctga ccaaaccagc ttctgcaggc cagctgggag gccacaactc ctacctacgg  52680
gaaaactgaa gggcatctct atttttagat tagcaaaaga aaataaattt aagtttgagt  52740
ctcctttgca acttttaaaa gacatcttta ttgagatgat cattcacatt ctataaaatt  52800
cccccacttt gagttacaat tcagtggttt tagtcttcct tgatgatttt gatggtcttt  52860
tcttaaggct cttggaagac ccagaagcct ctcagacaca ggtgggtgtg gagggcgtag  52920
cacagaggca gacttctcat ttcctgggtc tcccctttaa tgactctcag agacccctcc  52980
ttccccctgc ccctggcttc taccccaggg gtgtagagtt ttgccatttt ccaagcagaa  53040
cttcatttcc tcttctgtgt ctacactctt tgtgcttctt tcttgccagc tttttctcct  53100
ttgcccgccc ttccttcctt ccttccctcc ctcccccctt ccctccttcc ctctttccct  53160
ccttcccccc ttccaccctt ccccccttcc cccttccct ccttccttcc ttccttcctg  53220
cctgccttcc ttccttcctt ccttccttcc ttccttcctt ccttccttcc ttcctggtat  53280
gtgactaatt tctgtttcag gacataaatg ttgtccaggc tgttctttgg tctttctgtt  53340
ggataatgga catttggcat tgagagaggc tgctttttct gaaatcatgt tcttggggcc  53400
cagaacctag gtgtgtgctt ctgactttgt tttcttcctg atccaaattc tgatatgtcc  53460
atttaaattg atctagaccc acagggcact gtgggacaga tcctcagtgg aacatgactc  53520
tgtaacgaga gcattttgtt ttgtcaaaat gagaacatat tattgccttt catctgattg  53580
taaacataat acatgtttat aaaacagtat aatgagacaa aaatgtagac actaataagg  53640
gaaaatctcc ctaattgtat ttctcttcac agagaaagcc cctgttgggc atatatactc  53700
tagtttgttt atttgtttga ctacacatat atgtattctt ttcttatgta taaaaattct  53760
gaacatgcac atttctgcaa ctactgtttt cacttgatga tgcatggacc tctctagagt  53820
```

gtacgtttct tcttccttac aaagcagttg gcttcgccca gggtgcacca ggacacggtt 53880
ttggctctgt ccccagggtg tcacgggacc aggggatgat ctcacagggt ctgccatctg 53940
ccctgcctgg ccggaggctg catcgagagg gccaaggggc accacgtgtc gtgggtactg 54000
tcaaacaaga gccttcagag ccttccacag tctttctttt gcttcccagc attgcttccc 54060
cgctggtgga ctctgaatct agaactagct ccaggcgcct ctccaaattc agacgggagc 54120
tggggcacta ttataatgca aatctaggca aagccctccc aataccagga tccagaatgg 54180
ggtggggccc tttgccctga aaagctgttt agtttgaaaa tacaaacagg agacagaaaa 54240
gtttggctaa attaatggat aaagttttaa cgatggtaac catagtaggg ttcatcgaca 54300
gccagcgatg gttctgaaca cttgacatgt attaactcac ctaatcccca cattttacag 54360
acaatgcaaa ggaggctctg ggaggttgag tgacttgccc caaagtcgca cagctcctaa 54420
gtgaaggatt cggagtggac tccaggcagc ctggtctgac tccctgcact gcgctgtgct 54480
tatctctggc cccaatgccg ccatgcagaa gtgtctgggg gcactttgtc tctgtcagac 54540
agaattcgga gatgtgtatg cttgccctgg tatggcactt ctcttttttt gagacagaat 54600
ctcactctgt caccctggct ggagtgcagt ggcatgatct cagctcactg caacctccgc 54660
ctcccaggtt caagcaattc ttgtgcctca gcctcccaag tagctgggat tatagatgtg 54720
caccatcgtg cctagctaaa tttttgtact tttagtaaag atgttgtttt gctgtgttgg 54780
ccaagctgat ctcgaacttt tggcctcaag tgatctgcct acctcagcct cccaaagtgc 54840
tgggattaca ggcatgagcc accatgcctg gcagtgtggc acttcttacg tgtgttcagc 54900
ggacactgtt tatcttctgt ccctccaaga cggtgctgag ctcaggtcgt tcattactgg 54960
cagacaactg ctgatttcca acagaattgc catcctcttc tcccctgcga ctttcagagt 55020
gtgacctcag actcaaaaat tagaagtgaa aacatcttaa aaactatcac cttttcttcc 55080
taatcctcct ctcccctccc tgtcttcctt gttgtcccca tctaatgaac tatcatggca 55140
aaaagagccc atttctggtc attttctgtg gcctttcaaa ctcccaccta ccccactgct 55200
cctgggtgca ttacccgaaa gctgagactt cagtgcagaa agtgccaggc cctctgtccc 55260
cccagatcgc cttccttgtc ttccctgtgc ttgcctgtca cattgtgtgg gttccagcgc 55320
tggaaggaat gaggaacaga ttctctggtt ctccttttga agtttacctt cgctccacca 55380
cttctgagac cttcccggaa gttgcccctt gtttctctcc tctccagggc tgccccagag 55440
ctgcctctca cctcttcctg ctgtcacccc accaccatca gggcagaagt tgggacaaag 55500
cctctcctac tggctcctgc ttttctccct taggtccagc ctcctcttct ccatcttcag 55560
gagtctcctt ctccactcac acgtcatgac ttcagcacct cgcatcagtc cagaatatga 55620
ctgcttgttc aagtgccacc tttctcatgc attttttttct agtgacaatc acagccaccc 55680
tgtggggcag gagtgtcatc atccccatgt ttcaaatgaa gaattgcagt tcagagaggg 55740
caagtgactg gcccagcctc aacagctagc cagtggaccc caccagggct tctgactcca 55800
gtccgggttc cctttccacc caaatccatg gagggagctg agccgagaac aggtgtcctt 55860
caggaagacg tgaagccaaa gcctccacct ccaaactcag gggcccaggg agtccaggca 55920
cccatccact cacaaggctg gatatggtgc attccaggag aggggttggg ggcgagtggc 55980
ctctctgtgt acccgtgggg atagatgcgc aagtggcatc gccacatcgt gagtcctggc 56040
ttcatgggtg agctccaggt ccaacgagaa gccaagcagg gggcccttca agctcagctt 56100
tgggcccggg tcggggtaca gggtagagcg ggcctcccca gcccctgcca tgaggccaag 56160

-continued

```
gcagtgcatc gttcgcagcg tacattcaga aaccaaagcc taggagctgg ttatcattcc  56220
ggtttacagc tgatggaaga gcaggtgctt ccgagaaccc acagtgctct ttggccagtg  56280
acccaagggt gcctctgaga ggcctcgcag cacccggagg tgctgctgag gcaacgccct  56340
gactgtaaga aggaccattc atcctcagag agtggccgtg atgctgctgc gacagtccca  56400
ccatccctcc cgactctcac tcccaacaga cttcccactg taaagctgaa ctctccagca  56460
aatcacctct cgccagactc tctcctcact ctctctgggt ccactagagg ttcctcagcc  56520
tctctttgcc ttggttttcc cagctgtaaa atggagcaaa gagggcctat gtacccacaa  56580
aggtgtggtt ggagcgactc ctcctacatt agggcctcga gtggggcttc atgattggtt  56640
ggtggaggtc tccaaaccca cccagtgcca ccgaaggctg agactgcaga tgcaatgcca  56700
caggtgtcct tcctcagcct gggcagctga acatcatgtg taaaacgggg ataataagat  56760
aataacagcc ccttgcacct atgtggctgt gaggattaaa caagataaat gtgtaacagt  56820
gcctggctat agaaatattt actcttgtta ttaagggaag aatatgtgtg gctaaaaagg  56880
gatcgaagat gtaaaagcca atccctcccc ctctagcata tttaagggta atgttgagtt  56940
ggtttgtgga ccatttgctg cctgttagag ctggaaggta gggaccccct ctcaacagcg  57000
atgctacaaa ttatacccat tggaggtcaa ccaaaagaca aagcttattg gctggacatg  57060
gtggctcaca cctgtaatcc tagcactttg ggaggccaag gcaggcggat cacttgagat  57120
caggagttcg agaccagcct ggccaacatg gtgaaacccc atccctacta aaaatacaaa  57180
aattagctgg gcgtggtggt gcacacctgt aatcccagct actcaggagg ctgaggcagg  57240
agaatcacta gaacccagga ggtgaaggtt gcagtgagcc gagatcgcac cactgtactc  57300
aaaccgaggc aacagaggga gacgcaatct caaaaaaaaa gaaaaaaaga caaagcttgt  57360
taataccagc atattgttaa gggaataaag taggctgcag aacaactggt gtaatatggt  57420
gccatgtagg gaaaattaca tgtgtgcata ggagaggggt ctgcaaggtt gtgccctaag  57480
atgttagagt ggttcctttg cttttctctt ttataatttt gtatttgact tttaaataag  57540
gaccataaat cacttttata aaatacattc tctccagccc ctactactcc tttaaagaat  57600
aagagtggtt tgcccaagaa agacagtttt ttttgctctg gttttcttga ttctgacatc  57660
agaggaaact gcttctcatc cacttggggc tctgggttca ggggattcat ttcaggcaga  57720
ttaaagtggt gaccaggggc attcgtggac acagggaggg acaggagcac catcagtttg  57780
tctcacacaa ccactgtcat cctcactgaa ggctgttgcc tgatcaaaaa cagtattggg  57840
ccaggcacgg tggctcacac ctgtaatacc accactttgg gaggctgagg tgagtggatc  57900
acttgaggtc aggagttcga gatcaacctg gccaacatgg tgaaaccttg tctctactaa  57960
aagttcaaaa attagccagg cgtggtgggt gcctgtagtc ccagctactt gggaggctga  58020
ggcaggagaa ttgcttgaac ccgagaggta gaggttgcag tgagccgaga tggcaccacc  58080
acactccagc ctgggcgacc gagggggact ctgtcttaaa aaaaaaaaaa aaaaatatat  58140
atatatatat atatatatgt caaaaatggg gtagttttta gatctatagt agttctaaaa  58200
acaaaggcca tccaagcatg acagatttac aagcactatt ggctattcca gtagttacaa  58260
tggaggagag aagcttttag ttaaaacaaa caaacaacac aacaaaccca gaaaccttag  58320
gtcaaaacca aaattgtcct ctcagacaca atctgggaat tttctcatga cagtgggcat  58380
tagccaactg acatcagcag caaccatccg tgtgcacaca gtggcaccac ctcctcccaa  58440
aaagcagcct tcatctatgc cctcatacaa tcgttgatta ttctctttgg attgaggccc  58500
ggaattattt aagtttcttc ttgccagcat gagtctttcc tttctgtatg ctccttatct  58560
```

-continued tctctcttta atttggcagt tctgcttgaa atctgggtct ttcattagta gtagttcaat 58620
ttggttccag aacattctgt ggtgtgatgc aatgtgacca gagctcacac ttcagagctc 58680
ttcaagggcc agtcttactg agcacctccc agtggctgcc tgtgtgctgg gcgccacttg 58740
tggtgggcag gagagaggag gggacacaaa aggagacaca gctccttctt agaagctcaa 58800
agttggggac cagctgccac agaagagtat gtttagcatc tgagacacca agatccagcg 58860
tcacaagggt gtttattaag cctcctcatc tctttctttt tctttttttt tttttttttc 58920
ctcaggcagt cttactctgt cacccaggct ggagtgcagt ggcatgatct cggctcactg 58980
catgcaacca ccacctcccg ggtttaagca attctcctgc ctcagcctcc ccagtagctg 59040
ggattacagg tgcccaccac cacacccagc taatttttgt gtttttagta gagacagggt 59100
ttcaccatgt tggtcaggct ggtctcgaac tcctgacctc agatgattca cccacctcgg 59160
cctcccagtg tgctgggatt acaggtgtga gccaccgcgc ctggccttgc tgttgattca 59220
tctatagtat gtttgacttg atgacctcca gttaccttag acagaggttc tcatctaagc 59280
tccaactttc catttccttt gtcctcgtct ttccccttaa cccctccaca tttctctcaa 59340
aatcacccca cttctaaaaa atactgttta tttttctttt aaatttcaaa ttatctatac 59400
tcattgaaat aaatcaaaat agcatggaat aagcgaaaaa aatggatccc acccttcccc 59460
actcccattc cctagggcta accatagtta accatttaat gactaggttt ttttgttgtt 59520
gttatttttt atttatttat tttgagacag agtcttactc tgtcacccag gctggagtgc 59580
agtggtgtga tctcggctca ctgcaacctc tgcctcccag gttcaagcat tctcctgcct 59640
ctgcctcctg agtagctggg attacaggtg cctgccacca cacctggcta atttttgtac 59700
ttttggtaga gacagggttt ctcaatgtta gccaggctgg tctcgaactc ctggcctcaa 59760
gtgatctgcc caccttggcc ttccaaaata ctgggattaa ggtatgagcc accgcaccca 59820
gccctcctgg gctcttttcc tttagttgca ctcgctcccc gctcctggag tagagggatt 59880
tccgagagac tgtgggctcc agccttcacc taggcccagg actaggatgc ctgccctaac 59940
atttatcttt ataccttaaa gcaaaacagc tggaccataa gcattcaaga acaaactgtg 60000
aataaggaga aagttctccc aggaaacaag agctttagtt ctgttgggcc agcccttata 60060
ttccttagct gttaccagtc actgcttgat ttaatctcgg ctatcacttg gcctgacagg 60120
tctgctgctg gtgccaggat gtctgggttt tgaagcctgg ctccattaca tacttcctgt 60180
gtgaccttgg gcaacttact caacctgtct gttcctcagt ttccccagct gtattatgtc 60240
agcataatag tttgttgtgt gaattaaatg aggtaataac tggaaatgct tcaaacatgg 60300
ttcctatcat gagaaatcct gctttccgcc taaatgtgct ggaaaattcc tggtggtgca 60360
gaacaggaga ccagagcaaa ggaaagacag ggtgcagaag ccaaaaaatta ccttggagaa 60420
caaagcgcat gttaaggtta tttttggatt ctaggtttat ctctgcttgg tcttcagtta 60480
cctgcaagag atccatttag gggatttttg tttgttttta acgatagctt tattgagata 60540
taattcatat gccataaaag tcactctttt aaaatgtttc cggtatattc acaaggctgt 60600
gcagccttcc ctgtccttga ttccagtctg agtttttaac tgaagggata aggaggacca 60660
cgctttcccc agaccagaac cgcgggccag ggggcgattc tgctgagtca ccgcgggcgc 60720
ctggtgcgcg gcggcggagc ccgggacctt ccttggctgc cccctagcga gggccgcagc 60780
gcagcctgag acacccgccg gggccgctcc acggccgtcg gatttagact ggaagctcgg 60840
tccaggtccc cagcttgatg cgcccgcggt gtaggagacc agcccgactc gggcttcccc 60900

-continued

```
tgagcccctg gactcttgac tccagcaggg cctgggtaat gaacgtcagc tccccctttcc  60960
caaaggggtt gctctgttgg gaaggcaccc gtttgataca gtagcataga gatgggtttt  61020
agcatcaaaa tatcagaatt caagccttgc tctctgctta ctagctgtgt gaccctaaaa  61080
aggtttctga acgtctctga gcttcagttt cctcatcatt ccttctcacg gggtggttgt  61140
gagcattaca gagatcctct ctgtgaagcc cctgtgagtg gctcatcctg agggctgaaa  61200
taaacatgtt attaataatc caaaactggc aagggatgtt gactggtccc cctcccttgc  61260
ccaaggagct ttctagaacc tgagttatca ttaccaaact gtactgcctt gagtaagaaa  61320
gttagaagga atgggaagga tggtggcagg tggaggaagg cggattggtc atcacctcct  61380
tgcagcaaga aacagcccca gatcgtggga aacctacaga cctgctagac agactaggag  61440
caaaagctgg ggctttaaga atccccaggg aggttctcct gagagagtag ccagttggat  61500
tttgtaagca gagatttgtt tggggaggag gtgacaacgt agggagcaga ggggcaaagc  61560
tgtcgggaat cctgccttga gggcagggat gtgtgttggg gggagttggg tcactggggc  61620
tcggtggcct tgggcaagtt tctacctctc aggtccttta cccacctagg gtcgccatcc  61680
tgcccacctc acaggttaca gtgagcctgg atgcactgtc atgggcaggt gcccaggaaa  61740
atggcagaca tgttccaaac agcacgcagc attccccagt gatgcccagg gtcaccttgg  61800
aggtgggcga gatgcctggg gtttctcgtc caccccacaa cacctcaggg gacagccaaa  61860
gctgtccctt caggtaagct gcacagaaga tgtgaactct gctgcaaaga ctctattctt  61920
tgggagcaaa agggacccag ggtctcacct gcacatccct gtccctgagg gcctaggggt  61980
tcttggaggc cccagccttg gcaaaatgag gaagaaggtg aaggttgtct gggcccctgc  62040
caggctcctt cctcggccac gcactcccct tcctgcacac acacccttct ccctccaccc  62100
catctccatt gttgtcagaa aagtcacaat aaaaaggtcc atattgtcta gttcccatac  62160
ttttaatttt taaaatttta tttatttatt tatttatgta ttttttgaga cagagtctta  62220
acccaggctg gagttcagtg gcatgatcta ggctcactgc aacctctccc tcctgggttc  62280
aagtgattct catgcctcag cctcccgagt agctgagatt acagatatgt gccactatgc  62340
ccagctaatt tttgtatttt tagtagagac ggggtttcac catgttggcc aggctggtct  62400
cgaactcctg gcctcaagtg atctgcctgc ctgagcctcc ggaagtgctg ggatttcagg  62460
tgtgagccac cgcactcggc tccacacttt tcacttatta aaagactgtg gtgtccatca  62520
atggatgaat gaataaacca atgtggacta tccctcccat tacccaagga atgaagcacg  62580
gagccgtgcc aagatctgga ttcacagtga aagaagccag tcaccaaaag ccacgtgctg  62640
tgtgacttcc cttatacgaa atatccagaa gagatacatc catggtgaca gaaagtagat  62700
gagcagctgg ggactggcga aggggagaag ggggagcagc tgtctatgag gtccagcctt  62760
tcttctgggt ttggtgagaa tgttttggaa ctagatagag gtgatagttg tacaacattg  62820
tgaatgtact aaatgccact gaatcattca ttttaaatcg ttctttacgt tgcatgaatt  62880
ttaagtcaat caaaaacagt tgtttgaaaa gagaaaagcc tatgggtagc ggcagcagtg  62940
attggattta tgattcgatt ccatggctca tccctcccct gcctcacccc ctcgccctcc  63000
gacgtcttct tcttttactc tgaactgtta tctttgttct catctctctc tctctctctc  63060
aaccctgcag acacttttcc ctttctttgt ctgcccccac cctccagatt tccgtgtctc  63120
cagtgtctcc ctacgaggca tgaattgaga ctgggagggt gtgattctga agaaggcacc  63180
aacagtgact cagctagccc cttcccccac cccgcccccc gggcctcaat ttagctaaaa  63240
aaccacaggg acggactcag gaggcaatac ctttccaagg gtccctaaaa aatgtcccat  63300
```

-continued

```
tttagtgtcc aggtttcact caactttagt gcctccccta aaatgtgttc cttacctccc  63360
accccactgc atctaagtca ctgcctgaga aaacaggatt gaggaaagga gaaaggaaga  63420
gagagagaga ggaggagaga gagagagagg gaggaaggct gatggattta gaaaagaaga  63480
aaacaagtgg tctgaggaaa acagccttgg tgtgtttatt ttcctgtctg tgtatcgctt  63540
ctcggccttt tggctaagat caagtgtatt ttcctgtctg tgtgtctcgc ttagattaca  63600
gggatctgtg ggtgatgaca cgtctggtcc aggctgcgta gtcacctcaa gggcatgctt  63660
attgatgtgt ttttcaattc actatctttg catgggagtc ccaggccaag aggcacagct  63720
gcgccatttg tctgttggtt tagatatcct ttatccagtt cttccagaga aatcatcctg  63780
cccttctgga ggaggtgggc agcaggggtc agagatggga gggaaaggaa ggagccaggt  63840
ccttggctag gatgccaggg tcccctgcct ctcacctggc ctgggctgga ggcctcctgc  63900
tgtcctgtca ctgatcacta ccccgcccca gcctcctgag ttagaagaca caggctaaag  63960
tagagtattt cttcattgaa aaacccatac aaaataaagg ttcataaaaa ataaaaattt  64020
agactgggtg ctgtggctca cacctgtgat cccagcactt tgggaggcca aggcaggtgg  64080
atcgcttgag ccctggggtt catgaccagc ctgggcaaca tagtgaaacc ccatctctac  64140
aaaaaataca aaaaattagc caggcatggt ggtgcatacc tgtggtccca gcttctcagc  64200
ctatggaccc acatagaata caatgtcagc ataagaaggg agccctgggg tcaccaaatg  64260
gtttgggcgg caaagaacct gaaggttgag agaagtggct tggttaccca gctgttggat  64320
gtgagacctg gccactgctt cttccatacc ctagacctgc accctgacat ctcaagtaaa  64380
aagttggggg atgttttatg gtccaggatg aaggaagggc agtgaggggc agcggagcat  64440
cactttgcat ttctgtctgc ctcttactgg ctgtgtgacc tggggcaggt aacttcccag  64500
actcctggga atcataacac ctatgatgat gatgatgatg atgatgatga tgacacctac  64560
ctcaaggatt gccctgaagg gtcacagaga tgcctgcaag gcacctgcat ggagcaagcg  64620
ccccttctct ggcaggtgct gggtgagcac tacctgctgc caggccctgg ggctatggca  64680
ctgcgtgacc ctgcaagtcc tacctggcga agctgtcgtt cttgtgctca gtcagtgttg  64740
gttgtaagac tgagaagagt cacttcattt tgctctccag ggacatcttt ctgggtccta  64800
ttttctgcct atgtcaagta gcgcctcaag gatgctcctg aaaatgggct tgtctttctt  64860
aacatggcag gtaggtccca aagcattagc atggggcagc tgacctagcc cagccaatgc  64920
agtgcagtga ctcttgcaac cgagtctaat cagaaggtcc atgaacctac gagcatttcc  64980
tgtcccagga tcagggtgga ggctgagcct ccctgcttag agattcttcc catgcattcc  65040
actttttcc ccaaaagaaa atattgaccc ttgagaggca cacagtttat ttattttgca  65100
tagtaaatag tagcctgtat tttaaggatg agttgatttc tgcatcagcc cctgtaggtc  65160
atcagccttc tattggtgca tctgactctc tctagccctg cagggatggt ggagggggag  65220
gggaaggagg gatctttatt ggaaaccagg acagtgagac tcattgccct gtcatctgct  65280
ctgtggtgct gaatgaggca gcccaacaga gaaataccct gagcgagcat ccccagcctc  65340
caaaacagtg gcgcattgcc ctgagtcctg ggaatgacct ttgattctcc tgctcctgac  65400
ttggaaccca tggaaacctc tagaagcagc tgaggaaaac ccaacatgaa aagcagaact  65460
ccacactgag aatataggag gtgatcggaa catacaatga ttcttgctaa gaccgattca  65520
cagtttttct ttttttcga tcgaagaaat actggagaag cctaaagaag gagtctaaaa  65580
actctggcac gtgggccaaa actgtccttg agctaagaat gattttcaca tttttaagtg  65640
```

```
gttgaaaaat gaaataaaat aagatgatgt tttgtgacac atgaaagcta tgggaaattc  65700
aaattctaat atctataaat agtgttttat cagaacacag tcatgctcat ttatttatgc  65760
tcgatggctg ctttcccgct acaattacgt tgagcagtta caacagagac cacgtggccc  65820
acaaagcctt acaatattta ctatctggcc ctttccagaa aaaaatgtgc cgactcttga  65880
ccttaacctc agcaatttgg gaggccgagg caggcggatc gcttgagctc tggagttcat  65940
gaccagcctg ggcaacatag taagactcca tctctacaaa aaatacaaaa cattagccag  66000
gcatggtggt gcacacctgt ggtcctagcc actcgggaga ctgaggtggg aggatcgcct  66060
gagcccagga agtcgaggct gcagtgagct gtgatggcac cactgcacct cagcctgggc  66120
gacagagcaa gaccttgtct ccaaataaat aaataatgca aagtaaaata aataaaacca  66180
tataaaaagg aatcaattta aaattataat gaaagctggc cgggcatggt ggctcacgcc  66240
tgtaatccca gcactttggg aggctgaggt gggtggatca cgaggccagg agatcgagac  66300
catcttggct aacacggtga aaccccgtct ctactaaaaa tacaaaaaaa aaattagccg  66360
ggcacagtgg cgggcgcctg tagtcccagc tactcgggag gctgaggcag gagaatgtct  66420
tgaacccggg aggtggagct tgcagtgagc cgagatcgtg ccacttgcag tccagcctgg  66480
gcgaaagagc gagactccgt ctcaaaaaca aaaacaaaaa caaaaacaaa aaaaaattat  66540
aatgaaagcc aaggggcata gtagaacaaa ttttctagag ctcattaagt caaatgagtc  66600
accagttagt aaaacgcagt cacggggaag agagggcagg attctttgaa gcagcggctc  66660
tcctaaaaac aacccaccct tgtccagctg ccttccctcc tgagggtgtt ccctttgact  66720
gtgtgacccc catcccctat ttcccaaccg tccaagccca cctctagcat aatacgagct  66780
tttaatccct ctccctgacc ccaacccgat tttgaagccc agtctagtat tttctcaaat  66840
acacttcttg gctccattcc ttcctttcca tcacctctgc cttttcactg catgcttgga  66900
ccactgcagt cagctcccta tgaacagttg ctctctaccc atccaatcgg ccccgcctgc  66960
tgctgccaaa ttcaccgagg gcacctctgt ggtgctgcct gtggacaaag tccaagccag  67020
ccacctcacc cacctacagg tgagtgggga gcagccagcg tgtccagtgg tttaccccat  67080
cgccacagac ttggtgatgt gtcgatgtgc agagaagggg tgttggcagc cacaacacaa  67140
gcaaccccgc cccatgtgag atctaagatg ggcgtgctgg gagccacctc tgagaatcca  67200
acagaaggca gaggggagaa cggctcacac ggcacaaaca ctccttcctt tttttttttt  67260
ctttttcctt tttgaaagga gtctcactct attgcccagg caggagtgca gtggtgcaat  67320
ctcagctcac tgcaacctcc gcctcctagg ttcaagcgat tctccagcct cagcttccca  67380
agtagctggg attacaggta cactccacca tgcccggcta atttttgtgt ttttagtaga  67440
gacggggttt ccctatgttg gccaggctgg tcttgagctc ctgacctcag gtgatctgcc  67500
tgccttggcc tcccaaagtg ctgggattac aggtgtgagc catggggcct agcctccttc  67560
catttaaatg tatgcctaat ttgcccattg agaacggctg agacgcattt taagtggcca  67620
gggtctactt agagttagtg ctcatgacca ggcccaggtc aagcctggct ggccagatgg  67680
tgcctttgac ctgctctgtc tctgtgcaaa ggaatgagct gaaggatggg ggtgcagtgt  67740
gtgggcagtg ggctggggct ggcaggactc agtgactaag ggaagagaac tttcctcact  67800
accagcctgt cttttcaggg caccgcgggg ggctttggga cttggtgatg aacacagcac  67860
agagagctgt ccagcatgcg ggtccctggc ttctcacact tcccaggctc cttcagaggc  67920
tctctccaaa gggagctgct ctctctagaa cccatgaatt tggaatatag gcaaccactg  67980
cattggggac cactgacctc aaacatagag accagagcaa atggggctca tcacgtgaaa  68040
```

ctcatctgga actctagcag gttcttttat atatatatat atatatatat atatatatat 68100
atatatatat atatatatat tttttattat tatactttaa gttctagggt acatgtgcac 68160
aacatgcagg tttgttacat atgtatacat gtgccatgtt ggtgtgctgc acccattaat 68220
tcatcattta cattaggtat atctcctaat gctatccctc cccactcccc ccaccccaca 68280
acaggcccca gtgtgtgatg ttccccttcc tgtgtccaag tgttctcatt gttcaattcc 68340
cacctacgag tgagaacatg ctgtgtttgg tttttttgtc cttgcgatag tttgctgaga 68400
atgatggttt ccagcttcat ccatgtccct acaaaggaca tgaactcatc atttttttatg 68460
gctgcatagt attccatggt gtatatgtgc cacattttct taatccagtc tatcattgtt 68520
ggacatttgg gttggttcca agtctttgct attgtgaata gtgccgcaat aaacatacgt 68580
gtgcatgtgt ctttataaca gcatgattta tattcctttg gttatatacc cagtaatgag 68640
atggctgggt caaatggtat ttctagttct agatccctga ggaatcgcca cactgtcttc 68700
cacaatggtt gaactagttt acagtcctac caacagtgta aaagtgttcc tatttctcca 68760
catcctctcc agcagctgtt gtttcctgac tttttaatga tcgccattct aactggtgtg 68820
agatgttatc tcatggtggt tttgatttgc atttctctga tggccagtga tgatgagcat 68880
tttttcacgt gtctgttggc gaactctagc agcttctttt cacaagttca tggagagagg 68940
tttcccactg agggaatcac atctgtctga tcaaaagagg cttgggaaat ggctctcctg 69000
ttcattccct gaaaacctct gatggaacca ctgccactgt ggcagcccca gcactggcac 69060
cccagccatg attggtgccc cagccacatc tctgctgtga gccccagagc cctggttaat 69120
taatcatcca cgtgttgatg gggagaggcc cattcacaaa agcgacataa agcccaggga 69180
gacgtggccg tggcaagaag ggtgtgggac tacattccgc ccccaactga gagattcaga 69240
aaccagaaaa aaatggaaaa acatactgtg ctcttgggtg ggaaaactaa atatcatgaa 69300
gggagcaatt tttatagttt tggcctataa tacaattcca gccgaaatcc cagtggaact 69360
ttgagaattt gcaggaaaaa aaaaaatgtc taaagtacat ctggaagaca aacttacaag 69420
aaggtcaaat aattttgaaa aagaaaatga tatctaagcc cacctagaga ataagacttg 69480
agatccaaag ctaaatcagg aggctctagc aaaattgaca gataagcagg acagagtgca 69540
tggtgcattc acctggggaa gagggcagat tggtctacaa ataggcctgg gtccactgac 69600
tttagctgtt atatttgggg agaaactttt caacctcact ccatcttaaa cctaaaaata 69660
ttccagatga attaataaat ataaaaaatt agaccactaa aaatgtagaa gaaaatggat 69720
gatctttcta taccatagag caatggaata aatcacaaag gaaaacagat ttgactatat 69780
aaaacttaaa ccctgcccat caaaaaccat cagaaaccaa aataaaaggc aaccaactgg 69840
agaagatagt tgccacaaat atgatcaagg gttaatgtta ttcataaatt aagagcccac 69900
acaagtcatt agaataagca ctgagacctg aacagacaag caaaaagaat gagagtgggt 69960
cggcgcggcg gctcatgcct gtaatcccag cactttggaa ggctgaagca ggcggatcac 70020
ttgatcccag gagttccaac accagcctga gcaacatggt gaaaccctgc ctctacaaaa 70080
gtcataaata ttagccgggt gtgatggcac acgcctgtag tcccagctac tcaggaggct 70140
gaggtgggtg gatcacttga gcccgggagg tagagtctgc agtgagccaa gatcacaccg 70200
ctgcactcca gctggagcaa cagagtgaga ccctgactta aaagaaaaaa aaaaaaaaag 70260
aggagaaaaa tgctgatctc actagtaatt aaaacatcag gccaggcgca gtggctcaca 70320
cctttaatcc cagcactctg ggaggctgag gcaggcagat cacttgagat caggagttct 70380

-continued agaccagctt ggccaacatg gtgaaatccc gtctctacaa aaaatacaaa aattcgccaa 70440
gcgtggtggc acatgcctgt gatcccagct actcgggagg ctgagacagg agaattgctt 70500
gaacacggga ggcagaggtt gcagtaagct gagatcgtac cattccagtc cagcctgggc 70560
tacagagcga gactctgtcc cagaaaaaat taaaacatca catatttaaa caactctagg 70620
atatcattta aaaaaacatt aatagactgt tttttagagc acttttaggt tcacagtgaa 70680
actgagtgga aggtacagag acttcccgta tgttccctgc cctccacgta cagcctcccc 70740
cactgccaac gtcctgcacc agagtggtac acttgttaca accaatgaat cctcattaac 70800
atatcattat cacccaagtt catagtttac attagtaaaa catcatcttt catctataag 70860
cacaaaaatt ttttggcatt tatttaggtg tatgattaac tcagtgttga caagactcac 70920
acttcatacc cacttgcact gcatctgaga agcaattggt gtctacagcc gctacaccct 70980
caacaagccc gatcttgttt gaaaagcaat tggtgatgct tctcaaaatt ctatggacaa 71040
agtcagccgg gcatggtggc tcatgcctgt aatccctaaa ctttgggagg ccgaggcagg 71100
cagatcacct gaggtctggt gaaaccctgt ctctactaaa aatgcaaaaa ttacccaggc 71160
atggtggctg gggcctgtaa tcccagctac tcgggaggct gaggcaggag aatcgcttga 71220
agcaaggagg cggaggtttc agtgagccaa gattgcacca ctgcactcca gcctgggtga 71280
caagagtgaa actccatcta aaaaaaaaaa attatggaca aagtttttca aaaagatatt 71340
taatgcaact ttatttgtaa tattggaaca tctgaggcca tttcagtgct aactattagg 71400
ggatggttag gaaaatatgg tacatatgtg gaaaggaaca tttggtagtt agtgcccctg 71460
atgtttacaa aggcttttag tgaccaacaa atgctcatgc tataatctta tgtgaaaaaa 71520
gcaagtagca taattgcaac tatattttta atgcatagaa taaaaggcta gaaggaaata 71580
tcacagatcc ttgacataca ttcccaaacc tttgtaaatc cgcggattca tgaaaacaga 71640
cacatttgca caagtgcctg atcttttctg ttatacattc attagaagtc aagccctggt 71700
gccacaaagt atctgccttt tcaaatgtga tcagaatgtt ctcttttgct tcaaggccat 71760
ttttcacgaa gcagtggcat ttttgcctct tcatcagagt caccgtgtgc cctggaggac 71820
tgagaacagc agagccgttt taggatggga cagggcagcc aggaggattg ggctcactcc 71880
ctactgagtg cctcactccc gtacagcccc catagaggaa gaggggttca aatttattcc 71940
tcagccagat ggcatgtgcc gcctgtcctg gaatttcaca tcacttatga tggaccaaaa 72000
ttccaaaagc tgaatccatg attgtcaaag tctggtatgg caggatgtca acagtaatcg 72060
tttctgggca gagggatgat tttctcttcc catcttgctt tgtataaata cattttctat 72120
aataaggttg tattactttt ctcatcaaga aatagcaaag tactgtttta ctcaaaatat 72180
gaatagagcc aggcatggtg gcagcttatg cctgtaatcc caacactttg agaggcggat 72240
atgggaggat cactttagcc caggagtttg agaccagcct gggcaacata gtgagacccc 72300
cgtccccact cccccaaaga aaacccacaa agcatttatc ctggattatt cacaggggcc 72360
aaaaaaaaaa aaaaaaattc aggcctccta tagccatgag ctacgaatat gaaaatatgc 72420
aaatgtgtaa gaaaagccag cacatccgat ttttactttt actttcacac ctctgtccac 72480
catgttccaa gagaagaaac ttggtcattg aaaggaatag atcaaatcca aagaacaaaa 72540
ccactgtgct cattaaactt cttagtgttc acaaagcttt agctgcaggt tgaatggggc 72600
aacccgaatt ggctggctca cctgggctgc agggagcaga gatcgcgaca ctgcactcca 72660
gcctgggcaa caaagcgaga ctctatctca aaaaaaaaaa agttcataaa ttcaaagtta 72720
tgaattattt ttaaaataat aataatttac aataaagatg aggacaaagt gtgagtaaat 72780
ggtggtttct atccagctct gttgagctga agtggcatct ccctgctggg gcttttgggg 72840
aagaagggtg tgtgttgctc ttcagatccc aagcctcatg cccctactgg gccctgtggg 72900
gtgcttctca gcccaccagg agagccaccg ttggaacaca cacgtggggg acctggtggg 72960
tgccggtgtg gtgaatgggg gccacagcct gactccagga agccagcaaa ctcggagctg 73020
gaggagtcag gacacccccg atgagtcaag agttggtttt gctgccagtt gacatctgat 73080
tgaaccatct cttcacttct ccgtgcctca ctttccttac cagacaggct ctgctgatgc 73140
tgtccctctc ctgttcagtc gtgccctcac cgttaaagag aaagagcaaa ctgctgggca 73200
gcagcattga ttttttaat gaagtggaaa gagagctggg aataacaagt cgggcccacc 73260
tcacctgcct cacctggtgg gtttatttgt tttgtttttt tttttttgtt ttgagacaga 73320
gtttcaccct gtcacccagg ctggagtgca gtggtgtaat ctcagctcac tgcaacctcc 73380
acctgccagg ttcaattgat tctcctgcct cagcctcccc agtagctggg attacaggca 73440
cctgccacat gcctggctaa ttattgtatt tttagtagag atggggtttt accatgttgg 73500
ccaggctggt ctcgatcccc tgacctcagg tgatccaccc acctcggcct cccaaagtgc 73560
tgagatcaca ggcgtgagcc accatgcctg gccgtcacct ggtggtgttg aatatgaact 73620
gctgcggtgt tggtaaatta agcaagcaga tagatgtaaa taacgcttgg gcaggaatat 73680
ggagcacggg atgaggatgg gcggccaact gttagagagg gtagcaggga ggctgagatc 73740
tgcctgccat gaactgggag gagaggctcc tctctctctt cacccccact ctgcccccca 73800
acactcctca gaacttatcc tctcctcttc tttccccagg tgaactttga accaggatgg 73860
ctgagccccg ccaggagttc gaagtgatgg aagatcacgc tgggacgtac gggttggggg 73920
acaggaaaga tcagggggc tacaccatgc accaagacca agagggtgac acggacgctg 73980
gcctgaaagg ttagtggaca gccatgcaca gcaggcccag atcactgcaa gccaaggggt 74040
ggcgggaaca gtttgcatcc agaattgcaa agaaatttta aatacattat tgtcttagac 74100
tgtcagtaaa gtaaagcctc attaatttga gtgggccaag ataactcaag cagtgagata 74160
atggccagac acggtggctc acgcctgtaa tcccagcact ttggaaggcc caggcaggag 74220
gatcccttga ggccaggaat ttgagaccgg cctgggcaac atagcaagac cccgtctcta 74280
aaataattta aaaattagcc aggtgttgtg gtgcatgtct atagtcctag ctactcagga 74340
tgctgaggca gaaggatcac ttgagcccag gagttcaagg ttgcagtaag ctgtgattat 74400
aaaactgcac tccagcctga gcaacagagc aagaccctgt caaaaaaaaa agaaaagaaa 74460
aaagaaagaa agaaatttac cttgagttac ccacatgagt gaatgtaggg acagagattt 74520
tagggcctta acaatctctc aaatacaggg tactttttga ggcattagcc acacctgtta 74580
gcttataaat cagtggtatt gattagcatg taaaatatgt gactttaaac attgcttttt 74640
atctcttact tagatcaggc ctgagtggcc tctctttagc aagagttggt tagccctggg 74700
attcttactg tagccacatt aataaacaac atcgacttct aaacattcta taataccatc 74760
ttttggccaa attgacttcg cctcttcctc tctctttcca aatgaaatgt gtttcatttc 74820
actgtcagac cacatggttg gggaccccac agagcacaca gccctccctc tgccttccca 74880
tgctggccct tcacccactg ctggagtgcc aggttggtcc aagggttgga ccaagttgtc 74940
tgaggttgtc tcaaggttgg tcgaggctgt ctccgcgctg ggttgtgcta caaggagccc 75000
ttctttccat gggtgtggct ggcagtgagt gctcacagca acagcccaca gtgcagcccg 75060
agggcaggat ggactcagtc cctgcctcca tacccatttc taaggaggca aaatggcaaa 75120
cactctactt ttctctttta atgctaaaaa taagaaaaca ccttgcagcc cagggtatgg 75180
gtagtgcatg gaagccgtgg agttgtgagg tgggaagtga cctctgctgg atatgtctat 75240
tcaggaagat tgctggagtg ggtggggtct ctgggaggtc ccctgagtgt gggaagctgg 75300
gaccaccagc tttctcgcac agggagtggc catcccagct tggagaggtt ccaggactgg 75360
ttgggaggca cgtttcagat ttctatctgt tgaatcagcg aagatattgg attatgagga 75420
atttgggaat taggaaagtg ggtgcaggtg ggttgggggt aggtgaagga agacatgggc 75480
gtattggggg agcaggggct gctcagaggt gttccagaag ctctgggtga ggaggtgaga 75540
gggaccgggg aatgcagctc ggcccagcct ccctgcctga ggtcagccat cacgtggtga 75600
tggcaagatg gaaatgtgct ttctgactgc tccagccagt gctgccagat tcagctcccc 75660
agggagggca cctgagaggc tccaagccag gagatctgtt ttctcctttg ttttgttttt 75720
ttttgttttg ttttgtttta ttatacttta agttctaggg tacatgtgca caacgtgcag 75780
gtttgttaca tatgtataca tgtgccatgt tggtgtgctg cacccatcaa cttgtcattt 75840
acattaggta tatctcctaa tgctatccct ccccccctccc cccacccccct gttttctcct 75900 ttgaatcctt cttagaggcc gggcgcggtg gctcacgcct gtaatcccag cactttggga 75960
ggctgcggca ggaggattgc ttgagcccag gagttccaga ccagcctggg caacatagtg 76020
agacctcgtc tctacagata ataattttaa aaattatccg ggcatagtgg catgcaccta 76080
tagtcccagc tactcaagag gcagaggcag gaggatcact tgagcccagg aggcggaggt 76140
tgccgtgagc caagatccca ccactgcact ccagcctggg cgacagagac ccccatgtca 76200
aataataata ataataaata aatccttctc agtcccttcc tcactgtgtc cccctccact 76260
gaatttttcc acctcctctc ccacttcccc cactcccgct ttccctctcc ttctctcccc 76320
actccatctt tttctttctc tgctgtttct cgtccctccc tcctctccat cccacaacac 76380
tgcctaccct gtccctgccc caccctggtg ctcaggatgt gtgaagtgag ggtggtagc 76440 ccccaagacc tcaaccccga aggttagcct gttgaaacca ctttctccca gctgcccccc 76500
tggcagttgg tgctgctggg ggaaactggg attgggggcc agattttgcc tcttttcctg 76560
acaaagagag atgaagagtt ctctcaccag gtgcctggga ctggggtgtg ggtgtcccag 76620
cctatcccag cgcatctgtt ctgcatcatg attaatagtg ctgctttcag ccgggcgcgg 76680
tggctcacac ctgtaatccc agcactttgg gaggctaagg tgggcagatc acaaggtcag 76740
gagttcgaga ccagcctggc caacatggtg aaacctcgtc tctactaaaa atacaaaaat 76800
taaccaggtg tggtggtggg tgcctgtagt cccagctact tgggaggctg aggcaggaga 76860
atcacttgaa tctgggaagc agaggttgca gtgagccaag atcgtgccac tgcactccag 76920
cctgggtgac agagtgagac tccgtcctaa aaaaaaagga gttttgctct gtcgcccagg 76980
ctggagtgta gtggcgccat ctcggctcac cgcaacctgc gcctcccggg tgcaagcgat 77040
tctcctgcct cagcctccca agtagctagg attacaggcg cctaccacca cgcctggcca 77100
gttcttgtat ttttagaaga gacggggttt caccctgttg gccaggctcg tctgggactc 77160
ctgacctcag gtaatccgcc cacctcagcc tcccaaagtg ctgggattgc aggcatgagc 77220
caccgtgccc agtcaactcc ttctcaaaaa aaaaaaaata gtgctgcttt ctctttcaag 77280
tgtcctgatt tgggtgatag taaatgccac tctacttata agggatctac ctcagaatgc 77340
taattgggac atttttgtag cactctactg ttggcagcag gtgatgctca caacagcccg 77400
tgagggtgga tgacgtccgc ttcacagatg acaaaggagc ctcatgctca gaccgtgggc 77460
tgccagagca ggtccatggc tgcagcccca catggaccat atttccccct tgtcactctt 77520

```
tccaccaagc tcccttggaa cttcagttat taagctctct tgggtggaat ccaagttaga  77580
atcacaacat gtgcctcata tggattgtgc cagtgaaaaa tgacattcta tttagaggca  77640
gggcagcctg gcttagagtc agtttaaaat atgtattatg ctgcaacaaa tgtaccatga  77700
tcctgtaaga tgttcacaac aagggaactg gatgtggggt atactgtctg tactaacttc  77760
acaagttttc tgtaaatcta aaactgttcc aaaataacaa gttcgtttaa aattaactcc  77820
aggagaccag gtacggtagc taatgcctat aatcccagca cttcggaagg ctgaggcagg  77880
tggattgctt gagcccagga gtttgagaca agcctgggca acatggtgaa atcctgtctc  77940
taaaaaaaat cacaaaaatt agccaggtgt ggtggcgcat tcctgtagtc ccagctactt  78000
gcggggctga ggtgggagaa tcatctgagc ccaggagttt gaggctgcag tgagctgtga  78060
ttgtaccact gcactccaac ctgggcaaca gagcaagacc ctgtctcaaa aaacaaaaat  78120
gaaataaagt ccaggaaaga agtaggtttt accactctta ttttctgaag agaaaactaa  78180
atttaatgtg taaagtgagg acaagttcac caagttagtg tttgagttgc ctaaaatatg  78240
tttgctaaaa ctattcaaag ctttcacata aaacatgatc agaagttcta tgccaaaaca  78300
tatgtgtgtg tatatatata tgcactatat atactgtata taaaaatgca aaatctaaat  78360
tgccaacctt ttagaaattg ctctgaaagg aaagcatttc aagataattt gcttacccaa  78420
agaatatact ttccaagaaa gcaagtaata cttaaggtgt tcataatcct catcaaatta  78480
attcttgcta ctgaaagctt acaaggagct gttttgatgt cgggtgtgac aggtttgact  78540
tggcagaagg tgtcacttta ctaacaacat tttaaataag tgacagaaga caagaaacta  78600
cacgttaaat gccagaacaa agagtgtcta agtggatgct aagagttgaa atatggctgg  78660
atacctgccc aagagagctg aaaagtagat gaaagttggt tacctataaa ctagtgcacc  78720
ctaatgaatt aaaaggtgtt gatgagttaa cttgttatgc cttccagata agacatgcaa  78780
atggggcttc ttcctccttc actacttcca agggatttaa caaggagacc aatgcaaatg  78840
ataaggactg tagggctcaa gctggggaca gattggggaa agggggacca tcatgcccat  78900
atagatgtcc ctgtgccctg gcagtcaagg ctgctgaaaa ataacaaaac ccagaagtct  78960
gcgtgatgct gcctctccat ttgtccaaag ccttcttgcg gcagtttgca ggcttttgca  79020
aaagctccag gaccaaggag ctatgttcat gctggaagct tgttcaggat tagctgttct  79080
ttgtgggatg ggtgcagcca gggccaggtg tccagggaca gtgttttaac aaagggcatg  79140
aggtgtctga tctcacagtg gaactccact tgcctttttt tcatcttctc attctgcttc  79200
atgcacagaa ccagccccat cctgaaactg actctaaatt actcccgccc caggtggagt  79260
gcctttctcg gagttcaaca gagccttcct gtcgcccaag ggacaactcc actgaatgcc  79320
caagccacac ccaaaaccta acaagtaaaa accaaattct gtgctccccc atcctgggcc  79380
attcctggtt tctctactgc tgttggtgat accaccatca gcttgtccat catgaccctg  79440
gccagttcct cccacaaccc tccacagcac ccagggacct cacctccatt ccatccgaca  79500
cagatctcct caccacaaac cttggttttg caacagcagc catgagacct ttacaccctc  79560
cgcccttcat cctgtccccc actgaggccc cagagccatt ccttaaagca gcgcgccaca  79620
aactataacc cacaagccaa ttctggtacc cagcctgttt tgcacagcca gtgaactgac  79680
aatgatcttt tcatacagcc agaaaaacaa aacaaaacaa aaaacaacaa aaaaaaaccc  79740
caccattctg agcatgtgac ttccatgttc aagatgtctc atgttcagaa aggcccctgg  79800
aaaaggagga aggggagctg ggcacaaagg gagaccctct cagctgagct cctcccatcc  79860
```

agacattttc ctggacttcc tatccaatga cttcccttag cttcttatca gccacccctg 79920
tctgcccagg aggctggaag atgtggcctt ttaactgggc acagctctgt cctctatcat 79980
atcagggctc tgttcccaag gagggtagag agaatggaca ccaggtggac cctcagcagt 80040
ctgtgccaca gagggagtgt ttgcaatttc cagactaaaa gtccccatgt gcttgacggg 80100
gtatgtgact acaacgtgat gcttgacttt tcctcatatg accagagcca ctttgtccat 80160
ctggtacaat gtcagctatc tgctaggggc cctccaggat tcccagtcaa ttccatatct 80220
gcatcaccac cattggcact aaataaaata aaatactcaa gttcctgctg gtgagcatga 80280
gcagtgctac actgggccct tcaaccaagg tgacatgata atgactgaaa ataatcactg 80340
ccacttattg gggacgtctc atctgccagg catggtacaa agtgctttaa ataagcattc 80400
aacaatttca tgctgacaga agccctgtga gccagtggag ctactactat gcccattata 80460
caggggagaa aactgaggca gagagaggtt aggtaattcg ctcagcctca cacaaccaat 80520
aggtggtgga gccaggattt gggccccatc tgcctgactc tctagaggct ctatcttcca 80580
gtcttccaga gttgagtcta agccatgaat aggacaatta gacagcagag gaaacccatt 80640
cagccaccat gtgcatgaag agtaaggaat ttctgtcata cagaggggag tgaattcact 80700
gagctgagag ctgaggaacc attgatctga tggctgagac accactggga agactggaga 80760
ggcttttctg ggcatgcagt gccaggcaca ggaggagctg agggaagatg actaagaggt 80820
actggcaaag aattcagaaa ttctgatgga agctttacat gttaccatca catccatcca 80880
tctatccacc catccatcca cccatatctt cctccctcca cccaatcatg catacatcca 80940
gtcatctata caccacccac ccacccatcc atccatccat ccatcccttc atccatccca 81000
tcatccatcc aattatacat acatccaatc atatatctgt acataatcca ttcttccctc 81060
ggttcatcca tccatccatt catccatcca tccacccatc ccttccttca tccttcctat 81120
catccatcca atcatatatc tgtacataat ccattcttcc ctcggttcat ccatccatcc 81180
attcatccat ccatccaccc atcccttcct tcatccttcc tatcatccat ccaatcatac 81240
atatatccaa tcatacatct gcacatcacc agctcatcca tctatccatt tatccatcca 81300
tccttccttc catccatcat tcatccatca tacatacatc taaccataca tctctacatc 81360
attcattctt ccatcgattc atccaattat ccatcattcc ttcctccatc catcccatta 81420
tccatttgat catacatata tcatctatac atcatccatt catccatcca tccatccatc 81480
cacccatatc ttcatccaat caatcataca tacatcgaat catctacaca tcacccatcc 81540
atccatccat ccattcatct atccacccat ccatccatcc atccatccat tcatctatcc 81600
acccatccat ccatccatcc atccatccat ccatgtaacc atccagtcat atatccaatt 81660
acacatccat ccagttatac attcatacat gcatctaatc attcaattat acatacacac 81720
atccatataa ttctacatcc aattatacct ccatccaatt acacattcat acacccacct 81780
aataaattat taattcatat atccatccat ataattatac atcaattata catccatcta 81840
atcattcagt aattcaccca ccatccagtc atctatccaa taatacattc atccaatcat 81900
ccatccatcc atccacccat tcatccatcc atccgtccgt ccacccatca tggtatgagc 81960
catgatttac cacgatggtc ccctgtggac agcccaggtg gggcagaact gaagggaagc 82020
ccagggctgc ccccataaac atttgcctcc tttacatgga tgagaactag atccacatgt 82080
ataaatcctc atgatttgaa ggtgctttta ccaacattca ctcatgggat tctcccagga 82140
gctctaggag gaggcaggta gagttgaggt catctcacgc attttacaga tgaggaaacg 82200
gaggccctga gaggcaggtc caaggccacc tgaccagaaa gaagtggaac tgggacttga 82260
acccagccat cttgcccctt ggtcccatgc tctctagcct gtaactcctg cttcctggtg 82320
gggcatctcc aggaggaccc tatcggctgg ccatgggcct gccctggagt cttttgctct 82380
gtgtggccat ccttcctccc tcaggagagt gtgtgctccc agagcacagg ctgtatcttc 82440
tgagcatttt gtcccttccc agtacctagc actcagctct gtatacattg ggctctcaag 82500
aattctcaac cttccagagt gtaaggcctt gacctgctca gccctggata ctgcatgatg 82560
cattgataag cccataaaat aaccagggca gattgactcc cagtggccaa agtgccacag 82620
ggaagggaca attcagccct tctaggagga ggaggaggta gttttctcat ttctattaag 82680
gcaacaaaag ctgccttact aaggacattc ttggtggagg gcgtgactgt caaccactgt 82740
gatcatttgg gcctctcttg cccaggcttc ccattctgaa aggacagttt tattgtaggt 82800
acacatggct gccatttcaa atgtaactca cagcttgtcc atcagtcctt ggaggtcttt 82860
ctatgaaagg agcttggtgg cgtccaaaca ccacccaatg tccacttaga agtaagcacc 82920
gtgtctgccc tgagctgact ccttttccaa ggaaggggtt ggatcgctga gtgtttttcc 82980
aggtgtctac ttgttgttaa ttaatagcaa tgacaaagca gaaggttcat gcgtagctcg 83040
gctttctggt atttgctgcc cgttgaccaa tggaagataa acctttgcct caggtggcac 83100
cactagctgg ttaagaggca ctttgtcctt tcacccagga gcaaacgcac atcacctgtg 83160
tcctcatctg atggccctgg tgtggggcac agtcgtgttg gcagggaggg aggtggggtt 83220
ggtccccttt gtgggtttgt tgcgaggccg tgttccagct gtttccacag ggagcgattt 83280
tcagctccac aggacactgc tccccagttc ctcctgagaa caaaaggggg cgctggggag 83340
aggccaccgt tctgagggct cactgtatgt gttccagaat ctcccctgca gacccccact 83400
gaggacggat ctgaggaacc gggctctgaa acctctgatg ctaagagcac tccaacagcg 83460
gaaggtgggc ccccccttcag acgccccctc catgcctcca gcctgtgctt agccgtgctt 83520
tgagcctccc tcctggctgc atctgctgct ccccctggct gagagatgtg ctcactcctt 83580
cggtgctttg caggacagcg tggtgggagc tgagccttgc gtcgatgcct tgcttgctgg 83640
tgctgagtgt gggcaccttc atcccgtgtg tgctctggag gcagccaccc ttggacagtc 83700
ccgcgcacag ctccacaaag ccccgctcca tacgattgtc ctcccacacc cccttcaaaa 83760
gccccctcct ctctctttct tcaggggcca gtaggtccca gagcagccat ttggctgagg 83820
gaaggggcag gtcagtggac atctgatctt ggtttagtat ccttcatttt gggggctctg 83880
ggtgtggcct gggcctctgg actttggcca cggtgtttgt tccagccctt ctcctaacct 83940
gtcctttcca gacactcggc atctaggtta ttagcacctc gcatactttc tgacatgctc 84000
ctcagtcctg attttgacca tcttctcttg cttcccatct gtgtcagtca agactgcatt 84060
tggctgtaag aaacagaaac cccaactaac tgtggcattt acatgaagag gtttactttt 84120
ctcacataat cagatgtcta gacttggcca gcacctcaag ggtcattgat gctctcctgt 84180
ctttattttc tgtcatcttt agtggttgga ttgttgcctc atggttacaa agtggctgct 84240
gcacttccag gcatcacatc tgcctttgaa gcaggaacaa gttgcaaagt aaagtggcca 84300
aaagggccct gaaactaaat gtgtcccctt aggaaagcag gagttttctt gcaagtggca 84360
atcttctgct tatgtctcat tggccagagc tgggtcttac ggccacccct tgctgcgagc 84420
aaggctggga cattgagcat tttgccgtcc aacctcttta gcagaataaa ccaaggggga 84480
agaacgttaa tagtggcttt tgagtcacta gttggcagta tctgcccctc tatctttcca 84540
tcctccccat ggagtttcaa ggttcctttc tcagtacttc ttcaggctct gcacgttcat 84600

-continued ttggatcttg tgtcttgggg tgaaaaactg gcccaagtgt ctccccaagc atccaccttt 84660
ggattaattt ggaaaatggc tgtcaagtgc ccgcctcttg cttggtataa tgctacagct 84720
ttagaggacg cagcaggcat gggccttgcc gctgaggttc ttagcctcat gagaatatcc 84780
agatcagatt ctcttggctc cttcttagag ccagtgatgc aagacacttc ctgctcatct 84840
tgtcgggacg gttttacaag ttgcctgcca tcctgagaaa gtctacaaaa cgatgccaga 84900
cctcatgcca gcttcccaag ccttgactct cagtgctccc tcaacaggat tctggaagaa 84960
tctcccaaac aagtcgcaat gccctctgga ccctgtgcag gcatgagact caagagcatt 85020
ggctcccacc cctggtggag ggaacactgc tggggctggg atcttgcctg gttgctccgc 85080
ctgcacccaa gacaaccata attaaaatgt ccttcattga acttggaaag ccttcaaagc 85140
tgacaactcc ttatgtgtac ccggaaaggc ctgggagtgt gccagggcat tgctcgggag 85200
ggacgctgat ttggaagcat ttacctgatg agagactgac agcagctcct ggtagccgag 85260
ctttccctcc tgcctctgct gtgaaggtgg acccatccaa cagtcaaatg cctgactctg 85320
gacaggagcg gacctattta ttgccatgca agggactctg cacttttgaa ttgtgggtca 85380
tgggcttgga tttaggggtt agagctggga gaagtcttgg aagtcaccta gagatgacac 85440
tgccattttg cagatgagga aaccgtccaa tcaaaatgga ccaaggactt gcccaaagcc 85500
tcacagcaaa accataggcc cccgcactaa ccccagagtc cctgtgctgt cttaaggatc 85560
atatagttgt aagcaatcat ctggttttca gtatttcttc ttttaaaatg cctggggcca 85620
tgcccagcag tctgtttcac tgcagcgttt acacagggct gccgggcttt cctggtggat 85680
gagctgggcg gttcatgagc cagaaccact cagcagcatg tcagtgtgct tcctggggag 85740
ctggtagcag gggctccggg ccctacttca gggctgcttt ctggcatatg gctgatcccc 85800
tcctcactcc tcctccctgc attgctcctg cgcaagaagc aaaggtgagg ggctgggtat 85860
ggctcgtcct ggcccctcta aggtggatct cggtggtttc tagatgtgac agcaccctta 85920
gtggatgagg gagctcccgg caagcaggct gccgcgcagc cccacacgga gatcccagaa 85980
ggaaccacag gtgagggtaa gccccagaga cccccaggca gtcaaggccc tgctgggtgc 86040
cccagctgac ctgtgacaga agtgagggag ctttgcgtgt ttatcctcct gtggggcagg 86100
aacatgggtg gattctggct cctgggaatc ttgggttgtg agtagctcga tgccttggtg 86160
ctcagttacc tccctggctg cctgccagcc tctcagagca tttagggcct tctggacttc 86220
tagatgctcc tcatcttgcc tcagtcagcg cgtcagttcc agagacttct ctgcagggtt 86280
ttctggggca ggtggtggca gacccgtgcc ttcttgacac ctgaggtcag tccaccctcc 86340
tgctcagact gcccagcaca gggtcacctc ccaaggggtg gaccccaaga tcacctgagc 86400
gcacagaggg tgcagatgac tggaccacac cttttggtga tcttaatgag gtggtcccag 86460
aggagctcag acatgcaatc tagcatccag ttctgggact ctgtctcctt ttcaaacgta 86520
ttcatgtaga acaggcatga cgagaatgcc ttgtcaacat gggtgatggg gaatcaatca 86580
gacagggcgc cgggctcaag gctgcagtca cccaagagtg gctcagccca ccaggcccta 86640
ggaaacgcct gcacagcctg gagctcctgg agtcatttcc ttcatgtctt cttcactgca 86700
cttacgtaaa gatgccagcc attggtttgg tgatttggag ggtgcccagt tgcccaacaa 86760
gaaatgcaga agaggcctag ccaggatttc accagcagtg gagagtagag aagatgtggc 86820
cagaaaagag tttcctttcc ctcctaaaga tggtactccc tgcagctact ggggaagcct 86880
gcagcattct ctagggctct gtgtgttgag agcagcccca ccctggcccc ttctgagtgc 86940
atttctgctt tgtgacttga tccgtgaagt cccctgagat gggcagaggg gatgtcctcg 87000

-continued

```
aagctggggc agagcctcat ccttgaacgt gaaggacgtt tgaagactgt ggcatgatca  87060
caggatgaga tcacagggaa cttgagtttc tctcctcctc tcccttcaca gttatttcac  87120
tgagggaaat ccctcccctg cccagaatga aaactctagc caactcttga cttttccatc  87180
actccaaagt agttgaaagt acattagtct ccacagtggc aaaacagtgt gcaaaagcta  87240
aataattaga acagccagtc ccatgtgaca gtcaaagctt ctaactccat tcaaagttgc  87300
agccattccc ctcgagggct ggcagggagg ggaggggtaa gagaaacagg aaggttctta  87360
ctgagttggt cctggtgtga gctgcgtcac actccctgca gaggtttcaa ggagactctc  87420
tctctctctg tctccatggg gaccttattt gaattcttct actcttaccc cagcctgcca  87480
tctccagcta tcctcccctg aagagccctt ctgctgcgct ggattctggt ggccatgtca  87540
tctcctcggc cccgtgggag tctgaagatc tggctgcagc ctcacctctg aggtcctgct  87600
agttgccacc tcttaaacat gatctgaggc tcccatgcac tctgacctgt gcccacatgg  87660
ggcccacggg aaacacgctg gcaagcaaac tgtgggtgtg cagacggttc tcagggctgc  87720
agcacctgtc ctttgctctg cccccaaagc aaggccagcc catcttccat cctctagtgt  87780
tccttggtgg ggccctgacc acagtccacc aggtccctaa ccagagggga cacacaccag  87840
gtgtcctcaa tgtattgcct tgaaacagtt gtgctgggac tgtgatgggg ggtggccatg  87900
tagccacccc caccaccccc aagccactct ctccaaggaa atcctcctaa agatcccttt  87960
acatcctcca tgtggtgggg aggttctaga gttgggtgca tgtgtcttca gctactgaca  88020
atgcagacct tagttggcac ctcgctctgg cctatcctgt ttgctgttct tggcgctcca  88080
gtgaaactcc ccatgggcca tccagttggg gtgcagtgtg gccaccccct tgcaggttcc  88140
tgccttgctg gagagcacag ggccctcctg gctcttgtaa aacactcccc atggtacaga  88200
gaggccagca gtgatgtgag gcccaacctc cctccatggt gttcccaagc agctcccttt  88260
ctggggtcaa ggggtggcaa agacagtgca gcgtccaatt tctgactcaa gccgggcctg  88320
gctatcgcag ctctgcactg tgtgtgacag caaggcaact cacccagtgc cgtggcagtg  88380
accgtgtccg aggaagcctc ctcacaccct ctgtctcaag gactctggca tttagctgga  88440
cttgctgtag ctctgagcct ttctgccatt gccatcacct tgtcagaaac tcaggccgaa  88500
tctgcactca gagttgtgcc caggcagttg agccaacact tgctcagcga tattgtcaca  88560
tgacaaggca ctgtcaccac tgggcatcgt gggtagcgca gtgtcggctg gatggacccg  88620
gagggtgtct gtgtcatgct agtgctagtg atgggagccc cgtgagccca ttgcccgccc  88680
tcccatgccc tcagcagctg cctggggaca gccaatggcc tgggtgtttc tgaggctacc  88740
acatggcttc caggaaactc gagaaccttt ctctcccttg cctacactct tcacacaggc  88800
ctgtgctggc cagcggtggg gatccggcat tcctatctta ggtgcagaga gtgactgact  88860
cattgcaggc ctgggagata agactgatgg cccagccagc aagatgtatg gatttctcag  88920
aggcagtggc ctctgtcatt gtcctcagga aatgctggtg attctggtgg cctgaggtca  88980
atgcatgtca acgtggccaa cttgccttat aaactttttt tctggacaat tgcgtgcact  89040
gtcctgtaac agtgtcctgt tgtttatgat gcagaaatag gtgtttttaa agcctattga  89100
ttttggtact attaatgtgg tcaggaactt tctcagtctt tcttgtttgg ggtgagctgt  89160
ggcttcctaa acaggaaccc aagacacccc caaaagctgc tcaccagcac tgccagcctc  89220
cctcttacca agtagcaccc gttcaggaca ttctgcgaaa ggcatttgcc cagaagttgg  89280
gaggaaggaa atgtaacatt ttggggcacc taccatatgc caggcaccag gctaaacgtg  89340
```

ttcacacaaa ttctcttact aaccctcacc atccttctac aagacaaact agtatcttca 89400
tcttggggtt caagatgagg aaatggaggc tcagagaggt tgaatgaatg ccggtgcctg 89460
gatatgaacc ccatctgcct gactccgcaa cccaggcaaa gtctttcctt gaacttccca 89520
gcagccactg cttagacaca gcctccacaa ccatggctca gcagcaaatt gcttctctga 89580
cctcactcag cctgtgtgtc cttgttgagt gaggcattca ggaccctggt cccaaagtgg 89640
agaaagtctt tcctactagg tcatagctac acctgcatgt gggtgctgtg ccttttgttt 89700
agtgaacttt tatcaccagc atcctcagca atgacatttg cagagaagcc agagctgagg 89760
caccttggta ttcttgggat gtgactttcc tgaatgttta agggaaaatg cccgaaggta 89820
cagagagctt ggtttctagt aaacaataac tgtcttgctt ttaccccccct tcatttgctg 89880
acacatacac cagctgaaga agcaggcatt ggagacaccc ccagcctgga agacgaagct 89940
gctggtcacg tgacccaagg tcagtgaact ggaattgcct gccatgactt gggggttggg 90000
gggagggaca tggggtgggc tctgccctga aaagatcatt tggacctgag ctctaattca 90060
caagtccagg agattttagg gagttggttc ttatcaaagg ttggctactc agatatagaa 90120
agagccctag tggtttttttt ctaataccat ttctgggtaa ttcctaaggc atttagtgtt 90180
ctgaaagatg ctagccttgt ccagcctggg agttgagaat gaatgtctaa cagaaactct 90240
aggccgggcc tggtggctca cgcctctaat cccagcacta tgggagaccc aggtgggcag 90300
atcacctgag gtcaggagtt tgagaccagc ctggccaaca tgtgaaatcc tgtctcacta 90360
caaataaaaa aattagccgg gtgtggtggt aggtgcctat aatcccagct actcaggagg 90420
ctgaggcagg acaatcgctc gaacccagga ggtggacgtt gcagtgagcc gagatcgcat 90480
cattgcactc cagcctgggc aacaaaagca aaactccgtc tcaaaaaaaa aaaagaaact 90540
caaatatgtg tgacaggcga ttctcactgc aggctgccct gtggctgatc caggagcaag 90600
gccttaacca tgtcatcccc aagcgattgc ttgtaaactt tcttctgtgc agccttcaac 90660
ccttattatg attttcttct caggaaccaa actgctgtat tcaagaaagg cagctttgtg 90720
taatcattta tcataaatat cttaagaaaa atcctagaga ttcctaattt taggaaatgg 90780
gagacctatg gtactgatat aatgtgggct gggcttgttt tctgtcattt gctagataaa 90840
tgaacttgag agcctactgt aaaatgtgga agcttctaga ttgcagaagg gctggaaaga 90900
cactgttctt ttctcccgag tgatgggatc tgtccagtat ttagagctgc ctctgaggcc 90960
atctgattct aggagactct gcctcgttga ggatattttg aggcctaact acacattcct 91020
gcccccagag aggtcacagc ctatagcagg ctgatgtttc tcatgtcaca tggcacagaa 91080
aggcacattt tcgttctcag gctaacaaag agcttcaaaa actattagaa gggacagtgg 91140
ctataagaga agaacctcag tcaatgtgtg aaattaacta ggaacctggc tcctgtttct 91200
tttaggtcat gtttttcagc ttaggtaaaa ctagaggctt tgataaagca tgacctctag 91260
aaatcattgc ttttcataaa tggaagtggg tttgagtttt ttctactgat tgttagtgca 91320
ggtgatgtct acatgccccc agaacatatt ccatgcaaca aaaaaagccc aggtcaccgt 91380
ctttgctggg aacttgactt ttgtgctcac tgaattttaa gctttctgac agcagcctgg 91440
aatcatggag ggataaagta cctattagta agatggaaaa aggtgtttca ggttggagct 91500
gcagtctgtt gagagtaagc tatgggaagg cctgtatacg aggggtggac ttttcttctg 91560
taagtgtcca gagaccaggc ctcctgaaga gggcatgggg gcttaactta cctggactac 91620
tgtgtttaca atactcattt atcttgaact cctcctaacc cctgagaatt gctacattta 91680
gtatttgctg agtacttcct agcatcctag ggaatcaata gaacattctc ccaaccaggc 91740
tgggtgcggt ggctcatgtc tgtaatccca gcactttggg aggccaaggt aggcagatcc 91800
cttgaggcca ggagtgcaag actagcctgg ctgacatggt gaaaccccgt ctttactaaa 91860
aatacaaaag ttagccaggc atggtggtac acacctgtaa tcccagctac atgggaggag 91920
taggaggcag gagaattgct tgaacctggg aggtggaggt tgctgtgagc cgagatcatg 91980
ccactgcact ccagcctggg cgacagagtg agtgagactc tgtttaaaaa aaaaaaaaaa 92040
aagaacattc tcctaacctg gcttcttcct ccaggggtgt aattaatcat gtcagtttcc 92100
tcattgatac acacacacac acactacaat cctgtatcca ttacttttca aggtacattt 92160
actatttacg tttggggtcc ttgtctcttt tttaatagtg tttcttaaag tcttgtatta 92220
tatcagagta cagtaacatc ccagtcaaga gcactctagt aagctctagg aggaaagcga 92280
cttccggaag gcagtggaga cctgtcctgt tggggcagca taggggcagc ccctgcctct 92340
ggtcagttct ggcgctcagg ctcagggttg cctctgggct gttcttccca gagactgaca 92400
aagggctccc ataaggcacc tgcagagcct gtgagaagct gaagtcaatg ttttcctgac 92460
accagttgat ctgtgcagga tccattgatt taaccacctg ctgtgtggca tgcactgtgg 92520
tcgatgccag gaacaggaat tggaggggcc catgagcatg gccagtatca caggctggag 92580
gtgctgctgc gctctgaccg ggcctcttgg ggatgagccc atgtcaacca ccttgcctcc 92640
gatggggtcg ggcccacagg ttacctttgt gtgtccatga ccacaccttc ctccccgacc 92700
tcatccaaat ctctttcttt tccaagcccc tgaatccttc agggctgcag gttttgttta 92760
aagcagagct ggtgagttgc ataggttgtt gcattgggac tagatggggt gttcaaagag 92820
ttgggagtta aaaaacataa agggtattta ttaggagaac caaggagtgt aattctcctg 92880
ttcttaatat gcggccaggt taatgaatgt cacgtgaatg aaccagaaaa aaatgaagtg 92940
tgcccttgat cagctgggtt ggtgtgcagc aagctgtgtg accaggggac agcagtggtc 93000
ctgagggccg tcactgtctg ccgtgcagag cccttcctcc cacgggggcc tacctcacct 93060
gtgccaaggg cttgtctgtg gtcagtgacc tggatagatc tgaatggggc ttctttttcg 93120
aggagtctta tggcaggtct ctcagtaaag actccattct tgatgatcac acattttgga 93180
ttttccaaat ctgtcagaga atgggcttga ggcggggttt gtgggcacta gtttcactgg 93240
tttcatttac caaaaagggg agcagaagtc aagtatggtg gctcatccct gtaatcccag 93300
aggcaagaga attgcttgag cccaggagtt cgagaccagc ctgagcaaca taaggagacc 93360
ccgtctccac aaaaatgaaa aataacattt tagtcagacg tggtggcatg catctgtggt 93420
cccagctgct tgggagggtg agatgggagg gttgtttgag ccctggagtt aaagttgcaa 93480
tgagctgtga ttgcaccact gcactctagc ctgggtgaca gaacgagacc ctgtctcaaa 93540
aaaaaaaaaa aagaaagaaa gaaaggaaaa aaaaaactca tgcctgtaat cccagcactt 93600
tggggaccgg ggtgggcaga tcacgaggtc aggagatcaa gactatcctg gccaacatgg 93660
tgaaaccccg tttctactaa aaatacaaaa attagccagg tgtggtggca cgtgcctgta 93720
atcccagtta ctcgggaggc tgaggcagga gaatcgcttg aaccagggag tcagaggttg 93780
cagtgagctg agatcgtgcc actgtactcc agcctgggcg acagagtgag actctgtctc 93840
aaaccaaaaa aaaggggtgg ggggcggggg caggagaaca gtgagaggta gggagaggaa 93900
aggggattct cgctacaccc aaaccagata ccatctagag gctagaatct ttgggaggct 93960
caaattccct agaaagcagg agaagcttct gtagccctcc cgctttccca gtagattaag 94020
cccagggcgg ctccagatgt gtgacatgct ctgtgcccaa ccagagccca tcataggcag 94080

-continued

```
aggaataaca cccacaccag aagggccctc ggaggtcacc acgtccaaga accctcttta  94140
cagatgagga aactgaggcc cagagagggg agagccacct agcgagctgg tggcggctag  94200
accaggagag ctgtcattcc aagcaagcaa aggcaacgag acgagcccag agctgtgctc  94260
ccatctcttt gttagggggc ctgggatgcc ctctcagtgt cattttgtcc aggatgatgc  94320
tccctctctt aagcgattaa tgcgcccttg ctaacctttt gctatcgctg cctcttcaaa  94380
ccagaggagt tgagagttcc gggccggcag aggaaggcgc ctgaaaggcc cctggccaat  94440
gagattagcg cccacgtcca gcctggaccc tgcggagagg cctctggggt ctctgggccg  94500
tgcctcgggg agaaagagcc agaagctccc gtcccgctga ccgcgagcct tcctcagcac  94560
cgtcccgttt gcccagcgcc tcctccaaca ggaggccctc aggagccctc cctggagtgg  94620
ggacaaaaag gcggggactg ggccgagaag ggtccggcct ttccgaagcc cgccaccact  94680
gcgtatctcc acacagagcc tgaaagtggt aaggtggtcc aggaaggctt cctccgagag  94740
ccaggccccc caggtctgag ccaccagctc atgtccggca tgcctggggc tcccctcctg  94800
cctgagggcc ccagagaggc cacacgccaa ccttcgggga caggacctga ggacacagag  94860
ggcggccgcc acgcccctga gctgctcaag caccagcttc taggagacct gcaccaggag  94920
gggccgccgc tgaagggggc agggggcaaa gagaggccgg ggagcaagga ggaggtggat  94980
gaagaccgcg acgtcgatga gtcctccccc caagactccc ctccctccaa ggcctcccca  95040
gcccaagatg ggcggcctcc ccagacagcc gccagagaag ccaccagcat cccaggcttc  95100
ccagcggagg gtgccatccc cctccctgtg gatttcctct ccaaagtttc cacagagatc  95160
ccagcctcag agcccgacgg gcccagtgta gggcgggcca aagggcagga tgcccccctg  95220
gagttcacgt ttcacgtgga aatcacaccc aacgtgcaga aggagcaggc gcactcggag  95280
gagcatttgg gaagggctgc atttccaggg gcccctggag aggggccaga ggcccggggc  95340
ccctctttgg gagaggacac aaaagaggct gaccttccag agccctctga aaagcagcct  95400
gctgctgctc cgcgggggaa gcccgtcagc cgggtccctc aactcaaagg tctgtgtctt  95460
gagcttcttc gctccttccc tggggacctc ccaggcctcc caggctgcgg gcactgccac  95520
tgagcttcca ggcctcccga ctcctgctgc ttctgacgtt cctaggacgc cactaaatcg  95580
acacctgggt gcagctgctc cactccctcg gcctcctccc gtgctcaggc tgtggccgca  95640
cgcgcccctc acgcttgccc gccactctgc atgtcaccag cacccccgct ccgtgctacc  95700
caccttgttt gactctctgg ccacttgatt tgtccacaac ggcccatcag cccacaggag  95760
gtttggtggg tgccttccac cgacaggatg acgggtgccc tcatggtgtc tagaactctc  95820
caaccctccc atgtaggcat aagcagcccc actttgcaga tgaggaaacg gaggctcaga  95880
gaagtacagt aacttgccga aggccaatga gtagtaagtg acagagccag gtttgggatc  95940
caggtaggtt gtctctgaaa gacacgcctg tcctgcatcc cacaacgcct cccaggaggt  96000
gctggagtgt ggacgcctaa cacagagatg tgcagggcac acacagcagg tgacacacac  96060
agcatccaga ggtggcccag agctcatgct gtgcctttgg cccagtgccc tgcccccacc  96120
cactctgcct tgtggcagga agacaaggag cagacacaag atctccctgg tccacatgcc  96180
accacctccc tctgcagagg acaaggggat cctcatgctg gcattggagg gggttgagca  96240
gggcccacct tgagccctca ggagcacgac cacagcagcc ctgcagggag ggattggtgg  96300
gaggagagtc ccaagtatca gggagaggag agttggtgtc ccacaggaga cctcagagcc  96360
acaaggcgag cttgttcata aatttgggac ccttagcatt tcacagttat ttgcagagcc  96420
cagaaatgga tgttactgaa gctcacagtt gcaagcatct gttaaatttt tattagattt  96480
```

tacttttagg gaaaactttg aaatgctata aagaagcctg tgtttaaaag ttaagacaga 96540
ggctgggggc gatggctcac gcctgtaatc tcagcacttt gggaggccaa ggcaggtgga 96600
tcatttgagg ttaggagttc gagaccagcc tggccaacat ggtgagaccc tgtctctact 96660
aaaattacaa aaaattagct gggcgtggtg gcgggcacct gtagtcccag ctactgggga 96720
ggctgaagca ggataagtgc ttgaacccag gaggcagagg ttacagtgag ccaagatcac 96780
accactgtac cctaagcctg ggcgacagag tgagactctg tctcaaaaaa taaaataaaa 96840
taaagttaag agagaaaaaa atatatccta tatcctttgt taaattccaa aacagtaggg 96900
gacaaataac tgacttgaca ggttactaca atatttcctg aaatgatgtt ttcttgaata 96960
ctggcctact agaggttcat aggtgtgttt ggattaaaaa agagttccat ggcccagtga 97020
ctgggggaaa aaaataaaag actaaagtaa gttaaacagg cttttctgct gcaggacttg 97080
tcagagcctt taatgtacta atggccattg tgaccctctg agaaggtcac agagtgggtt 97140
tcccaaactt acttgattct acctgctaac atttcctgga ggaagtttgg gaaatgccga 97200
tttagcagat tcttttgttg tgccgtggat ggtgctggtt gatgtgggca aaacaaagaa 97260
cacgtgagtc agatccgcct ggggctctta ctaaagtgca ggttcccagg tgccacttta 97320
ggcttacaga cccagttgtg gggtaagcct gggagtcttt tagcaggtga ttctgccaca 97380
tagtatagtt ggaaaacctc tgggcatact cattgctggt ccctctagaa atccaggtga 97440
caatagccaa tgagaagctc caagagaccc agttgtccat ggggtagagg gaatgtgata 97500
ttgaaaccaa agaagaaaat ctatgatcag ttttcagcag tgactgtcaa gagaaggaga 97560
agggtgagtt agcgctgatg ctggctgaca ggtcagcggg ttggtttcac caaggagtgt 97620
gatgaaggct gatgttgtct gtgggaatgt atgatggtaa ctggtttgta gctaatttgg 97680
ggaagcagtg agaattcgtg ccctttgaag accagtaagt ggcaagaaac ccaccaggcc 97740
tggctcaggg ctgggctggg cttggctcgt ctcagagcag ctggggctgg tggccaaagc 97800
caccattagt gaggggcagg ccctgggggt acaaccagca actaggggac aaagacaacc 97860
ctgccagcct ctcctattct ggaggcgtgt gaccagaaat ggagatgggt tggtcagcat 97920
aagatggcca ggaaggtgga aatcaggact gctggcaatc tagccacatg ggcaggggag 97980
ccgggtggtt ccaggcagtt tccaaggcca agagggtgag caggcacctc acagggaatc 98040
agggccaagc ctggctgcag tgtggagaca atgcacccac ccccatcctt ggatcttgca 98100
ggaggctggg tcctcactga gctaccaaca tccatggccc tgaggctttt aaaacaccca 98160
tccatggagt ggggctggtc ccagtggggt gaggctgacc ctggcagaaa cagggcagga 98220
gcctgtgggt tagggagact gcaccttcct tagatagcct ccatgccatc atgtccccgt 98280
gacagtttct gctgcgtccc ctctgcatgg tcccaccctc ggccagcctg ctgccccctc 98340
ttgccaggtt gcgctaatca gtgaccccag tgtgctgtgt tgatactaac aatgcgaggc 98400
ctagcagatt caagggaaaa gagaaccaac tgggtttcca ccagacccaa ctaaacaaac 98460
atggacctat cccagagaaa tccagcttca ccacagctgg ctttctgtga acagtgaaaa 98520
tggagtgtga caagcattct tattttatat tttatcagct cgcatggtca gtaaaagcaa 98580
agacgggact ggaagcgatg acaaaaaagc caaggtaagc tgacgatgcc acggagctct 98640
gcagctggtc aagtttacag agaagctgtg ctttatgtct gattcattct catatataat 98700
gtggggagta tttgtcacta aagtacagct gtcatttaaa gtgctttgta ttttggggca 98760
ggcttttaaa aagtccagca tttattagtt ttgatactta ccccagggaa gagcagttgg 98820

-continued

```
caggttcatg aagtcatgct cctaattcca gctttcttag tgtactttca gtgagaccct  98880
gacagtaaat gaaggtgtgt ttgaaaacca aacccaggac agtaaatgaa ggtgtgtttg  98940
aaaaccagcc ctaggacagt aaatgaagcc atcttctcac tgcataaact gcacccagat  99000
cttcgcccat ccttctcagt atttcacttc acccattgtt tactgtctca atgactgggg  99060
aaatgtctgg ggaaatgctc ccgtaattgc acagtggcgt ttttcctgga aaatcccacc  99120
atggctctag ataagaccta tttttcttaa aggtatctaa aatttccagc ataaattctg  99180
tctgaaacac ctgaatttta atcagtactg gagcccggag ggcatctcca gttgccacat  99240
agctctgagc attcagtggt gtgttgaggg ctgctcccgg aagtgcctgc agagtcaggg  99300
ctccccagcc tcatctagtg aggcagtgga agggcctgtg gggatttgga gagctggcct  99360
gggtctctga agtgatagtg acagctgctt gtcaatcacg gtgcacattt agtgctgggg  99420
gcagggggca gggaatacca gcctcatgca tgcatgcatt catttgttcc ttccttcatt  99480
cattcattca gtacacatgg gtacaacatc cctgccctgg agttgcccag agtctaggga  99540
ggggaaagat ctattaccct gggcctcggc cagctgggga gtgctgctgg tggagagggg  99600
ccgtgtgcag cgagggaagg aggagtcgtc aatacccccca ccccagcttt gctttcttgt  99660
catcagcccc agggccccag cctgtgtccc tcctctccca ttgctacttc atctcctggg  99720
tcctccttac caagcctgac cacacagagg gccttggccg cttccatggg gaattggaaa  99780
gcaataagat agcatcccct agaagcccag tgaagtctgg gacaggaccc ttctctgagc  99840
tctgacttgc tcttggaaac acttcgaggc ttagcctccc cactttgttt cccgagagtg  99900
tgacctgttc ccctccaaac accccccttct cctccagggc catgcccacc cgtcaaaatc  99960
ccccacgggc aggacgaact gtgggtgtca gtcaccatct atcctgcatc ctggttccag 100020
ggcccccccc agccccgcct ccatagggac aggcgtgcag acacccgtcc ctggctgctt 100080
cctcttgtgg aatgggttca aaagtaagca gtgttgttta cactgacaaa ctgaaaaaaa 100140
aagaaaaaga gataacattg gaggcttggc acagtggctc atgcctgtaa tcccagcact 100200
ttgggaggct aaggtgggag gatgtcccca gcccaagagt tctagaccag cctgggcaac 100260
atagcaagac cccatctcaa aaaaaaaatt taattggcca ggcagaggtg ggaggatcac 100320
ttgaacccaa agggtggagg ctgcagtgag ccgtgatggc accactgcac tccagccagg 100380
gcaacagagg gagaccctgt ctctaaaaca aacaaacaaa caaacaaaca aaagagttaa 100440
cattggccag attaggattc accagatagt gttaatatta gtttgatttg agactttaat 100500
cagaaagcac atgtgtggtg ggggtgggtg taacctaagt caggtagaat ctttccaact 100560
tggggggggc acactcctga ttgtagccat atgagtctgt cagtgtggtg gaagaggcca 100620
tgggttaatg ggcaggtaaa aaagcacctt gcctggaatt gagtagaaag taaggccctt 100680
cagaccccgt gacacacttg ggacatttt cttgagtaac atcctaagat tcatgtacct 100740
tgatgatctc catcaactta ctcatgtgaa gcacctttaa accagtcgtc tccaaattca 100800
ggggcacagt aacatccaac aggctggaga aagaacgtac tagaacttcc attccttttt 100860
catgtcctct tctaaaagct ttgtcagggc caggcgcggt ggctcacgcc tgtaatccca 100920
gcactttggg aggccgagac gggtggatca cgaggtcagg agatcgagac catcctggct 100980
aacacagtga aaccccatct ctactaaaaa tacaaaaaaa cgagccgggc gtggtggtgg 101040
gcgcctgtag tcccagctac tcgggaggct gaggcaggag aatggcgtga acccaggagg 101100
cagagcttgc agtgagccga gattgcacca ctgcagtcca gcctgggcga cagagcgaga 101160
ctccgtctca aaaaagaaaa agaaaaagaa aaagaactgt gattggggag gacggtcact 101220
```

```
ttcctgttct tactgatcag aagggatatt aagggtacct gattcaaaca gcctggagat 101280
cactgctttc aaccattacc tgccttattt atttttagtt actgtccttt tttcagtttg 101340
tttccctcct ccatgtgctg acttttattt tgattttatt tatgtttatg tttaagacat 101400
ccacacgttc ctctgctaaa accttgaaaa ataggccttg ccttagcccc aaacacccca 101460
ctcctggtag ctcagaccct ctgatccaac cctccagccc tgctgtgtgc ccagagccac 101520
cttcctctcc taaatacgtc tcttctgtca cttcccgaac tggcagttct ggagcaaagg 101580
agatgaaact caaggtaagg aaaccacctt tgaaaagaac caggctgctc tgctgtggtt 101640
tgcaaatgtg gggtttgttt atttgttttt tagcctcaaa gacctttctt caaatgagtt 101700
ctggcataga agcaccgtgt aaaatagtta gaattctggg caaaggggaa aagagagctg 101760
ggggccatcc ctctcagcac cccacaggct ctcatagcag cagctcctaa gacacctggt 101820
gggaccttgg tttcgaaatc gctactctaa ggctgggcac ggtggctcac acctgtaatc 101880
ccagctcttt aggaggccga ggagggtgga tcacctgaga tcaggagttc gagaccagcc 101940
tggctaacat ggcaaaaccc tgtctctact aaaaatacaa aaattagccg ggcgtggtgg 102000
tatgcgtggt ggtaatcgca gctactcggg aggctgaggc acaaggattg cttgaacccc 102060
agaggcagag gttgtagtta gctccagctt gggcgacaga gcaagaccct gtcgcaaaaa 102120
ttgtttaaaa aacaaaccca aaattgctac tctcattggg ttcctttgcc cattcctgat 102180
tttggcaaga gaaatgcttc cagattgccc tgatctgggt aggacagcat cacgccatag 102240
caacactgcc ccgtgagctc actgccccct caactagctt gtggtccttg gttaatgtca 102300
gtttcttttt tgagtttgtg ttatgtctaa gggtcatctg ctgggtaacg gaacccaggg 102360
actgccctag tccctagact gtgccatgcc cgactctgcc agctttgtca gtgatgctgg 102420
tgctcgcctc ctcgggtgct cgcctggtct gagcacaccc aaggagttct tgaggcctta 102480
gggttgtttg cgagagaatg aaagaacacg acctagctct ctttagcatc cttggtcagg 102540
ttcaacactg cccccagggg cctctggtgg agccaaccac catcagccaa ataaatccat 102600
aattagagtc agaaaatgga tgtctgcata tgtgtagtgc actaatgtcc tgccgatgat 102660
tgacatggag tggagagtga cctgatcatt gctgtgagct ctgctggcct tggcacaact 102720
catgctgata actaatgcac acagttcctc tgggaggaaa tgtcctcagg gaacttggag 102780
tttgggtggg gatgtgggtt tgtgtgccca gcaagccctt gtggttgtag cagacactag 102840
tggcatctag gaggcaaagg gtcaccccag tcttagccac gttttgagtc aaggtggcgg 102900
agtggggctg gtgttgactc ttggtggcag taacttttcc caatggtgaa aaaccccctct 102960
atcatgtttc atttacaggg ggctgatggt aaaacgaaga tcgccacacc gcggggagca 103020
gcccctccag gccagaaggg ccaggccaac gccaccagga ttccagcaaa aaccccgccc 103080
gctccaaaga caccacccag ctctggtaag aagaacgttc tcttgaatct tagaggaagc 103140
tgaagctctc agaggtacag ccttcatttt aggaggcctt aggccactga gaatgaataa 103200
cccctggcag ctggtcagca gcttgcagtt tactaagcac tggagtcttc attgccttct 103260
cagtcctttt gatttctgag gcaaatgttg aatccctacc tttttttttt tttttctttt 103320
gagacagagt ttcgcttttg ttatccaggc cggagtgcag tggtgtgatc tcagctcact 103380
gcatcctcca cctcccaggt tcaagcgatt ctcctacctc agcctcccta gtagctggga 103440
ttacaggcac ctgccactat gcccggctaa ttttttgtat ttttagtaga gacagggttt 103500
caccatgttg gccaggctgg tctcgaacgc ctgacctcag gtgatccacc tgcctcggcc 103560
```

-continued tcccaaagtg ctgggattac aggcatgagc caccactccc agcctgaatc ctcacttttt 103620
atcaatgaag aaattgaggc tgattctgca gcatgataaa aaaaaataca gaaaaaggaa 103680
aaaaaagaaa gaaatcgagc ctctgagagt ttgcttgact gagtctaacc agctcatttt 103740
aaacccgagg aaaatgcagt cacatgacta ctaagtggca gctctcggag cctctctggc 103800
cccaagtcca gggttccata gaggcagccc cagcatggca tgttttcagt ccccaaatga 103860
gactctggag acaaatgtct ctggagacag agcagcagcc tggataagtc acaatgggtg 103920
acgtcactca gggctcaacc cctgggcagc ttaacttgct agggacgtta ggagtctgct 103980
gcaaaacctg agggtcttag ctgagcagtc acaggctggg cccgttgccc tgggctcctg 104040
tgagtaaaac ccagtcaatt ttgagtaccc agtaaggcat ccattgagtt attttgcagc 104100
caggagtgct attaagaaca gtcgcggctg ggcgtggtgg ctcatgcctg taatcccagc 104160
actttgggag gccaaggtgg gcggatcacc tgaggtcagg agttcgagac cagcttggcc 104220
aacatggcaa aaccccgtct ctaataaaaa tacaaaataa ttagctgggc gtggtggcgg 104280
gcgcctgtaa tcccagcttc tcaggagggt gaggaaggag aatcacttga acccaggagg 104340
cagaggttgc agtgagctga gatcgcacca ttgcactcca gcctggatga caaaagtgag 104400
attccttctc aaaaaaaaaa aaaaaaaaac agtcgtcctc tttggggatt agggacagcc 104460
tgcctgcctg cccgagcact tctctcttcc attgccccag tgaagtattc caggcccctg 104520
ggtttagact ctgcaccatg taggggtgtc tgacctgcac ttgctccttg gtggcacggg 104580
cagcctatgg cacttgctgc gggctgtgac caaagcctgg cctggatctt ggatcttggt 104640
gactctgctt ctccctggcc tgagggagct gcccagagcc tgcccaccac ctgctgcgtg 104700
tctttgcggt ggcatttctc gcacacatgc cgtgcagtgg cacccccaag gatggccatt 104760
cactaaggcc cattgttttt gtcttttcgc ttcgtgtttt ctggcctggt gtttttctca 104820
tatacatgtg atccagggat aattcccaga attttgacag gattttaagt agcgtttgga 104880
tcctgctgtt ttttttcac ttaacatcgg gccagttgac tcacactctg tttttgttg 104940
ttgtttttt gagacggagt ctcactgtgt cacccaggct gaagtgcagt ggcacaatct 105000
tggcatactg caacctctgc ttcccaaatt caagcagttt tcctgcctca gcctcctgag 105060
tagctgggac tacaggcaca ggccaccacg ccctgctaat ttttgtattt ttagtaaaga 105120
cagggtttca ccattttggc cagcctagtc tcgaactcct gacctcaagt gatccgccca 105180
cctcggcctc ccaaagtgct gggattacag gggactcaca ctttgtaaca acctgaaaca 105240
acgtgatgca tttccctttg ggtcttacct gctcttcggt ggctgcctgc aggtggagag 105300
accctccccc ttgggcccct cgaccttgtt tcagaatggg gcccctgctg ggccagctgt 105360
gggtgcctgc cacgtgaagg actcattaag gccctgttta agcctgatga taataaggct 105420
ttcgtggatt tttctcttta agcgactaag caagtccaga gaagaccacc ccctgcaggg 105480
cccagatctg agagaggtac tcgggagcct acttcgctgg gagcagcctc cctttgcgtg 105540
tgtggccatt cactggcttg tgtttctaga gccgggagga ccctttctg caatgcaggg 105600
ttcacacagg gttcgcagcc tgaagatgga gcagtccgaa ttctcttccc tgtgcagttt 105660
gcgcagctgt gtttgtctga tgggctttct aatcctgtgt gctctccttg acttcaggga 105720
caatggcatt acaggcatga gccaccatgc ctggctgtct ccctatgttt cagatgaaga 105780
cataggctta aggaggtcag gtgacttgcc cacgaccact ctgtaaataa gaggcatgaa 105840
aagtatttgg agccaccacc accaagccca ctggtcaccc tgggtctctg aagtcaggga 105900
ggcaggagga tgggaggtct gaggaggcag agaggctgag cctggaggcc ctggaggccg 105960
aggccccatc tgttgtttcc ttatgtggaa aataagaggc ttcgtttgtc ctattgccac 106020
agagcgtact acttcaggaa catccaagac atggaaatcc gcagggcacg gtggctcacg 106080
tctataatcc cggcactttg ggaggttgag gtgggagaat cgcttgaggc cagaagttca 106140
agaccagcct gagcaacata gtcagacccc gtctctataa aaaacattat ttttaaaaaa 106200
gacatggaag tcaaattcta aaaactggtg ctggctgggt gcggtggctc atgcctataa 106260
tcccagcact ttgggaggcc gaggcgggtg gatcacctga ggtcaggagt tcaagaccag 106320
cctggccaac atggtaaaac ctctactaaa gaaatcttta ctgaaaatac aaaaatccag 106380
tctctactaa aataagtctc tactaaaaat acaaaaatta gccaggcgtg gtgctgcaca 106440
cctgtaatat cagctactcg ggaggctgag gcaggagact cgcttgatcc catgcagcgg 106500
aggttgcagt gagccgagat cacgccattg cactccagcc tgggcatcag aataagactc 106560
cgtctcaaaa aaaaaaccac aaaaaaacaa aacaacaaca aaagaaaact agtgcttatt 106620
cgtcactggc caagctgccc attggctaca tgggtgcttc aaagagctgc ccttctccag 106680
gtctggccag caggtatgtg ttacagcaaa tgcctggggc agcggcaggg gcattgctgc 106740
gggaagcttc tggacttgca ggaaagctaa gttctcagac tgcaggggag ctaagcacac 106800
ctcggcacag ggtgaggcct gcggttctca gacttcagtc tttgtggagc ttgagaaaaa 106860
tgaggctttg caggtcccac ccctagagat tctgctctat ccactcttga aggggatcga 106920
gaaatttgca ttttgcaact cccactttcc tccttgaaag ctccggagat tctgacgcag 106980
ggttccgtgg gccacacttt ggaaaataca gacccatgag atagaatacc agactgttga 107040
agtgtaacgg gggcctggga agtgcagtaa cagaagcaag tttgagggta aaggacaccc 107100
agaggaggga gggacagcat ctgcatggag aggagaagag accccccagc agcttccagg 107160
gtgttggaag ggtgcgctag taactgctat gcatggcagg tggggaactg tacgtcaggg 107220
cacagcagca tgaagcggta tggctcgtgt ggacagctag ggacaggcag gcgtggagca 107280
ggcatcctgt tctgaaggcc aaatcccaca gaggagccag ggtgctggca ggagccctga 107340
actagccgaa cagctgaaca gctgaacatt caccctgtgg ggaaagggtc agaagcgtcc 107400
aggcttgagg gcacagctgg gtctcgtcac tgcatcaccc ttatttagga taaaggccct 107460
gaagaattgt attagaggtt ggcaaagcat atctaccacc tcctggagcc acgctggccg 107520
cagggattat aattatttcc attttcaaat taaggcctct gagctcagag aggggaagtt 107580
acttgtctga ggccacacag cttgttggag cccatctctt gacccaaaga ctgtggagcc 107640
gagttggcca cctctctggg agcgggtatt ggatggtggt tgatggtttt ccattgcttt 107700
cctgggaaag gggtgtctct gtccctaagc aaaaaggcag ggaggaagag atgcttcccc 107760
agggcagccg tctgctgtag ctgcgcttcc aacctggctt ccacctgcct aacccagtgg 107820
tgagcctggg aatggaccca cgggacaggc agcccccagg gccttttctg accccaccca 107880
ctcgagtcct ggcttcactc ccttccttcc ttcccaggtg aacctccaaa atcaggggat 107940
cgcagcggct acagcagccc cggctcccca ggcactcccg gcagccgctc ccgcaccccg 108000
tcccttccaa ccccacccac ccgggagccc aagaaggtgg cagtggtccg tactccaccc 108060
aagtcgccgt cttccgccaa gagccgcctg cagacagccc ccgtgcccat gccagacctg 108120
aagaatgtca agtccaagat cggctccact gagaacctga agcaccagcc gggaggcggg 108180
aaggtgagag tggctggctg cgcgtggagg tgtgggggc tgcgcctgga ggggtagggc 108240
tgtgcctgga agggtagggc tgcgcctgga ggtgcgcggt tgagcgtgga gtcgtgggac 108300
tgtgcatgga ggtgtggggc tccccgcacc tgagcacccc cgcataacac cccagtcccc 108360
tctggaccct cttcaaggaa gttcagttct ttattgggct ctccactaca ctgtgagtgc 108420
cctcctcagg cgagagaacg ttctggctct tctcttgccc cttcagcccc tgttaatcgg 108480
acagagatgg cagggctgtg tctccacggc cggaggctct catagtcagg gcacccacag 108540
cggttcccca cctgccttct gggcagaata cactgccacc cataggtcag catctccact 108600
cgtgggccat ctgcttaggt tgggttcctc tggattctgg ggagattggg ggttctgttt 108660
tgatcagctg attcttctgg gagcaagtgg gtgctcgcga gctctccagc ttcctaaagg 108720
tggagaagca cagacttcgg gggcctggcc tggatccctt tccccattcc tgtccctgtg 108780
cccctcgtct gggtgcgtta gggctgacat acaaagcacc acagtgaaag aacagcagta 108840
tgcctcctca ctagccaggt gtgggcgggt gggtttcttc caaggcctct ctgtggccgt 108900
gggtagccac ctctgtcctg caccgctgca gtcttccctc tgtgtgtgct cctggtagct 108960
ctgcgcatgc tcatcttctt ataagaacac catggcagct gggcgtagtg gctcacgcct 109020
ataatcccag cactttggga ggctgaggca ggcagatcac gaggtcagga gttcgagacc 109080
aacctgacca acagggtgaa acctcgtctc tactaaaaat acaaaaatac ctgggcgtgg 109140
tggtggtgcg cgcctataat cccagctact caggaggctg aggcaggaga atcgcttgaa 109200
cccaggaggc agaggttgca gtgagccgag atagtgccac tgcactccag tttgagcaac 109260
agagcgagac tctgtctcaa aacaaaataa aacaaaccaa aaaaacccac catggcttag 109320
ggcccagcct gatgacctca tttttcactt agtcacctct ctaaaggccc tgtctccaaa 109380
tagagtcaca ttctaaggta cgggggtgtt ggggaggggg gttagggctt caacatgtga 109440
atttgcgggg accacaattc agcccaggac cccgctcccg ccacccagca ctggggagct 109500
ggggaagggt gaagaggagg ctgggggtga gaaggaccac agctcactct gaggctgcag 109560
atgtgctggg ccttctgggc actgggcctc ggggagctag ggggctttct ggaaccctgg 109620
gcctgcgtgt cagcttgcct cccccacgca ggcgctctcc acaccattga agttcttatc 109680
acttgggtct gagcctgggg catttggacg gagggtggcc accagtgcac atgggcacct 109740
tgcctcaaac cctgccacct ccccccaccc aggatccccc ctgcccccga acaagcttgt 109800
gagtgcagtg tcacatccca tcgggatgga aatggacggt cgggttaaaa gggacgcatg 109860
tgtagaccct gcctctgtgc atcaggcctc ttttgagagt ccctgcgtgc caggcggtgc 109920
acagaggtgg agaagactcg gctgtgcccc agagcacctc ctctcatcga ggaaaggaca 109980
gacagtggct cccctgtggc tgtggggaca agggcagagc tccctggaac acaggaggga 110040
gggaaggaag agaacatctc agaatctccc tcctgatggc aaacgatccg ggttaaatta 110100
aggtccggcc ttttcctgct caggcatgtg gagcttgtag tggaagaggc tctctggacc 110160
ctcatccacc acagtggcct ggttagagac cttggggaaa taactcacag gtgacccagg 110220
gcctctgtcc tgtaccgcag ctgagggaaa ctgtcctgcg cttccactgg ggacaatgcg 110280
ctccctcgtc tccagacttt ccagtcctca ttcggttctc gaaagtcgcc tccagaagcc 110340
ccatcttggg accaccgtga ctttcattct ccagggtgcc tggccttggt gctgcccaag 110400
accccagagg ggccctcact ggcctttcct gccttttctc ccattgccca cccatgcacc 110460
cccatcctgc tccagcaccc agactgccat ccaggatctc ctcaagtcac ataacaagca 110520
gcacccacaa ggtgctccct tccccctagc ctgaatctgc tgctccccgt ctggggttcc 110580
ccgcccatgc acctctgggg gcccctgggt tctgccatac cctgccctgt gtcccatggt 110640
ggggaatgtc cttctctcct tatctcttcc cttcccttaa atccaagttc agttgccatc 110700
tcctccagga agtcttcctg gattcccctc tctcttctta aagcccctgt aaactctgac 110760
cacactgagc atgtgtctgc tgctccctag tctgggccat gagtgagggt ggaggccaag 110820
tctcatgcat ttttgcagcc cccacaagac tgtgcaggtg gccggccctc attgaatgcg 110880
gggttaattt aactcagcct ctgtgtgagt ggatgattca ggttgccaga gacagaaccc 110940
tcagcttagc atgggaagta gcttccctgt tgaccctgag ttcatctgag gttggcttgg 111000
aaggtgtggg caccatttgg cccagttctt acagctctga agagagcagc aggaatgggg 111060
ctgagcaggg aagacaactt tccattgaag gccccctttca gggccagaac tgtccctccc 111120
accctgcagc tgccctgcct ctgcccatga ggggtgagag tcaggcgacc tcatgccaag 111180
tgtagaaagg ggcagatggg agccccaggt tatgacgtca ccatgctggg tggaggcagc 111240
acgtccaaat ctactaaagg gttaaaggag aaagggtgac ttgacttttc ttgagatatt 111300
ttgggggacg aagtgtggaa aagtggcaga ggacacagtc acagcctccc ttaaatgcca 111360
ggaaagccta gaaaaattgt ctgaaactaa acctcagcca taacaaagac caacacatga 111420
atctccagga aaaaagaaaa agaaaaatgt catacagggt ccatgcacaa gagcctttaa 111480
aatgacccgc tgaagggtgt caggcctcct cctcctggac tggcctgaag gctccacgag 111540
cttttgctga gacctttggg tccctgtggc ctcatgtagt acccagtatg cagtaagtgc 111600
tcaataaatg tttggctaca aaagaggcaa agctggcgga gtctgaagaa tccctcaacc 111660
gtgccggaac agatgctaac accaaaggga aaagagcagg agccaagtca cgtttgggaa 111720
cctgcagagg ctgaaaactg ccgcagattg ctgcaaatca ttgggggaaa aacggaaaac 111780
gtctgttttc ccctttgtgc ttttctctgt tttcttcttt gtgcttttct ctgttttcag 111840
gatttgctac agtgaacata gattgctttg gggccccaaa tggaattatt ttgaaaggaa 111900
aatgcagata atcaggtggc cgcactggag caccagctgg gtaggggtag agattgcagg 111960
caaggaggag gagctgggtg gggtgccagg caggaagagc ccgtaggccc cgccgatctt 112020
gtgggagtcg tgggtggcag tgttccctcc agactgtaaa agggagcacc tggcgggaag 112080
agggaattct tttaaacatc attccagtgc ccgagcctcc tggacctgtt gtcatcttga 112140
ggtgggcctc ccctgggtga ctctagtgtg cagcctggct gagactcagt ggccctgggt 112200
tcttactgct gacacctacc ctcaacctca accactgcgg cctcctgtgc accctgatcc 112260
agtggctcat tttccacttt cagtcccagc tctatcccta tttgcagttt ccaagtgcct 112320
ggtcctcagt cagctcagac ccagccaggc cagcccctgg ttcccacatc ccctttgcca 112380
agctcatccc cgccctgttt ggcctgcggg agtgggagtg tgtccagaca cagagacaaa 112440
ggaccagctt ttaaaacatt ttgttggggc caggtgtggt ggctcacacc taatcccaac 112500
acctggggag gccaaggcag aaggatcact tgagtccagg agttcaagac cagcctgggc 112560
aacataggga gaccctgtct ctacaatttt ttttttaatt agctgggcct gttggcactc 112620
tcctgtagtt ccagctactc tagaggctga ggtgggagga ctgcttgagc ctgggaggtc 112680
agggctgcaa tgagccatgt tcacaccact gaacgccagc ctgggcgaga ccctgtatca 112740
aaaaagtaaa gtaaaatgaa tcctgtacgt tatattaagg tgccccaaat tgtacttaga 112800
aggatttcat agttttaaat acttttgtta tttaaaaaat taaatgactg cagcatataa 112860
attaggttct taatggaggg gaaaaagagt acaagaaaag aaataagaat ctagaaacaa 112920
agataagagc agaaataaac cagaaaacac aaccttgcac tcctaactta aaaaaaaaaa 112980
tgaagaaaac acaaccagta aaacaacata taacagcatt aagagctggc tcctggctgg 113040
gcgcggtggc gcatgcctgt aatcccaaca ctttgggagg ccgatgctgg aggatcactt 113100
gagaccagga gttcaaggtt gcagtgagct atgatcatac cactacaccc tagcctgggc 113160
aacacagtga gactgagact ctattaaaaa aaaaatgctg gttccttcct tatttcattc 113220
ctttattcat tcattcagac aacatttatg gggcacttct gagcaccagg ctctgtgcta 113280
agagcttttg cccccagggt ccaggccagg ggacaggggc aggtgagcag agaaacaggg 113340
ccagtcacag cagcaggagg aatgtaggat ggagagcttg gccaggcaag gacatgcagg 113400
gggagcagcc tgcacaagtc agcaagccag agaagacagg cagacccttg tttgggacct 113460
gttcagtggc ctttgaaagg acagccccca cccggagtgc tgggtgcagg agctgaagga 113520
ggatagtgga acactgcaac gtggagctct tcagagcaaa agcaaaataa acaactggag 113580
gcagctgggg cagcagaggg tgtgtgttca gcactaaggg gtgtgaagct tgagcgctag 113640
gagagttcac actggcagaa gagaggttgg ggcagctgca agcctctgga catcgcccga 113700
caggacagag ggtggtggac ggtggccctg aagagaggct cagttcagct ggcagtggcc 113760
gtgggagtgc tgaagcaggc aggctgtcgg catctgctgg ggacggttaa gcaggggtga 113820
gggcccagcc tcagcagccc ttcttggggg gtcgctggga aacatagagg agaactgaag 113880
aagcagggag tcccagggtc catgcagggc gagagagaag ttgctcatgt ggggcccagg 113940
ctgcaggatc aggagaactg gggaccctgt gactgccagc ggggagaagg gggtgtgcag 114000
gatcatgccc agggaagggc ccaggggccc aagcatgggg gggcctggtt ggctctgaga 114060
agatggagct aaagtcactt tctcggagga tgtccaggcc aatagttggg atgtgaagac 114120
gtgaagcagc acagagcctg gaagcccagg atggacagaa acctacctga gcagtggggc 114180
tttgaaagcc ttggggcggg gggtgcaata ttcaagatgg ccacaagatg gcaatagaat 114240
gctgtaactt tcttggttct gggccgcagc ctgggtggct gcttccttcc ctgtgtgtat 114300
tgatttgttt ctcttttttg agacagagtc ttgctgggtt gcccaggctg gagtgcagtg 114360
gtgcgatcat agctcactgc agccttgaag tcctgagctc aagagatcct tccacctcag 114420
cctcctgagt agttgggacc acaggcttgc accacagtgc ccaactaatt tcttatattt 114480
tttgtagaga tggggtttca ctgtgtcgcc caggatggtc ttgaactcct gggctcaagt 114540
gatcctcctg cctcagcctc gcaaattgct gggattacag gtgtgagcca ccatgcccga 114600
ccttctcttt ttaagggcgt gtgtgtgtgt gtgtgtgtgt gggcgcactc tcgtcttcac 114660
cttcccccag ccttgctctg tctctaccca gtcacctctg cccatctctc cgatctgttt 114720
ctctctcctt ttacccctct ttcctccctc ctcatacacc actgaccatt atagagaact 114780
gagtattcta aaaatacatt ttatttattt attttgagac agagtctcac tctgtcaccc 114840
aggctggagt gcagtggtgc aatctcggct cactgcaacc tccgcctccc aggttgaagc 114900
aactctcctg cctcagcctc cctagtagct gggattacaa gcacacacca ccatgcctag 114960
caaattttta tatttttagt agaggagggg tgtcaccatg tttgccaagc tggtctcaaa 115020
ctcctggcct caggtgatct gcctaccttg gtctcccaaa gtgctgggat tacaggtgtg 115080
agccaccacg cctgccctta aaaatacatt atatttaata gcaaagcccc agttgtcact 115140
ttaaaaagca tctatgtaga acatttatgt ggaataaata cagtgaattt gtacgtggaa 115200
tcgtttgcct ctcctcaatc agggccaggg atgcaggtga gcttgggctg agatgtcaga 115260
ccccacagta agtggggggc agagccaggc tgggaccctc ctctaggaca gctctgtaac 115320
tctgagaccc tccaggcatc ttttcctgta cctcagtgct tctgaaaaat ctgtgtgaat 115380
caaatcattt taaaggagct tgggttcatc actgtttaaa ggacagtgta aataattctg 115440
aaggtgactc taccctgtta tttgatctct tctttggcca gctgacttaa caggacatag 115500
acaggttttc ctgtgtcagt tcctaagctg atcaccttgg acttgaagag gaggcttgtg 115560
tgggcatcca gtgcccaccc cgggttaaac tcccagcaga gtattgcact gggcttgctg 115620
agcctggtga ggcaaagcac agcacagcga gcaccaggca gtgctggaga caggccaagt 115680
ctgggccagc ctgggagcca actgtgaggc acggacgggg ctgtggggct gtggggctgc 115740
aggcttgggg ccagggaggg agggctgggc tctttggaac agccttgaga gaactgaacc 115800
caaacaaaac cagatcaagg tctagtgaga gcttagggct gctttgggtg ctccaggaaa 115860
ttgattaaac caagtggaca cacaccccca gccccacctc accacagcct ctccttcagg 115920
gtcaaactct gaccacagac atttctcccc tgactaggag ttccctggat caaaattggg 115980
agcttgcaac acatcgttct ctcccttgat ggtttttgtc agtgtctatc cagagctgaa 116040
gtgtaatata tatgttactg tagctgagaa attaaatttc aggattctga tttcataatg 116100
acaaccattc ctcttttctc tcccttctgt aaatctaaga ttctataaac ggtgttgact 116160
taatgtgaca attggcagta gttcaggtct gctttgtaaa tacccttgtg tctattgtaa 116220
aatctcacaa aggcttgttg cctttttttgt ggggttagaa caagaaaaag ccacatggaa 116280
aaaaaatttc tttttgttt ttttgtttgc ttgtttttttt gagacagagt ttcactctgt 116340
cgcccaggct ggagtgcagt ggtgcgatct ccgcccactg caagctccac ctcccgggtt 116400
catgctattc tcctgtctca gcctcccaag tagctgggac tgcaggtgcc cgccaccaca 116460
cctggctaat ttttttgtat ttttagtaga gacggggttt caccgtgtta gccaggatgg 116520
tctcaatctc ctgacctcgt catctgcctg cctcggcctc ccaaagtgct gagattacag 116580
gcgtgagcca ccgtgcccgg ccagaaaaaa acatttctaa gtatgtggca gatactgaat 116640
tattgcttaa tgtcctttga ttcatttgtt taatttcttt aatggattag tacagaaaac 116700
aaagttctct tccttgaaaa actggtaagt tttctttgtc agataaggag agttaaataa 116760
cccatgacat ttcccttttt gcctcggctt ccaggaagct caaagttaaa tgtaatgatc 116820
actcttgtaa ttatcagtgt tgatgccctt cccttcttct aatgttactc tttacatttt 116880
cctgctttat tattgtgtgt gttttctaat tctaagctgt tcccactcct ttctgaaagc 116940
aggcaaatct tctaagcctt atccactgaa aagttatgaa taaaaaatga tcgtcaagcc 117000
tacaggtgct gaggctactc cagaggctga ggccagagga ccacttgagc ccaggaattt 117060
gagacctggg ctgggcagca tagcaagact ctatctccat taaaactatt tttttttatt 117120
taaaaaataa tccgcaaaga aggagtttat gtgggattcc ttaaaatcgg agggtggcat 117180
gaattgattc aaagacttgt gcagagggcg acagtgactc cttgagaagc agtgtgagaa 117240
agcctgtccc acctccttcc gcagctccag cctgggctga ggcactgtca cagtgtctcc 117300
ttgctggcag gagagaattt caacattcac caaaaagtag tattgttttt attaggttta 117360
tgaggctgta gccttgagga cagcccagga caactttgtt gtcacataga tagcctgtgg 117420
ctacaaactc tgagatctag attcttctgt ggctgcttct gacctgagaa agttgcggaa 117480
cctcagcgag cctcacatgg cctccttgtc cttaacgtgg ggacggtggg caagaaaggt 117540
gatgtggcac tagagattta tccatctcta aaggaggagt ggattgtaca ttgaaacacc 117600
agagaaggaa ttacaaagga agaatttgag tatctaaaaa tgtaggtcag gcgctcctgt 117660
gttgattgca gggctattca caatagccaa gatttggaag caacccaagt gtccatcaac 117720
agacaaatgg ataaagaaaa tgtggtgcat atacacaatg gaatactatt cagccatgaa 117780
aaagaatgag aatctgtcat ttgaaacaac atggatggaa ctggaggaca ttatgttaag 117840
tgaaataagc cagacagaag gacagacttc acatgttctc acacatttgt gggagctaaa 117900
aattaaactc atggagatag agagtagaag gatggttacc agaggctgag gagggtggag 117960
gggagcaggg agaaagtagg gatggttaat gggtacaaaa acgtagttag catgcataga 118020
tctagtattg gatagcacag cagggtgacg acagccaaca gtaatttata gtacatttaa 118080
aaacaactaa aagagtgtaa ttggactggc taacatggtg aaaccccgtc tctactaaaa 118140
atacaaaaat tagctgggca tggtggctca cgcctgtaat cccagcactt tgggaggccg 118200
aggcgggccg atcacgaggt caggagatcg agaccatcct agctaacatg gtgaaacccc 118260
gtctctacta caaatacaaa aaaaagaaaa aattagccgg gcatggtggt gggcgcctgt 118320
agtcccagct actcgggagg ctgaggcagg agaatggcgt gaacccggga ggcggagctt 118380
gcagtgagcc gagatcgcgc cactgcactc cagcctgggc gacaaggcaa gattctatct 118440
caaaaaaata aaaataaaat aaaataaaat aataaaataa aataaaataa aataaaataa 118500
ataaaataaa ataaaatgta taattggaat gtttataaca caagaaatga taaatgcttg 118560
aggtgataga taccccattc accgtgatgt gattattgca caatgtatgt ctgtatctaa 118620
atatctcatg taccccacaa gtatatacac ctactatgta cccatataaa tttaaaatta 118680
aaaaattata aaacaaaaat aaataagtaa attaaaatgt aggctggaca ccgtggttca 118740
cgcctgtaat cccagtgctt tgtgaggctg aggtgagaga atcacttgag cccaggagtt 118800
tgagaccggc ctgggtgaca tagcgagacc ccatcatcac aaagaatttt taaaaattag 118860
ctgggcgtgg tagcacatac cggtagttcc agctacttgg gagaccgagg caggaggatt 118920
gcttgagccc aggagtttaa ggctgcagtg agctacgatg gcgccactgc attccagcct 118980
gggtgacaga gtgagagctt gtctctattt taaaaataat aaaaagaata aataaaaata 119040
aattaaaatg taaatatgtg catgttagaa aaaatacacc catcagcaaa aagggggtaa 119100
aggagcgatt tcagtcataa ttggagagat gcagaataag ccagcaatgc agtttctttt 119160
attttggtca aaaaaaataa gcaaaacaat gttgtaaaca cccagtgctg gcagcaatgt 119220
ggtgaggctg gctctctcac cagggctcac agggaaaact catgcaaccc ttttagaaag 119280
ccatgtggag agttgtaccg agaggtttta gaatatttat aactttgacc cagaaattct 119340
attctaggac tctgtgttat gaaaataacc catcatatgg aaaaagctcc tttcagaaag 119400
aggttcatgg gaggctgttt gtattttttt tttctttgca tcaaatccag ctcctgcagg 119460
actgtttgta ttattgaagt acaaagtgga atcaatacaa atgttggata gcaggggaac 119520
aatattcaca aaatggaatg ggacatagta ttaaacatag tgcttctgat gaccgtagac 119580
catagacaat gcttaggata tgatatcact tcttttgttg ttttttgtat tttgagacga 119640
agtctcattc tgtcacccag gctggagttc agtggcgcca tctcagctca ctgcaacctc 119700
catctcccgg gttcaagcta ttctccttcc tcaacctccc gagtagctgg gttgcgcacc 119760
accatgcctg gctaactttt gtatttttag tacagacggg gtttcaccac gttggccagg 119820
ctgctcttga actcctgacg tcaggtgatc caccagcctt gacctcccaa agtgctagga 119880
ttacaggagc cactgtaccc agcctaggat atgatatcac ttcttagagc aagatacaaa 119940
attgcatgtg cacaataatt ctaccaagta taggtataca ggggtagtta tatataaatg 120000
agacttcaag gaaatacaac aaaatgcaat cgtgattgtg ttagggtggt aagaaaacgg 120060
tttttgcttt gatgagctct gttttttaaa atcgttatat tttctaataa aaatacatag 120120
tcttttgaag gaacataaaa gattatgaag aaatgagtta gatattgatt cctattgaag 120180
attcagacaa gtaaaattaa ggggaaaaaa aacgggatga accagaagtc aggctggagt 120240
tccaacccca gatccgacag cccaggctga tggggcctcc agggcagtgg tttccaccca 120300
gcattctcaa aagagccact gaggtctcag tgccattttc aagatttcgg aagcggcctg 120360
ggcacggctg gtccttcact gggatcacca cttggcaatt atttacacct gagacgaata 120420
aaaaccagag tgctgagatt acaggcatgg tggcttacgc ttgtaatcgg ctttgggaag 120480
ccgaggtggg ctgattgctt gagcccagga gtttcaaact atcctggaca acatagcatg 120540
acctcgtctc tacaaaaaat acaaaaaatt tgccaggtgt ggtggcatgt gcctgtggtc 120600
ccagctactt gggaggctga agtaggagaa tcccctgagc cctgggaagt cgaggctgca 120660
ctgagccgtg atggtgtcac tgcactccag cctgggtgac aaagtgagac cctatctcac 120720
aaagaaaaaa aacaaaacaa aaaacccaaa gcacactgtt tccactgttt ccagagttcc 120780
tgagaggaaa ggtcaccggg tgaggaagac gttctcactg atctggcaga gaaaatgtcc 120840
agtttttcca actccctaaa ccatggtttt ctatttcata gttcttaggc aaattggtaa 120900
aaatcatttc tcatcaaaac gctgatattt tcacacctcc ctggtgtctg cagaaagaac 120960
cttccagaaa tgcagtcgtg ggagacccat ccaggccacc cctgcttatg gaagagctga 121020
gaaaaagccc cacgggagca tttgctcagc ttccgttacg cacctagtgg cattgtgggt 121080
gggagagggc tggtgggtgg atggaaggag aaggcacagc ccccccttgc agggacagag 121140
ccctcgtaca gaagggacac cccacatttg tcttccccac aaagcggcct gtgtcctgcc 121200
tacggggtca gggcttctca aacctggctg tgtgtcagaa tcaccagggg aacttttcaa 121260
aactagagag actgaagcca gactcctaga ttctaattct aggtcagggc taggggctga 121320
gattgtaaaa atccacaggt gattctgatg cccggcaggc ttgagaacag ccgcagggag 121380
ttctctggga atgtgccggt gggtctagcc aggtgtgagt ggagatgccg gggaacttcc 121440
tattactcac tcgtcagtgt ggccgaacac atttttcact tgacctcagg ctggtgaacg 121500
ctcccctctg gggttcaggc ctcacgatgc catccttttg tgaagtgagg acctgcaatc 121560
ccagcttcgt aaagcccgct ggaaatcact cacacttctg ggatgccttc agagcagccc 121620
tctatccctt cagctcccct gggatgtgac tcaacctccc gtcactcccc agactgcctc 121680
tgccaagtcc gaaagtggag gcatccttgc gagcaagtag gcgggtccag ggtggcgcat 121740
gtcactcatc gaaagtggag gcgtccttgc gagcaagcag gcgggtccag ggtggcgtgt 121800
cactcatcct tttttctggc taccaaaggt gcagataatt aataagaagc tggatcttag 121860
caacgtccag tccaagtgtg gctcaaagga taatatcaaa cacgtcccgg gaggcggcag 121920
tgtgagtacc ttcacacgtc ccatgcgccg tgctgtggct tgaattatta ggaagtggtg 121980
tgagtgcgta cacttgcgag acactgcata gaataaatcc ttcttgggct ctcaggatct 122040
ggctgcgacc tctgggtgaa tgtagcccgg ctccccacat tcccccacac ggtccactgt 122100
tcccagaagc cccttcctca tattctagga gggggtgtcc cagcatttct gggtccccca 122160
gcctgcgcag gctgtgtgga cagaataggg cagatgacgg accctctctc cggaccctgc 122220
ctgggaagct gagaataccc atcaaagtct ccttccactc atgcccagcc ctgtccccag 122280
gagccccata gcccattgga agttgggctg aaggtggtgg cacctgagac tgggctgccg 122340
cctcctcccc cgacacctgg gcaggttgac gttgagtggc tccactgtgg acaggtgacc 122400
cgtttgttct gatgagcgga caccaaggtc ttactgtcct gctcagctgc tgctcctaca 122460
cgttcaaggc aggagccgat tcctaagcct ccagcttatg cttagcctgc gccaccctct 122520

-continued ggcagagact ccagatgcaa agagccaaac caaagtgcga caggtccctc tgcccagcgt 122580
tgaggtgtgg cagagaaatg ctgcttttgg cccttttaga tttggctgcc tcttgccagg 122640
agtggtggct cgtgcctgta attccagcac tttgggagac taaggcggga ggttcgcttg 122700
agcccaggag ttcaagacca gcctgggcaa caatgagacc cctgtgtcta caaaaagaat 122760
taaaattagc caggtgtggt ggcacgcacc tgtagtccca gctacttggg aggctgaggt 122820
gggaggattg cctgagtccg ggaggcggaa gttgcaagga gccatgatcg cgccactgca 122880
cttcaaccta ggcaacagag tgagactttg tctcaaaaaa caatcatata ataattttaa 122940
aataaataga tttggcttcc tctaaatgtc cccggggact ccgtgcatct tctgtggagt 123000
gtctccgtga gattcgggac tcagatcctc aagtgcaact gacccacccg ataagctgag 123060
gcttcatcat cccctggccg gtctatgtcg actgggcacc cgaggctcct ctcccaccag 123120
ctctcttggt cagctgaaag caaactgtta acaccctggg gagctggacg tatgagaccc 123180
ttggggtggg aggcgttgat ttttgagagc aatcacctgg ccctggctgg cagtaccggg 123240
acactgctgt ggctccgggg tgggctgtct ccagaaaatg cctggcctga ggcagccacc 123300
cgcatccagc ccagagggtt tattcttgca atgtgctgct gcttcctgcc ctgagcacct 123360
ggatcccggc ttctgccctg aggccccttg agtcccacag gtagcaagcg cttgccctgc 123420
ggctgctgca tggggctaac taacgcttcc tcaccagtgt ctgctaagtg tctcctctgt 123480
ctcccacgcc ctgctctcct gtccccccag tttgtctgct gtgaggggac agaagaggtg 123540
tgtgccgccc ccacccctgc ccgggccctt gttcctggga ttgctgtttt cagctgtttg 123600
agctttgatc ctggttctct ggcttcctca aagtgagctc ggccagagga ggaaggccat 123660
gtgctttctg gttgaagtca agtctggtgc cctggtggag gctgtgctgc tgaggcggag 123720
ctggggagag agtgcacacg ggctgcgtgg ccaacccctc tgggtagctg atgcccaaag 123780
acgctgcagt gcccaggaca tctgggacct ccctggggcc cgcccgtgtg tcccgcgctg 123840
tgttcatctg cgggctagcc tgtgacccgc gctgtgctcg tctgcgggct agcctgtgtc 123900
ccgcgctctg cttgtctgcg gtctagcctg tgacctggca gagagccacc agatgtcccg 123960
ggctgagcac tgccctctga gcaccttcac aggaagccct tctcctggtg agaagagatg 124020
ccagcccctg gcatctgggg gcactggatc cctggcctga gccctagcct ctccccagcc 124080
tgggggcccc ttcccagcag gctggccctg ctccttctct acctgggacc cttctgcctc 124140
ctggctggac cctggaagct ctgcagggcc tgctgtcccc ctccctgccc tccaggtatc 124200
ctgaccaccg gccctggctc ccactgccat ccactcctct cctttctggc cgttccctgg 124260
tccctgtccc agcccccctc cccctctcac gagttacctc acccaggcca gagggaagag 124320
ggaaggaggc cctggtcata ccagcacgtc ctcccacctc cctcggccct ggtccacccc 124380
ctcagtgctg gcctcagagc acagctctct ccaagccagg ccgcgcgcca tccatcctcc 124440
ctgtccccca acgtccttgc cacagatcat gtccgccctg acacacatgg gtctcagcca 124500
tctctgcccc agttaactcc ccatccataa agagcacatg ccagctgaca ccaaaataat 124560
tcgggatggt tccagtttag acctaagtgg aaggagaaac caccacctgc cctgcacctt 124620 gtttttttggt gaccttgata aaccatcttc agccatgaag ccagctgtct cccaggaagc 124680
tccagggcgg tgcttcctcg ggagctgact gataggtggg aggtggctgc ccccttgcac 124740
cctcaggtga ccccacacaa ggccactgct ggaggccctg gggactccag gaatgtcaat 124800
cagtgacctg ccccccaggc cccacacagc catggctgca tagaggcctg cctccaaggg 124860
acctgtctgt ctgccactgt ggagtcccta cagcgtgccc cccacagggg agctggttct 124920
ttgactgaga tcagctggca gctcagggtc atcattccca gagggagcgg tgccctggag 124980
gccacaggcc tcctcatgtg tgtctgcgtc cgctcgagct tactgagaca ctaaatctgt 125040
tggtttctgc tgtgccacct acccaccctg ttggtgttgc tttgttccta ttgctaaaga 125100
caggaatgtc caggacactg agtgtgcagg tgcctgctgg ttctcacgtc cgagctgctg 125160
aactccgctg ggtcctgctt actgatggtc tttgctctag tgctttccag ggtccgtgga 125220
agcttttcct ggaataaagc ccacgcatcg accctcacag cgcctcccct ctttgaggcc 125280
cagcagatac cccactcctg cctttccagc aagatttttc agatgctgtg catactcatc 125340
atattgatca ctttttttctt catgcctgat tgtgatctgt caatttcatg tcaggaaagg 125400
gagtgacatt tttacactta agcgtttgct gagcaaatgt ctgggtcttg cacaatgaca 125460
atgggtccct gtttttccca gaggctcttt tgttctgcag ggattgaaga cactccagtc 125520
ccacagtccc cagctcccct ggggcagggt tggcagaatt tcgacaacac atttttccac 125580
cctgactagg atgtgctcct catggcagct gggaaccact gtccaataag ggcctgggct 125640
tacacagctg cttctcattg agttacaccc ttaataaaat aatcccattt tatccttttt 125700
gtctctctgt cttcctctct ctctgccttt cctcttctct ctcctcctct ctcatctcca 125760
ggtgcaaata gtctacaaac cagttgacct gagcaaggtg acctccaagt gtggctcatt 125820
aggcaacatc catcataaac caggtagccc tgtggaaggt gagggttggg acgggagggt 125880
gcagggggtg gaggagtcct ggtgaggctg gaactgctcc agacttcaga aggggctgga 125940
aaggatattt taggtagacc tacatcaagg aaagtgttga gtgtgaaact tgcgggagcc 126000
caggaggcgt ggtggctcca gctcgctcct gcccaggcca tgctgcccaa gacaaggtga 126060
ggcgggagtg aagtgaaata aggcaggcac agaaagaaag cacatattct cggccgggcg 126120
ctgtggctca cgcctgtaat tccagcactt tgggaggcca aggtgggtgg atcatgaggt 126180
caggagattg agaccatcct ggctaacaca gtgaaacccc gtctctacta aaaatacaaa 126240
aaattagccg ggcgtggtgg tgggcgcctg tagtcccagc tactccggag gctgaggcag 126300
gaaaatggcg tgaacccgga aggcggagct tgcagtgagc ggagtgagca gagatcgcgc 126360
cactgcactc cagcctgggc gacagagcga gactccgtct caaaaaaaaa aagcacatgt 126420
tctcgcttct ttgtgggatc caggagatag agaatagaag gatggttacc agaggctggg 126480
aagggtagtg aggggatggt gggggatgg tcaatgggta caaaaaaaat agaataagac 126540
ctagtatttg atagtgcaac agggtgacta tagtcaataa taatttaatt gtacatttaa 126600
aaataactaa aagatagccg ggtgcagtgg cttacgtctg taatcccagt actttgggag 126660
gctgaggtgg gcgtttgaga ccagcctggc caacatggtg aaaccccatc tctactaaaa 126720
atacaaaaat tagccaggca tggtggcggg cgcctgtaat cccagctact cgggaggctg 126780
aggcaggaga atcacttgaa cctgggaggc agaggttgca gtgagccgag atcttgccac 126840
tgcactccag cctgggtgac agtgaaactc cgtctcaaaa ataaaaataa aaatacagct 126900
gggcacggtg gctcacgcct gtaatcccag cactttggga ggccgaggcg agcggatcac 126960
aaggtcagga gatatagacc atcctggcta acacggtgaa acccggtctc tactaaaaat 127020
acaaaaaatt agccaggcgt ggtggcaggt gcctatagtc ccagctactc acaaggctga 127080
ggcaggagaa tggcatgaac ctgggaggcg gagcttgcag tgagccgaga ttgtgccact 127140
gcactccagc ctgggcgaga gagtgagact ccgtctcaaa acaaaaacaa aaacaaaaac 127200
aaaaacaaac acacaacaaa aacctaaaag aatataaatg gattgtttgt aacacaaagg 127260
acaaatgttt gaggggatgg ataccccatt ttccatgatg tgattattat acattgtgtg 127320
tctgtatcaa aacatctcat gagccccata aatatataca cctaactatg tacccacaaa 127380
aattaaaaaa atatattttt taaggtgaag agggaggcga gatgctggcc ttaaccccta 127440
acccgttgtt ctccctgcaa gctgtccaca gggcctctca gactcgaggt tcagctatat 127500
ggatgcatga gcttggtccc cagccaacat gggagacact tcaccatcgg cagcagctac 127560
agcacaggaa ccctgggtca ctgccatgtc ccctctgtga ctttgtttaa acagaaaatg 127620
atgctctggg ccggctgtgg tggcccacac ctataatccc agcaccttgg gaggcggggg 127680
tgggcagatt gcctgaggtc aggagttgga gatcagcctg gccgacatgg cgaaacccca 127740
tgtctactaa aaatacaaaa actagccagg catggtggca catgcctgta atcccagcta 127800
cttgggaggc tgaagcagga gaatcacttg aacccaggag gcagaggctg agtgagccaa 127860
gatcgtgcca atgcactcca gcttgggtga gggagtgaga ctccgtctca aaaaaaaaaa 127920
aaaagaaaga aaaagaaaag aaagtgatcc tactggaacc atgcttactc ccctccccac 127980
ctcacactgt gtagaaatta gtgctgtcgg ccaggcgcgg tggctcatgc ctgtaatcgc 128040
agcactttgg gaggccaagg caggcggatc acgaggtcag gagatcaaga ccatcctggc 128100
taacacagtg aaaccctgtc tctactaaaa atacaaaaaa ttagccgggc atggtggcag 128160
gcacctgtag tcccaactac ttgggaggct gaggcaggag aatggcatga acctgggagg 128220
cggagcttgc agtgagccaa gatcgcgcca ctgcatacca gcctaggtga cagagtgaga 128280
ctcagcaaaa aaagaaagaa agaaagaaag aaatcagtgc tgtctatact tctttctgca 128340
gtgatggaaa tattctgtat ctgtgctgtc cagtatagta gccactagct acatgtggca 128400
cttgaaacat ggctggtaca gttgaggaag agtggctgcc atatcggacg acacagctat 128460
agattctgtc accccacccc gagagtccag agcggggact tctgccttag gccctattca 128520
gggctgattt ttacttgaac ccttactgtg ggaagagaag gccatgagaa gttcagtcta 128580
gaatgtgact ccttattttc tggctccctt ggacactttg tgggatttag tctccctgtg 128640
gaaagtattc cacaagtggt gccaccaccc cagctgtgag agcagctggg agctgctttt 128700
gtcatctttc cctggaaagt cctgtgggct gtctcttcct catgccttgt cccatgcttg 128760
ggcatggtgt caagcgtcag gagggagaaa gggtccttat ttatttattt agagagggac 128820
ccttcttctg ttcccaggct ggagtgcagt ggtgcgatct cggctcactg caacctccgc 128880
ctcctgggtt caagtgattc tcctgcctca gcctcctgag tagctgagat tacaggcaca 128940
tgccaacatg cctggctaat tttttttttt tttttttttt tttttttttg agatggagtt 129000
gtactctcat tgcccaggct ggaatgtaat ggcacaatct cggctcactg caacctccac 129060
ctcctggatt caagcaattc tcctgtctca gcttcccaag tagctgggat tacaggtgcc 129120
cgccaccatg ctcaactaat ttttgtattt ttttttagt agagacgagg tttcaccatg 129180
ttggtcagac tggtctcaaa ctcctgacct caggtgatcc acctgcctcg gcctcccaaa 129240
gtgctaggat tacaggcatg agccaccacg cccggcctga aagggttctt atttagtgtg 129300
cattttgaca ttcaatttaa ttccaaggtc ttgtggggtc atggtttaca ggatgttgat 129360
atagaaaaga cttcacttaa tgggccgggc gcagtggctc atgcctgtaa tcccagcact 129420
ttgggaggcc gaggcaggca gatcaggagg tcaggagatt gagaccatcc tggctaacac 129480
agtgaaaccc catctctact gaaaatacaa aaaattagct gggcgtggtg gcaggcacct 129540
gtagtcccag ccactcggtt ggctgaggca ggagaatggc atgaacccgg gaggcggagc 129600
ttgcagtgag cagagaccat gccactgcac tccagcctgg gcgacagagc aagactctgt 129660
ctcaagaaaa aaaaaaaaaa aacagacttt acttactgga agccaaccaa tgtatattta 129720
gagtaatttt tcctgggctg agctgtcatt tacttttgca gtatctcaag aagaagagtt 129780
tacagtgtaa atatttgatg cacactttga ttatatagat gaagcaaact attttcaaga 129840
gctttgcaag gacttacttg tatccaaaca ccattctaaa ggagtcttac ctacttctaa 129900
aggctggtct ctacttggaa ccacttgctt ggccctggtt caagtcctgc tgcaaacctg 129960
gaagtcctgt cattgtcttc ttccctccag agcagtggca cccaatctaa tttttgctgt 130020
gccccagcag cccctggcac tttgccctgt agactgcaga cctcatgtaa tgtatgttaa 130080
gtccacagaa ccacagaaga tgatggcaag atgctcttgt gtgtgttgtg ttctaggagg 130140
tggccaggtg gaagtaaaat ctgagaagct tgacttcaag gacagagtcc agtcgaagat 130200
tgggtccctg gacaatatca cccacgtccc tggcggagga aataaaaagg taaagggggt 130260
agggtgggtt ggatgctgcc cttgggtata tgggcattaa tcaagttgag tggacaaagg 130320
ctggtccagt tcccagagga ggaaaacaga ggcttctgtg ttgactggct ggatgtgggc 130380
cctcagcagc atccagtggg tctccactgc ctgtctcaat cacctggagc tttagcacgt 130440
ttcacacctg ggccccaacc tggagaggct gaccaatggg tctcaggggc agctcggttg 130500
ctggagtttt tgtttttatt tatttttatg tatttaaggc agggtctctg tattagtcca 130560
ttctcacact gctaataaag acatacccaa gactgggtaa tttataaagg aaagaggttt 130620
aatggactca cagttccaca tggctgggga ggcctcaaaa tcatggcgga aggcaaagga 130680
gaagcaaagg catttcttac atggcgacag gcaagagagc gtgtgcaggg gaactcccat 130740
ttataaaacc atcagacctc atgagattta ttcactatca tgagaacagc atgggaaaga 130800
cccgccccca tgattcagtt acctcccact gggtccctcc catgacacat ggaattatgg 130860
gagctacaat tcaagatgag atttgggtgg ggacacagcc aaaccatatc agtctccctc 130920
tgtcatccag gctggagtgc actggcatga tctcggctca ctgcagcctc tacctccctg 130980
ggtcaggtga tcttcccacc tcagcctccc aggtagctgg aactacaggt acctgccact 131040
atgcctggct aaatattttg tatttcctgt ggagacgagg ttttgccacg ttgcccaggc 131100
tggtcttgaa ctcctgaggt caagcaatat gcccacctcg gcctcccaag gtgctgggat 131160
tacaggtgtg agccacagtg ctcggcctaa gtcactgcag tttttaaagc tcccaggtga 131220
ttcttcagtg cagtcaaaag tgagaactgg ctgggtgcgg tggctcatgc ctgtaatccc 131280
agcaccttgg gaggcgaagg tggcagatg gcttgaggtc aggagttcaa gaccagcctg 131340
gccaacatgg taaaacccca tctctactaa aaatacaaaa gttagctggg tgtggtggtg 131400
cgtgcctgta atcccagcta cttgggaggc tgaggcatga gaattgcttg aacccagggg 131460
acagaggttg tagtgagccg agatcgtgcc actgcactcc agcctgggca acagagtgag 131520
attccatctc acaaaaaaaa aaaaaaaagc gagaaccact gtcctaggcc ctgatgtttg 131580
caggcaacta aaaaaggaag tggacatccc cagtcagctg tggcgcacca agaacaagtc 131640
atgggaacat aacctaattt tctaaatggg ttactaggca cttagagcaa aacaatgatg 131700
ccgaaatcct gatttcagca aagcctctgc ctgcctgtct tggaagtatc cacatgaggc 131760
tgctggggcc ttggtgtccc cagcagtttc tagtctctag gtcttgctgt gggtgtctgt 131820
gcagtgaggg tgtgtgtggc gctgggtgag ctctgtctag gcctggcaca ggatgcggtc 131880
tggtagctgc tgcttctctt ctgcagaagc gcagccaagc accctctggg gtttcaggcc 131940
cacacccagc ctgaagttct gggagtggct cactttccaa ccttcagggt ctcccagcag 132000

-continued ctgactgggg agtggtggag ggaaaaggga ttgtattagt ccgttttcac gccgctgatg 132060
aagacatacc cgatactggg cagtctaaaa gatagaggtc tgatggactc acagttccac 132120
gtgactgggg aggcctgaca atcatggtgg aaggtgaaag gcttgtctca cacggtggca 132180
gacaagagaa aagagcttgt gcaggggaac tcccctttat aaaaccatca gatctcggga 132240
gacttattca ctatcatgag aacagcacgg gaaagaccct cctctatgat tcaattacct 132300
cccaccaggt ccctcccaca acatgtagga attgtgggaa ctacaattca agatgacatt 132360
tgggtgggga cacagccaaa ccatatcagg gcgtcccaga aagggtatag ggtctgagac 132420
ccaagtcagc atgagaaagt atgcttctca tggtggccca gttgggtgga agtggcagcc 132480
gggccgtctt tccaccaggc cactcaagta gcagctgaga gacccctgcc ctggccagtc 132540
cccgccctcc cctcttgcca ctgcctctgg ttctgaacag atgggcaccc tcatcttgta 132600
tttgtgatta atgtctaaca atgtagtttt gtgagaaggg tttgctgata cagccttgct 132660
gcagatgctg cgaactgtgg cctggggcag accttacctc cagacacgcc ctgaggcagg 132720
ggagggcact ggcccgtagc tggccgagag ctctcgggtt gcgcgacagg gatacttttc 132780
agcggctggg tcgctatcca aagtgagaaa acgaggaggg accaggaggc tgtccgcctc 132840
aagagatgtg gggggccaggt ccagttatct ggggaagcag taagcttctc tgctgtttct 132900
aaccccaggc ctcccctggt ctaaggcagg gcctcccagc ctcggggcac tttaaagata 132960
tctgggcctg gccccatccc cacagtctga ctgagtgggt ctggataggg cctgagcatt 133020
ggtgatttcc tgggtgaaag gaggcccctc acagtctctg gaagcttctc tgtgttagga 133080
aaagctctgg gcttgactct gctttgaaag tcaagatccg caaatcctct cagcctcagt 133140
ttctccttca gcaagatgaa atggaaatgc tgtacctacg tcccggggtg gttgtgagac 133200
ccaaaaaaga caatgttctg gaaggttcct ggtgcgttgc agtcctctaa gaacctgagt 133260
tagagccacg ctgagtctca gcttcttggc tccttctgtt tcaaactcgt ccatgtgata 133320
gctcaggaag ggtaggcagg gccctgcccc ctactcagaa aacaccatcc tggtcctggg 133380
gatccccgca gcattagtcc cctgttttcc cagtgtattg agaaaaattg ctaacaagca 133440
gtggggcaca ccaccagcct cctgggttcc tttcagtttg gggatttttg gacattccca 133500
ggaatgtctt aaaaaacact tcaaaaaaca ttaacataaa tatttttatc aaagcctgta 133560
ttaaatggtc tttcaagaaa atacagtaac aggtcaggca tggtggctca tgcctgtaac 133620
cccagcactt tgggaggcca aggcaggcag atcacctgaa atcaggagtt caagaccaac 133680
ctggccaaca cagccaaatc ccatctctac aaaaaataca aaaattagct gggtgtggtg 133740
gcacacacct gtagtcccag ctacttggga ggccgaggca ggagaattgc ttgatcccgg 133800
aggcggaggt tgcagtgagc tgagatcgtg ccactgcact ccagcgtggg tgacaaggtg 133860
aatctttgtc tcaaaaaaaa aaaaaaaaaa aagataaaat acagtataca gtaatagaga 133920
acaatccttt tttcaaagta gtgaccccaa atgaacaaaa tatgcatcta gcttaaatgc 133980
gaacctggtt ttctctacgc ccattcaagc ccctgcaata ggggcccttc accccgcatc 134040
catggactcc taaaattata tggaaaatgg ctgtgtgtga gtgtggatgg acatgtgcac 134100
acatattttt ggctttacca gatgctcaaa gagcctagga cccaaaaagg gctgagaatg 134160
accgtgtcgg ccacttcagg gtcatcagga attgctgtgc actgctcact tctccagtga 134220
acactttctg cttctgtgtt tcctggtatc ctttgggact cctggctagg tcatgtgttt 134280
ctctactttc aaaagggctt cagccaggca cgatggcatg agcctgtagt cccagttgct 134340
ctggaggtta aggtgggaag attgcttgag cccaggaatt tgaggccagc ctgggcaagt 134400

-continued agataggtag atgattgata gatagataga tagataaata gatggataga taagtcgcta 134460
gacagtcatc catccaccca tccacacata aaaaggcctt tgtcatgtca tgttttgtgg 134520
cccacctgcc agtgttgccc acagttgctg cccctccaaa ctcatcagtc actggcaaac 134580
aggaggaatg tgtggctcat gtctgggcat cagtggctgt gggagacatc cttgatcttc 134640
tccagcttct ccttccacat tttcctttgc aatctggcaa tatctattaa aataaaatgt 134700
gcatgccttt tgacctaaga gcttcacttc taggacccac ttacacgtgt gtgacatgat 134760
gttcatacgg gtttatttat ctgaggttgt tcatacacac cattgcctgt aatcactaaa 134820
ggcgggagca gcctacacat ccatccacag aggagtagat gccttttggt acatccgtgg 134880
cgacggaata ctaagcagcc tgtgtatcta tacactcaca cgtgtttgtt tatgtgtgga 134940
atatctctgg agggtacaca agaaacttaa aatgatcact gtctctgggg agggtacctg 135000
ggtgcctggg aggcaggtca gggaaggagt gggcacaggt attaccaatt ggaagacaat 135060
aaaaacaaca gctcctggcc aggcgcagtg gctcacgcct gtaatggcag cactctgaga 135120
ggctgaggcg ggcagattgc ttgcgtccag gagttcaaga ccagcctggg caacatagca 135180
aaaccccgtt tctattaaaa atacaaaaaa ttagccaggt gtggtggcat gcacctgtaa 135240
tcccagctac tcgggaggct gaggtgggag aatcacctga gcctgggagg tcaaggctgc 135300
agtgaggtga gattgtgcca ccgcactcta gcctgggcga tagagcaaga ccctgtctca 135360
aaaacaaaca aaaaacagtc cctggcactc tgggccaggc ctggcagggc agttggcagg 135420
gctggtcttt ctctggcact tcatctcacc ctccctccct tcctcttctt gcagattgaa 135480
acccacaagc tgaccttccg cgagaacgcc aaagccaaga cagaccacgg ggcggagatc 135540
gtgtacaagt cgccagtggt gtctggggac acgtctccac ggcatctcag caatgtctcc 135600
tccaccggca gcatcgacat ggtagactcg ccccagctcg ccacgctagc tgacgaggtg 135660
tctgcctccc tggccaagca gggtttgtga tcaggcccct ggggcggtca ataattgtgg 135720
agaggagaga atgagagagt gtggaaaaaa aaagaataat gacccggccc ccgccctctg 135780
cccccagctg ctcctcgcag ttcggttaat tggttaatca cttaacctgc ttttgtcact 135840
cggctttggc tcgggacttc aaaatcagtg atgggagtaa gagcaaattt catctttcca 135900
aattgatggg tgggctagta ataaaatatt taaaaaaaaa cattcaaaaa catggccaca 135960
tccaacattt cctcaggcaa ttccttttga ttcttttttc ttccccctcc atgtagaaga 136020
gggagaagga gaggctctga aagctgcttc tgggggattt caagggactg ggggtgccaa 136080
ccacctctgg ccctgttgtg ggggtgtcac agaggcagtg gcagcaacaa aggatttgaa 136140
acttggtgtg ttcgtggagc cacaggcaga cgatgtcaac cttgtgtgag tgtgacgggg 136200
gttggggtgg ggcgggaggc cacgggggag gccgaggcag gggctgggca gaggggagag 136260
gaagcacaag aagtgggagt gggagaggaa gccacgtgct ggagagtaga catccccctc 136320
cttgccgctg ggagagccaa ggcctatgcc acctgcagcg tctgagcggc cgcctgtcct 136380
tggtggccgg gggtgggggc ctgctgtggg tcagtgtgcc accctctgca gggcagcctg 136440
tgggagaagg gacagcgggt aaaaagagaa ggcaagctgg caggagggtg gcacttcgtg 136500
gatgacctcc ttagaaaaga ctgaccttga tgtcttgaga gcgctggcct cttcctccct 136560
ccctgcaggg tagggggcct gagttgaggg gcttccctct gctccacaga aaccctgttt 136620
tattgagttc tgaaggttgg aactgctgcc atgattttgg ccactttgca gacctgggac 136680
tttagggcta accagttctc tttgtaagga cttgtgcctc ttgggagacg tccacccgtt 136740

-continued tccaagcctg ggccactggc atctctggag tgtgtggggg tctgggaggc aggtcccgag 136800
ccccctgtcc ttcccacggc cactgcagtc accccgtctg cgccgctgtg ctgttgtctg 136860
ccgtgagagc ccaatcactg cctatacccc tcatcacacg tcacaatgtc ccgaattccc 136920
agcctcacca ccccttctca gtaatgaccc tggttggttg caggaggtac ctactccata 136980
ctgagggtga aattaaggga aggcaaagtc caggcacaag agtgggaccc cagcctctca 137040
ctctcagttc cactcatcca actgggaccc tcaccacgaa tctcatgatc tgattcggtt 137100
ccctgtctcc tcctcccgtc acagatgtga gccagggcac tgctcagctg tgaccctagg 137160
tgtttctgcc ttgttgacat ggagagagcc ctttcccctg agaaggcctg gccccttcct 137220
gtgctgagcc cacagcagca ggctgggtgt cttggttgtc agtggtggca ccaggatgga 137280
agggcaaggc acccagggca ggcccacagt cccgctgtcc cccacttgca ccctagcttg 137340
tagctgccaa cctcccagac agcccagccc gctgctcagc tccacatgca tagtatcagc 137400
cctccacacc cgacaaaggg gaacacaccc ccttggaaat ggttcttttc ccccagtccc 137460
agctggaagc catgctgtct gttctgctgg agcagctgaa catatacata gatgttgccc 137520
tgccctcccc atctgcaccc tgttgagttg tagttggatt tgtctgttta tgcttggatt 137580
caccagagtg actatgatag tgaaaagaaa aaaaaaaaaa aaaaaggacg catgtatctt 137640
gaaatgcttg taaagaggtt tctaacccac cctcacgagg tgtctctcac ccccacactg 137700
ggactcgtgt ggcctgtgtg gtgccaccct gctggggcct cccaagtttt gaaaggcttt 137760
cctcagcacc tgggacccaa cagagaccag cttctagcag ctaaggaggc cgttcagctg 137820
tgacgaaggc ctgaagcaca ggattaggac tgaagcgatg atgtcccctt ccctacttcc 137880
ccttggggct ccctgtgtca gggcacagac taggtcttgt ggctggtctg gcttgcggcg 137940
cgaggatggt tctctctggt catagcccga agtctcatgg cagtcccaaa ggaggcttac 138000
aactcctgca tcacaagaaa aaggaagcca ctgccagctg gggggatctg cagctcccag 138060
aagctccgtg agcctcagcc acccctcaga ctgggttcct ctccaagctc gccctctgga 138120
ggggcagcgc agcctcccac caagggccct gcgaccacag cagggattgg gatgaattgc 138180
ctgtcctgga tctgctctag aggcccaagc tgcctgcctg aggaaggatg acttgacaag 138240
tcaggagaca ctgttcccaa agccttgacc agagcacctc agcccgctga ccttgcacaa 138300
actccatctg ctgccatgag aaaagggaag ccgcctttgc aaaacattgc tgcctaaaga 138360
aactcagcag cctcaggccc aattctgcca cttctggttt gggtacagtt aaaggcaacc 138420
ctgagggact tggcagtaga aatccagggc ctcccctggg gctggcagct tcgtgtgcag 138480
ctagagcttt acctgaaagg aagtctctgg gcccagaact ctccaccaag agcctccctg 138540
ccgttcgctg agtcccagca attctcctaa gttgaaggga tctgagaagg agaaggaaat 138600
gtggggtaga tttggtggtg gttagagata tgccccccctc attactgcca acagtttcgg 138660
ctgcatttct tcacgcacct cggttcctct tcctgaagtt cttgtgccct gctcttcagc 138720
accatgggcc ttcttatacg gaaggctctg ggatctcccc cttgtggggc aggctcttgg 138780
ggccagccta agatcatggt ttagggtgat cagtgctggc agataaattg aaaaggcacg 138840
ctggcttgtg atcttaaatg aggacaatcc ccccagggct gggcactcct cccctcccct 138900
cacttctccc acctgcagag ccagtgtcct tgggtgggct agataggata tactgtatgc 138960
cggctccttc aagctgctga ctcactttat caatagttcc atttaaattg acttcagtgg 139020
tgagactgta tcctgtttgc tattgcttgt tgtgctatgg ggggaggggg gaggaatgtg 139080
taagatagtt aacatgggca aagggagatc ttggggtgca gcacttaaac tgcctcgtaa 139140

```
ccctttcat gatttcaacc acatttgcta gagggaggga gcagccacgg agttagaggc 139200
ccttggggtt tctcttttcc actgacaggc tttcccaggc agctggctag ttcattccct 139260
ccccagccag gtgcaggcgt aggaatatgg acatctggtt gctttggcct gctgccctct 139320
ttcaggggtc ctaagcccac aatcatgcct ccctaagacc ttggcatcct tccctctaag 139380
ccgttggcac ctctgtgcca cctctcacac tggctccaga cacacagcct gtgcttttgg 139440
agctgagatc actcgcttca ccctcctcat ctttgttctc caagtaaagc cacgaggtcg 139500
gggcgagggc agaggtgatc acctgcgtgt cccatctaca gacctgcagc ttcataaaac 139560
ttctgatttc tcttcagctt tgaaaagggt taccctgggc actggcctag agcctcacct 139620
cctaatagac ttagccccat gagtttgcca tgttgagcag gactatttct ggcacttgca 139680
agtcccatga tttcttcggt aattctgagg gtggggggag ggacatgaaa tcatcttagc 139740
ttagctttct gtctgtgaat gtctatatag tgtattgtgt gttttaacaa atgatttaca 139800
ctgactgttg ctgtaaaagt gaatttggaa ataaagttat tactctgatt aaataaggtc 139860
tccattcatg gattccaagg acaagaaagt catatagaat gtctattttt taagttcttt 139920
cccacgcacc cttagataat ttagctcaga acaggaaatg atagtattaa taaaagctgg 139980
acatcaggat taacagctct ctctggggcc ctgaaggtga gagttctcag acttgctcat 140040
ttgcagttgc ttctttgtga tgctggcaaa ccatcctagt cccattcaaa gggcaataca 140100
aagccttgtg gctgacctca cgatgcagca ctcagtttgc aagaccggca ccagtgtatg 140160
caaacctgag aaggttgggg atgaggatat gggatctttc atccctggaa atttagtcca 140220
gaggcctggg gctggagcag aacaccaagc caatcagctt aatgaatggc ttagattcct 140280
gctaggtttg cagagctgcc ttctttcctt tggtacctta ttatagattg aggagtattt 140340
ctgctaaacc aagataggga taaccagata gcatcttcat agcaatgcca caaaggaaaa 140400
caaaaacaaa acagtaatcc atcatattat tccttagtaa ctatgccaag gtcatgatac 140460
tgaatcctta gattgtttca aaatactact tttctttgct cttcctgatg tgtttgccac 140520
cgcaggcaga tgtttaagta aaacagattt taactgcagc tacaaaagca gcaacaggcc 140580
agcaaaagag aagtgctatc tcagagagca tggctttcag agccacaaga gacagcctca 140640
ctggctgttt cagcttgact gccatgcaaa gaagagagca gagggagaac cagcccccacc 140700
cacttattca tcttgtacaa aaaaaaagca cctaccagcc taggctacat agtgagacac 140760
tatctccaca aaaaacccac gaaaactagc tgggtatggt ggcacatgcc tacagtccca 140820
gctactggta aggctgtggt gggaggatct cttgaggcca ggaaggagat ccaggctgca 140880
gtgagccaag attgcaccac tgcactccag tctggacaat cgagcaagat cccatctcaa 140940
acaataaaaa aaaaaagcgt gtaacctcct cagaagaaag atgttataat ctcaggcagc 141000
a                                                                 141001
```

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2

```
cactgagaac ctgaagcacc                                               20
```

<210> SEQ ID NO 3

```
<211> LENGTH: 21
<212> TYPE: DNA
<213> ORGANISM: Artificial sequence
<220> FEATURE:
<223> OTHER INFORMATION: Primer

<400> SEQUENCE: 3

ggactggacg ttgctaagat c                                              21

<210> SEQ ID NO 4
<211> LENGTH: 26
<212> TYPE: DNA
<213> ORGANISM: Artificial sequence
<220> FEATURE:
<223> OTHER INFORMATION: Probe

<400> SEQUENCE: 4

ttaattatct gcaccttccc gcctcc                                         26

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5

ggataatatc aaacacgtcc cg                                             22

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6

tgcctaatga gccacacttg                                                20

<210> SEQ ID NO 7
<211> LENGTH: 24
<212> TYPE: DNA
<213> ORGANISM: Artificial sequence
<220> FEATURE:
<223> OTHER INFORMATION: Probe

<400> SEQUENCE: 7

gtctacaaac cagttgacct gagc                                           24

<210> SEQ ID NO 8
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 8

cccgcctact tgctcgca                                                  18

<210> SEQ ID NO 9
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 9
```

tggacccgcc tacttgct 18

<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 10
accctggacc cgcctact 18

<210> SEQ ID NO 11
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 11
catgcgccac cctggacc 18

<210> SEQ ID NO 12
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 12
gtgacatgcg ccaccctg 18

<210> SEQ ID NO 13
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 13
atgagtgaca tgcgccac 18

<210> SEQ ID NO 14
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 14
ttcgatgagt gacatgcg 18

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15
cactttcgat gagtgaca 18

<210> SEQ ID NO 16
<211> LENGTH: 18
<212> TYPE: DNA

<213> ORGANISM: Artificial sequence
<220> FEATURE:
<223> OTHER INFORMATION: Synthetic oligonucleotide

<400> SEQUENCE: 16
cctccacttt cgatgagt 18

<210> SEQ ID NO 17
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 17
gacgcctcca ctttcgat 18

<210> SEQ ID NO 18
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 18
caaggacgcc tccacttt 18

<210> SEQ ID NO 19
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 19
ctcgcaagga cgcctcca 18

<210> SEQ ID NO 20
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 20
cttgctcgca aggacgcc 18

<210> SEQ ID NO 21
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 21
cctgcttgct cgcaagga 18

<210> SEQ ID NO 22
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 22
cccgcctgct tgctcgca 18

<210> SEQ ID NO 23
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 23
tggacccgcc tgcttgct 18

<210> SEQ ID NO 24
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 24
accctggacc cgcctgct 18

<210> SEQ ID NO 25
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 25
cgccaccctg gacccgcc 18

<210> SEQ ID NO 26
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 26
gacacgccac cctggacc 18

<210> SEQ ID NO 27
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 27
gagtgacacg ccaccctg 18

<210> SEQ ID NO 28
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 28
ggatgagtga cacgccac 18

<210> SEQ ID NO 29
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 29
aaaaggatga gtgacacg 18

<210> SEQ ID NO 30
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 30
agaaaaaagg atgagtga 18

<210> SEQ ID NO 31
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 31
agccagaaaa aaggatga 18

<210> SEQ ID NO 32
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 32
tggtagccag aaaaaagg 18

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
ttatcctttg agccacac 18

<210> SEQ ID NO 34
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 34
gatattatcc tttgagcc 18

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 35
gtttgatatt atcctttg 18

-continued

<210> SEQ ID NO 36
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 36
acgtgtttga tattatcc 18

<210> SEQ ID NO 37
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 37
cgggacgtgt ttgatatt 18

<210> SEQ ID NO 38
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 38
ctcccgggac gtgtttga 18

<210> SEQ ID NO 39
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 39
ccgcctcccg ggacgtgt 18

<210> SEQ ID NO 40
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 40
actgccgcct cccgggac 18

<210> SEQ ID NO 41
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 41
tcacactgcc gcctcccg 18

<210> SEQ ID NO 42
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 42
gtactcacac tgccgcct 18

<210> SEQ ID NO 43
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 43
gaaggtactc acactgcc 18

<210> SEQ ID NO 44
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 44
gtgtgaaggt actcacac 18

<210> SEQ ID NO 45
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 45
ggacgtgtga aggtactc 18

<210> SEQ ID NO 46
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 46
catgggacgt gtgaaggt 18

<210> SEQ ID NO 47
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 47
ggcgcatggg acgtgtga 18

<210> SEQ ID NO 48
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 48
gcacggcgca tgggacgt 18

<210> SEQ ID NO 49
<211> LENGTH: 18

<212> TYPE: DNA
<213> ORGANISM: Artificial sequence
<220> FEATURE:
<223> OTHER INFORMATION: Synthetic oligonucleotide

<400> SEQUENCE: 49
cacagcacgg cgcatggg 18

<210> SEQ ID NO 50
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 50
aagccacagc acggcgca 18

<210> SEQ ID NO 51
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 51
attcaagcca cagcacgg 18

<210> SEQ ID NO 52
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 52
aataattcaa gccacagc 18

<210> SEQ ID NO 53
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 53
tcctaataat tcaagcca 18

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 54
cacttcctaa taattcaa 18

<210> SEQ ID NO 55
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 55
acaccacttc ctaataat 18

<210> SEQ ID NO 56
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 56
actcacacca cttcctaa 18

<210> SEQ ID NO 57
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 57
gtgtacgcac tcacacca 18

<210> SEQ ID NO 58
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 58
gcaagtgtac gcactcac 18

<210> SEQ ID NO 59
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 59
tctcgcaagt gtacgcac 18

<210> SEQ ID NO 60
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 60
agtgtctcgc aagtgtac 18

<210> SEQ ID NO 61
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 61
atgcagtgtc tcgcaagt 18

<210> SEQ ID NO 62
<211> LENGTH: 18
<212> TYPE: DNA
<213> ORGANISM: Artificial sequence -continued
<220> FEATURE:
<223> OTHER INFORMATION: Synthetic oligonucleotide

<400> SEQUENCE: 62
ttctatgcag tgtctcgc 18

<210> SEQ ID NO 63
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 63
tttattctat gcagtgtc 18

<210> SEQ ID NO 64
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 64
aggatttatt ctatgcag 18

<210> SEQ ID NO 65
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 65
aagaaggatt tattctat 18

<210> SEQ ID NO 66
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 66
gcccaagaag gatttatt 18

<210> SEQ ID NO 67
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 67
gagagcccaa gaaggatt 18

<210> SEQ ID NO 68
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 68
tcctgagagc ccaagaag 18

<210> SEQ ID NO 69
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 69
cagatcctga gagcccaa 18

<210> SEQ ID NO 70
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 70
cctttggtag ccagaaaa 18

<210> SEQ ID NO 71
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 71
tgcacctttg gtagccag 18

<210> SEQ ID NO 72
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 72
taattatctg cacctttg 18

<210> SEQ ID NO 73
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 73
ttcttaatta tctgcacc 18

<210> SEQ ID NO 74
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 74
cttcttctta attatctg 18

<210> SEQ ID NO 75
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 75
ccagcttctt cttaatta 18

<210> SEQ ID NO 76
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 76
agatccagct tcttctta 18

<210> SEQ ID NO 77
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 77
gctaagatcc agcttctt 18

<210> SEQ ID NO 78
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 78
cgttgctaag atccagct 18

<210> SEQ ID NO 79
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 79
tggacgttgc taagatcc 18

<210> SEQ ID NO 80
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 80
ggactggacg ttgctaag 18

<210> SEQ ID NO 81
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 81
acttggactg gacgttgc 18

<210> SEQ ID NO 82

<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 82
ccacacttgg actggacg 18

<210> SEQ ID NO 83
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 83
tgagccacac ttggactg 18

<210> SEQ ID NO 84
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 84
aaaaaggatg agtgacac 18

<210> SEQ ID NO 85
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 85
aaaaaaggat gagtgaca 18

<210> SEQ ID NO 86
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 86
gaaaaaagga tgagtgac 18

<210> SEQ ID NO 87
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 87
cagaaaaaag gatgagtg 18

<210> SEQ ID NO 88
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 88
ccagaaaaaa ggatgagt 18

<210> SEQ ID NO 89
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 89
gccagaaaaa aggatgag 18

<210> SEQ ID NO 90
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 90
tagccagaaa aaaggatg 18

<210> SEQ ID NO 91
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 91
gtagccagaa aaaaggat 18

<210> SEQ ID NO 92
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 92
ggtagccaga aaaaagga 18

<210> SEQ ID NO 93
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 93
ttggtagcca gaaaaaag 18

<210> SEQ ID NO 94
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 94
tttggtagcc agaaaaaa 18

<210> SEQ ID NO 95
<211> LENGTH: 18
<212> TYPE: DNA

<213> ORGANISM: Artificial sequence
<220> FEATURE:
<223> OTHER INFORMATION: Synthetic oligonucleotide

<400> SEQUENCE: 95
ctttggtagc cagaaaaa 18

<210> SEQ ID NO 96
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 96
acctttggta gccagaaa 18

<210> SEQ ID NO 97
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 97
cacctttggt agccagaa 18

<210> SEQ ID NO 98
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 98
gcacctttgg tagccaga 18

<210> SEQ ID NO 99
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 99
ctgcaccttt ggtagcca 18

<210> SEQ ID NO 100
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 100
tctgcacctt tggtagcc 18

<210> SEQ ID NO 101
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 101
atctgcacct ttggtagc 18

<210> SEQ ID NO 102
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 102
tatctgcacc tttggtag 18

<210> SEQ ID NO 103
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 103
ttatctgcac ctttggta 18

<210> SEQ ID NO 104
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 104
attatctgca cctttggt 18

<210> SEQ ID NO 105
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 105
aattatctgc acctttgg 18

<210> SEQ ID NO 106
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 106
ttaattatct gcaccttt 18

<210> SEQ ID NO 107
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 107
attaattatc tgcacctt 18

<210> SEQ ID NO 108
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 108
tattaattat ctgcacct 18

<210> SEQ ID NO 109
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 109
ttattaatta tctgcacc 18

<210> SEQ ID NO 110
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 110
cttattaatt atctgcac 18

<210> SEQ ID NO 111
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 111
tcttattaat tatctgca 18

<210> SEQ ID NO 112
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 112
ttcttattaa ttatctgc 18

<210> SEQ ID NO 113
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 113
cttcttatta attatctg 18

<210> SEQ ID NO 114
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 114
gcttcttatt aattatct 18

<210> SEQ ID NO 115
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 115
agcttcttat taattatc 18

<210> SEQ ID NO 116
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 116
cagcttctta ttaattat 18

<210> SEQ ID NO 117
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 117
ccagcttctt attaatta 18

<210> SEQ ID NO 118
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 118
tccagcttct tattaatt 18

<210> SEQ ID NO 119
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 119
atccagcttc ttattaat 18

<210> SEQ ID NO 120
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 120
gatccagctt cttattaa 18

<210> SEQ ID NO 121
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 121
agatccagct tcttatta 18

<210> SEQ ID NO 122
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 122
aagatccagc ttcttatt 18

<210> SEQ ID NO 123
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 123
taagatccag cttcttat 18

<210> SEQ ID NO 124
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 124
ctaagatcca gcttctta 18

<210> SEQ ID NO 125
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 125
tgctaagatc cagcttct 18

<210> SEQ ID NO 126
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 126
ttgctaagat ccagcttc 18

<210> SEQ ID NO 127
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 127
gttgctaaga tccagctt 18

<210> SEQ ID NO 128
<211> LENGTH: 18

<212> TYPE: DNA
<213> ORGANISM: Artificial sequence
<220> FEATURE:
<223> OTHER INFORMATION: Synthetic oligonucleotide

<400> SEQUENCE: 128
acgttgctaa gatccagc 18

<210> SEQ ID NO 129
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 129
gacgttgcta agatccag 18

<210> SEQ ID NO 130
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 130
ggacgttgct aagatcca 18

<210> SEQ ID NO 131
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 131
ctggacgttg ctaagatc 18

<210> SEQ ID NO 132
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 132
actggacgtt gctaagat 18

<210> SEQ ID NO 133
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 133
gactggacgt tgctaaga 18

<210> SEQ ID NO 134
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 134
tggactggac gttgctaa 18

<210> SEQ ID NO 135
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 135
ttggactgga cgttgcta 18

<210> SEQ ID NO 136
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 136
cttggactgg acgttgct 18

<210> SEQ ID NO 137
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 137
cacttggact ggacgttg 18

<210> SEQ ID NO 138
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 138
acacttggac tggacgtt 18

<210> SEQ ID NO 139
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 139
cacacttgga ctggacgt 18

<210> SEQ ID NO 140
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 140
gccacacttg gactggac 18

<210> SEQ ID NO 141
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 141
agccacactt ggactgga 18

<210> SEQ ID NO 142
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 142
gagccacact tggactgg 18

<210> SEQ ID NO 143
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 143
ttgagccaca cttggact 18

<210> SEQ ID NO 144
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 144
tttgagccac acttggac 18

<210> SEQ ID NO 145
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 145
ctttgagcca cacttgga 18

<210> SEQ ID NO 146
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 146
cctttgagcc acacttgg 18

<210> SEQ ID NO 147
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 147
tcctttgagc cacacttg 18

<210> SEQ ID NO 148
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 148
atcctttgag ccacactt 18

<210> SEQ ID NO 149
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 149
tatcctttga gccacact 18

<210> SEQ ID NO 150
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 150
attatccttt gagccaca 18

<210> SEQ ID NO 151
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 151
tattatcctt tgagccac 18

<210> SEQ ID NO 152
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 152
atattatcct ttgagcca 18

<210> SEQ ID NO 153
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 153
tgatattatc ctttgagc 18

<210> SEQ ID NO 154
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 154
ttgatattat cctttgag 18

<210> SEQ ID NO 155
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 155
tttgatatta tcctttga 18

<210> SEQ ID NO 156
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 156
tgtttgatat tatccttt 18

<210> SEQ ID NO 157
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 157
gtgtttgata ttatcctt 18

<210> SEQ ID NO 158
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 158
cgtgtttgat attatcct 18

<210> SEQ ID NO 159
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 159
gacgtgtttg atattatc 18

<210> SEQ ID NO 160
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 160
ggacgtgttt gatattat 18

<210> SEQ ID NO 161

<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 161
gggacgtgtt tgatatta 18

<210> SEQ ID NO 162
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 162
ccgggacgtg tttgatat 18

<210> SEQ ID NO 163
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 163
cccgggacgt gtttgata 18

<210> SEQ ID NO 164
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 164
tcccgggacg tgtttgat 18

<210> SEQ ID NO 165
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 165
cactgccgcc tcccggga 18

<210> SEQ ID NO 166
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 166
acactgccgc ctcccggg 18

<210> SEQ ID NO 167
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 167
cacactgccg cctcccgg 18

<210> SEQ ID NO 168
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 168
ctcacactgc cgcctccc 18

<210> SEQ ID NO 169
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 169
actcacactg ccgcctcc 18

<210> SEQ ID NO 170
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 170
tactcacact gccgcctc 18

<210> SEQ ID NO 171
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 171
ggtactcaca ctgccgcc 18

<210> SEQ ID NO 172
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 172
aggtactcac actgccgc 18

<210> SEQ ID NO 173
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 173
aaggtactca cactgccg 18

<210> SEQ ID NO 174
<211> LENGTH: 18
<212> TYPE: DNA

-continued

<213> ORGANISM: Artificial sequence
<220> FEATURE:
<223> OTHER INFORMATION: Synthetic oligonucleotide

<400> SEQUENCE: 174
tgaaggtact cacactgc 18

<210> SEQ ID NO 175
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 175
gtgaaggtac tcacactg 18

<210> SEQ ID NO 176
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 176
tgtgaaggta ctcacact 18

<210> SEQ ID NO 177
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 177
cgtgtgaagg tactcaca 18

<210> SEQ ID NO 178
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 178
acgtgtgaag gtactcac 18

<210> SEQ ID NO 179
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 179
gacgtgtgaa ggtactca 18

<210> SEQ ID NO 180
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 180
gggacgtgtg aaggtact 18

<210> SEQ ID NO 181
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 181
tgggacgtgt gaaggtac 18

<210> SEQ ID NO 182
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 182
atgggacgtg tgaaggta 18

<210> SEQ ID NO 183
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 183
gcatgggacg tgtgaagg 18

<210> SEQ ID NO 184
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 184
cgcatgggac gtgtgaag 18

<210> SEQ ID NO 185
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 185
gcgcatggga cgtgtgaa 18

<210> SEQ ID NO 186
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 186
cggcgcatgg gacgtgtg 18

<210> SEQ ID NO 187
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 187
acggcgcatg ggacgtgt 18

<210> SEQ ID NO 188
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 188
cacggcgcat gggacgtg 18

<210> SEQ ID NO 189
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 189
agcacggcgc atgggacg 18

<210> SEQ ID NO 190
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 190
cagcacggcg catgggac 18

<210> SEQ ID NO 191
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 191
acagcacggc gcatggga 18

<210> SEQ ID NO 192
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 192
atcctgagag cccaagaa 18

<210> SEQ ID NO 193
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 193
gatcctgaga gcccaaga 18

<210> SEQ ID NO 194
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 194
agatcctgag agcccaag 18

<210> SEQ ID NO 195
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 195
ccagatcctg agagccca 18

<210> SEQ ID NO 196
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 196
gccagatcct gagagccc 18

<210> SEQ ID NO 197
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 197
agccagatcc tgagagcc 18

<210> SEQ ID NO 198
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 198
ugaagguacu cacacugccg c 21

<210> SEQ ID NO 199
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 199
uaucugcacc uuugguag 18

<210> SEQ ID NO 200
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 200
tcttattaat tatctgcacc 20

<210> SEQ ID NO 201
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 201
acgcactcac accacttc 18

<210> SEQ ID NO 202
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 202
cgcctacttg ctcgcaag 18

<210> SEQ ID NO 203
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 203
gacccgccta cttgctcg 18

<210> SEQ ID NO 204
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 204
gacccgcctg cttgctcg 18

<210> SEQ ID NO 205
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 205
cctggacccg cctgcttg 18

<210> SEQ ID NO 206
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 206
cgccuacuug cucgcaag 18

<210> SEQ ID NO 207
<211> LENGTH: 18

<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (17)..(17)
<223> OTHER INFORMATION: bases at these positions are DNA

<400> SEQUENCE: 207
ccuggacccg ccugcutg 18

<210> SEQ ID NO 208
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are DNA

<400> SEQUENCE: 208
tgauauuauc cuuugagc 18

<210> SEQ ID NO 209
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are DNA

<400> SEQUENCE: 209
ttgauauuau ccuuugag 18

<210> SEQ ID NO 210
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are DNA

<400> SEQUENCE: 210
ttugauauua uccuuuga 18

<210> SEQ ID NO 211
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 211
cacuuccuaa uaauucaa 18

<210> SEQ ID NO 212
<211> LENGTH: 18
<212> TYPE: DNA
<213> ORGANISM: Artificial sequence
<220> FEATURE:

<223> OTHER INFORMATION: Synthetic oligonucleotide
<220> FEATURE:
<221> NAME/KEY: misc_feature
<222> LOCATION: (18)..(18)
<223> OTHER INFORMATION: bases at these positions are DNA

<400> SEQUENCE: 212
acaccacuuc cuaauaat 18

<210> SEQ ID NO 213
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 213
acucacacca cuuccuaa 18

<210> SEQ ID NO 214
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 214
cccgccuacu ugcucgca 18

<210> SEQ ID NO 215
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 215
gacccgccua cuugcucg 18

<210> SEQ ID NO 216
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 216
gacccgccug cuugcucg 18

<210> SEQ ID NO 217
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are DNA
<220> FEATURE:
<221> NAME/KEY: misc_feature
<222> LOCATION: (18)..(18)
<223> OTHER INFORMATION: bases at these positions are DNA

<400> SEQUENCE: 217
tggacccgcc ugcuugct 18

<210> SEQ ID NO 218
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 218
ucuuauuaau uaucugcacc 20

<210> SEQ ID NO 219
<211> LENGTH: 20
<212> TYPE: DNA
<213> ORGANISM: Artificial sequence
<220> FEATURE:
<223> OTHER INFORMATION: Primer

<400> SEQUENCE: 219
cactgagaac ctgaagcacc 20

<210> SEQ ID NO 220
<211> LENGTH: 21
<212> TYPE: DNA
<213> ORGANISM: Artificial sequence
<220> FEATURE:
<223> OTHER INFORMATION: Primer

<400> SEQUENCE: 220
gttgctaaga tccagcttct t 21

<210> SEQ ID NO 221
<211> LENGTH: 26
<212> TYPE: DNA
<213> ORGANISM: Artificial sequence
<220> FEATURE:
<223> OTHER INFORMATION: Probe

<400> SEQUENCE: 221
ttaattatct gcaccttccc gcctcc 26

<210> SEQ ID NO 222
<211> LENGTH: 22
<212> TYPE: DNA
<213> ORGANISM: Artificial sequence
<220> FEATURE:
<223> OTHER INFORMATION: Primer

<400> SEQUENCE: 222
aatatcaaac acgtcccggg ag 22

<210> SEQ ID NO 223
<211> LENGTH: 20
<212> TYPE: DNA
<213> ORGANISM: Artificial sequence
<220> FEATURE:
<223> OTHER INFORMATION: Primer

<400> SEQUENCE: 223
tgcctaatga gccacacttg 20

<210> SEQ ID NO 224
<211> LENGTH: 24
<212> TYPE: DNA
<213> ORGANISM: Artificial sequence
<220> FEATURE:
<223> OTHER INFORMATION: Probe

<400> SEQUENCE: 224
gtctacaaac cagttgacct gagc 24

<210> SEQ ID NO 225
<211> LENGTH: 21
<212> TYPE: DNA
<213> ORGANISM: Artificial sequence
<220> FEATURE:
<223> OTHER INFORMATION: Primer

<400> SEQUENCE: 225
aagattgggt ccctggacaa t 21

<210> SEQ ID NO 226
<211> LENGTH: 26
<212> TYPE: DNA
<213> ORGANISM: Artificial sequence
<220> FEATURE:
<223> OTHER INFORMATION: Primer

<400> SEQUENCE: 226
agcttgtggg tttcaatctt tttatt 26

<210> SEQ ID NO 227
<211> LENGTH: 19
<212> TYPE: DNA
<213> ORGANISM: Artificial sequence
<220> FEATURE:
<223> OTHER INFORMATION: Probe

<400> SEQUENCE: 227
cacccacgtc cctggcgga 19

<210> SEQ ID NO 228
<211> LENGTH: 20
<212> TYPE: DNA
<213> ORGANISM: Artificial sequence
<220> FEATURE:
<223> OTHER INFORMATION: Primer

<400> SEQUENCE: 228
ggcaaattca acggcacagt 20

<210> SEQ ID NO 229
<211> LENGTH: 20
<212> TYPE: DNA
<213> ORGANISM: Artificial sequence
<220> FEATURE:
<223> OTHER INFORMATION: Primer

<400> SEQUENCE: 229
gggtctcgct cctggaagat 20

<210> SEQ ID NO 230
<211> LENGTH: 27
<212> TYPE: DNA
<213> ORGANISM: Artificial sequence
<220> FEATURE:
<223> OTHER INFORMATION: Probe

<400> SEQUENCE: 230
aaggccgaga atgggaagct tgtcatc 27

<210> SEQ ID NO 231
<211> LENGTH: 20

-continued

```
<212> TYPE: DNA
<213> ORGANISM: Artificial sequence
<220> FEATURE:
<223> OTHER INFORMATION: Synthetic oligonucleotide

<400> SEQUENCE: 231

ccagcttctt attaattatc                                     20


<210> SEQ ID NO 232
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 232

taagatccag cttcttatta                                     20
```

COMPOSITIONS AND METHODS FOR MODULATING TAU EXPRESSION

SEQUENCE LISTING

The present application is being filed along with a Sequence Listing in electronic format. The Sequence Listing is provided as a file entitled BIOL0220USASEQ_ST25.txt created Sep. 14, 2015, which is approximately 228 KB in size. The information in the electronic format of the sequence listing is incorporated herein by reference in its entirety.

BACKGROUND

1. Field

Disclosed herein are compositions and methods related to the fields of antisense compounds biochemistry, molecular biology, and medicine. Embodiments described herein relate to compounds, compositions, and methods for treating, preventing, or ameliorating neurodegenerative diseases, including tauopathies, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome by inhibiting expression of Tau or modulating the splicing of Tau in a cell and/or in an animal.

2. Description

The primary function of Tau is to bind to and stabilize microtubules, which are important structural components of the cytoskeleton involved in mitosis, cytokinesis, and vesicular transport. Tau is found in multiple tissues, but is particularly abundant in axons of neurons. In humans, there are six isoforms of Tau that are generated by alternative splicing of exons 2, 3, and 10. Splicing of exons 2 and 3 at the N-terminus of the protein leads to inclusion of zero, one, or two 29 amino acid acidic domains and is termed 0N, 1N, or 2N Tau respectively. The influence of these domains on Tau function is not fully clear, though may play a role in interactions with the plasma membrane. Inclusion of exon 10 at the C-terminus leads to inclusion of the microtubule binding domain encoded by exon 10. Since there are 3 microtubule binding domains elsewhere in Tau, this Tau isoform (with exon 10 included) is termed 4R Tau, where 'R' refers to the number of repeats of microtubule binding domains. Tau without exon 10 is termed 3R Tau. Since more microtubule binding domains (4R compared with 3R) increases the binding to microtubules, 4R Tau presumably significantly increases microtubule binding and assembly. The ratio of 3R/4R Tau is developmentally regulated, with fetal tissues expressing exclusively 3R Tau and adult human tissues expressing approximately equal levels of 3R/4R Tau. Deviations from the normal ratio of 3R/4R Tau are characteristic of neurodegenerative FTD Tauopathies. It is not known how changing the 3R/4R Tau ratio at a later stage in the adult animal will affect Tau pathogenesis.

Serine-threonine directed phosphorylation regulates the microtubule binding ability of Tau. Hyperphosphorylation promotes detachment of Tau from microtubules. Other post translational modifications of Tau have been described; however the significance of these is unclear. Phosphorylation of Tau is also developmentally regulated with higher phosphorylation in fetal tissues and much lower phosphorylation in the adult. One characteristic of neurodegenerative disorders is aberrantly increased Tau phosphorylation.

The microtubule network is involved in many important processes within the cell including structural integrity needed for maintaining morphology of cells and operating transport machinery. Since binding of Tau to microtubules stabilizes microtubules, Tau is likely to be a key mediator of some of these processes and disruption of normal Tau in neurodegenerative diseases may disrupt some of these key cellular processes.

One of the early indicators that Tau may be important in neurodegenerative syndromes was the recognition that Tau is a key component of neurofibrillary inclusions in Alzheimer's disease. In fact, neurofibrillary inclusions are aggregates of hyperphosphorylated Tau protein. Along with amyloid beta containing plaques, neurofibrillary inclusions are a hallmark of Alzheimer's disease and correlate significantly with cognitive impairment. 95% of Tau accumulations in AD are found in neuronal processes and is termed neuritic dystrophy. The process(es) whereby this microtubule associated protein becomes disengaged from microtubules and forms accumulations of proteins and how this relates to neuronal toxicity is not well understood.

Neuronal Tau inclusions are a pathological characteristic of not only Alzheimer's disease, but also a subset of Frontotemporal dementia (FTD), PSP, and CBD. The link between Tau and neurodegeneration was solidified by the discovery that mutations in the Tau gene cause a subset of FTD. These genetic data have also highlighted the importance of the 3R:4R ratio of Tau. Many of the Tau mutations that cause FTD lead to a change in Tau splicing which leads to preferential inclusion of exon 10, and thus to increased 4R Tau. The overall Tau levels are normal. Whether the Tau isoform change or the amino acid change or both cause neurodegeneration remains unknown. Recent data suggest that PSP may also be associated with an increased 4R:3R Tau ratio and thus may be amenable to a similar splicing strategy.

To help understand the influence of Tau ratios on neurodegeneration, a mouse model based on one of the splicing Tau mutations (N279K) has been generated using a minigene that includes the Tau promoter and the flanking intronic sequences of exon 10. As in humans, these mice demonstrate increased levels of 4R Tau compared with transgenics expressing WT Tau and develop behavioral and motor abnormalities as well as accumulations of aggregated Tau in the brain and spinal cord.

The protein "Tau" has been associated with multiple diseases of the brain including Alzheimer's disease, frontotemporal dementia, progressive supranuclear palsy, corticobasal ganglionic degeneration, dementia pugilistica, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, corticobasal degeneration or frontotemporal lobar degeneration and others. Tau-associated disorders such as AD are the most common cause of dementia in the elderly. AD affects an estimated 15 million people worldwide and 40% of the population above 85 years of age. AD is characterized by two pathological hallmarks: Tau neurofibrillary inclusions (NFT) and amyloid-β (Aβ)plaques.

In seizure disorders, the brain's electrical activity is periodically disturbed, resulting in some degree of temporary brain dysfunction. Normal brain function requires an orderly, organized, coordinated discharge of electrical impulses. Electrical impulses enable the brain to communicate with the spinal cord, nerves, and muscles as well as within itself. Seizures may result when the brain's electrical activity is disrupted. There are two basic types of seizures;

epileptic and nonepileptic. Epileptic seizures have no apparent cause or trigger and occur repeatedly. Nonepileptic seizures are triggered orprovoked by a disorder or another condition that irritates the brain. Certain mental disorders can cause seizure symptoms referred to as psychogenic nonepileptic seizures.

Alzheimer's Disease(AD) is known to be a clinical risk factor for late onset seizures. Multiple AD mouse models recapitulate this increased seizure susceptibility. Within the last 5 years, many of these AD models have been studied in the setting of mouse tau knockout (tau−/−). Increased seizure susceptibility was ameliorated in these amyloid-depositing tau knockout lines. Further, tau−/− alone interestingly appeared to be protective against chemically induced seizures.

Anticonvulsants represent the common treatment regime for seizures. However, anticonvulsants are ineffective in a significant percent of people with a seizure disorder and for these individuals, surgery is the only option. Amidst the lack of available treatments for seizure disorders and neurodegenerative diseases, certain methods of the present embodiments provide methods for treating, preventing or ameliorating a seizure disorder and neurodegenerative diseases by inhibiting expression of Tau or modulating the splicing of Tau in an animal.

SUMMARY

Provided herein are methods for modulating splicing of Tau mRNA in cells, tissues, and animals. Also provided herein are methods for modulating the expression product of a Tau mRNA in cells, tissues, and animals.

In certain embodiments, modulation can occur in a cell or tissue. In certain embodiments, the cell or tissue is in an animal. In certain embodiments, the animal is human. In certain embodiments, Tau mRNA levels are reduced. In certain embodiments, Tau protein levels are reduced. In certain embodiments, splicing of Tau mRNA is modulated. In certain embodiments, the expression product of a Tau mRNA is modulated. In certain embodiments, exclusion of Tau exon 10 is promoted. In certain embodiments, expression of the 4R isoform of Tau RNA or protein is reduced. In certain embodiments, expression of the 3R isoform of Tau RNA or protein is increased. In certain embodiments, expression of the 4R isoform of Tau RNA or protein is reduced and expression of the 3R isoform of Tau RNA or protein is increased. In certain embodiments, hyperphosphorylated Tau is reduced. Such reduction and modulation can occur in a time-dependent manner or in a dose-dependent manner.

Several embodiments are drawn to methods of reducing or decreasing one or more symptoms of a tau-associated disorder. In certain embodiments, the symptom is a seizure. In certain embodiments, the tau-associated disorder or neurodegenerative disorder is Alzheimer's disease, frontotemporal dementia, progressive supranuclear palsy, corticobasal ganglionic degeneration, dementia pugilistica, parkinsonism linked to chromosome, Lytico¬Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, corticobasal degeneration or frontotemporal lobar degeneration. Certain embodiments are drawn to a method of decreasing seizures in a subject with a high 4R:3R tau isoform ratio. In certain embodiments, the methods comprise administering an antisense agent to the subject, wherein the agent decreases expression of tau or decreases the 4R:3R tau ratio in the central nervous system of the subject.

Also provided are methods useful for preventing, treating, and ameliorating diseases, disorders, and conditions associated with Tau. In certain embodiments, such diseases, disorders, and conditions associated with Tau are neurodegenerative diseases. In certain embodiments, the neurodegenerative disease is any of Alzheimer's Disease, Fronto-temporal Dementia (FTD), FTDP-17, Progressive Supranuclear Palsy, Chronic Traumatic Encephalopathy, Epilepsy, or Dravet's Syndrome. In certain embodiments, one or more symptoms of a neurodegenerative disease is ameliorated, prevented, or delayed (progression slowed). In certain embodiments, the symptom is memory loss, anxiety, or loss of motor function. In certain embodiments, neurodegenerative function is improved. In certain embodiments, neurofibrillary inclusions are reduced.

Such diseases, disorders, and conditions can have one or more risk factors, causes, or outcomes in common Certain risk factors and causes for development of a neurodegenerative disease include genetic predisposition and older age.

In certain embodiments, methods of treatment include administering a Tau antisense compound to an individual in need thereof. The antisense compound may inhibit expression of Tau or modulate splicing of Tau. In certain embodiments, the antisense compound is a single-stranded antisense oligonucleotide. In certain embodiments, the single-stranded antisense oligonucleotide is complementary to a Tau nucleic acid.

In certain embodiments, the present invention provides compounds comprising oligonucleotides. In certain embodiments, such oligonucleotides are complementary to a Tau transcript. In certain such embodiments, oligonucleotides are complementary to a target region of the Tau transcript comprising exon 10. In certain such embodiments, oligonucleotides are complementary to a target region of the Tau transcript comprising an intron adjacent to exon 10. In certain such embodiments, oligonucleotides are complementary to a target region of the Tau transcript comprising an intron adjacent to exon 10 and downstream of exon 10. In certain such embodiments, oligonucleotides are complementary to a target region of the Tau transcript comprising an intron adjacent to exon 10 and upstream of exon 10. In certain embodiments, the Tau transcript comprises an exonic splice silencer for exon 10. In certain embodiments, oligonucleotides inhibit inclusion of exon 10. In certain embodiments, oligonucleotides promote skipping of exon 10. In certain such embodiments, 3R Tau mRNA is increased. In certain such embodiments, Tau mRNA with exon 10 mRNA is decreased. In certain embodiments, the 4R isoform of the Tau protein is decreased. In certain embodiments, the 3R isoform of the Tau protein is increased.

In certain embodiments, including, but not limited to any of the above numbered embodiments, the Tau transcript is in a human. In certain embodiments, including, but not limited to any of the above numbered embodiments, the Tau transcript is in a mouse.

The present disclosure provides the following non-limiting numbered embodiments:

Embodiment 1. A compound comprising a modified oligonucleotide consisting of 8 to 30 linked nucleosides and having a nucleobase sequence comprising a complementary region comprising at least 8 contiguous nucleobases complementary to a target region of equal length of a Tau transcript.

Embodiment 2. The compound of embodiment 1, wherein the complementary region of the modified oligonucleotide is 100% complementary to the target region.

Embodiment 3. The compound of embodiment 1 or 2, wherein the complementary region of the nucleobase sequence of the modified oligonucleotide comprises at least 10 contiguous nucleobases.

Embodiment 4. The compound of embodiment 1 or 2, wherein the complementary region of the nucleobase sequence of the modified oligonucleotide comprises at least 15 contiguous nucleobases.

Embodiment 5. The compound of embodiment 1 or 2, wherein the complementary region of the nucleobase sequence of the modified oligonucleotide comprises at least 18 contiguous nucleobases.

Embodiment 6. The compound of any of embodiments 1-5, wherein the nucleobase sequence of the modified oligonucleotide is at least 80% complementary to an equal-length region of the Tau transcript, as measured over the entire length of the oligonucleotide.

Embodiment 7. The compound of any of embodiments 1-5, wherein the nucleobase sequence of the modified oligonucleotide is at least 90% complementary to an equal-length region of the Tau transcript, as measured over the entire length of the oligonucleotide.

Embodiment 8. The compound of any of embodiments 1-5, wherein the nucleobase sequence of the modified oligonucleotide is 100% complementary to an equal-length region of the Tau transcript, as measured over the entire length of the oligonucleotide.

Embodiment 9. The compound of any of embodiments 1-8, wherein the target region is within exon 10 of the Tau transcript.

Embodiment 10. The compound of any of embodiments 1-8, wherein the target region is within intron 9 of the Tau transcript.

Embodiment 11. The compound of any of embodiments 1-8, wherein the target region is within intron 10 of the Tau transcript.

Embodiment 12. The compound of any of embodiments 1-8, wherein the target region comprises a portion of intron 9 and a portion of exon 10.

Embodiment 13. The compound of any of embodiments 1-8, wherein the target region comprises a portion of exon 10 and a portion of intron 10.

Embodiment 14. The compound of any of embodiments 1-8, wherein the target region comprises a portion of exon 10 and a portion of the intron at the 5'-end of exon 10.

Embodiment 15. The compound of any of embodiments 1-8, wherein the target region comprises a portion of exon 10 and a portion of the intron at the 3'-end of exon 10.

Embodiment 16. The compound of any of embodiments 1-15, wherein the target region is within nucleobase 121708 and nucleobase 122044 of SEQ ID NO.: 1.

Embodiment 17. The compound of any of embodiments 1-9, wherein the target region is within nucleobase 121796 and nucleobase 122044 of SEQ ID NO.: 1.

Embodiment 18. The compound of any of embodiments 1-9, wherein the target region is within nucleobase 121796 and nucleobase 121885 of SEQ ID NO.: 1.

Embodiment 19. The compound of any of embodiments 1-9, wherein the target region is within nucleobase 121873 and nucleobase 121898 of SEQ ID NO.: 1.

Embodiment 20. The compound of any of embodiments 1-9, wherein the target region is within nucleobase 121869 and nucleobase 121943 of SEQ ID NO.: 1.

Embodiment 21. The compound of any of embodiments 1-9, wherein the target region is within nucleobase 122020 and nucleobase 122044 of SEQ ID NO.: 1.

Embodiment 22. The compound of any of embodiments 1-9, wherein the target region is within nucleobase 121881 and nucleobase 121898 of SEQ ID NO.: 1.

Embodiment 23. The compound of any of embodiments 1-9, wherein the target region is within nucleobase 121880 and nucleobase 121897 of SEQ ID NO.: 1.

Embodiment 24. The compound of any of embodiments 1-9, wherein the target region is within nucleobase 121879 and nucleobase 121896 of SEQ ID NO.: 1.

Embodiment 25. The compound of any of embodiments 1-9, wherein the target region is within nucleobase 121878 and nucleobase 121895 of SEQ ID NO.: 1.

Embodiment 26. The compound of any of embodiments 1-9, wherein the target region is within nucleobase 121877 and nucleobase 121894 of SEQ ID NO.: 1.

Embodiment 27. The compound of any of embodiments 1-9, wherein the target region is within nucleobase 121876 and nucleobase 121893 of SEQ ID NO.: 1.

Embodiment 28. The compound of any of embodiments 1-9, wherein the target region is within nucleobase 121875 and nucleobase 121892 of SEQ ID NO.: 1.

Embodiment 29. The compound of any of embodiments 1-9, wherein the target region is within nucleobase 121874 and nucleobase 121891 of SEQ ID NO.: 1.

Embodiment 30. The compound of any of embodiments 1-9, wherein the target region is within nucleobase 121873 and nucleobase 121890 of SEQ ID NO.: 1.

Embodiment 31. The compound of any of embodiments 1-15, wherein the nucleobase sequence of the modified oligonucleotide comprises the nucleobase sequence of any of SEQ ID NOs: 8-200.

Embodiment 32. The compound of any of embodiments 1-15, wherein the nucleobase sequence of the modified oligonucleotide consists of the nucleobase sequence of any of SEQ ID NOs: 8-200.

Embodiment 33. The compound of any of embodiments 1-15, wherein the nucleobase sequence of the modified oligonucleotide comprises the nucleobase sequence of any of SEQ ID NOs: 33, 34, 147, 148, 149, 150, 151, 152, or 153.

Embodiment 34. The compound of any of embodiments 1-15, wherein the nucleobase sequence of the modified oligonucleotide consists of the nucleobase sequence of any of SEQ ID NOs: 33, 34, 147, 148, 149, 150, 151, 152, or 153.

Embodiment 35. The compound of any of embodiments 1-15, wherein the nucleobase sequence of the modified oligonucleotide comprises the nucleobase sequence of any of SEQ ID NOs: 31, 33, 34, 35, 36, 37, 45, 72, 79, 82, 83, 97, 106, 107, 112, 113, 130, 140, 141, 142, 143, 144, 145, 146, 147, 148, 149, 150, 151, 152, 153, 154, 157, 158, 160, or 200.

Embodiment 36. The compound of any of embodiments 1-15, wherein the nucleobase sequence of the modified oligonucleotide consists of the nucleobase sequence of any of SEQ ID NOs: 31, 33, 34, 35, 36, 37, 45, 72, 79, 82, 83, 97, 106, 107, 112, 113, 130, 140, 141, 142, 143, 144, 145, 146, 147, 148, 149, 150, 151, 152, 153, 154, 157, 158, 160, or 200.

Embodiment 37. The compound of any of embodiments 1-36, wherein the modified oligonucleotide comprises at least one modified nucleoside.

Embodiment 38. The compound of embodiment 37, wherein at least one modified nucleoside comprises a modified sugar moiety.

Embodiment 39. The compound of embodiment 37, wherein at least one modified sugar moiety is a 2'-substituted sugar moiety.

Embodiment 40. The compound of embodiment 39, wherein the 2'-substitutent of at least one 2'-substituted sugar moiety is selected from among: 2'-OMe, 2'-F, and 2'-MOE.

Embodiment 41. The compound of embodiment 39, wherein the 2'-substituent of at least one 2'-substituted sugar moiety is a 2'-MOE.

Embodiment 42. The compound of any of embodiments 37-38, wherein at least one modified sugar moiety is a bicyclic sugar moiety.

Embodiment 43. The compound of embodiment 42, wherein at least one bicyclic sugar moiety is LNA or cEt.

Embodiment 44. The compound of any of embodiments 37-43, wherein at least one sugar moiety is a sugar surrogate.

Embodiment 45. The compound of embodiment 44, wherein at least one sugar surrogate is a morpholino.

Embodiment 46. The compound of embodiment 44, wherein at least one sugar surrogate is a modified morpholino.

Embodiment 47. The compound of any of embodiment 1-46, wherein the modified oligonucleotide comprises at least 5 modified nucleosides, each independently comprising a modified sugar moiety.

Embodiment 48. The compound of embodiment 47, wherein the modified oligonucleotide comprises at least 10 modified nucleosides, each independently comprising a modified sugar moiety.

Embodiment 49. The compound of embodiment 47, wherein the modified oligonucleotide comprises at least 15 modified nucleosides, each independently comprising a modified sugar moiety.

Embodiment 50. The compound of embodiment 47, wherein each nucleoside of the modified oligonucleotide is a modified nucleoside and each independently comprises a modified sugar moiety, wherein the modified sugar moieties of each modified nucleosides are each the same as one another.

Embodiment 51. The compound of embodiment 47, wherein each nucleoside of the modified oligonucleotide is a modified nucleoside, each independently comprising a modified sugar moiety.

Embodiment 52. The compound of any of embodiments 1-51, wherein the modified oligonucleotide comprises at least two modified nucleosides comprising modified sugar moieties that are the same as one another.

Embodiment 53. The compound of any of embodiments 1-52, wherein the modified oligonucleotide comprises at least two modified nucleosides comprising modified sugar moieties that are different from one another.

Embodiment 54. The compound of any of embodiments 1-53, wherein the modified oligonucleotide comprises a modified region comprising at least 5 contiguous modified nucleosides.

Embodiment 55. The compound of embodiment 54, wherein the modified oligonucleotide comprises a modified region comprising at least 10 contiguous modified nucleosides.

Embodiment 56. The compound of embodiment 54, wherein the modified oligonucleotide comprises a modified region comprising at least 15 contiguous modified nucleosides.

Embodiment 57. The compound of embodiment 54, wherein the modified oligonucleotide comprises a modified region comprising at least 18 contiguous modified nucleosides.

Embodiment 58. The compound of embodiment 54, wherein the modified oligonucleotide comprises a modified region comprising at least 20 contiguous modified nucleosides.

Embodiment 59. The compound of any of embodiments 53-58, wherein each modified nucleoside of the modified region has a modified sugar moiety independently selected from among: 2'-F, 2'-OMe, 2'-MOE, cEt, LNA, morpholino, and modified morpholino.

Embodiment 60. The compound of any of embodiments 54-59, wherein the modified nucleosides of the modified region each comprise the same modification as one another.

Embodiment 61. The compound of embodiment 60, wherein the modified nucleosides of the modified region each comprise the same 2'-substituted sugar moiety.

Embodiment 62. The compound of embodiment 61, wherein the 2'-substituted sugar moiety of the modified nucleosides of the region of modified nucleosides is selected from 2'-F, 2'-OMe, and 2'-MOE.

Embodiment 63. The compound of embodiment 61, wherein the 2'-substituted sugar moiety of the modified nucleosides of the region of modified nucleosides is 2'-MOE.

Embodiment 64. The compound of embodiment 59, wherein the modified nucleosides of the region of modified nucleosides each comprise the same bicyclic sugar moiety.

Embodiment 65. The compound of embodiment 64, wherein the bicyclic sugar moiety of the modified nucleosides of the region of modified nucleosides is selected from LNA and cEt.

Embodiment 66. The compound of embodiment 59, wherein the modified nucleosides of the region of modified nucleosides each comprises a sugar surrogate.

Embodiment 67. The compound of embodiment 66, wherein the sugar surrogate of the modified nucleosides of the region of modified nucleosides is a morpholino.

Embodiment 68. The compound of embodiment 66, wherein the sugar surrogate of the modified nucleosides of the region of modified nucleosides is a modified morpholino.

Embodiment 69. The compound of any of embodiments 1-68, wherein the modified nucleotide comprises no more than 4 contiguous naturally occurring nucleosides.

Embodiment 70. The compound of any of embodiments 1-68, wherein each nucleoside of the modified oligonucleotide is a modified nucleoside.

Embodiment 71. The compound of embodiment 70 wherein each modified nucleoside comprises a modified sugar moiety.

Embodiment 72. The compound of embodiment 71, wherein the modified nucleosides of the modified oligonucleotide comprise the same modification as one another.

Embodiment 73. The compound of embodiment 72, wherein the modified nucleosides of the modified oligonucleotide each comprise the same 2'-substituted sugar moiety.

Embodiment 74. The compound of embodiment 73, wherein the 2'-substituted sugar moiety of the modified oligonucleotide is selected from 2'-F, 2'-OMe, and 2'-MOE.

Embodiment 75. The compound of embodiment 74, wherein the 2'-substituted sugar moiety of the modified oligonucleotide is 2'-MOE.

Embodiment 76. The compound of embodiment 72, wherein the modified nucleosides of the modified oligonucleotide each comprise the same bicyclic sugar moiety.

Embodiment 77. The compound of embodiment 76, wherein the bicyclic sugar moiety of the modified oligonucleotide is selected from LNA and cEt.

Embodiment 78. The compound of embodiment 72, wherein the modified nucleosides of the modified oligonucleotide each comprises a sugar surrogate.

Embodiment 79. The compound of embodiment 78, wherein the sugar surrogate of the modified oligonucleotide is a morpholino.

Embodiment 80. The compound of embodiment 78, wherein the sugar surrogate of the modified oligonucleotide is a modified morpholino.

Embodiment 81. The compound of any of embodiments 1 to 36, wherein the modified oligonucleotide has an $A-B_2-A-B_2-A-B_2-A-B_2-A-B_2-A-B_2-A_2$ motif, wherein each A comprises a bicyclic sugar moiety, and wherein each B is selected from a 2'-substituted sugar moiety and an unmodified 2'-deoxy sugar moiety.

Embodiment 82. The compound of embodiment 81, wherein each A is a cEt sugar moiety.

Embodiment 83. The compound of embodiment 81, wherein each A is an LNA sugar moiety.

Embodiment 84. The compound of any of embodiments 81 to 83, wherein each B is an unmodified 2'-deoxy sugar moiety.

Embodiment 85. The compound of any of embodiments 81 to 83, wherein each B is 2'-MOE sugar moiety.

Embodiment 86. The compound of any of embodiments 1-85, wherein the modified oligonucleotide comprises at least one modified internucleoside linkage.

Embodiment 87. The compound of embodiment 86, wherein each internucleoside linkage is a modified internucleoside linkage.

Embodiment 88. The compound of embodiment 86 or 87, comprising at least one phosphoro-thioate internucleoside linkage.

Embodiment 89. The compound of any of embodiments 1-85, wherein each internucleoside linkage is a modified internucleoside linkage and wherein each internucleoside linkage comprises the same modification.

Embodiment 90. The compound of embodiment 89, wherein each internucleoside linkage is a phosphorothioate internucleoside linkage.

Embodiment 91. The compound of embodiment 86, wherein the modified oligonucleotide comprises 4 phosphodiester internucleoside linkages.

Embodiment 92. The compound of embodiment 86, wherein the modified oligonucleotide comprises 5 phosphodiester internucleoside linkages.

Embodiment 93. The compound of embodiment 86, wherein the modified oligonucleotide comprises 6 phosphodiester internucleoside linkages.

Embodiment 94. The compound of embodiment 86, wherein the modified oligonucleotide comprises 7 phosphodiester internucleoside linkages.

Embodiment 95. The compound of any of embodiments 91 to 94, wherein each remaining internucleoside linkage is a phosphodiester internucleoside linkage.

Embodiment 96. The compound of any of embodiments 1-85, wherein the compound has an $N_SN_SN_ON_SN_O N_SN_ON_SN_ON_SN_ON_SN_ON_SN_ON_SN_SN$ internucleoside linkage motif, wherein each N represents a nucleoside, each S represents a phosphorothioate internucleoside linkage, and each 0 represents a phosphodiester internucleoside linkage.

Embodiment 97. The compound of any of embodiments 1-85, wherein the compound has an $N_SN_ON_ON_ON_SN_S$ $N_SN_SN_SN_SN_SN_SN_ON_ON_ON_SN_SN$ internucleoside linkage motif, wherein each N represents a nucleoside, each S represents a phosphorothioate internucleoside linkage, and each 0 represents a phosphodiester internucleoside linkage.

Embodiment 98. The compound of any of embodiments 1-97 comprising at least one conjugate.

Embodiment 99. The compound of any of embodiments 1-98 consisting of the modified oligonucleotide.

Embodiment 100. The compound of any of embodiments 1-99, wherein the compound modulates splicing of the Tau transcript.

Embodiment 101. The compound of any of embodiments 1-99, wherein the compound decreases expression of the 4R Tau isoform.

Embodiment 102. The compound of any of embodiments 1-99, wherein the compound decreases expression Tau mRNA comprising exon 10.

Embodiment 103. The compound of any of embodiments 1-99, wherein the compound decreases expression Tau protein comprising amino acids encoded from exon 10 mRNA.

Embodiment 104. The compound of any of embodiments 1-8 or 30-103, having a nucleobase sequence comprising any of the sequences as set forth in SEQ ID NOs. 8-200.

Embodiment 105. The compound of any of embodiments 1-8 or 30-103, having a nucleobase sequence comprising any of the sequences as set forth in SEQ ID NOs. 33, 34, 147, 148, 149, 150, 151, 152, or 153.

Embodiment 106. The compound of any of embodiments 1-8 or 30-103, having a nucleobase sequence consisting of any of the sequences as set forth in SEQ ID NOs. 8-200.

Embodiment 107. The compound of any of embodiments 1-8 or 30-103, having a nucleobase sequence consisting of any of the sequences as set forth in SEQ ID NOs. 33, 34, 147, 148, 149, 150, 151, 152, or 153.

Embodiment 108. A double stranded compound comprising the compound of any of embodiments 1-107.

Embodiment 109. A compound consisting of ISIS 670011.

Embodiment 110. A compound consisting of ISIS 670012.

Embodiment 111. A compound consisting of ISIS 670013.

Embodiment 112. A compound consisting of ISIS 670014.

Embodiment 113. A compound consisting of ISIS 670015.

Embodiment 114. A compound consisting of ISIS 670016.

Embodiment 115. A compound consisting of ISIS 670017.

Embodiment 116. A compound consisting of ISIS 670018.

Embodiment 117. A compound consisting of ISIS 670019.

Embodiment 118. A compound consisting of ISIS 670020.

Embodiment 119. A compound consisting of ISIS 670021.

Embodiment 120. A compound consisting of ISIS 670022.

Embodiment 121. A compound consisting of ISIS 670023.

Embodiment 122. A compound consisting of ISIS 670024.

Embodiment 123. A compound consisting of ISIS 670025.

Embodiment 124. A compound consisting of ISIS 670026.

Embodiment 125. A compound consisting of ISIS 670027.

Embodiment 126. A compound consisting of ISIS 670028.

Embodiment 127. A compound consisting of ISIS 678329.

Embodiment 128. A compound consisting of ISIS 678330.

Embodiment 129. A compound consisting of ISIS 678331.

Embodiment 130. A compound consisting of ISIS 678332.

Embodiment 131. A compound consisting of ISIS 678333.

Embodiment 132. A compound consisting of ISIS 678334.

Embodiment 133. A compound consisting of ISIS 693840.

Embodiment 134. A compound consisting of ISIS 693841.

Embodiment 135. A compound consisting of ISIS 693842.

Embodiment 136. A compound consisting of ISIS 693843.

Embodiment 137. A compound consisting of ISIS 693844.

Embodiment 138. A compound consisting of ISIS 693845.

Embodiment 139. A compound consisting of ISIS 693846.

Embodiment 140. A compound consisting of ISIS 693847.

Embodiment 141. A compound consisting of ISIS 693848.

Embodiment 142. A compound consisting of ISIS 693849.

Embodiment 143. A compound consisting of ISIS 549577.

Embodiment 144. A compound consisting of ISIS 549580.

Embodiment 145. A compound consisting of ISIS 549581.

Embodiment 146. A compound consisting of ISIS 549582.

Embodiment 147. A compound consisting of ISIS 549583.

Embodiment 148. A compound consisting of ISIS 549584.

Embodiment 149. A compound consisting of ISIS 549585.

Embodiment 150. A compound consisting of ISIS 549586.

Embodiment 151. A compound consisting of ISIS 617341.

Embodiment 152. A compound consisting of ISIS 617351.

Embodiment 153. A compound consisting of ISIS 617352.

Embodiment 154. A compound consisting of ISIS 617353.

Embodiment 155. A compound consisting of ISIS 617358.

Embodiment 156. A compound consisting of ISIS 617360.

Embodiment 157. A compound consisting of ISIS 617361.

Embodiment 158. A compound consisting of ISIS 617362.

Embodiment 159. A method of modulating splicing of a Tau transcript in a cell comprising contacting the cell with a compound according to any of embodiments 1-158.

Embodiment 160. The method of embodiment 158, wherein the cell is in vitro.

Embodiment 161. The method of embodiment 158, wherein the cell is in an animal.

Embodiment 162. A method of modulating the expression of Tau protein in a cell, comprising contacting the cell with a compound according to any of embodiments 1-158.

Embodiment 163. The method of embodiment 162, wherein expression of the 4R isoform of Tau protein is decreased.

Embodiment 164. The method of embodiment 162, wherein expression of the 3R isoform of Tau protein is increased.

Embodiment 165. The method of any of embodiments 162 to 164, wherein the cell is in vitro.

Embodiment 166. The method of any of embodiments 162 to 164, wherein the cell is in an animal.

Embodiment 167. A method of reducing or ameliorating one or more symptoms associated with a tau-associated disorder, comprising contacting a cell with a compound according to any of embodiments 1-158.

Embodiment 168. The method of embodiment 167, wherein the symptom is seizure.

Embodiment 169. The method of any of embodiments 167-168, wherein the cell is in an animal.

Embodiment 170. A pharmaceutical composition comprising a compound according to any of embodiments 1-158 and a pharmaceutically acceptable carrier or diluent.

Embodiment 171. The pharmaceutical composition of embodiment 170, wherein the pharmaceutically acceptable carrier or diluent is sterile saline.

Embodiment 172. A method comprising administering the pharmaceutical composition of embodiments 170 or 171 to an animal.

Embodiment 173. The method of embodiment 172, wherein the administration is by injection.

Embodiment 174. The method of embodiment 172 or 173, wherein the administration is systemic.

Embodiment 175. The method of embodiment 172 or 173, wherein the administration is to the CNS.

Embodiment 176. The method of any of embodiments 172-175, wherein the animal has one or more symptoms associated with one or more tau-associated disorders.

Embodiment 177. The method of embodiment 176, wherein the administration results in amelioration of one or more symptoms associated with one or more tau-associated disorders.

Embodiment 178. The method of any of embodiments 172-175, wherein the animal has one or more symptoms associated with Alzheimer's disease.

Embodiment 179. The method of embodiment 178, wherein the administration results in amelioration of one or more symptoms associated with Alzheimer's disease.

Embodiment 180. The method of any of embodiments 172-179, wherein the animal is a mouse.

Embodiment 181. The method of any of embodiments 172-179, wherein the animal is a human.

Embodiment 182. Use of the compound of any of embodiments 1 to 158 or the composition of embodiments 170-171 for the preparation of a medicament for use in the treatment of a tau-associated disorder.

Embodiment 183. Use of the compound of any of embodiments 1 to 158 or the composition of embodiments 170-171 for the preparation of a medicament for use in the amelioration of one or more symptoms associated a tau-associated disorder.

Embodiment 184. The compound, composition, or method of any of embodiments 1-183, wherein the nucleobase sequence does not consist of the nucleobase sequence as set forth in SEQ ID NO.: 45, 66, 68, 69, or 200.

Embodiment 185. The compound, composition, or method of any of embodiments 1-183, wherein the nucleobase sequence does not consist of the nucleobase sequence CCAGCTTCTTATTAATTATC
or

TAAGATCCAGCTTCTTATTA.

Embodiment 186. The compound, composition, or method of any of embodiments 1-183, wherein the target region is not within nucleobase 121828 and nucleobase 121847 of SEQ ID NO.: 1.

Embodiment 187. The compound, composition, or method of any of embodiments 1-183, wherein the target region is not within nucleobase 121834 and nucleobase 121853 of SEQ ID NO.: 1.

Embodiment 188. The compound, composition, or method of any of embodiments 1-183, wherein the target region is not within nucleobase 121840 and nucleobase 121859 of SEQ ID NO.: 1.

Embodiment 189. The compound, composition, or method of any of embodiments 1-183, wherein the target region is not within nucleobase 121924 and nucleobase 121941 of SEQ ID NO.: 1.

Embodiment 190. The compound, composition, or method of any of embodiments 1-183, wherein the target region is not within nucleobase 121012 and nucleobase 121029 of SEQ ID NO.: 1.

Embodiment 191. The compound, composition, or method of any of embodiments 1-183, wherein the target region is not within nucleobase 121020 and nucleobase 121037 of SEQ ID NO.: 1.

Embodiment 192. The compound, composition, or method of any of embodiments 1-183, wherein the target region is not within nucleobase 121024 and nucleobase 121041 of SEQ ID NO.: 1.

BRIEF DESCRIPTION OF THE FIGURES

FIG. 1 depicts a graphical representation of Tau isoforms. The isoforms can differ from each other in the number of tubulin-binding domains (three or four repeats located in the C-terminal half of the protein) and are referred to as 3R or 4R Tau isoforms, respectively. They can also differ in the presence or absence of either one or two 29-amino-acid-long, highly acidic inserts at the N-terminal portion of the protein (the projection domain). Between the projection domain and the microtubule-binding domain lies a basic proline-rich region.

DETAILED DESCRIPTION

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., $21^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to, furanosyls comprising substituents at the 2'-position, the 3'-position, the 5'-position and/or the 4'-position.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means $-OCH_2CH_2OCH_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-$CH(CH_3)$—O-2'bridge.

As used herein, "locked nucleic acid nucleoside" or "LNA" means a nucleoside comprising a bicyclic sugar moiety comprising a 4'-$CH_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "transcript" means an RNA molecule transcribed from DNA. Transcripts include, but are not limited to mRNA, pre-mRNA, and partially processed RNA.

As used herein, "Tau transcript" means a transcript transcribed from a Tau gene. In certain embodiments, a Tau transcript is represented by GENBANK Accession No NT_010783.15, truncated from nucleotides 9240000 to 9381000 (SEQ ID NO: 1), or a variant thereof.

As used herein, "Tau gene" means a gene that encodes a Tau protein and any Tau protein isoforms. In certain embodiments, Tau protein isoforms include the 3R isoform and the 4R isoform.

As used herein, "3R" means a Tau transcript that includes does not include exon 10.

As used herein, "3R Tau isoform" means a Tau protein isoform that does not include amino acids encoded from exon 10.

As used herein, "4R" means a Tau transcript that includes exon 10.

As used herein, "4R Tau isoform" means a Tau protein isoform that includes amino acids encoded from exon 10.

As used herein, "Tau-associated disease" means any neurological or neurodegenerative disease associated with Tau. Non-limiting examples of Tau-associated disorders include Alzheimer's disease, progressive supranuclear palsy, dementia pugilistica, frontotemporal dementia, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal ganglionic degeneration, argyrophilic grain disease, supranuclear palsy, corticobasal degeneration, frontotemporal dementia, or frontotemporal lobar degeneration.

As used herein, "Tauopathy" means disorders characterized by a build-up of Tau protein in the brain.

As used herein, "Tau-specific inhibitor" includes but is not limited to a "antisense compound" targeted to Tau.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl ($-C(O)R_{aa}$), carboxyl ($-C(O)O-R_{aa}$), aliphatic groups, alicyclic groups, alkoxy, substituted oxy ($-O-R_{aa}$), aryl, aralkyl, heterocyclic radical, heteroaryl, heteroarylalkyl, amino ($-N(R_{bb})(R_{cc})$), imino($=NR_{bb}$), amido ($-C(O)N(R_{bb})(R_{cc})$ or $-N(R_{bb})C(O)R_{aa}$), azido ($-N_3$), nitro ($-NO_2$), cyano ($-CN$), carbamido ($-OC(O)N(R_{bb})(R_{cc})$ or $-N(R_{bb})C(O)OR_{aa}$), ureido ($-N(R_{bb})C(O)N(R_{bb})(R_{cc})$), thioureido ($-N(R_{bb})C(S)N(R_{bb})(R_{cc})$), guanidinyl ($-N(R_{bb})C(=NR_{bb})N(R_{bb})(R_{cc})$), amidinyl ($-C(=NR_{bb})N(R_{bb})(R_{cc})$ or $-N(R_{bb})C(=NR_{bb})(R_{aa})$), thiol ($-SR_{bb}$), sulfinyl ($-S(O)R_{bb}$), sulfonyl ($-S(O)_2R_{bb}$) and sulfonamidyl ($-S(O)_2N(R_{bb})(R_{cc})$ or $-N(R_{bb})S(O)_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula $-C(O)-X$ where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-$OCH_3$ ("OMe" or "O-methyl"), and 2'-$O(CH_2)_2OCH_3$ ("MOE"). In certain embodiments, sugar substituents at the 2' position is selected from allyl, amino, azido, thio, O-allyl, O—$C_1$-$C_{10}$ alkyl, O—$C_1$-$C_{10}$ substituted alkyl; O—$C_1$-$C_{10}$ alkoxy; O—$C_1$-$C_{10}$ substituted alkoxy, $OCF_3$, $O(CH_2)_2SCH_3$, $O(CH_2)_2$—O—N(Rm)(Rn), and O—$CH_2$—C(=O)—N(Rm)(Rn), where each Rm and Rn is, independently, H or substituted or unsubstituted $C_1$-$C_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—$C_1$-$C_{10}$ alkoxy; O—$C_1$-$C_{10}$ substituted alkoxy, SH, CN, OCN, $CF_3$, $OCF_3$, O-alkyl, S-alkyl, N($R_m$)-alkyl; O-alkenyl, S-alkenyl, or N($R_m$)-alkenyl; O-alkynyl, S-alkynyl, N($R_m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R_m$)($R_n$) or O—$CH_2$—C(=O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH=$CH_2$, O—$CH_2$—CH=$CH_2$, $OCH_2CH_2OCH_3$, $O(CH_2)_2SCH_3$, O—$(CH_2)_2$—O—N($R_m$)($R_n$), $O(CH_2)_2O(CH_2)_2N(CH_3)_2$, and N-substituted acetamide (O—$CH_2$—C(=O)—N($R_m$)($R_n$) where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, $O(CH_2)_2$ $SCH_3$, O—$(CH_2)_2$—O—$N(CH_3)_2$, —$O(CH_2)_2O(CH_2)_2N(CH_3)_2$, and O—$CH_2$—C(=O)—N(H)$CH_3$.

In certain embodiments, a 2'-substituted nucleoside comprises a sugar moiety comprising a 2'-substituent group selected from F, O—$CH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C($R_a$)($R_b$)]$_n$—, —[C($R_a$)($R_b$)]$_n$—O—, —C($R_aR_b$)—N(R)—O— or, —C($R_aR_b$)—O—N(R)—; 4'-$CH_2$-2', 4'-$(CH_2)_2$-2', 4'-$(CH_2)_3$-2', 4'-($CH_2$)—O-2' (LNA); 4'-($CH_2$)—S-2; 4'-$(CH_2)_2$ —O-2' (ENA); 4'-CH($CH_3$)—O-2' (cEt) and 4'-CH($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya, et al., *J. Org. Chem.,* 2009, 74, 118-134); and 4'-$CH_2$—C(=$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C($R_a$)($R_b$)]$_n$—, —C($R_a$)=C($R_b$)—, —C($R_a$)=N—, —C(=N$R_a$)—, —C(=O)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-($CH_2$)$_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-CH2-N(R)-2') BNA, (I) methyl carbocyclic (4'-$CH_2$—CH($CH_3$)-2') BNA, and (J) propylene carbocyclic (4'-($CH_2$)$_3$-2') BNA as depicted below.

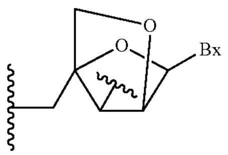

(A)

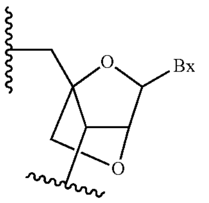

(B)

-continued

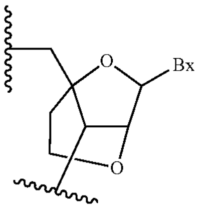

(C)

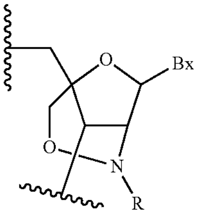

(D)

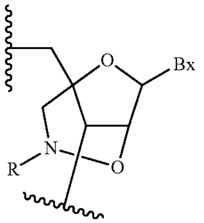

(E)

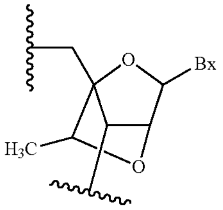

(F)

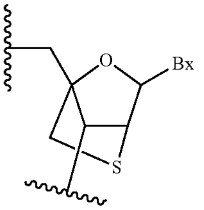

(G)

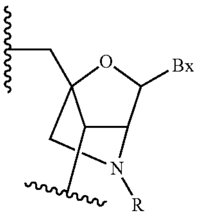

(H)

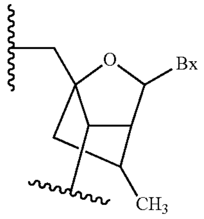

(I)

-continued (J)

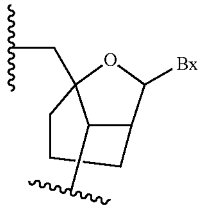

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

VII

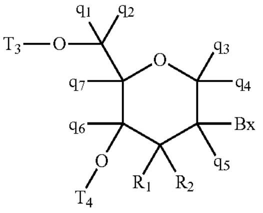

wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, OC(═X)$J_1$, OC(═X)$NJ_1J_2$, $NJ_3$C(═X)$NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry*, 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166,315; 5,185,444; and 5,034,506). As used here, the term "morpholino" means a sugar surrogate having the following structure:

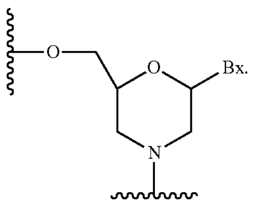

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)$_2$—O—); and N,N'-dimethylhydrazine (—$CH_2$—N($CH_3$)—N($CH_3$)—). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, or 20 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisesense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, compounds and compositions, including modified oligonucleotides, are delivered to the CNS. In certain embodiments, compounds and compositions, including modified oligonucleotides, are delivered to the CNS via intracerebroventricular administration or intracerebroventricular bolus administration. In certain embodiments, one or more modified oligonucleotides may exhibit high potency and high selectivity toward a nucleic acid target, but may possess certain degrees of acute toxicity when delivered into the CNS via intracerebroventricular administration. In certain embodiments, introduction of one or more modifications to the internucleoside linkages of the modified oligonucleotide ameliorates or reduces acute toxicity associated with CNS delivery via intracerebroventricular administration. In certain embodiments, introduction of one or more phosphodiester internucleoside linkages into the modified oligonucleotide ameliorates or reduces acute toxicity associated with CNS delivery via intracerebroventricular administration.

In certain embodiments, an oligomeric compound has an internucleoside linkage motif selected from the table below, wherein each "N" represents a nucleoside, each subscript "s" represents a phosphorothioate internucleoside linkage, and each subscript "o" represents a phosphodiester internucleoside linkage:

| Internucleoside Linkage Motifs |
| --- |
| $N_SN_SN_ON_SN_ON_SN_ON_SN_ON_SN_ON_SN_ON_SN_ON_SN_SN$ |
| $N_SN_ON_ON_ON_SN_SN_SN_SN_SN_SN_SN_SN_ON_ON_ON_SN_SN$ |

In certain embodiments, the inclusion of 3, 4, 5, 6, 7, 8, or 9 phosphodiester internucleoside linkages into the modified oligonucleotide ameliorates or reduces acute toxicity associated with CNS delivery via intracerebroventricular administration.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that $X \leq Y$. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments antisense compounds and antisense oligonucleotides comprise single-strand compounds. In certain embodiments antisense compounds and antisense oligonucleotides comprise double-strand compounds.

Certain Modified Oligonucleotides

In certain embodiments, a modified oligonucleotide has the sequence of SEQ ID NO. 31. In certain embodiments, a modified oligonucleotide has the sequence of SEQ ID NO. 33. In certain embodiments, a modified oligonucleotide has the sequence of SEQ ID NO.34. In certain embodiments, a modified oligonucleotide has the sequence of SEQ ID NO.35. In certain embodiments, a modified oligonucleotide has the sequence of SEQ ID NO. 36. In certain embodiments, a modified oligonucleotide has the sequence of SEQ ID NO. 37. In certain embodiments, a modified oligonucleotide has the sequence of SEQ ID NO. 45.

In certain embodiments, a modified oligonucleotide has the sequence of SEQ ID NO. 72. In certain embodiments, a modified oligonucleotide has the sequence of SEQ ID NO. 79. In certain embodiments, a modified oligonucleotide has the sequence of SEQ ID NO. 82. In certain embodiments, a modified oligonucleotide has the sequence of SEQ ID NO. 83. In certain embodiments, a modified oligonucleotide has the sequence of SEQ ID NO. 97. In certain embodiments, a modified oligonucleotide has the sequence of SEQ ID NO. 106. In certain embodiments, a modified oligonucleotide has the sequence of SEQ ID NO. 107. In certain embodiments, a modified oligonucleotide has the sequence of SEQ ID NO. 112. In certain embodiments, a modified oligonucleotide has the sequence of SEQ ID NO. 113. In certain embodiments, a modified oligonucleotide has the sequence of SEQ ID NO. 130. In certain embodiments, a modified oligonucleotide has the sequence of SEQ ID NO. 140.

In certain embodiments, a modified oligonucleotide has the sequence of SEQ ID NO. 141. In certain embodiments, a modified oligonucleotide has the sequence of SEQ ID NO. 142. In certain embodiments, a modified oligonucleotide has the sequence of SEQ ID NO. 143. In certain embodiments, a modified oligonucleotide has the sequence of SEQ ID NO. 144. In certain embodiments, a modified oligonucleotide has the sequence of SEQ ID NO. 145. In certain embodiments, a modified oligonucleotide has the sequence of SEQ ID NO. 146. In certain embodiments, a modified oligonucleotide has the sequence of SEQ ID NO. 147. In certain embodiments, a modified oligonucleotide has the sequence of SEQ ID NO. 148. In certain embodiments, a modified oligonucleotide has the sequence of SEQ ID NO. 149.

In certain embodiments, a modified oligonucleotide has the sequence of SEQ ID NO. 150. In certain embodiments, a modified oligonucleotide has the sequence of SEQ ID NO. 151. In certain embodiments, a modified oligonucleotide has the sequence of SEQ ID NO. 152. In certain embodiments, a modified oligonucleotide has the sequence of SEQ ID NO. 153. In certain embodiments, a modified oligonucleotide has the sequence of SEQ ID NO. 157. In certain embodiments, a modified oligonucleotide has the sequence of SEQ ID NO. 158. In certain embodiments, a modified oligonucleotide has the sequence of SEQ ID NO. 160. In certain embodiments, a modified oligonucleotide has the sequence of SEQ ID NO. 200.

Certain Pathways and Mechanisms Associated with Neurodegenerative Disorders

In certain embodiments, a neurodegenerative syndrome or disorder may be any neurodegenerative syndrome or disorder associated with Tau. Non limiting examples of a neurodegenerative disorder associated with Tau may include Alzheimer's disease, progressive supranuclear palsy, dementia pugilistica, frontotemporal dementia, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal ganglionic degeneration, argyrophilic grain disease, supranuclear palsy, corticobasal degeneration, frontotemporal dementia, or frontotemporal lobar degeneration. In some embodiments, the method of the invention comprises modifying frontotemporal dementia (FTD). In other embodiments, the method of the invention comprises modifying Alzheimer's disease (AD). In yet other embodiments, the method of the invention comprises modifying progressive supranuclear palsy. In other embodiments, the method of the invention comprises modifying corticobasalganglionic degeneration.

In certain embodiments, described herein are compositions and methods of modifying a neurodegenerative syndrome by altering the splicing of a nucleic acid encoding Tau. Tau is a protein found in multiple tissues, but is particularly abundant in axons of neurons. The primary function of Tau is to bind to and stabilize microtubules, which are important structural components of the cytoskeleton involved in mitosis, cytokinesis and vesicular transport. In humans, there are six isoforms of Tau that are generated by alternative splicing of exons 2, 3, and 10. Splicing of exons 2 and 3 at the N-terminus of the protein leads to inclusion of zero, one or two 29 amino acid, acidic domains and is termed 0N, 1N, or 2N Tau respectively. Inclusion of exon 10 at the C-terminus leads to inclusion of the microtubule binding domain encoded by exon 10. Since there are 3 mictrotubule binding domains elsewhere in Tau, this Tau isoform (with exon 10 included) is termed 4R Tau, where R refers to the number of repeats of microtubule binding domains. (FIG. 1). Tau without exon 10 is termed 3R Tau. In healthy subjects, the ratio of 3R:4R Tau is developmentally regulated, with fetal tissues expressing almost exclusively 3R Tau and adult human tissues expressing approximately equal levels of 3R/4R Tau. Deviations from the normal ratio of 3R/4R Tau are characteristic of neurodegenerative syndromes such as FTD Tauopathies.

In certain embodiments, the 4R:3R Tau ratio in the central nervous system of the subject may be normal, low or high. As used herein, a "normal 4R:3R Tau ratio" in the central nervous system signifies a 4R:3R Tau ratio in the central nervous system that is substantially the same as the 4R:3R Tau ratio in the central nervous system of a subject from the same species and of approximately the same age not suffering from a neurodegenerative disease. In certain embodiments, certain antisense oligonucleotide compositions and/or methods decrease the normal 4R:3R Tau ratio in the central nervous system of a subject. In other embodiments, certain antisense oligonucleotide compositions and/or methods decreases a low 4R:3R Tau ratio in the central nervous system of a subject.

In certain embodiments, certain antisense oligonucleotide compositions and/or methods decrease a high 4R:3R Tau ratio in the central nervous system of a subject. In certain embodiments, certain antisense oligonucleotide compositions and/or methods decreases a high 4R:3R Tau ratio caused by a defect in splicing of the nucleic acid encoding Tau in the subject. Defects in splicing of the nucleic acid encoding Tau in the subject may be caused, for instance, by genetic mutations altering the splicing of the nucleic acid encoding Tau and leading to a high 4R:3R Tau ratio. A mutation may be either a substitution mutation or a deletion mutation which creates a new, aberrant, splice element. Non-limiting examples of genetic mutations that may alter the splicing of the nucleic acid encoding Tau and lead to a high 4R:3R Tau ratio may include N279K, P301S, 280, L284L, N296H, N296N, 296N, P301S, G303V, E10+11, E10+12, E10+13, E+10+14 and E10+16, and E10+19.

In certain embodiments, administration of an antisense oligonucleotide decreases the 4R:3R Tau ratio in the central nervous system of a subject by altering the splicing of a nucleic acid encoding Tau.

In certain embodiments, increasing exclusion of exon 10 of a Tau transcript inhibits one or more tau-associated disorders. In certain embodiments, the tau-associated disorder may be any of Alzheimer's Disease, frontotemporal Dementia (FTD), FTDP-17, Progressive Supranuclear Palsy (PSP), Chronic Traumatic Encephalopathy (CTE), Corticobasal Ganglionic Degeneration (CBD), epilepsy, Dravet's Syndrome, dementia pugilistica, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, supranuclear palsy, corticobasal degeneration, or frontotemporal lobar degeneration.

Certain Target Nucleic Acids and Mechanisms

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a pre-mRNA. In certain embodiments, the target nucleic acid is a tau transcript. In certain embodiments, the target RNA is a Tau pre-mRNA.

In certain embodiments, an antisense compound is complementary to a region of Tau pre-mRNA. In certain embodiments, an antisense compound is complementary within a region of Tau pre-mRNA comprising an exon encoding the 4R isoform. In certain embodiments, an antisense compound is complementary to a region of Tau pre-mRNA comprising an intron-exon splice junction. In certain embodiments, an antisense compound is complementary to a region of Tau pre-mRNA comprising the intron-exon splice junction adjacent to exon 10. In certain embodiments, an antisense compound is complementary to a region of Tau pre-mRNA comprising the intron-exon splice junction between intron 9 and exon 10. In certain embodiments, an antisense compound is complementary to a region of Tau pre-mRNA comprising the intron-exon splice junction between exon 10 and intron 10. In certain embodiments, an antisense compound is complementary within a region of Tau pre-mRNA consisting of exon 10.

In certain embodiments, an antisense compound is complementary within a region of Tau pre-mRNA comprising an exonic splicing silencer within exon 10. In certain embodiments, an antisense compound is complementary within a region of Tau pre-mRNA comprising an exonic splicing enhancer within exon 10.

In certain embodiments, an antisense compound comprises a modified oligonucleotide consisting of 8 to 30 linked nucleosides and having a nucleobase sequence comprising a complementary region comprising at least 8 contiguous nucleobases complementary to a target region of equal length of a Tau transcript.

In certain embodiments, the target region is within nucleobase 121708 and nucleobase 122044 of SEQ ID NO.: 1. In certain embodiments, the target region is within nucleobase 121796 and nucleobase 122044 of SEQ ID NO.: 1. In certain embodiments, the target region is within nucleobase 121796 and nucleobase 121885 of SEQ ID NO.: 1. In certain embodiments, the target region is within nucleobase 121873 and nucleobase 121898 of SEQ ID NO.: 1. In certain embodiments, the target region is within nucleobase 121869 and nucleobase 121943 of SEQ ID NO.: 1. In certain embodiments, the target region is within nucleobase 122020 and nucleobase 122044 of SEQ ID NO.: 1. In certain embodiments, the target region is within nucleobase 121881 and nucleobase 121898 of SEQ ID NO.: 1. In certain embodiments, the target region is within nucleobase 121880 and nucleobase 121897 of SEQ ID NO.: 1. In certain embodiments, the target region is within nucleobase 121879 and nucleobase 121896 of SEQ ID NO.: 1.

In certain embodiments, the target region is within nucleobase 121878 and nucleobase 121895 of SEQ ID NO.: 1. In certain embodiments, the target region is within nucleobase 121877 and nucleobase 121894 of SEQ ID NO.: 1. In certain embodiments, the target region is within nucleobase 121876 and nucleobase 121893 of SEQ ID NO.: 1. In certain embodiments, the target region is within nucleobase 121875 and nucleobase 121892 of SEQ ID NO.: 1. In certain embodiments, the target region is within nucleobase 121874 and nucleobase 121891 of SEQ ID NO.: 1. In certain embodiments, the target region is within nucleobase 121873 and nucleobase 121890 of SEQ ID NO.: 1.

In certain embodiments, an antisense oligonucleotide modulates splicing of a pre-mRNA. In certain embodiments, an antisense oligonucleotide modulates splicing a Tau pre-mRNA. In certain embodiments, an antisense oligonucleotide increases the amount of Tau 3R mRNA. In certain embodiments, an antisense oligonucleotide increases the exclusion of exon 10 in Tau mRNA. In certain embodiments, an antisense oligonucleotide decreases the inclusion of exon 10 in Tau mRNA. In certain embodiments, an antisense oligonucleotide increases the amount of 3R Tau mRNA. In certain embodiments, an antisense oligonucleotide decreases the amount of 4R Tau mRNA.

In certain embodiments it is desirable to alter the splicing of Tau pre-mRNA to exclude exon 10. By altering the splicing of Tau pre-mRNA to exclude exon 10, expression of 3R Tau will increase and expression of 4R Tau will decrease. In certain embodiments it is desirable to alter the splicing of Tau pre-mRNA to decrease expression of 4R Tau.

In certain embodiments, an antisense oligonucleotide decreases the amount of Tau 3R mRNA. In certain embodiments, an antisense oligonucleotide decreases the exclusion of exon 10 in Tau mRNA. In certain embodiments, an antisense oligonucleotide increases the inclusion of exon 10 in Tau mRNA. In certain embodiments, an antisense oligonucleotide decreases the amount of 3R Tau mRNA. In certain embodiments, an antisense oligonucleotide increases the amount of 4R Tau mRNA. In certain embodiments it is desirable to alter the splicing of Tau pre-mRNA to include exon 10, for example to produce a phenotypic effect in a mouse or animal model.

Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the eyes, ears).

In certain embodiments, a pharmaceutical composition is administered to an animal having at least one Tau-associated disorder. In certain embodiments, such administration results in reduction in expression of the 4R isoform. In certain embodiments, a pharmaceutical composition is administered to an animal having at least one symptom associated with a Tau-associated disorder. In certain embodiments, such administration results in amelioration of at least one symptom. In certain embodiments, administration of a pharmaceutical composition to an animal results in a decrease of 4R mRNA in a cell of the animal. In certain embodiments, such administration results in an increase in 3R mRNA. In certain embodiments, such administration results in a decrease in 4R protein and an increase 3R protein. In certain embodiments, a 3R protein is preferred over a 4R protein. In certain embodiments, the administration of certain antisense oligonucleotides delays the onset of one or more Tau-associated disorders. In certain embodiments, the administration of certain antisense oligonucleotides prevents or reduces seizures. In certain embodiments, the administration of certain antisense oligonucleotides causes the amount of 4R protein to decrease in the CNS. In certain embodiments, the administration of certain antisense oligonucleotides rescues cellular phenotype.

Nonlimiting disclosure and incorporation by reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine(methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

Non-limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Effects of Uniform 2'-MOE Modified Oligonucleotides on Human Tau Exon 10

A series of modified oligonucleotides were designed to target exon 10 of human Tau and were screened for their effects in reducing exon 10 inclusion in vitro. These modified oligonucleotides were designed by shifting 4 nucleotides upstream or downstream (i.e. microwalk) across the target site. They are 18 nucleosides in length, wherein each nucleoside has a 2'-MOE modification. Each internucleoside linkage throughout the modified oligonucleotide are phosphorothioate internucleoside linkages (P═S). All cytosine residues throughout the modified oligonucleotides are 5-methylcytosines.

"Start site" indicates the 5'-most nucleoside to which the modified oligonucleotide is targeted. "Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

A172 cells were transfected using Lipofectamine2000® with 5 nM concentration of modified oligonucleotide. After a treatment period of approximately 24 hours, RNA was isolated from the cells and the mRNA levels of Tau transcripts containing exon 10 were measured by quantitative real-time PCR. Human primer probe set 9_10 or 10_11 was used to measure mRNA levels. Tau exon 10 mRNA levels were adjusted according to total RNA content, as measured by RIBOGREEN®. Results are presented as percent of Tau exon 10 mRNA expression, relative to untreated control levels and is denoted as "% UTC."

Human primer probe set 9_10 (forward sequence CACTGAGAACCTGAAGCACC, designated herein as SEQ ID NO: 2; reverse sequence GGACTGGACGTTGCTAAGATC, designated herein as SEQ ID NO: 3; probe sequence TTAATTATCTGCACCTTCCCGCCTCC, designated herein as SEQ ID NO: 4).

Human primer probe set 10_11 (forward sequence GGATAATATCAAACACGTCCCG, designated herein as SEQ ID NO: 5; reverse sequence TGCCTAATGAGCCACACTTG, designated herein as SEQ ID NO: 6; probe sequence GTCTACAAACCAGTTGACCTGAGC, designated herein as SEQ ID NO: 7).

As illustrated in Tables 1 and 2, ISIS 549583, 549584, 549585, 549586, 549595, 549571, 549566, 549570, 549587, 549568, 549617, 549567, 549576, 549577, 549580, and 549581 show 70% or greater reduction in human Tau exon 10 inclusion comparing to untreated control.

TABLE 1

Effects of uniform 2'-MOE modified oligonucleotides on human Tau exon 10 using Primer Probe Set 9_10

| ISIS NO | Sequence | % UTC | SEQ ID NO: 1 Start Site | SEQ ID NO: 1 Stop Site | SEQ ID NO |
|---|---|---|---|---|---|
| 549543 | CCCGCCTACTTGCTCGCA | 130 | 121708 | 121725 | 8 |
| 549544 | TGGACCCGCCTACTTGCT | 119 | 121712 | 121729 | 9 |
| 549545 | ACCCTGGACCCGCCTACT | 106 | 121716 | 121733 | 10 |
| 549546 | CATGCGCCACCCTGGACC | 84 | 121724 | 121741 | 11 |
| 549547 | GTGACATGCGCCACCCTG | 78 | 121728 | 121745 | 12 |
| 549548 | ATGAGTGACATGCGCCAC | 63 | 121732 | 121749 | 13 |
| 549549 | TTCGATGAGTGACATGCG | 70.0 | 121736 | 121753 | 14 |
| 549550 | CACTTTCGATGAGTGACA | 69 | 121740 | 121757 | 15 |
| 549551 | CCTCCACTTTCGATGAGT | 103 | 121744 | 121761 | 16 |
| 549552 | GACGCCTCCACTTTCGAT | 148 | 121748 | 121765 | 17 |
| 549553 | CAAGGACGCCTCCACTTT | 116 | 121752 | 121769 | 18 |

TABLE 1-continued

Effects of uniform 2'-MOE modified oligonucleotides on human Tau exon 10 using Primer Probe Set 9_10

| ISIS NO | Sequence | % UTC | SEQ ID NO: 1 Start Site | SEQ ID NO: 1 Stop Site | SEQ ID NO |
|---|---|---|---|---|---|
| 549554 | CTCGCAAGGACGCCTCCA | 80 | 121756 | 121773 | 19 |
| 549555 | CTTGCTCGCAAGGACGCC | 102 | 121760 | 121777 | 20 |
| 549556 | CCTGCTTGCTCGCAAGGA | 109 | 121764 | 121781 | 21 |
| 549557 | CCCGCCTGCTTGCTCGCA | 100 | 121768 | 121785 | 22 |
| 549558 | TGGACCCGCCTGCTTGCT | 111 | 121772 | 121789 | 23 |
| 549559 | ACCCTGGACCCGCCTGCT | 108 | 121776 | 121793 | 24 |
| 549560 | CGCCACCCTGGACCCGCC | 88 | 121720<br>121780 | 121737<br>121797 | 25 |
| 549561 | GACACGCCACCCTGGACC | 83 | 121784 | 121801 | 26 |
| 549562 | GAGTGACACGCCACCCTG | 77 | 121788 | 121805 | 27 |
| 549563 | GGATGAGTGACACGCCAC | 58 | 121792 | 121809 | 28 |
| 549564 | AAAAGGATGAGTGACACG | 49 | 121796 | 121813 | 29 |
| 549565 | AGAAAAAAGGATGAGTGA | 35 | 121800 | 121817 | 30 |
| 549566 | AGCCAGAAAAAAGGATGA | 21 | 121804 | 121821 | 31 |
| 549567 | TGGTAGCCAGAAAAAAGG | 32 | 121808 | 121825 | 32 |
| 549583 | TTATCCTTTGAGCCACAC | 11 | 121876 | 121893 | 33 |
| 549584 | GATATTATCCTTTGAGCC | 11 | 121880 | 121897 | 34 |
| 549585 | GTTTGATATTATCCTTTG | 13 | 121884 | 121901 | 35 |
| 549586 | ACGTGTTTGATATTATCC | 17 | 121888 | 121905 | 36 |
| 549587 | CGGGACGTGTTTGATATT | 24 | 121892 | 121909 | 37 |
| 549588 | CTCCCGGGACGTGTTTGA | 52 | 121896 | 121913 | 38 |
| 549589 | CCGCCTCCCGGGACGTGT | 57 | 121900 | 121917 | 39 |
| 549590 | ACTGCCGCCTCCCGGGAC | 84 | 121904 | 121921 | 40 |
| 549591 | TCACACTGCCGCCTCCCG | 48 | 121908 | 121925 | 41 |
| 549592 | GTACTCACACTGCCGCCT | 30 | 121912 | 121929 | 42 |
| 549593 | GAAGGTACTCACACTGCC | 35 | 121916 | 121933 | 43 |
| 549594 | GTGTGAAGGTACTCACAC | 63 | 121920 | 121937 | 44 |

TABLE 1-continued

Effects of uniform 2'-MOE modified oligonucleotides on human Tau exon 10 using Primer Probe Set 9_10

| ISIS NO | Sequence | % UTC | SEQ ID NO: 1 Start Site | SEQ ID NO: 1 Stop Site | SEQ ID NO |
|---|---|---|---|---|---|
| 549595 | GGACGTGTGAAGGTACTC | 20 | 121924 | 121941 | 45 |
| 549596 | CATGGGACGTGTGAAGGT | 125 | 121928 | 121945 | 46 |
| 549597 | GGCGCATGGGACGTGTGA | 216 | 121932 | 121949 | 47 |
| 549598 | GCACGGCGCATGGGACGT | 242 | 121936 | 121953 | 48 |
| 549599 | CACAGCACGGCGCATGGG | 158 | 121940 | 121957 | 49 |
| 549600 | AAGCCACAGCACGGCGCA | 162 | 121944 | 121961 | 50 |
| 549601 | ATTCAAGCCACAGCACGG | 175 | 121948 | 121965 | 51 |
| 549602 | AATAATTCAAGCCACAGC | 164 | 121952 | 121969 | 52 |
| 549603 | TCCTAATAATTCAAGCCA | 200 | 121956 | 121973 | 53 |
| 549604 | CACTTCCTAATAATTCAA | 133 | 121960 | 121977 | 54 |
| 549605 | ACACCACTTCCTAATAAT | 113 | 121964 | 121981 | 55 |
| 549606 | ACTCACACCACTTCCTAA | 136 | 121968 | 121985 | 56 |
| 549608 | GTGTACGCACTCACACCA | 80.6 | 121976 | 121993 | 57 |
| 549609 | GCAAGTGTACGCACTCAC | 49.9 | 121980 | 121997 | 58 |
| 549610 | TCTCGCAAGTGTACGCAC | 86.5 | 121984 | 122001 | 59 |
| 549611 | AGTGTCTCGCAAGTGTAC | 62.4 | 121988 | 122005 | 60 |
| 549612 | ATGCAGTGTCTCGCAAGT | 46.4 | 121992 | 122009 | 61 |
| 549613 | TTCTATGCAGTGTCTCGC | 46.6 | 121996 | 122013 | 62 |
| 549614 | TTTATTCTATGCAGTGTC | 33.2 | 122000 | 122017 | 63 |
| 549615 | AGGATTTATTCTATGCAG | 34.3 | 122004 | 122021 | 64 |
| 549616 | AAGAAGGATTTATTCTAT | 46.5 | 122008 | 122025 | 65 |
| 549617 | GCCCAAGAAGGATTTATT | 29.6 | 122012 | 122029 | 66 |
| 549618 | GAGAGCCCAAGAAGGATT | 38.6 | 122016 | 122033 | 67 |
| 549619 | TCCTGAGAGCCCAAGAAG | 36.9 | 122020 | 122037 | 68 |
| 549620 | CAGATCCTGAGAGCCCAA | 38.3 | 122024 | 122041 | 69 |

TABLE 2

Effects of uniform 2'-MOE modified oligonucleotides on human Tau exon 10 using Primer Probe Set 10_11

| ISIS No. | Sequence | % UTC | SEQ ID NO: 1 Start Site | SEQ ID NO: 1 Stop Site | Mismatches | SEQ ID No. |
|---|---|---|---|---|---|---|
| 549543 | CCCGCCTACTTGCTCGCA | 128 | 121708<br>121768 | 121725<br>121785 | 0<br>1 | 8 |
| 549544 | TGGACCCGCCTACTTGCT | 117 | 121712<br>121772 | 121729<br>121789 | 0<br>1 | 9 |
| 549545 | ACCCTGGACCCGCCTACT | 98 | 121716<br>121776 | 121733<br>121793 | 0<br>1 | 10 |

TABLE 2-continued

Effects of uniform 2'-MOE modified oligonucleotides on human Tau exon 10 using Primer Probe Set 10_11

| ISIS No. | Sequence | % UTC | SEQ ID NO: 1 Start Site | SEQ ID NO: 1 Stop Site | Mismatches | SEQ ID No. |
|---|---|---|---|---|---|---|
| 549546 | CATGCGCCACCCTGGACC | 78 | 121724 | 121741 | 0 | 11 |
| 549547 | GTGACATGCGCCACCCTG | 75 | 121728 | 121745 | 0 | 12 |
| 549548 | ATGAGTGACATGCGCCAC | 63 | 121732 | 121749 | 0 | 13 |
| 549549 | TTCGATGAGTGACATGCG | 74 | 121736 | 121753 | 0 | 14 |
| 549550 | CACTTTCGATGAGTGACA | 76 | 121740 | 121757 | 0 | 15 |
| 549551 | CCTCCACTTTCGATGAGT | 107 | 121744 | 121761 | 0 | 16 |
| 549552 | GACGCCTCCACTTTCGAT | 137 | 121748 | 121765 | 0 | 17 |
| 549553 | CAAGGACGCCTCCACTTT | 108 | 121692<br>121752 | 121709<br>121769 | 1<br>0 | 18 |
| 549554 | CTCGCAAGGACGCCTCCA | 71 | 121696<br>121756 | 121713<br>121773 | 1<br>0 | 19 |
| 549555 | CTTGCTCGCAAGGACGCC | 108 | 121700<br>121760 | 121717<br>121777 | 1<br>0 | 20 |
| 549556 | CCTGCTTGCTCGCAAGGA | 106 | 121704<br>121764 | 121721<br>121781 | 1<br>0 | 21 |
| 549557 | CCCGCCTGCTTGCTCGCA | 93 | 121708<br>121768 | 121725<br>121785 | 1<br>0 | 22 |
| 549558 | TGGACCCGCCTGCTTGCT | 111 | 121712<br>121772 | 121729<br>121789 | 1<br>0 | 23 |
| 549559 | ACCCTGGACCCGCCTGCT | 100 | 121716<br>121776 | 121733<br>121793 | 1<br>0 | 24 |
| 549560 | CGCCACCCTGGACCCGCC | 89 | 121720<br>121780 | 121737<br>121797 | 0<br>0 | 25 |
| 549561 | GACACGCCACCCTGGACC | 80 | 121784 | 121801 | 0 | 26 |
| 549562 | GAGTGACACGCCACCCTG | 81 | 121788 | 121805 | 0 | 27 |
| 549563 | GGATGAGTGACACGCCAC | 54 | 121792 | 121809 | 0 | 28 |
| 549564 | AAAAGGATGAGTGACACG | 45 | 121796 | 121813 | 0 | 29 |
| 549565 | AGAAAAAAGGATGAGTGA | 34 | 121800 | 121817 | 0 | 30 |
| 549566 | AGCCAGAAAAAAGGATGA | 19 | 121804 | 121821 | 0 | 31 |
| 549567 | TGGTAGCCAGAAAAAAGG | 31 | 121808 | 121825 | 0 | 32 |
| 549568 | CCTTTGGTAGCCAGAAAA | 23 | 121812 | 121829 | 0 | 70 |
| 549569 | TGCACCTTTGGTAGCCAG | 53 | 121816 | 121833 | 0 | 71 |
| 549570 | TAATTATCTGCACCTTTG | 26 | 121824 | 121841 | 0 | 72 |
| 549571 | TTCTTAATTATCTGCACC | 21 | 121828 | 121845 | 1 | 73 |
| 549572 | CTTCTTCTTAATTATCTG | 30 | 121832 | 121849 | 1 | 74 |
| 549573 | CCAGCTTCTTCTTAATTA | 34 | 121836 | 121853 | 1 | 75 |
| 549574 | AGATCCAGCTTCTTCTTA | 43 | 121840 | 121857 | 1 | 76 |
| 549575 | GCTAAGATCCAGCTTCTT | 25 | 121844 | 121861 | 0 | 77 |
| 549576 | CGTTGCTAAGATCCAGCT | 18 | 121848 | 121865 | 0 | 78 |
| 549577 | TGGACGTTGCTAAGATCC | 16 | 121852 | 121869 | 0 | 79 |
| 549578 | GGACTGGACGTTGCTAAG | 44 | 121856 | 121873 | 0 | 80 |

TABLE 2-continued

Effects of uniform 2'-MOE modified oligonucleotides on human Tau exon 10 using Primer Probe Set 10_11

| ISIS No. | Sequence | % UTC | SEQ ID NO: 1 Start Site | SEQ ID NO: 1 Stop Site | Mismatches | SEQ ID No. |
|---|---|---|---|---|---|---|
| 549579 | ACTTGGACTGGACGTTGC | 36 | 121860 | 121877 | 0 | 81 |
| 549580 | CCACACTTGGACTGGACG | 19 | 121864 | 121881 | 0 | 82 |
| 549581 | TGAGCCACACTTGGACTG | 16 | 121868 | 121885 | 0 | 83 |
| 549595 | GGACGTGTGAAGGTACTC | 20 | 121924 | 121941 | 0 | 45 |
| 549596 | CATGGGACGTGTGAAGGT | 128 | 121928 | 121945 | 0 | 46 |
| 549597 | GGCGCATGGGACGTGTGA | 199 | 121932 | 121949 | 0 | 47 |
| 549598 | GCACGGCGCATGGGACGT | 199 | 121936 | 121953 | 0 | 48 |
| 549599 | CACAGCACGGCGCATGGG | 149 | 121940 | 121957 | 0 | 49 |
| 549600 | AAGCCACAGCACGGCGCA | 156 | 121944 | 121961 | 0 | 50 |
| 549601 | ATTCAAGCCACAGCACGG | 166 | 121948 | 121965 | 0 | 51 |
| 549602 | AATAATTCAAGCCACAGC | 159 | 121952 | 121969 | 0 | 52 |
| 549603 | TCCTAATAATTCAAGCCA | 179 | 121956 | 121973 | 0 | 53 |
| 549604 | CACTTCCTAATAATTCAA | 123 | 121960 | 121977 | 0 | 54 |
| 549605 | ACACCACTTCCTAATAAT | 113 | 121964 | 121981 | 0 | 55 |
| 549606 | ACTCACACCACTTCCTAA | 119 | 121968 | 121985 | 0 | 56 |
| 549608 | GTGTACGCACTCACACCA | 77.2 | 121976 | 121993 | 0 | 57 |
| 549609 | GCAAGTGTACGCACTCAC | 53.0 | 121980 | 121997 | 0 | 58 |
| 549610 | TCTCGCAAGTGTACGCAC | 87.4 | 121984 | 122001 | 0 | 59 |
| 549611 | AGTGTCTCGCAAGTGTAC | 69.2 | 121988 | 122005 | 0 | 60 |
| 549612 | ATGCAGTGTCTCGCAAGT | 43.3 | 121992 | 122009 | 0 | 61 |
| 549613 | TTCTATGCAGTGTCTCGC | 41.4 | 121996 | 122013 | 0 | 62 |
| 549614 | TTTATTCTATGCAGTGTC | 29.2 | 122000 | 122017 | 0 | 63 |
| 549615 | AGGATTTATTCTATGCAG | 30.9 | 122004 | 122021 | 0 | 64 |
| 549616 | AAGAAGGATTTATTCTAT | 45.8 | 122008 | 122025 | 0 | 65 |
| 549617 | GCCCAAGAAGGATTTATT | 31.8 | 122012 | 122029 | 0 | 66 |
| 549618 | GAGAGCCCAAGAAGGATT | 41.8 | 122016 | 122033 | 0 | 67 |
| 549619 | TCCTGAGAGCCCAAGAAG | 41.7 | 122020 | 122037 | 0 | 68 |
| 549620 | CAGATCCTGAGAGCCCAA | 35.6 | 122024 | 122041 | 0 | 69 |

Example 2

Effects of Uniform 2'-MOE Modified Oligonucleotides on Human Tau Exon 10

A series of modified oligonucleotides were designed to target exon 10 of human Tau and were screened for their effects in reducing exon 10 inclusion in vitro. These modified oligonucleotides were designed by shifting 1 nucleotide upstream or downstream (i.e. microwalk) across the target site. They are 18 nucleosides in length, wherein each nucleoside has a 2'-MOE modification. Each internucleoside linkage throughout the modified oligonucleotide are phosphorothioate internucleoside linkages (P═S). All cytosine residues throughout the modified oligonucleotides are 5-methylcytosines.

"Start site" indicates the 5'-most nucleoside to which the modified oligonucleotide is targeted. "Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

A172 cells were transfected using Lipofectamine2000® with 5 nM concentration of modified oligonucleotide. After a treatment period of approximately 24 hours, RNA was isolated from the cells and the mRNA levels of Tau transcripts containing exon 10 were measured by quantitative real-time PCR. Human Tau primer probe set 10_11 or 9_10 R5 was used to measure mRNA levels. Tau exon 10 mRNA levels were adjusted according to total RNA content, as measured by RIBOGREEN®. Results are presented as percent of Tau exon 10 mRNA expression, relative to untreated control levels and is denoted as "% UTC."

Human primer probe set 10_11 (forward sequence GGATAATATCAAACACGTCCCG, designated herein as SEQ ID NO: 5; reverse sequence TGCCTAATGAGCCACACTTG, designated herein as SEQ ID NO: 6; probe sequence GTCTACAAACCAGTTGACCTGAGC, designated herein as SEQ ID NO: 7).

Human Tau primer probe set 9_10 R5 (forward sequence CACTGAGAACCTGAAGCACC, designated herein as SEQ ID NO: 2; reverse sequence GGACGTTGCTAAGATCCAGCT, designated herein as SEQ ID NO: 3; probe sequence TTAATTATCTGCACCTTCCCGCCTCC, designated herein as SEQ ID NO: 4).

TABLE 3

Effects of uniform 2'-MOE modified oligonucleotides on human Tau exon 10 using Human Tau primer probe set 10_11

| ISIS NO | Sequence | % UTC | SEQ ID NO: 1 Start Site | SEQ ID NO: 1 Stop Site | SEQ ID NO |
|---|---|---|---|---|---|
| 549564 | AAAAGGATGAGTGACACG | 43 | 121796 | 121813 | 29 |
| 617296 | AAAAAGGATGAGTGACAC | 38 | 121797 | 121814 | 84 |
| 617297 | AAAAAAGGATGAGTGACA | 40 | 121798 | 121815 | 85 |
| 617298 | GAAAAAAGGATGAGTGAC | 39 | 121799 | 121816 | 86 |
| 549565 | AGAAAAAAGGATGAGTGA | 45 | 121800 | 121817 | 30 |
| 617299 | CAGAAAAAAGGATGAGTG | 39 | 121801 | 121818 | 87 |
| 617300 | CCAGAAAAAAGGATGAGT | 34 | 121802 | 121819 | 88 |
| 617301 | GCCAGAAAAAAGGATGAG | 34 | 121803 | 121820 | 89 |
| 549566 | AGCCAGAAAAAAGGATGA | 21 | 121804 | 121821 | 31 |
| 617302 | TAGCCAGAAAAAAGGATG | 26 | 121805 | 121822 | 90 |
| 617303 | GTAGCCAGAAAAAAGGAT | 27 | 121806 | 121823 | 91 |
| 617304 | GGTAGCCAGAAAAAAGGA | 32 | 121807 | 121824 | 92 |
| 549567 | TGGTAGCCAGAAAAAAGG | 39 | 121808 | 121825 | 32 |
| 617305 | TTGGTAGCCAGAAAAAAG | 34 | 121809 | 121826 | 93 |
| 617306 | TTTGGTAGCCAGAAAAAA | 49 | 121810 | 121827 | 94 |
| 617307 | CTTTGGTAGCCAGAAAAA | 37 | 121811 | 121828 | 95 |
| 549568 | CCTTTGGTAGCCAGAAAA | 27 | 121812 | 121829 | 70 |
| 617308 | ACCTTTGGTAGCCAGAAA | 31 | 121813 | 121830 | 96 |
| 617309 | CACCTTTGGTAGCCAGAA | 23 | 121814 | 121831 | 97 |
| 617310 | GCACCTTTGGTAGCCAGA | 59 | 121815 | 121832 | 98 |
| 549569 | TGCACCTTTGGTAGCCAG | 59 | 121816 | 121833 | 71 |
| 617311 | CTGCACCTTTGGTAGCCA | 59 | 121817 | 121834 | 99 |
| 617312 | TCTGCACCTTTGGTAGCC | 58 | 121818 | 121835 | 100 |

TABLE 3-continued

Effects of uniform 2'-MOE modified oligonucleotides on human Tau exon 10 using Human Tau primer probe set 10_11

| ISIS NO | Sequence | % UTC | SEQ ID NO: 1 Start Site | SEQ ID NO: 1 Stop Site | SEQ ID NO |
|---|---|---|---|---|---|
| 617313 | ATCTGCACCTTTGGTAGC | 53 | 121819 | 121836 | 101 |
| 415866 | TATCTGCACCTTTGGTAG | 41 | 121820 | 121837 | 102 |
| 617314 | TTATCTGCACCTTTGGTA | 36 | 121821 | 121838 | 103 |
| 617315 | ATTATCTGCACCTTTGGT | 31 | 121822 | 121839 | 104 |
| 617316 | AATTATCTGCACCTTTGG | 38 | 121823 | 121840 | 105 |
| 549570 | TAATTATCTGCACCTTTG | 21 | 121824 | 121841 | 72 |
| 617317 | TTAATTATCTGCACCTTT | 23 | 121825 | 121842 | 106 |
| 617318 | ATTAATTATCTGCACCTT | 25 | 121826 | 121843 | 107 |
| 617319 | TATTAATTATCTGCACCT | 27 | 121827 | 121844 | 108 |
| 617320 | TTATTAATTATCTGCACC | 27 | 121828 | 121845 | 109 |
| 617321 | CTTATTAATTATCTGCAC | 26 | 121829 | 121846 | 110 |
| 617322 | TCTTATTAATTATCTGCA | 25 | 121830 | 121847 | 111 |
| 617323 | TTCTTATTAATTATCTGC | 25 | 121831 | 121848 | 112 |
| 617324 | CTTCTTATTAATTATCTG | 25 | 121832 | 121849 | 113 |
| 617325 | GCTTCTTATTAATTATCT | 26 | 121833 | 121850 | 114 |
| 617326 | AGCTTCTTATTAATTATC | 32 | 121834 | 121851 | 115 |
| 617327 | CAGCTTCTTATTAATTAT | 31 | 121835 | 121852 | 116 |
| 617328 | CCAGCTTCTTATTAATTA | 29 | 121836 | 121853 | 117 |
| 617329 | TCCAGCTTCTTATTAATT | 35 | 121837 | 121854 | 118 |
| 617330 | ATCCAGCTTCTTATTAAT | 29 | 121838 | 121855 | 119 |
| 617331 | GATCCAGCTTCTTATTAA | 33 | 121839 | 121856 | 120 |
| 617332 | AGATCCAGCTTCTTATTA | 33 | 121840 | 121857 | 121 |
| 617333 | AAGATCCAGCTTCTTATT | 37 | 121841 | 121858 | 122 |
| 617334 | TAAGATCCAGCTTCTTAT | 42 | 121842 | 121859 | 123 |
| 617335 | CTAAGATCCAGCTTCTTA | 34 | 121843 | 121860 | 124 |
| 549575 | GCTAAGATCCAGCTTCTT | 29 | 121844 | 121861 | 77 |
| 617336 | TGCTAAGATCCAGCTTCT | 42 | 121845 | 121862 | 125 |
| 617337 | TTGCTAAGATCCAGCTTC | 36 | 121846 | 121863 | 126 |
| 617338 | GTTGCTAAGATCCAGCTT | 35 | 121847 | 121864 | 127 |
| 549576 | CGTTGCTAAGATCCAGCT | 26 | 121848 | 121865 | 78 |
| 617339 | ACGTTGCTAAGATCCAGC | 25 | 121849 | 121866 | 128 |
| 617340 | GACGTTGCTAAGATCCAG | 30 | 121850 | 121867 | 129 |
| 617341 | GGACGTTGCTAAGATCCA | 24 | 121851 | 121868 | 130 |
| 549577 | TGGACGTTGCTAAGATCC | 25 | 121852 | 121869 | 79 |
| 617342 | CTGGACGTTGCTAAGATC | 27 | 121853 | 121870 | 131 |

TABLE 3-continued

Effects of uniform 2'-MOE modified oligonucleotides on human Tau exon 10 using Human Tau primer probe set 10_11

| ISIS NO | Sequence | % UTC | SEQ ID NO: 1 Start Site | SEQ ID NO: 1 Stop Site | SEQ ID NO |
|---|---|---|---|---|---|
| 617343 | ACTGGACGTTGCTAAGAT | 29 | 121854 | 121871 | 132 |
| 617344 | GACTGGACGTTGCTAAGA | 34 | 121855 | 121872 | 133 |
| 549578 | GGACTGGACGTTGCTAAG | 40 | 121856 | 121873 | 80 |
| 617345 | TGGACTGGACGTTGCTAA | 51 | 121857 | 121874 | 134 |
| 617346 | TTGGACTGGACGTTGCTA | 43 | 121858 | 121875 | 135 |
| 617347 | CTTGGACTGGACGTTGCT | 38 | 121859 | 121876 | 136 |
| 549579 | ACTTGGACTGGACGTTGC | 34 | 121860 | 121877 | 81 |
| 617348 | CACTTGGACTGGACGTTG | 39 | 121861 | 121878 | 137 |
| 617349 | ACACTTGGACTGGACGTT | 30 | 121862 | 121879 | 138 |
| 617350 | CACACTTGGACTGGACGT | 32 | 121863 | 121880 | 139 |
| 549580 | CCACACTTGGACTGGACG | 27 | 121864 | 121881 | 82 |
| 617351 | GCCACACTTGGACTGGAC | 23 | 121865 | 121882 | 140 |
| 617352 | AGCCACACTTGGACTGGA | 23 | 121866 | 121883 | 141 |
| 617353 | GAGCCACACTTGGACTGG | 26 | 121867 | 121884 | 142 |
| 549581 | TGAGCCACACTTGGACTG | 24 | 121868 | 121885 | 83 |

TABLE 4

Effects of uniform 2'-MOE modified oligonucleotides on human Tau exon 10 using Human Tau primer probe set 9_10 R5

| ISIS NO | Sequence | % UTC | SEQ ID NO: 1 Start Site | SEQ ID NO: 1 Stop Site | SEQ ID NO |
|---|---|---|---|---|---|
| 617354 | TTGAGCCACACTTGGACT | 21 | 121869 | 121886 | 143 |
| 617355 | TTTGAGCCACACTTGGAC | 22 | 121870 | 121887 | 144 |
| 617356 | CTTTGAGCCACACTTGGA | 16 | 121871 | 121888 | 145 |
| 549582 | CCTTTGAGCCACACTTGG | 14 | 121872 | 121889 | 146 |
| 617357 | TCCTTTGAGCCACACTTG | 17 | 121873 | 121890 | 147 |
| 617358 | ATCCTTTGAGCCACACTT | 17 | 121874 | 121891 | 148 |
| 617359 | TATCCTTTGAGCCACACT | 19 | 121875 | 121892 | 149 |
| 549583 | TTATCCTTTGAGCCACAC | 20 | 121876 | 121893 | 33 |
| 617360 | ATTATCCTTTGAGCCACA | 21 | 121877 | 121894 | 150 |
| 617361 | TATTATCCTTTGAGCCAC | 15 | 121878 | 121895 | 151 |
| 617362 | ATATTATCCTTTGAGCCA | 16 | 121879 | 121896 | 152 |
| 549584 | GATATTATCCTTTGAGCC | 17 | 121880 | 121897 | 34 |
| 565989 | TGATATTATCCTTTGAGC | 17 | 121881 | 121898 | 153 |
| 565990 | TTGATATTATCCTTTGAG | 20 | 121882 | 121899 | 154 |

TABLE 4-continued

Effects of uniform 2'-MOE modified oligonucleotides on human Tau exon 10 using Human Tau primer probe set 9_10 R5

| ISIS NO | Sequence | % UTC | SEQ ID NO: 1 Start Site | SEQ ID NO: 1 Stop Site | SEQ ID NO |
|---|---|---|---|---|---|
| 565991 | TTTGATATTATCCTTTGA | 28 | 121883 | 121900 | 155 |
| 549585 | GTTTGATATTATCCTTTG | 22 | 121884 | 121901 | 35 |
| 617363 | TGTTTGATATTATCCTTT | 25 | 121885 | 121902 | 156 |
| 617364 | GTGTTTGATATTATCCTT | 22 | 121886 | 121903 | 157 |
| 617365 | CGTGTTTGATATTATCCT | 20 | 121887 | 121904 | 158 |
| 549586 | ACGTGTTTGATATTATCC | 21 | 121888 | 121905 | 36 |
| 617366 | GACGTGTTTGATATTATC | 24 | 121889 | 121906 | 159 |
| 617367 | GGACGTGTTTGATATTAT | 16 | 121890 | 121907 | 160 |
| 617368 | GGGACGTGTTTGATATTA | 33 | 121891 | 121908 | 161 |
| 549587 | CGGGACGTGTTTGATATT | 20 | 121892 | 121909 | 37 |
| 617369 | CCGGGACGTGTTTGATAT | 25 | 121893 | 121910 | 162 |
| 617370 | CCCGGGACGTGTTTGATA | 43 | 121894 | 121911 | 163 |
| 617371 | TCCCGGGACGTGTTTGAT | 52 | 121895 | 121912 | 164 |
| 549588 | CTCCCGGGACGTGTTTGA | 53 | 121896 | 121913 | 38 |
| 549590 | ACTGCCGCCTCCCGGGAC | 48 | 121904 | 121921 | 40 |
| 617372 | CACTGCCGCCTCCCGGGA | 71 | 121905 | 121922 | 165 |
| 617373 | ACACTGCCGCCTCCCGGG | 60 | 121906 | 121923 | 166 |
| 617374 | CACACTGCCGCCTCCCGG | 40 | 121907 | 121924 | 167 |
| 549591 | TCACACTGCCGCCTCCCG | 47 | 121908 | 121925 | 41 |
| 617375 | CTCACACTGCCGCCTCCC | 33 | 121909 | 121926 | 168 |
| 617376 | ACTCACACTGCCGCCTCC | 34 | 121910 | 121927 | 169 |
| 617377 | TACTCACACTGCCGCCTC | 34 | 121911 | 121928 | 170 |
| 549592 | GTACTCACACTGCCGCCT | 31 | 121912 | 121929 | 42 |
| 617378 | GGTACTCACACTGCCGCC | 29 | 121913 | 121930 | 171 |
| 617379 | AGGTACTCACACTGCCGC | 34 | 121914 | 121931 | 172 |
| 617380 | AAGGTACTCACACTGCCG | 43 | 121915 | 121932 | 173 |
| 549593 | GAAGGTACTCACACTGCC | 33 | 121916 | 121933 | 43 |
| 617381 | TGAAGGTACTCACACTGC | 28 | 121917 | 121934 | 174 |
| 617382 | GTGAAGGTACTCACACTG | 41 | 121918 | 121935 | 175 |
| 617383 | TGTGAAGGTACTCACACT | 43 | 121919 | 121936 | 176 |
| 549594 | GTGTGAAGGTACTCACAC | 68 | 121920 | 121937 | 44 |
| 617384 | CGTGTGAAGGTACTCACA | 35 | 121921 | 121938 | 177 |
| 617385 | ACGTGTGAAGGTACTCAC | 34 | 121922 | 121939 | 178 |
| 617386 | GACGTGTGAAGGTACTCA | 29 | 121923 | 121940 | 179 |
| 549595 | GGACGTGTGAAGGTACTC | 26 | 121924 | 121941 | 45 |

TABLE 4-continued

Effects of uniform 2'-MOE modified oligonucleotides on human Tau exon 10 using Human Tau primer probe set 9_10 R5

| ISIS NO | Sequence | % UTC | SEQ ID NO: 1 Start Site | SEQ ID NO: 1 Stop Site | SEQ ID NO |
|---|---|---|---|---|---|
| 617387 | GGGACGTGTGAAGGTACT | 36 | 121925 | 121942 | 180 |
| 617388 | TGGGACGTGTGAAGGTAC | 36 | 121926 | 121943 | 181 |
| 617389 | ATGGGACGTGTGAAGGTA | 94 | 121927 | 121944 | 182 |
| 549596 | CATGGGACGTGTGAAGGT | 141 | 121928 | 121945 | 46 |
| 617390 | GCATGGGACGTGTGAAGG | 297 | 121929 | 121946 | 183 |
| 510184 | CGCATGGGACGTGTGAAG | 295 | 121930 | 121947 | 184 |
| 617391 | GCGCATGGGACGTGTGAA | 274 | 121931 | 121948 | 185 |
| 549597 | GGCGCATGGGACGTGTGA | 284 | 121932 | 121949 | 47 |
| 510185 | CGGCGCATGGGACGTGTG | 276 | 121933 | 121950 | 186 |
| 617392 | ACGGCGCATGGGACGTGT | 304 | 121934 | 121951 | 187 |
| 510186 | CACGGCGCATGGGACGTG | 268 | 121935 | 121952 | 188 |
| 549598 | GCACGGCGCATGGGACGT | 305 | 121936 | 121953 | 48 |
| 617393 | AGCACGGCGCATGGGACG | 237 | 121937 | 121954 | 189 |
| 510187 | CAGCACGGCGCATGGGAC | 144 | 121938 | 121955 | 190 |
| 617394 | ACAGCACGGCGCATGGGA | 170 | 121939 | 121956 | 191 |
| 549599 | CACAGCACGGCGCATGGG | 183 | 121940 | 121957 | 49 |
| 549619 | TCCTGAGAGCCCAAGAAG | 42 | 122020 | 122037 | 68 |
| 617395 | ATCCTGAGAGCCCAAGAA | 38 | 122021 | 122038 | 192 |
| 617396 | GATCCTGAGAGCCCAAGA | 44 | 122022 | 122039 | 193 |
| 617397 | AGATCCTGAGAGCCCAAG | 35 | 122023 | 122040 | 194 |
| 549620 | CAGATCCTGAGAGCCCAA | 35 | 122024 | 122041 | 69 |
| 617398 | CCAGATCCTGAGAGCCCA | 39 | 122025 | 122042 | 195 |
| 617399 | GCCAGATCCTGAGAGCCC | 47 | 122026 | 122043 | 196 |
| 617400 | AGCCAGATCCTGAGAGCC | 38 | 122027 | 122044 | 197 |

Example 3

Inhibitory Effect of Uniform 2'-MOE Modified Oligonucleotides on Human Tau Exon 10

Several modified oligonucleotides from Tables 3 and 4 were selected and further evaluated for their effects on inhibiting human Tau exon 10 expression in vitro. ISIS 549595 was included in the study for comparison.

"Start site" indicates the 5'-most nucleoside to which the modified oligonucleotide is targeted. "Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

A172 cells were transfected using Lipofectamine2000® with 0, 0.1, 0.3, 1, 3, 10, or 30 nM concentration of modified oligonucleotide as specified in the table below. After a treatment period of approximately 24 hours, RNA was isolated from the cells and the mRNA levels of Tau transcripts containing exon 10 were measured by quantitative real-time PCR. Human Tau primer probe set 9_10 R5 was used to measure mRNA levels, except for ISIS 549581. Human Tau primer probe set 10_11 was used for this oligonucleotide. Human Tau exon 10 mRNA levels were adjusted according to total RNA content, as measured by RIBOGREEN®.

The half maximal inhibitory concentration ($IC_{50}$) of each oligonucleotide is presented in the table below and was calculated by plotting the concentrations of oligonucleotides used versus the percent inhibition of human Tau exon 10 mRNA expression achieved at each concentration, and noting the concentration of oligonucleotide at which 50% inhibition of human Tau exon 10 mRNA expression was achieved compared to the control. Results are presented below.

TABLE 5

Inhibitory effect of uniform 2'-MOE modified oligonucleotides on human Tau exon 10 expression

| ISIS NO | Sequence | $IC_{50}$ (nM) | SEQ ID NO: 1 Start Site | SEQ ID NO: 1 Stop Site | SEQ ID NO |
|---|---|---|---|---|---|
| 549581 | TGAGCCACACTTGGACTG | 1.20 | 121868 | 121885 | 83 |
| 617354 | TTGAGCCACACTTGGACT | 1.39 | 121869 | 121886 | 143 |
| 617355 | TTTGAGCCACACTTGGAC | 1.08 | 121870 | 121887 | 144 |
| 617356 | CTTTGAGCCACACTTGGA | 0.74 | 121871 | 121888 | 145 |
| 549582 | CCTTTGAGCCACACTTGG | 0.49 | 121872 | 121889 | 146 |
| 617357 | TCCTTTGAGCCACACTTG | 0.64 | 121873 | 121890 | 147 |
| 617358 | ATCCTTTGAGCCACACTT | 0.44 | 121874 | 121891 | 148 |
| 617359 | TATCCTTTGAGCCACACT | 0.54 | 121875 | 121892 | 149 |
| 549583 | TTATCCTTTGAGCCACAC | 0.37 | 121876 | 121893 | 33 |
| 617360 | ATTATCCTTTGAGCCACA | 0.39 | 121877 | 121894 | 150 |
| 617361 | TATTATCCTTTGAGCCAC | 0.38 | 121878 | 121895 | 151 |
| 549595 | GGACGTGTGAAGGTACTC | 0.97 | 121924 | 121941 | 45 |

Example 4

Inhibitory Effect of Uniform 2'-MOE Modified Oligonucleotides on Human Tau Exon 10

Several modified oligonucleotides from Table 4 were selected and further evaluated for their effects on inhibiting human Tau exon 10 expression in vitro. ISIS 549595 was included in the study for comparison.

"Start site" indicates the 5'-most nucleoside to which the modified oligonucleotide is targeted. "Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

A172 cells were transfected using Lipofectamine2000® with 0, 0.1, 0.3, 1, 3, 10, or 30 nM concentration of modified oligonucleotide as specified in the table below. After a treatment period of approximately 24 hours, RNA was isolated from the cells and the mRNA levels of Tau transcripts containing exon 10 were measured by quantitative real-time PCR. Human Tau primer probe set 9_10 R5 was used to measure mRNA levels. Human Tau exon 10 mRNA levels were adjusted according to total RNA content, as measured by RIBOGREEN®.

The $IC_{50}$ of each oligonucleotide was calculated in the same manner as illustrated in Example 3 and the results are presented below.

TABLE 6

Inhibitory effect of uniform 2'-MOE modified oligonucleotides on human Tau exon 10 expression

| ISIS NO | Sequence | $IC_{50}$ (nM) | SEQ ID NO: 1 Start Site | SEQ ID NO: 1 Stop Site | SEQ ID NO |
|---|---|---|---|---|---|
| 617362 | ATATTATCCTTTGAGCCA | 0.27 | 121879 | 121896 | 152 |
| 549584 | GATATTATCCTTTGAGCC | 0.40 | 121880 | 121897 | 34 |
| 565989 | TGATATTATCCTTTGAGC | 0.58 | 121881 | 121898 | 153 |
| 565990 | TTGATATTATCCTTTGAG | 1.23 | 121882 | 121899 | 154 |
| 549585 | GTTTGATATTATCCTTTG | 0.71 | 121884 | 121901 | 35 |
| 617364 | GTGTTTGATATTATCCTT | 0.61 | 121886 | 121903 | 157 |
| 617365 | CGTGTTTGATATTATCCT | 0.74 | 121887 | 121904 | 158 |
| 549586 | ACGTGTTTGATATTATCC | 0.93 | 121888 | 121905 | 36 |
| 617367 | GGACGTGTTTGATATTAT | 0.64 | 121890 | 121907 | 160 |
| 549587 | CGGGACGTGTTTGATATT | 0.97 | 121892 | 121909 | 37 |
| 549620 | CAGATCCTGAGAGCCCAA | 3.46 | 122024 | 122041 | 69 |
| 549595 | GGACGTGTGAAGGTACTC | 1.25 | 121924 | 121941 | 45 |

Example 5

Inhibitory Effect of Uniform 2'-MOE Modified Oligonucleotides on Human Tau Exon 10

Several modified oligonucleotides from Tables 3 and 4 were selected and further evaluated for their effects on inhibiting human Tau exon 10 expression in vitro. ISIS 549595 was included in the study for comparison.

"Start site" indicates the 5'-most nucleoside to which the modified oligonucleotide is targeted. "Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

A172 cells were transfected using Lipofectamine2000® with 0, 0.1, 0.3, 1, 3, 10, or 30 nM concentrations of modified oligonucleotide as specified in the table below. After a treatment period of approximately 24 hours, RNA was isolated from the cells and the mRNA levels of Tau transcripts containing exon 10 were measured by quantitative real-time PCR. Human Tau primer probe set 10_11 was used to measure mRNA levels, except for ISIS 549595. Human Tau primer probe set 9_10 R5 was used for this oligonucleotide. Human Tau exon 10 mRNA levels were adjusted according to total RNA content, as measured by RIBOGREEN®.

The $IC_{50}$ of each oligonucleotide was calculated in the same manner as illustrated in Example 3 and the results are presented below.

TABLE 7

Inhibitory effect of uniform 2'-MOE modified oligonucleotides on human Tau exon 10 expression

| ISIS NO | Sequence | $IC_{50}$ (nM) | SEQ ID NO: 1 Start Site | SEQ ID NO: 1 Stop Site | SEQ ID NO |
|---|---|---|---|---|---|
| 549566 | AGCCAGAAAAAAGGATGA | 1.00 | 121804 | 121821 | 31 |
| 617309 | CACCTTTGGTAGCCAGAA | 1.11 | 121814 | 121831 | 97 |
| 549570 | TAATTATCTGCACCTTTG | 1.39 | 121824 | 121841 | 72 |
| 617317 | TTAATTATCTGCACCTTT | 1.26 | 121825 | 121842 | 106 |
| 617318 | ATTAATTATCTGCACCTT | 1.21 | 121826 | 121843 | 107 |
| 617323 | TTCTTATTAATTATCTGC | 0.96 | 121831 | 121848 | 112 |
| 617324 | CTTCTTATTAATTATCTG | 1.06 | 121832 | 121849 | 113 |
| 617341 | GGACGTTGCTAAGATCCA | 0.82 | 121851 | 121868 | 130 |
| 549577 | TGGACGTTGCTAAGATCC | 0.87 | 121852 | 121869 | 79 |
| 617351 | GCCACACTTGGACTGGAC | 0.91 | 121865 | 121882 | 140 |
| 617352 | AGCCACACTTGGACTGGA | 0.79 | 121866 | 121883 | 141 |
| 549595 | GGACGTGTGAAGGTACTC | 0.73 | 121924 | 121941 | 45 |

Example 6

Inhibitory Effect of Uniform 2'-MOE Modified Oligonucleotides on Human Tau Exon 10

Several modified oligonucleotides from Tables 1 and 4 were selected and further evaluated for their effect on inhibiting human Tau exon 10 expression in vitro. ISIS 617782, 617781, and 415833 were included in the study for comparison.

"Start site" indicates the 5'-most nucleoside to which the modified oligonucleotide is targeted. "Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

ISIS 617782 is 21 nucleosides in length, wherein each nucleoside has a 2'-$OCH_3$ modification and is denoted as the subscript "m". Each internucleoside linkage throughout the modified oligonucleotide are phosphorothioate internucleoside linkages (P═S).

ISIS 617781 is 18 nucleosides in length, wherein each nucleoside has a 2'-$OCH_3$ modification and is denoted as the subscript "m". Each internucleoside linkage throughout the modified oligonucleotide are phosphorothioate internucleoside linkages (P═S).

ISIS 415833 is 20 nucleosides in length, wherein each nucleoside has a 2'-MOE modification. Each internucleoside linkage throughout the modified oligonucleotide are phosphorothioate internucleoside linkages (P═S). All cytosine residues throughout the modified oligonucleotides are 5-methylcytosines.

A172 cells were transfected using Lipofectamine2000® with 0, 0.1, 0.3, 1, 3, 10, or 30 nM concentration of modified oligonucleotide as specified in the table below. After a treatment period of approximately 24 hours, RNA was isolated from the cells and the mRNA levels of Tau transcripts containing exon 10 were measured by quantitative real-time PCR. Human Tau primer probe set 9_10 R5 was used to measure mRNA levels, except for ISIS 617781 and 415883. Human Tau primer probe set 10_11 was used for these two oligonucleotides. Human Tau exon 10 mRNA levels were adjusted according to total RNA content, as measured by RIBOGREEN®.

The $IC_{50}$ of each oligonucleotide was calculated in the same manner as illustrated in Example 3 and the results are presented below.

TABLE 8

Inhibitory effect of uniform 2'-MOE modified oligonucleotides on human Tau exon 10 expression

| ISIS NO | Sequence | $IC_{50}$ (nM) | SEQ ID NO: 1 Start Site | SEQ ID NO: 1 Stop Site | SEQ ID NO |
|---|---|---|---|---|---|
| 617357 | TCCTTTGAGCCACACTTG | 0.48 | 121873 | 121890 | 147 |
| 617358 | ATCCTTTGAGCCACACTT | 0.34 | 121874 | 121891 | 148 |
| 617359 | TATCCTTTGAGCCACACT | 0.41 | 121875 | 121892 | 149 |
| 549583 | TTATCCTTTGAGCCACAC | 0.27 | 121876 | 121893 | 33 |
| 617360 | ATTATCCTTTGAGCCACA | 0.33 | 121877 | 121894 | 150 |
| 617361 | TATTATCCTTTGAGCCAC | 0.24 | 121878 | 121895 | 151 |
| 617362 | ATATTATCCTTTGAGCCA | 0.27 | 121879 | 121896 | 152 |
| 549584 | GATATTATCCTTTGAGCC | 0.19 | 121880 | 121897 | 34 |

TABLE 8-continued

Inhibitory effect of uniform 2'-MOE modified oligonucleotides on human Tau exon 10 expression

| ISIS NO | Sequence | $IC_{50}$ (nM) | SEQ ID NO: 1 Start Site | SEQ ID NO: 1 Stop Site | SEQ ID NO |
|---|---|---|---|---|---|
| 565989 | TGATATTATCCTTTGAGC | 0.39 | 121881 | 121898 | 153 |
| 617782 | $U_{m}G_{m}A_{m}A_{m}G_{m}G_{m}U_{m}A_{m}C_{m}U_{m}C_{m}A_{m}C_{m}A_{m}C_{m}U_{m}G_{m}C_{m}C_{m}G_{m}C_{m}$ | 4.33 | 121914 | 121934 | 198 |
| 617781 | $U_{m}A_{m}U_{m}C_{m}U_{m}G_{m}C_{m}A_{m}C_{m}C_{m}U_{m}U_{m}U_{m}G_{m}G_{m}U_{m}A_{m}G_{m}$ | 20.25 | 121820 | 121837 | 199 |
| 415883 | TCTTATTAATTATCTGCACC | 0.65 | 121828 | 121847 | 200 |

Example 7

Modified Oligonucleotides Targeting Exon 10 of Human Tau

A series of modified oligonucleotides were designed to target exon 10 of human Tau. "Start site" indicates the 5'-most nucleoside to which the modified oligonucleotide is targeted. "Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

In the table below, "${}^{m}C$" indicates 5-methylcytosine, subscript "e" indicates 2'-O-methoxyethyl, subscript "f" indicates 2'-deoxyfluoro, subscript "d" indicates 2'-deoxy, subscript "p" indicates a peptide nucleic acid monomer, subscript "s" indicates a phosphorothioate internucleoside linkage, subscript "o" indicates a phosphodiester internucleoside linkage, "P-" indicates an O-linker at the 5'-end (PNA Bio, Thousand Oaks, Calif.), "-N" indicates a 3'-end carboxy amide.

TABLE 9

Modified oligonucleotides targeting human Tau

| ISIS NO | Sequence | SEQ ID NO: 1 Start Site | SEQ ID NO: 1 Stop Site | SEQ ID NO |
|---|---|---|---|---|
| 549607 | $A_{es}{}^{m}C_{es}G_{es}{}^{m}C_{es}A_{es}{}^{m}C_{es}T_{es}{}^{m}C_{es}A_{es}{}^{m}C_{es}A_{es}{}^{m}C_{es}{}^{m}C_{es}A_{es}{}^{m}C_{es}T_{es}T_{es}{}^{m}C_{e}$ | 121972 | 121989 | 201 |
| 565985 | ${}^{m}C_{es}G_{es}{}^{m}C_{es}{}^{m}C_{es}T_{es}A_{es}C_{es}T_{es}T_{es}G_{es}{}^{m}C_{es}T_{es}C_{es}G_{es}{}^{m}C_{es}A_{es}A_{es}G_{e}$ | 121706 | 121723 | 202 |
| 565986 | $G_{es}A_{es}{}^{m}C_{es}{}^{m}C_{es}{}^{m}C_{es}G_{es}{}^{m}C_{es}{}^{m}C_{es}T_{es}A_{es}{}^{m}C_{es}T_{es}T_{es}G_{es}{}^{m}C_{es}T_{es}{}^{m}C_{es}G_{e}$ | 121710 | 121727 | 203 |
| 565987 | $G_{es}A_{es}{}^{m}C_{es}{}^{m}C_{es}{}^{m}C_{es}sG_{es}{}^{m}C_{es}{}^{m}C_{es}T_{es}G_{es}{}^{m}C_{es}T_{es}T_{es}G_{es}{}^{m}C_{es}T_{es}{}^{m}C_{es}G_{e}$ | 121770 | 121787 | 204 |
| 565988 | ${}^{m}C_{es}{}^{m}C_{es}T_{es}G_{es}G_{es}A_{es}{}^{m}C_{es}{}^{m}C_{es}{}^{m}C_{es}G_{es}{}^{m}C_{es}{}^{m}C_{es}T_{es}G_{es}{}^{m}C_{es}T_{es}T_{es}G_{e}$ | 121774 | 121791 | 205 |
| 566007 | ${}^{m}C_{es}G_{es}C_{fs}C_{fs}U_{fs}A_{fs}C_{fs}U_{fs}U_{fs}G_{fs}C_{fs}U_{fs}C_{fs}G_{fs}C_{fs}A_{fs}A_{es}G_{e}$ | 121706 | 121723 | 206 |
| 566012 | ${}^{m}C_{es}{}^{m}C_{es}U_{fs}G_{fs}G_{fs}A_{fs}C_{fs}C_{fs}C_{fs}G_{fs}C_{fs}C_{fs}U_{fs}G_{fs}C_{fs}U_{fs}T_{es}G_{e}$ | 121774 | 121791 | 207 |
| 566013 | $T_{es}G_{es}A_{fs}U_{fs}A_{fs}U_{fs}U_{fs}A_{fs}mU_{fs}C_{fs}C_{fs}U_{fs}U_{fs}U_{fs}G_{fs}A_{fs}G_{es}{}^{m}C_{e}$ | 121881 | 121898 | 208 |

TABLE 9-continued

Modified oligonucleotides targeting human Tau

| ISIS NO | Sequence | SEQ ID NO: 1 Start Site | SEQ ID NO: 1 Stop Site | SEQ ID NO |
|---|---|---|---|---|
| 566014 | $T_{es}T_{es}G_{fs}A_{fs}U_{fs}A_{fs}U_{fs}U_{fs}A_{fs}U_{fs}C_{fs}C_{fs}U_{fs}U_{fs}U_{fs}G_{fs}A_{es}G_{e}$ | 121882 | 121899 | 209 |
| 566015 | $T_{es} T_{es} U_{fs} G_{fs} A_{fs} U_{fs} A_{fs} U_{fs} U_{fs} A_{fs} U_{fs} C_{fs} C_{fs} U_{fs} U_{fs} U_{fs} G_{es} A_{e}$ | 121883 | 121900 | 210 |
| 566016 | ${}^{m}C_{es} A_{es} C_{fs} U_{fs} U_{fs} C_{fs} C_{fs} U_{fs} A_{fs} A_{fs} U_{fs} A_{fs} A_{fs} U_{fs} U_{fs} C_{fs} A_{es} A_{e}$ | 121960 | 121977 | 211 |
| 566017 | $A_{es} {}^{m}C_{es} A_{fs} C_{fs} C_{fs} A_{fs} C_{fs} U_{fs} U_{fs} C_{fs} C_{fs} U_{fs} A_{fs} A_{fs} U_{fs} A_{fs} A_{es} T_{e}$ | 121964 | 121981 | 212 |
| 566018 | $A_{es} {}^{m}C_{es} U_{fs} C_{fs} A_{fs} C_{fs} A_{fs} C_{fs} C_{fs} A_{fs} C_{fs} U_{fs} U_{fs} C_{fs} C_{fs} U_{fs} A_{es} A_{e}$ | 121968 | 121985 | 213 |
| 568409 | ${}^{m}C_{es} {}^{m}C_{es} C_{fs} G_{fs} C_{fs} C_{fs} U_{fs} A_{fs} C_{fs} U_{fs} U_{fs} G_{fs} C_{fs} U_{fs} C_{fs} G_{fs} {}^{m}C_{es} A_{e}$ | 121708 | 121725 | 214 |
| 568410 | $G_{es} A_{es} C_{fs} C_{fs} C_{fs} G_{fs} C_{fs} C_{fs} U_{fs} A_{fs} C_{fs} U_{fs} U_{fs} G_{fs} C_{fs} U_{fs} {}^{m}C_{es} G_{e}$ | 121710 | 121727 | 215 |
| 568411 | $G_{es} A_{es} C_{fs} C_{fs} C_{fs} G_{fs} C_{fs} C_{fs} U_{fs} G_{fs} C_{fs} U_{fs} U_{fs} G_{fs} C_{fs} U_{fs} {}^{m}C_{es} G_{e}$ | 121770 | 121787 | 216 |
| 568412 | $T_{es} G_{es} G_{fs} A_{fs} C_{fs} C_{fs} C_{fs} G_{fs} C_{fs} C_{fs} U_{fs} G_{fs} C_{fs} U_{fs} U_{fs} G_{fs} {}^{m}C_{es} T_{e}$ | 121772 | 121789 | 217 |
| 624464 | $U_{ms} C_{ms} U_{ms} U_{ms} A_{ms} U_{ms} U_{ms} A_{ms} A_{ms} U_{ms} U_{ms} A_{ms} U_{ms} C_{ms} U_{ms} G_{ms} C_{ms} A_{ms} C_{ms} C_{m}$ | 121828 | 121847 | 218 |
| 624465 | $T_{ks} {}^{m}C_{ds} T_{ds} T_{ks} A_{ds} T_{ds} T_{ks} A_{ds} A_{ds} T_{ks} T_{ds} A_{ds} T_{ks} {}^{m}C_{ds} T_{ds} G_{ks} {}^{m}C_{ds} A_{ds} {}^{m}C_{ks} {}^{m}C_{k}$ | 121828 | 121847 | 200 |
| 624466 | $T_{ks} {}^{m}C_{es} T_{es} T_{ks} A_{es} T_{es} T_{ks} A_{es} A_{es} T_{ks} T_{es} A_{es} T_{ks} {}^{m}C_{es} T_{es} G_{ks} {}^{m}C_{es} A_{es} {}^{m}C_{ks} {}^{m}C_{k}$ | 121828 | 121847 | 200 |
| 624467 | $T_{ks} {}^{m}C_{es} T_{es} T_{ko} A_{es} T_{es} T_{ko} A_{es} A_{es} T_{ko} T_{es} A_{es} T_{ko} {}^{m}C_{es} T_{es} G_{ko} {}^{m}C_{es} A_{es} {}^{m}C_{ks} {}^{m}C_{k}$ | 121828 | 121847 | 200 |
| 624468 | $T_{ks} {}^{m}C_{ds} T_{ds} T_{ko} A_{ds} T_{ds} T_{ko} A_{ds} A_{ds} T_{ko} T_{ds} A_{ds} T_{ko} mC_{ds} T_{ds} G_{ko} {}^{m}C_{ds} A_{ds} {}^{m}C_{ks} {}^{m}C_{k}$ | 121828 | 121847 | 200 |
| 626881 | $P\text{-}T_{p} C_{p} T_{p} T_{p} A_{p} T_{p} T_{p} A_{p} A_{p} T_{p} T_{p} A_{p} T_{p} C_{p} T_{p} G_{p} C_{p} A_{p} C_{p} C_{p}\text{-}N$ | 121828 | 121847 | 200 |
| 670011 | $G_{es} G_{es} A_{eo} {}^{m}C_{es} G_{eo} T_{es} T_{eo} G_{es} {}^{m}C_{eo} T_{es} A_{eo} A_{es} G_{eo} A_{es} T_{eo} {}^{m}C_{es} {}^{m}C_{es} A_{e}$ | 121851 | 121868 | 130 |
| 670012 | ${}^{m}C_{es} {}^{m}C_{es} T_{eo} T_{es} T_{eo} G_{es} A_{eo} G_{es} {}^{m}C_{eo} {}^{m}C_{es} A_{eo} {}^{m}C_{es} A_{eo} {}^{m}C_{es} T_{eo} T_{es} G_{es} G_{e}$ | 121872 | 121889 | 146 |
| 670013 | $A_{es} T_{es} {}^{m}C_{eo} {}^{m}C_{es} T_{eo} T_{es} T_{eo} G_{es} A_{eo} G_{es} {}^{m}C_{eo} {}^{m}C_{es} A_{eo} {}^{m}C_{es} A_{eo} {}^{m}C_{es} T_{es} T_{e}$ | 121874 | 121891 | 148 |
| 670014 | $T_{es} T_{es} A_{eo} T_{es} {}^{m}C_{eo} {}^{m}C_{es} T_{eo} T_{es} T_{eo} G_{es} A_{eo} G_{es} {}^{m}C_{eo} {}^{m}C_{es} A_{eo} {}^{m}C_{es} A_{es} {}^{m}C_{e}$ | 121876 | 121893 | 33 |
| 670015 | $A_{es} T_{es} T_{eo} A_{es} T_{eo} {}^{m}C_{es} {}^{m}C_{eo} T_{es} T_{eo} T_{es} G_{eo} A_{es} G_{eo} {}^{m}C_{es} {}^{m}C_{eo} A_{es} {}^{m}C_{es} A_{e}$ | 121877 | 121894 | 150 |
| 670016 | $T_{es} A_{es} T_{eo} T_{es} A_{eo} T_{es} {}^{m}C_{eo} {}^{m}C_{es} T_{eo} T_{es} T_{eo} G_{es} A_{eo} G_{es} {}^{m}C_{eo} {}^{m}C_{es} A_{es} {}^{m}C_{e}$ | 121878 | 121895 | 151 |
| 670017 | $A_{es} T_{es} A_{eo} T_{es} T_{eo} A_{es} T_{eo} {}^{m}C_{es} {}^{m}C_{eo} T_{es} T_{eo} T_{es} G_{eo} A_{es} G_{eo} {}^{m}C_{es} {}^{m}C_{es} A_{e}$ | 121879 | 121896 | 152 |
| 670018 | $G_{es} A_{es} T_{eo} A_{es} T_{eo} T_{es} A_{eo} T_{es} {}^{m}C_{eo} {}^{m}C_{es} T_{eo} T_{es} T_{eo} G_{es} A_{eo} G_{es} {}^{m}C_{es} {}^{m}C_{e}$ | 121880 | 121897 | 34 |
| 670019 | $G_{es} T_{es} T_{eo} T_{es} G_{eo} A_{es} T_{eo} A_{es} T_{eo} T_{es} A_{eo} T_{es} {}^{m}C_{eo} {}^{m}C_{es} T_{eo} T_{es} T_{es} G_{e}$ | 121884 | 121901 | 35 |
| 670020 | $G_{es} G_{eo} A_{eo} {}^{m}C_{eo} G_{es} T_{es} T_{es} G_{es} {}^{m}C_{es} T_{es} A_{es} A_{es} G_{eo} A_{eo} T_{eo} {}^{m}C_{es} {}^{m}C_{es} A_{e}$ | 121851 | 121868 | 130 |

TABLE 9-continued

Modified oligonucleotides targeting human Tau

| ISIS NO | Sequence | SEQ ID NO: 1 Start Site | SEQ ID NO: 1 Stop Site | SEQ ID NO |
|---|---|---|---|---|
| 670021 | $^{m}C_{es}\ ^{m}C_{eo}\ T_{eo}\ T_{eo}\ T_{es}\ G_{es}\ A_{es}\ G_{es}\ ^{m}C_{es}\ ^{m}C_{es}\ A_{es}\ ^{m}C_{es}\ A_{eo}\ ^{m}C_{eo}\ T_{eo}\ T_{es}\ G_{es}\ G_{e}$ | 121872 | 121889 | 146 |
| 670022 | $A_{es}\ T_{eo}\ ^{m}C_{eo}\ ^{m}C_{eo}\ T_{es}\ T_{es}\ T_{es}\ G_{es}\ A_{es}\ G_{es}\ ^{m}C_{es}\ ^{m}C_{es}\ A_{eo}\ ^{m}C_{eo}\ A_{eo}\ ^{m}C_{es}\ T_{es}\ T_{e}$ | 121874 | 121891 | 148 |
| 670023 | $T_{es}\ T_{eo}\ A_{eo}\ T_{eo}\ ^{m}C_{es}\ ^{m}C_{es}\ T_{es}\ T_{es}\ T_{es}\ G_{es}\ A_{es}\ G_{es}\ ^{m}C_{eo}\ ^{m}C_{eo}\ A_{eo}\ ^{m}C_{es}\ A_{es}\ ^{m}C_{e}$ | 121876 | 121893 | 33 |
| 670024 | $A_{es}\ T_{eo}\ T_{eo}\ A_{eo}\ T_{es}\ ^{m}C_{es}\ ^{m}C_{es}\ T_{es}\ T_{es}\ T_{es}\ G_{es}\ A_{es}\ G_{eo}\ ^{m}C_{eo}\ ^{m}C_{eo}\ A_{es}\ ^{m}C_{es}\ A_{e}$ | 121877 | 121894 | 150 |
| 670025 | $T_{es}\ A_{eo}\ T_{eo}\ T_{eo}\ A_{es}\ T_{es}\ ^{m}C_{es}\ ^{m}C_{es}\ T_{es}\ T_{es}\ T_{es}\ G_{es}\ A_{eo}\ G_{eo}\ ^{m}C_{eo}\ ^{m}C_{es}\ A_{es}\ ^{m}C_{e}$ | 121878 | 121895 | 151 |
| 670026 | $A_{es}\ T_{eo}\ A_{eo}\ T_{eo}\ T_{es}\ A_{es}\ T_{es}\ ^{m}C_{es}\ ^{m}C_{es}\ T_{es}\ T_{es}\ T_{es}\ G_{eo}\ A_{eo}\ G_{eo}\ ^{m}C_{es}\ ^{m}C_{es}\ A_{e}$ | 121879 | 121896 | 152 |
| 670027 | $G_{es}\ A_{eo}\ T_{eo}\ A_{eo}\ T_{es}\ T_{es}\ A_{es}\ T_{es}\ ^{m}C_{es}\ ^{m}C_{es}\ T_{es}\ T_{es}\ T_{eo}\ G_{eo}\ A_{eo}\ G_{es}\ ^{m}C_{es}\ ^{m}C_{e}$ | 121880 | 121897 | 34 |
| 670028 | $G_{es}\ T_{eo}\ T_{eo}\ T_{eo}\ G_{es}\ A_{es}\ T_{es}\ A_{es}\ T_{es}\ T_{es}\ A_{es}\ T_{es}\ ^{m}C_{eo}\ ^{m}C_{eo}\ T_{eo}\ T_{es}\ T_{es}\ G_{e}$ | 121884 | 121901 | 35 |
| 678329 | $G_{es}\ ^{m}C_{es}\ ^{m}C_{eo}\ A_{es}\ ^{m}C_{eo}\ A_{es}\ ^{m}C_{eo}\ T_{es}\ T_{eo}\ G_{es}\ G_{eo}\ A_{es}\ ^{m}C_{eo}\ T_{es}\ G_{eo}\ G_{es}\ A_{es}\ ^{m}C_{e}$ | 121865 | 121882 | 140 |
| 678330 | $A_{es}\ G_{es}\ ^{m}C_{eo}\ ^{m}C_{es}\ A_{eo}\ ^{m}C_{es}\ A_{eo}\ ^{m}C_{es}\ T_{eo}\ T_{es}\ G_{eo}\ G_{es}\ A_{eo}\ ^{m}C_{es}\ T_{eo}\ G_{es}\ G_{es}\ A_{e}$ | 121866 | 121883 | 141 |
| 678331 | $T_{es}\ G_{es}\ A_{eo}\ G_{es}\ ^{m}C_{eo}\ ^{m}C_{es}\ A_{eo}\ ^{m}C_{es}\ T_{eo}\ T_{es}\ G_{eo}\ G_{es}\ A_{eo}\ ^{m}C_{es}\ T_{es}\ G_{e}$ | 121868 | 121885 | 83 |
| 678332 | $G_{es}\ ^{m}C_{eo}\ ^{m}C_{eo}\ A_{eo}\ ^{m}C_{es}\ A_{es}\ ^{m}C_{es}\ T_{es}\ T_{es}\ G_{es}\ G_{es}\ A_{es}\ ^{m}C_{eo}\ T_{eo}\ G_{eo}\ G_{es}\ A_{es}\ ^{m}C_{e}$ | 121865 | 121882 | 140 |
| 678333 | $A_{es}\ G_{eo}\ ^{m}C_{eo}\ ^{m}C_{eo}\ A_{es}\ ^{m}C_{es}\ A_{es}\ ^{m}C_{es}\ T_{es}\ T_{es}\ G_{es}\ G_{es}\ A_{eo}\ ^{m}C_{eo}\ T_{eo}\ G_{es}\ G_{es}\ A_{e}$ | 121866 | 121883 | 141 |
| 678334 | $T_{es}\ G_{eo}\ A_{eo}\ G_{eo}\ ^{m}C_{es}\ ^{m}C_{es}\ A_{es}\ ^{m}C_{es}\ A_{es}\ ^{m}C_{es}\ T_{es}\ T_{es}\ G_{eo}\ G_{eo}\ A_{eo}\ ^{m}C_{es}\ T_{es}\ G_{e}$ | 121868 | 121885 | 83 |
| 693840 | $T_{es}\ G_{es}\ G_{eo}\ A_{es}\ ^{m}C_{eo}\ G_{es}\ T_{eo}\ T_{es}\ G_{eo}\ ^{m}C_{es}\ T_{eo}\ A_{es}\ A_{eo}\ G_{es}\ A_{eo}\ T_{es}\ ^{m}C_{es}\ ^{m}C_{e}$ | 121852 | 121869 | 79 |
| 693841 | $^{m}C_{es}\ ^{m}C_{es}\ A_{eo}\ ^{m}C_{es}\ A_{eo}\ ^{m}C_{es}\ T_{eo}\ T_{es}\ G_{eo}\ G_{es}\ A_{eo}\ ^{m}C_{es}\ T_{eo}\ G_{es}\ G_{eo}\ A_{es}\ ^{m}C_{es}\ G_{e}$ | 121864 | 121881 | 82 |
| 693842 | $A_{es}\ ^{m}C_{es}\ G_{eo}\ T_{es}\ G_{eo}\ T_{es}\ T_{eo}\ T_{es}\ G_{eo}\ A_{es}\ T_{eo}\ A_{es}\ T_{eo}\ T_{es}\ A_{eo}\ T_{es}\ ^{m}C_{es}\ ^{m}C_{e}$ | 121888 | 121905 | 36 |
| 693843 | $G_{es}\ G_{es}\ A_{eo}\ ^{m}C_{es}\ G_{eo}\ T_{es}\ G_{eo}\ T_{es}\ G_{eo}\ A_{es}\ A_{eo}\ G_{es}\ G_{eo}\ T_{es}\ A_{eo}\ ^{m}C_{es}\ T_{es}\ ^{m}C_{e}$ | 121924 | 121941 | 45 |
| 693844 | $G_{es}\ A_{es}\ G_{eo}\ ^{m}C_{es}\ ^{m}C_{eo}\ A_{es}\ ^{m}C_{eo}\ A_{es}\ ^{m}C_{eo}\ T_{es}\ T_{eo}\ G_{es}\ G_{eo}\ A_{es}\ ^{m}C_{eo}\ T_{es}\ G_{es}\ G_{e}$ | 121867 | 121884 | 142 |
| 693845 | $T_{es}\ G_{eo}\ G_{eo}\ A_{eo}\ ^{m}C_{es}\ G_{es}\ T_{es}\ T_{es}\ G_{es}\ ^{m}C_{es}\ T_{es}\ A_{es}\ A_{eo}\ G_{eo}\ A_{eo}\ T_{es}\ ^{m}C_{es}\ ^{m}C_{e}$ | 121852 | 121869 | 79 |
| 693846 | $^{m}C_{es}\ ^{m}C_{eo}\ A_{eo}\ ^{m}C_{eo}\ A_{es}\ Mc_{es}\ T_{es}\ T_{es}\ G_{es}\ G_{es}\ A_{es}\ ^{m}C_{es}\ T_{eo}\ G_{eo}\ G_{eo}\ A_{es}\ ^{m}C_{es}\ G_{e}$ | 121864 | 121881 | 82 |
| 693847 | $A_{es}\ ^{m}C_{eo}\ G_{eo}\ T_{eo}\ G_{es}\ T_{es}\ T_{es}\ T_{es}\ G_{es}\ A_{es}\ T_{es}\ A_{es}\ T_{eo}\ T_{eo}\ A_{eo}\ T_{es}\ ^{m}C_{es}\ ^{m}C_{e}$ | 121888 | 121905 | 36 |
| 693848 | $G_{es}\ G_{eo}\ A_{eo}\ ^{m}C_{eo}\ G_{es}\ T_{es}\ G_{es}\ T_{es}\ G_{es}\ A_{es}\ A_{es}\ G_{es}\ G_{eo}\ T_{eo}\ A_{eo}\ ^{m}C_{es}\ T_{es}\ ^{m}C_{e}$ | 121924 | 121941 | 45 |
| 693849 | $G_{es}\ A_{eo}\ G_{eo}\ ^{m}C_{eo}\ ^{m}C_{es}\ A_{es}\ ^{m}C_{es}\ A_{es}\ ^{m}C_{es}\ T_{es}\ T_{es}\ G_{es}\ G_{eo}\ A_{eo}\ ^{m}C_{eo}\ T_{es}\ G_{es}\ G_{e}$ | 121867 | 121884 | 142 |

Example 8

In Vivo Analysis of Oligonucleotides Targeting Human Tau Exon 10

Sprague Dawley rats were separated into groups of 3 rats for the experiment presented in Table 11 and into groups of 2 or 4 rats for the experiment presented in Table 12. Each rat in each group of rats was administered a single 3 mg intrathecal (IT) dose of an oligonucleotide selected from Table 3, 4, or 9. At various time points after injection from 3 hours to 8 weeks, the movement of 7 different parts of the body was evaluated for each rat. The 7 body parts are (1) the rat's tail; (2) the rat's posterior posture; (3) the rat's hind limbs; (4) the rat's hind paws; (5) the rat's forepaws; (6) the rat's anterior posture; and (7) the rat's head. For each of the 7 different body parts, each rat was given a sub-score of 0 if the body part was moving or 1 if the body part was paralyzed. After each of the 7 body parts were evaluated, the sub-scores were summed for each rat and then averaged for each group. For example, if a rat's tail, head, and all other evaluated body parts were moving 3 hours after the 3 mg IT dose, it would get a summed score of 0. If another rat was not moving its tail 3 hours after the 3 mg IT dose but all other evaluated body parts were moving, it would receive a score of 1. Saline treated rats generally receive a score of 0. A score of at the top end of the range would be suggestive of toxicity. Results are presented as the average score for each treatment group in Tables 11 and 12.

TABLE 11

3 mg IT bolus in vivo study

| ISIS No. | Score 3 hours after injection | Score 2 weeks after injection | Score 8 weeks after injection | SEQ ID NO. |
|---|---|---|---|---|
| 670020 | 1.0 | 2.7 | 2.7 | 130 |
| 670011 | 2.3 | 2.3 | 2.3 | 130 |
| 617341 | 3.0 | 0.0 | 0.0 | 130 |
| 678329 | 2.3 | 0.0 | 0.0 | 140 |
| 678332 | 3.0 | 0.0 | 1.3 | 140 |
| 617351 | 7.0 | 0.0 | 4.0 | 140 |
| 678330 | 2.7 | 2.3 | 3.0 | 141 |
| 678333 | 2.7 | 2.3 | 2.3 | 141 |
| 617352 | 7.0 | 0.0 | 2.0 | 141 |
| 678331 | 3.0 | 0.0 | 0.0 | 83 |
| 678334 | 4.3 | 2.3 | 2.3 | 83 |
| 549581 | 7.0 | 0.0 | 0.3 | 83 |
| 670012 | 2.7 | 0.0 | 0.0 | 146 |
| 670021 | 3.0 | 0.0 | 1.0 | 146 |
| 549582 | 4.3 | 0.0 | 0.0 | 146 |
| 670013 | 0.3 | 2.3 | 2.3 | 148 |
| 670022 | 2.0 | 2.3 | 3.0 | 148 |
| 617358 | 3.7 | 0.0 | 1.3 | 148 |
| 670014 | 0.0 | 0.0 | 0.0 | 33 |
| 670023 | 2.0 | 1.0 | 0.3 | 33 |
| 549583 | 2.3 | 0.0 | 0.0 | 33 |
| 670015 | 1.0 | 2.0 | 0.7 | 150 |
| 670024 | 1.0 | 0.7 | 0.0 | 150 |
| 617360 | 5.3 | 0.0 | 1.0 | 150 |
| 670025 | 0.3 | 5.3 | 5.3 | 151 |
| 670016 | 2.3 | 1.3 | 1.7 | 151 |
| 617361 | 3.0 | 0.0 | 0.3 | 151 |
| 670017 | 0.0 | 1.7 | 1.3 | 152 |
| 670026 | 1.0 | 3.7 | 3.3 | 152 |
| 617362 | 4.7 | 3.7 | 2.7 | 152 |
| 670018 | 0.3 | 0.3 | 0.3 | 34 |
| 670027 | 1.0 | 0.7 | 0.7 | 34 |
| 549584 | 5.0 | 2.7 | 3.7 | 34 |
| 670028 | 2.0 | 0.0 | 0.0 | 35 |
| 670019 | 3.0 | 0.0 | 0.0 | 35 |
| 549585 | 4.7 | 5.3 | 7.0 | 35 |

TABLE 12

3 mg IT bolus in vivo study

| ISIS No. | No. of rats in treatment group | Score 3 hours after injection | SEQ ID NO. |
|---|---|---|---|
| 549577 | 4 | 3.3 | 79 |
| 693840 | 4 | 1.8 | 79 |
| 693845 | 4 | 0.0 | 79 |
| 549580 | 4 | 7.0 | 82 |
| 693841 | 4 | 1.8 | 82 |
| 693846 | 4 | 2.5 | 82 |
| 617353 | 4 | 7.0 | 142 |
| 693844 | 2 | 3.5 | 142 |
| 693849 | 4 | 5.0 | 142 |
| 549582 | 4 | 4.3 | 146 |
| 549586 | 4 | 5.0 | 36 |
| 693847 | 2 | 1.0 | 36 |
| 549595 | 4 | 6.5 | 45 |
| 693843 | 2 | 2.0 | 45 |
| 693848 | 2 | 7.0 | 45 |

Example 9

Inhibitory Effect In Vivo of a Modified Oligonucleotide Targeting Human Tau Exon 10

B6.Cg-Mapttm1(EGFP)Klt Tg(MAPT)8cPdav/J mice (The Jackson Laboratory) express the 3R and 4R isoforms of human Tau. The effect of oligonucleotides selected from Table 3, 4, or 8 on shifting of the 4R isoform to 3R isoform was assessed in this mouse model.

Groups of four B6.Cg-Mapttm1(EGFP)Klt Tg(MAPT) 8cPdav/J mice (3-4 months of age) were administered 500 μg of oligonucleotide via an intracerebroventricular (ICV) bolus injection. A control group of four mice was similarly treated with PBS. Two weeks after the dose, animals were sacrificed and RNA was extracted from the cerebral cortex, hippocampus, and/or spinal cord. mRNA expression of the 4R isoform and total human Tau were analyzed by qRT-PCR. The 4R isoform was analyzed using primer probe set hTau 9_10 junction (forward sequence 5'-CACTGAGAACCTGAAGCACC-3', SEQ ID NO: 219; reverse sequence 5'-GTTGCTAAGATCCAGCTTCTT-3', SEQ ID NO: 220; probe sequence 5'-TTAATTATCTGCACCTTCCCGCCTCC-3', SEQ ID NO: 221) or primer probe set hTau 10_11 junction (forward sequence 5'-AATATCAAACACGTCCCGGGAG-3', SEQ ID NO: 222; reverse sequence 5'-TGCCTAATGAGCCACACTTG-3', SEQ ID NO: 223; probe sequence 5'-GTCTACAAACCAGTTGACCTGAGC-3', SEQ ID NO: 224). Total Tau was analyzed using primer probe set RTS3104 (forward sequence 5'-AAGATTGGGTCCCTGGACAAT-3', SEQ ID NO: 225; reverse sequence 5'-AGCTTGTGGGTTTCAATCTTTTTATT-3', SEQ ID NO: 226; probe sequence 5'-CACCCACGTCCCTGGCGGA-3', SEQ ID NO: 227). The ratio of 4R isoform to total Tau mRNA levels was normalized to mouse GAPDH levels, which were analyzed using primer probe set mGapdh_LTS00102 (forward sequence 5'-GGCAAATTCAACGGCACAGT-3', SEQ ID NO: 228; reverse sequence 5'-GGGTCTCGCTCCTGGAAGAT-3', SEQ ID NO: 229; probe sequence 5'-AAGGCCGAGAATGGGAAGCTTGTCATC-3', SEQ ID NO: 230). The results are presented in Tables 13-15 as the average ratio of 4R isoform to total Tau mRNA normalized to GAPDH levels for each treatment group divided by the average ratio for the PBS group. "ND" indicates no data.

Inflammation was also assessed by performing RT-PCT to determine the expression levels of AIF1 in the cortex, hippocampus, and/or spinal cord. After normalization of all samples to GADPH, the average AIF1 value for each treatment group was divided by the average AIF1 value for the PBS control group. The results are presented in Tables 13-15.

TABLE 13

Effect of modified oligonucleotides on Tau exon 10 skipping in transgenic mice

| ISIS NO. | 4R cortex | 4R hippo | 4R spinal cord | AIF1 cortex | AIF1 hippo | AIF1 spinal cord | SEQ ID NO. |
|---|---|---|---|---|---|---|---|
| 415883 | 0.50 | 0.46 | 0.56 | 1.35 | 1.27 | 1.44 | 200 |
| 549566 | 0.54 | 0.54 | 0.66 | 1.09 | 1.13 | 1.46 | 31 |
| 549570 | 0.58 | 0.60 | 0.64 | 1.17 | 1.16 | 1.39 | 72 |
| 549577 | 0.25 | 0.30 | 0.38 | 2.92 | 3.27 | 4.39 | 79 |
| 549581 | 0.25 | ND | ND | 1.04 | 1.07 | 1.40 | 83 |
| 549582 | 0.07 | 0.10 | 0.12 | 0.89 | 0.95 | 1.15 | 146 |
| 549583 | 0.25 | 0.26 | 0.25 | 0.97 | 0.94 | 1.09 | 33 |
| 617309 | 0.36 | 0.36 | 0.51 | 1.06 | 1.06 | 1.09 | 97 |

TABLE 14

Effect of modified oligonucleotides on Tau exon 10 skipping in transgenic mice

| ISIS NO. | 4R cortex | 4R hippo | 4R spinal cord | AIF1 spinal cord | SEQ ID NO. |
|---|---|---|---|---|---|
| 549582 | 0.21 | 0.21 | 0.23 | 0.97 | 146 |
| 549584 | 0.32 | 0.28 | 0.28 | 1.12 | 34 |
| 549585 | 0.30 | 0.27 | 0.30 | 1.05 | 35 |
| 565989 | 0.36 | 0.32 | 0.36 | 1.03 | 153 |
| 565990 | 0.50 | 0.46 | 0.53 | 0.97 | 154 |
| 617341 | 0.25 | 0.28 | 0.28 | 1.16 | 130 |
| 617351 | 0.13 | 0.18 | 0.14 | 1.01 | 140 |
| 617352 | 0.09 | 0.13 | 0.09 | 1.06 | 141 |
| 617354 | 0.31 | ND | ND | 1.21 | 143 |
| 617355 | 0.43 | 0.50 | 0.37 | 1.18 | 144 |
| 617356 | 0.30 | 0.40 | 0.49 | 0.98 | 145 |
| 617357 | 0.33 | 0.33 | 0.27 | 1.31 | 147 |
| 617358 | 0.27 | 0.27 | 0.34 | 1.12 | 148 |
| 617359 | 0.32 | 0.32 | 0.37 | 0.95 | 149 |
| 617360 | 0.21 | 0.19 | 0.29 | 1.19 | 150 |
| 617361 | 0.26 | 0.21 | 0.37 | 1.04 | 151 |
| 617362 | 0.26 | 0.27 | 0.34 | 0.90 | 152 |
| 617364 | 0.39 | 0.33 | 0.43 | 1.09 | 157 |

TABLE 15

Effect of modified oligonucleotides on Tau exon 10 skipping in transgenic mice

| ISIS NO. | 4R cortex | 4R hippo | 4R spinal cord | AIF1 cortex | AIF1 spinal cord | SEQ ID NO. |
|---|---|---|---|---|---|---|
| 549582 | 0.26 | 0.34 | 0.29 | 0.74 | 1.03 | 146 |
| 549586 | 0.25 | 0.43 | 0.38 | 0.97 | 0.98 | 36 |
| 549587 | 0.39 | 0.47 | 0.46 | 0.96 | 1.17 | 37 |
| 549595 | 0.27 | 0.39 | 0.39 | 0.84 | 0.92 | 45 |
| 617317 | 0.62 | 0.83 | 0.53 | 0.88 | 1.05 | 106 |
| 617318 | 0.57 | 0.69 | 0.49 | 0.94 | 1.06 | 107 |
| 617323 | 0.60 | 0.82 | 0.49 | 0.92 | 1.10 | 112 |
| 617324 | 0.72 | 0.88 | 0.49 | 0.70 | 1.03 | 113 |
| 617365 | 0.31 | 0.42 | 0.27 | 0.79 | 0.87 | 158 |
| 617367 | 0.39 | 0.46 | 0.35 | 0.90 | 1.29 | 160 |

Example 10

Effect In Vivo of Mixed Backbone Oligonucleotides on Human Tau Exon 10 Skipping Groups of four B6.Cg-Mapttm1(EGFP)Klt Tg(MAPT) 8cPdav/J mice (see Example 9) were administered 125 μg of an oligonucleotide selected from Table 3, 4, or 9 or PBS via ICV bolus injection. Two weeks after the dose, animals were sacrificed and RNA was extracted from the cerebral cortex and/or hippocampus and analyzed as described in Example 9. The results are presented in Tables 16 and 17 as the average ratio of the 4R isoform to total Tau mRNA normalized to PBS for each treatment group.

Expression of allograft inflammatory factor (AIF1) was tested as a measure of inflammation by performing RT-PCT to determine the expression levels of AIF1 in the cortex and spinal cord. After normalization of all samples to GADPH, the average AIF1 value for each treatment group was divided by the average AIF1 value for the PBS control group. The results are presented in Tables 16 and 17.

TABLE 16

Effect of modified oligonucleotides on Tau exon 10 skipping in transgenic mice

| ISIS NO. | 4R Cortex | AIF1 cortex | AIF1 spinal cord | SEQ ID NO. |
|---|---|---|---|---|
| 549582 | 0.42 | 1.0 | 0.9 | 146 |
| 549583 | 0.71 | 0.9 | 1.2 | 33 |
| 617341 | 0.64 | 1.0 | 0.9 | 130 |
| 617361 | 0.63 | 1.1 | 1.1 | 151 |
| 670011 | 0.78 | 1.0 | 1.0 | 130 |
| 670012 | 0.47 | 0.9 | 1.1 | 146 |
| 670013 | 0.63 | 1.0 | 0.9 | 148 |
| 670014 | 0.90 | 0.9 | 1.0 | 33 |
| 670015 | 0.70 | 0.9 | 0.9 | 150 |
| 670018 | 0.75 | 1.0 | 1.0 | 34 |
| 670019 | 0.58 | 1.1 | 1.0 | 35 |
| 670020 | 0.67 | 0.9 | 0.9 | 130 |
| 670023 | 0.87 | 1.0 | 1.0 | 33 |
| 670024 | 0.60 | 1.0 | 1.1 | 150 |
| 670025 | 0.72 | 1.1 | 0.9 | 151 |
| 670027 | 0.79 | 1.0 | 0.9 | 34 |
| 670028 | 0.66 | 1.1 | 1.0 | 35 |
| 678329 | 0.13 | 1.0 | 1.0 | 140 |
| 678330 | 0.51 | 0.9 | 0.9 | 141 |
| 678331 | 1.12 | 0.9 | 1.0 | 83 |
| 678332 | 0.27 | 0.9 | 1.0 | 140 |
| 678333 | 0.56 | 0.9 | 0.9 | 141 |
| 678334 | 1.10 | 0.9 | 1.2 | 83 |

TABLE 17

Effect of modified oligonucleotides on Tau exon 10 skipping in transgenic mice

| ISIS No. | 4R Cortex | AIF1 cortex | AIF1 spinal cord | SEQ ID NO. |
|---|---|---|---|---|
| 549577 | 0.56 | 1.4 | 1.6 | 79 |
| 549580 | 0.52 | 0.9 | 1.2 | 82 |
| 549582 | 0.27 | 0.9 | 1.0 | 146 |
| 549586 | 0.90 | 1.1 | 1.3 | 36 |
| 549595 | 0.90 | 1.0 | 1.4 | 45 |
| 617353 | 1.35 | 1.0 | 1.3 | 142 |
| 693840 | 0.80 | 0.9 | 1.2 | 79 |
| 693841 | 0.91 | 1.1 | 1.1 | 82 |
| 693842 | 1.20 | 1.0 | 0.8 | 36 |
| 693843 | 1.31 | 1.0 | 1.6 | 45 |
| 693844 | 2.22 | 1.1 | 1.6 | 142 |
| 693845 | 0.86 | 1.0 | 1.4 | 79 |

TABLE 17-continued

Effect of modified oligonucleotides on Tau exon 10 skipping in transgenic mice

| ISIS No. | 4R Cortex | AIF1 cortex | AIF1 spinal cord | SEQ ID NO. |
|---|---|---|---|---|
| 693846 | 0.84 | 1.0 | 1.4 | 82 |
| 693847 | 0.89 | 1.0 | 1.8 | 36 |
| 693848 | 0.76 | 0.9 | 1.9 | 45 |
| 693849 | 2.08 | 0.8 | 1.8 | 142 |

The invention claimed is:

1. A compound comprising a modified oligonucleotide consisting of 15 to 30 linked nucleosides and having a nucleobase sequence comprising a complementary region comprising at least 15 contiguous nucleobases complementary to an equal length portion of nucleobases 121708 to 122044 of SEQ ID NO.: 1, wherein each nucleoside of the modified oligonucleotide comprises a 2'-substituted sugar moiety and wherein each 2'-substituted sugar moiety is 2'-MOE.

2. The compound of claim 1, wherein the modified oligonucleotide consists of 16 to 22 linked nucleosides.

3. The compound of claim 2, wherein at least one nucleobase of the modified oligonucleotide is a modified nucleobase.

4. The compound of claim 3, wherein the modified nucleobase is a 5-methylcytosine.

5. The compound of claim 4, wherein the modified oligonucleotide comprises at least one modified internucleoside linkage.

6. The compound of claim 5, wherein the modified internucleoside linkage is a phosphorothioate internucleoside linkage.

7. The compound of claim 4, wherein each internucleoside linkage is a modified internucleoside linkage.

8. The compound of claim 7, wherein each modified internucleoside linkage is a phosphorothioate internucleoside linkage.

9. A compound comprising a modified oligonucleotide consisting of 12 to 30 linked nucleosides and having a nucleobase sequence comprising a complementary region comprising at least 15 contiguous nucleobases complementary to an equal length portion of nucleobases 121873 to 121898 of SEQ ID NO: 1, wherein each nucleoside of the modified oligonucleotide comprises a modified sugar moiety.

10. The compound of claim 9, wherein the nucleobase sequence of the modified oligonucleotide is at least 90% complementary to SEQ ID NO: 1.

11. The compound of claim 10, wherein the modified oligonucleotide consists of 16 to 22 linked nucleosides.

12. The compound of claim 11, wherein at least one nucleobase of the modified oligonucleotide is a modified nucleobase.

13. The compound of claim 12, wherein the modified nucleobase is a 5-methylcytosine.

14. The compound of claim 13, wherein the modified oligonucleotide comprises at least one modified internucleoside linkage.

15. The compound of claim 14, wherein the modified internucleoside linkage is a phosphorothioate internucleoside linkage.

16. The compound of claim 13, wherein each internucleoside linkage is a modified internucleoside linkage.

17. The compound of claim 16, wherein each modified internucleoside linkage is a phosphorothioate internucleoside linkage.

18. The compound of claim 17, wherein the modified sugar moiety is a 2'-substituted sugar moiety.

19. The compound of claim 18, wherein the 2'-substituted sugar moiety is selected from among: 2'-OMe, 2'-F, and 2'-MOE.

20. The compound of claim 17, wherein the modified sugar moiety is a bicyclic sugar moiety.

21. The compound of claim 20, wherein the bicyclic sugar moiety is LNA or cEt.

22. The compound of claim 17, wherein the modified sugar moiety is a sugar surrogate.

23. The compound of claim 22, wherein the sugar surrogate is a morpholino.

24. A pharmaceutical composition comprising a compound according to claim 1 and a pharmaceutically acceptable carrier or diluent.

25. A method of reducing or ameliorating one or more symptoms associated with a tau-associated disorder, comprising contacting a cell with a compound according to claim 1.

26. The method of claim 25, wherein the cell is in an animal.

* * * * *